(12) United States Patent
Arista et al.

(10) Patent No.: US 11,613,543 B2
(45) Date of Patent: Mar. 28, 2023

(54) SUBSTITUTED PYRROLO[2,3-D]PYRIMIDINES AS BRUTON'S TYROSINE KINASE INHIBITORS

(71) Applicant: NOVARTIS AG, Basel (CH)

(72) Inventors: Luca Arista, Riehen (CH); Christina Hebach, Muenchenstein (CH); Gregory John Hollingworth, Kent (GB); Philipp Holzer, Sissach (CH); Patricia Imbach-Weese, Bielefeld (DE); Julien Lorber, Colmar (FR); Rainer Machauer, Freiburg (DE); Niko Schmiedeberg, Riehen (CH); Anna Vulpetti, Basel (CH); Thomas Zoller, Andolsheim (FR)

(73) Assignee: NOVARTIS AG, Basel (CH)

( * ) Notice: Subject to any disclaimer, the term of this patent is extended or adjusted under 35 U.S.C. 154(b) by 186 days.

(21) Appl. No.: 16/981,059

(22) PCT Filed: Mar. 22, 2019

(86) PCT No.: PCT/IB2019/052346
§ 371 (c)(1),
(2) Date: Sep. 15, 2020

(87) PCT Pub. No.: WO2019/186343
PCT Pub. Date: Oct. 3, 2019

(65) Prior Publication Data
US 2021/0002285 A1 Jan. 7, 2021

(30) Foreign Application Priority Data
Mar. 26, 2018 (EP) .................. 18164076

(51) Int. Cl.
A61K 31/519 (2006.01)
C07D 487/04 (2006.01)
C07D 519/00 (2006.01)
A61K 45/06 (2006.01)

(52) U.S. Cl.
CPC ......... C07D 487/04 (2013.01); C07D 519/00 (2013.01); A61K 45/06 (2013.01)

(58) Field of Classification Search
CPC ..................... A61K 31/519; C07D 487/04
USPC ....................... 514/265.1; 544/280
See application file for complete search history.

(56) References Cited

U.S. PATENT DOCUMENTS

| 2009/0118276 A1 | 5/2009 | Gopalsamy et al. |
| 2021/0251996 A1 | 8/2021 | Arista et al. |

FOREIGN PATENT DOCUMENTS

| WO | 2013008095 A1 | 1/2013 |
| WO | 2013157021 A1 | 10/2013 |
| WO | 2015197028 A1 | 12/2015 |
| WO | 2016169989 A1 | 10/2016 |
| WO | 2018033556 A1 | 2/2018 |
| WO | 2019186343 A1 | 10/2019 |
| WO | 2019186358 A1 | 10/2019 |

OTHER PUBLICATIONS

Huang, et al.; A Chemoproteomic Approach to Query the Degradable Kinome Using a Multi-kinase Degrader; Cell Chemical Biology; Jan. 18, 2018; vol. 25; pp. 1-12.
Doig, et al., Rational design of inhibitors of the bacterial cell wall synthetic enzyme GlmU using virtual screening and lead-hopping, Bioorganic & Medicinal Chemisty Letters, Sep. 16, 2014, 6256-6269, 22.
Donner, et al., High potency improvements to weak aryl uracil HCV polymerase inhibitor leads, Bioorganic & Medicinal Chemisty Letters, Jun. 4, 2013, 4367-4369, 23.
Randolph, et al., Synthesis and Biological Characterization of Aryl Uracil Inhibitors of Hepatitis C Virus NS5B Polymerase: Discovery od ABT-072, a trans-Stilbene Analog with Good Oral Bioavailability, Journal of Medicinal Chemistry, Jan. 17, 2018, 1153-1163, 61.

Primary Examiner — Douglas M Willis
(74) Attorney, Agent, or Firm — Elizabeth T. Karnas

(57) ABSTRACT

The invention relates to compounds of the formula (I) (I) or a pharmaceutically acceptable salt thereof, wherein the substituents are as defined in the specification; to intermediates in the preparation of the compounds, to pharmaceutical compositions comprising the compounds and to use of the compounds in the treatment of disease.

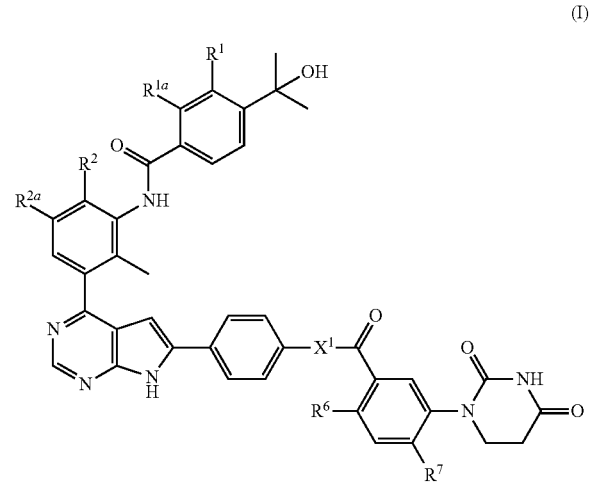

14 Claims, No Drawings
Specification includes a Sequence Listing.

SUBSTITUTED PYRROLO[2,3-D]PYRIMIDINES AS BRUTON'S TYROSINE KINASE INHIBITORS

CROSS-REFERENCE TO RELATED APPLICATIONS

This application is a national phase application, filed under 35 U.S.C. 371 of International Application No. PCT/IB2019/052346 filed Mar. 22, 2019, which claims the benefit to EP 18164076.4 filed Mar. 26, 2018, the content of which is incorporated by reference herein in its entirety

FIELD OF THE INVENTION

The present invention relates to N-(3-(7H-pyrrolo[2,3-d]pyrimidin-4-yl)phenyl)benzamide derivatives, to their preparation, to pharmaceutical compositions comprising them and to their use in the treatment of conditions, diseases and disorders mediated by Bruton's Tyrosine Kinase.

BACKGROUND OF THE INVENTION

Bruton's Tyrosine Kinase (BTK) is a critical node for B-cell receptor (BCR) signaling, and an important target in cancer. Many cancers and lymphomas express BTK and are dependent on BTK function, and BCR signaling in tumor infiltrating B-cells has also been implicated in the tumor-promoting microenvironment of solid cancers (J. A. Burger and A. Wiestner, *Nat Rev Cancer* 2018, 18, 148). Pharmacological blockade of BTK using inhibitors, particularly inhibitors which irreversibly bind BTK through cysteine-481 is an established strategy, BTK being a primary target of the molecule ibrutinib (J. A. Burger and J. J. Buggy, *Leukemia and Lymphoma* 2013, 54, 2385) which is indicated for the treatment of several cancers (C-S Lee et al., *J. Oncol. Pharm. Practice* 2016, 22, 92-104. V. Kaur & A. Swami, *Ann. Hematol.* 2017, 96, 1175), as well as for acalabrutinib which is indicated for the treatment of patients with mantle cell lymphoma who have received at least one prior treatment (Wang M et al, *Lancet* 2018, 391, Issue 10121, 659-667).

BTK also plays an essential role in autoimmune disease. BTK-deficient mice are protected in standard preclinical models for rheumatoid arthritis (L. Jansson and R. Holmdahl, *Clinical and experimental immunology* 1993, 94, 459; L. E. Nyhoff et al, *Arthritis Rheumatol.* 2016, 68, 1856), systemic lupus erythematosus (Steinberg, B. J. et al., *J. Clin. Invest.* 1982, 70, 587-597), as well as allergic disease and anaphylaxis (Hata, D. et al., *J. Exp. Med.* 1998, 187, 1235-1247), thus pharmacological blockade of BTK may be useful in the treatment of immune disorders.

In view of the above, modulators of BTK may be useful in the treatment of proliferative disorders such as cancer and of immune (e.g. autoimmune) disorders.

There remains a need for new medications to treat BTK-dependent diseases, particularly those resistant to or poorly responding to currently available medications.

A molecule designed to reduce or remove BTK protein by inducing its degradation (hereinafter referred to as a 'BTK degrader') may be efficacious in treating a range of BTK mediated diseases such as proliferative disorders (such as cancers) and immune disorders. Furthermore, BTK degraders may be effective in settings of resistance to irreversible BTK inhibitors (which bind covalently to BTK). Resistance may arise through, for example mutation of cysteine-481 to serine (or other amino acid substitutions).

Potential indications for a BTK degrader include, but are not limited to, cancers of hematopoietic origin such as Hodgkin lymphoma, non-Hodgkin lymphoma, post-transplant lymphoproliferative disorder, hairy cell leukemia, histiocytic and dendritic neoplasms and B-cell neoplasms such as chronic lymphocytic leukemia (CLL), mantle cell lymphoma (MCL), small lymphocytic lymphoma (SLL), Waldenstrom's macroglobulinemia, diffuse large B-cell lymphoma (DLBCL), follicular lymphoma, Burkitt lymphoma, Marginal Zone Lymphoma, immunoblastic large cell lymphoma, Richter Syndrome, and precursor B-lymphoblastic lymphoma, primary and secondary multiple myeloma, B-cell prolymphocytic leukemia, lymphoplasmacytic lymphoma, splenic marginal zone lymphoma, plasma cell myeloma, plasmacytoma, extranodal marginal zone B-cell lymphoma, nodal marginal zone B-cell lymphoma, mediastinal (thymic) large B-cell lymphoma, intravascular large B-cell lymphoma, primary effusion lymphoma, lymphomatoid granulomatosis, and acute lymphoblastic leukemia.

Potential indications for a BTK degrader also include, but are not limited to, autoimmune disorders such as rheumatoid arthritis, systemic lupus erythematosus, allergic diseases, anaphylaxis and inflammatory conditions. Furthermore, potential indications for a BTK degrader include chronic graft-versus-host disease (cGvHD) and immunoglobulin Light Chain Amyloidosis (AL).

The principle of induced degradation of protein targets as a potential therapeutic approach has been described in, for example, C. M. Crews, 2018, *J. Med. Chem.*, 61(2), 403-404 and references cited therein. A BTK degrader molecule which incorporates an ibrutinib substructure as the BTK binding moiety is described in WO 2016/169989 at page 12 and incorporates an E3 ligase IAP binding moiety for recruitment of the target protein to the E3 ubiquitin ligase IAP for degradation. Two further BTK degrader molecules are described in Huang et. al., 2018, *Cell Chemical Biology* 25, 88-99 which incorporate two structurally different moieties as the BTK binding components. The molecules described in that publication incorporate an immunomodulatory imide drug (IMiD) moiety (pomalidomide) for recruitment of BTK to the E3 ligase complex comprising cereblon (CRBN) for ubiquitination and consequent degradation. Also described in Huang et al. is a molecule (TL12-186) based on a promiscuous kinase binder which degrades multiple targets including BTK, and is reported to also degrade certain non-kinase targets including the zinc finger DNA-binding protein IKZF1 (Ikaros). IKZF1 and the related protein IKZF3 (Aiolos) are known to be degraded by pomalidomide and lenalidomide (Krönke, J. et. al. 2014, *Science* 343, 301-305; Petzold et. al., *Nature* 2016, 532, 127-130; Bjorklund et. al., 2015, *Blood Cancer Journal*, 5, e354; Lu et. al., 2014, *Science*, 343, 305-309; Gandhi et. al., 2014, *Br. J. Haematol.* 164, 811-821).

SUMMARY OF THE INVENTION

The present invention provides compounds of formula (I), or a pharmaceutically acceptable salt thereof, as defined herein below. The compounds of formula (I) are BTK degraders and are therefore potentially useful in the treatment of conditions, diseases and disorders mediated by BTK.

In one aspect of the present invention, a compound of formula (I) is provided, (I)

wherein:
$R^1$, $R^{1a}$, $R^2$ and $R^{2a}$ are independently at each occurrence selected from H and F;
$R^6$ is H or F;
$R^7$ is selected from H, F, C, —$CH_3$, —$OCH_3$, and —$OCH_2CH_3$;
$X^1$ is a group of formula (A) or (B):

*$X^{1a}$—$X^{2a}$— (A)

or

*$X^{1b}$—$X^{2b}$— (B)

wherein,
*$X^{1a}$ is selected from *—$(CH_2)_{1-3}$—, and *—$CH_2C(CH_3)_2$—, wherein the * indicates the point of attachment of the $X^{1a}$ group to the phenyl ring in formula (I);
*$X^{1b}$ is selected from *—O—, *—$OCH_2$—, and *—$CH_2O$— wherein the * indicates the point of attachment of the $X^{1b}$ group to the phenyl ring in formula (I);
$X^{2a}$ is selected from formula (C), (D), (E), (F), and (G):

(C)

(D)

(E)

(F)

(G)

wherein ** indicates the point of attachment to $X^{1a}$;
$X^{2b}$ is selected from formula (E1) and (F1):

(E1)

(F1)

wherein ** indicates the point of attachment to $X^{1b}$;
$X^5$ is CH or N;
$X^6$ is CH or N;
$R^3$ is H or —$CH_3$;
$R^4$ is H or —$CH_2OH$;
$R^5$ is H or —$CH_2OH$;
Z is absent or *—$(CH_2)_{2-3}NH$—, wherein * indicates the point of attachment of Z to the N atom in formula (C);
$Z^1$ is selected from *—O—, *—C(O)—, *—$(CH_2)_{1-3}$—, *—$(CH_2)_2O$—, and *—$CH_2CH(CH_2OH)O$—, wherein * indicates the point of attachment of $Z^1$ to $X^5$ in formula (E) and formula (E1);
$Z^{2a}$ is absent or —$NH(CH_2)_4$—**;
$Z^{2b}$ is —$(CH_2)_{3-4}NH(CH_2)_2$—**;
$Z^3$ is absent or —$(CH_2)_4NH$—, wherein $Z^{2a}$ and $Z^3$ are not both at the same time absent; and wherein  in each of $Z^{2a}$, $Z^{2b}$ and $Z^3$ indicates the point of attachment to the respective N atoms in formulae (F) and (F1);
q is 0 or 1; and
n and p are independently 0 or 1; and
wherein (i) when $Z^1$ in formula (E) or formula (E1) is *—O—, then $X^5$ and $X^6$ are not N, and (ii) when $Z^1$ in formula (E) or formula (E1) is *—$(CH_2)_2$—O— or *—$CH_2CH(CH_2OH)O$— then $X^6$ is not N;
or a pharmaceutically acceptable salt thereof.

The present invention relates to novel N-(3-(7H-pyrrolo [2,3-d]pyrimidin-4-yl)phenyl)benzamide compounds of formula (I) which bring about degradation of Bruton's Tyrosine Kinase (BTK). These compounds are designed to induce degradation of BTK by recruiting BTK (including BTK mutants, especially those that confer resistance to BTK inhibitors, in particular irreversible BTK inhibitors such as ibrutinib), to an E3 ligase, thus prompting ubiquitination of BTK and its subsequent degradation by the proteasome. The compounds of the present invention comprise a novel BTK-binding domain moiety joined to a novel ligand which binds to the E3-ligase cereblon (CRBN).

Accordingly, compounds of the present invention may therefore be potentially useful in the treatment of a range of diseases and disorders, including proliferative and autoimmune diseases, particularly disorders and diseases mediated by BTK, including those in which resistance has arisen, e.g. through mutation of cysteine-481 to serine (or other amino acid substitutions). The compounds of the present invention further may show selectivity for BTK degradation over other proteins, in particular over other tyrosine kinase proteins and/or the (non-tyrosine kinase) IKZF family of proteins such as IKZF1 and/or IKZF3, which have been shown to be degraded by IMiDs e.g. thalidomide, lenalidomide and pomalidomide, and also by the protein degrading molecule TL12-186 mentioned supra. The compounds of the present invention further may exhibit kinase selectivity and/or selectivity over other off target proteins such as ion channels and G-protein coupled receptor (GPCRs).

The compounds of formula (I), including their pharmaceutically acceptable salts, are therefore considered suitable for use in the treatment of conditions, diseases, and disorders mediated by BTK, especially proliferative conditions, diseases and disorders such as cancer, in particular, hematopoietic cancers, including B-cell neoplasms such as chronic lymphocytic leukemia (CLL), mantle cell lymphoma (MCL), small lymphocytic lymphoma (SLL), Waldenstrom's macroglobulinemia, diffuse large B-cell lymphoma (DLBCL), follicular lymphoma, Burkitt lymphoma, Marginal Zone Lymphoma, immunoblastic large cell lymphoma, Richter Syndrome, and precursor B-lymphoblastic lymphoma, primary and secondary multiple myeloma, B-cell prolymphocytic leukemia, lymphoplasmacytic lymphoma, splenic marginal zone lymphoma, plasma cell myeloma, plasmacytoma, extranodal marginal zone B-cell lymphoma, nodal marginal zone B-cell lymphoma, mediastinal (thymic) large B-cell lymphoma, intravascular large B-cell lymphoma, primary effusion lymphoma, lymphomatoid granulomatosis, and acute lymphoblastic leukemia.

In another aspect, the invention provides compounds of formula (I), or pharmaceutically acceptable salts thereof, for use in methods of treating, preventing, or ameliorating a BTK-mediated condition, disease, or disorder.

In another aspect, the invention provides compositions which comprise (e.g. a therapeutically effective amount of) a compound of formula (I), or a pharmaceutically acceptable salt thereof, and one or more pharmaceutically acceptable carriers.

In another aspect, the invention provides a combination, comprising (e.g. a therapeutically effective amount of) a compound of formula (I), or a pharmaceutically acceptable salt thereof, and one or more therapeutically active agents.

DETAILED DESCRIPTION OF THE INVENTION

Various embodiments of the invention are described herein. It will be recognized that features specified in each embodiment may be combined with other specified features to provide further embodiments of the present invention. Various (enumerated) embodiments of the invention are also described herein.

The definition of the substituents applies to compounds of formulae (I), (I'), (I''), (I'''), and (Ia) as applicable.

The definition of the substituents applies to the end-products as well as to the corresponding intermediates.

The invention therefore provides a compound of formula (I)

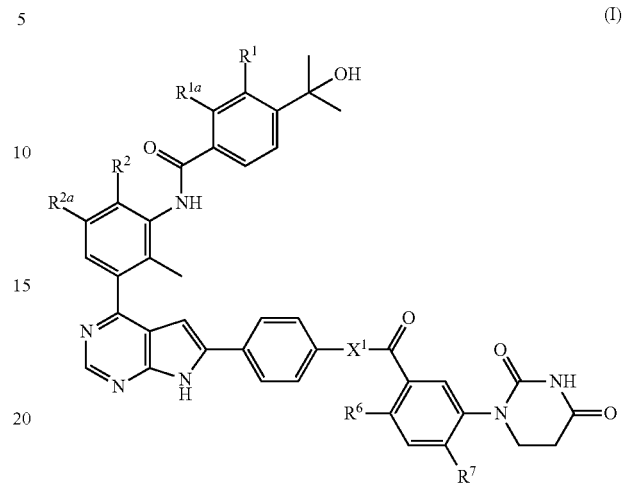

wherein:
$R^1$, $R^{1a}$, $R^2$ and $R^{2a}$ are independently at each occurrence selected from H and F;
$R^6$ is H or F;
$R^7$ is selected from H, F, C, —CH$_3$, —OCH$_3$, and —OCH$_2$CH$_3$;
$X^1$ is a group of formula (A) or (B):

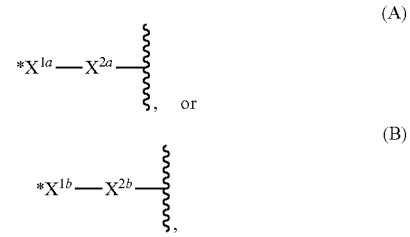

wherein,
*$X^{1a}$ is selected from *—(CH$_2$)$_{1-3}$—, and *—CH$_2$C(CH$_3$)$_2$—, wherein the * indicates the point of attachment of the $X^{1a}$ group to the phenyl ring in formula (I);
*$X^{1b}$ is selected from *—O—, *—OCH$_2$—, and *—CH$_2$O— wherein the * indicates the point of attachment of the $X^{1b}$ group to the phenyl ring in formula (I);
$X^{2a}$ is selected from formula (C), (D), (E), (F), and (G):

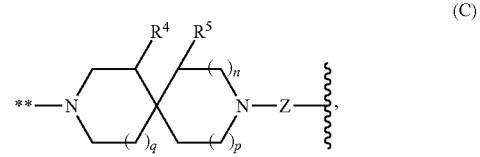

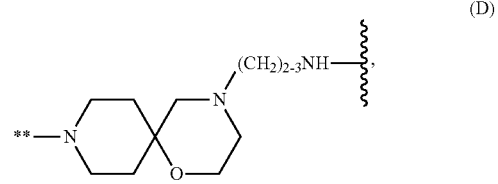

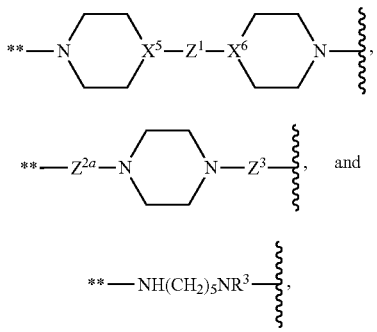

(E)

(F)

(G)

wherein ** indicates the point of attachment to $X^{1a}$;
$X^{2b}$ is selected from formula (E1) and (F1):

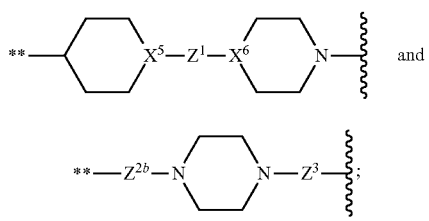

(E1)

(F1)

wherein ** indicates the point of attachment to $X^{1b}$;
$X^5$ is CH or N;
$X^6$ is CH or N;
$R^3$ is H or —$CH_3$;
$R^4$ is H or —$CH_2OH$;
$R^5$ is H or —$CH_2OH$;
Z is absent or *—$(CH_2)_{2-3}NH$—, wherein * indicates the point of attachment of Z to the N atom in formula (C);
$Z^1$ is selected from *—O—, *—C(O)—, *—$(CH_2)_{1-3}$—, *—$(CH_2)_2O$—, and *—$CH_2CH(CH_2OH)O$—, wherein * indicates the point of attachment of $Z^1$ to $X^5$ in formula (E) and formula (E1);
$Z^{2a}$ is absent or —$NH(CH_2)_4$—**;
$Z^{2b}$ is —$(CH_2)_{3-4}NH(CH_2)_2$—**;
$Z^3$ is absent or —$(CH_2)_4NH$—, wherein $Z^{2a}$ and $Z^3$ are not both at the same time absent; and wherein  in each of $Z^{2a}$, $Z^{2b}$ and $Z^3$ indicates the point of attachment to the respective N atoms in formulae (F) and (F1);
q is 0 or 1; and
n and p are independently 0 or 1; and
wherein (i) when $Z^1$ in formula (E) or formula (E1) is *—O—, then $X^5$ and $X^6$ are not N, and (ii) when $Z^1$ in formula (E) or formula (E1) is *—$(CH_2)_2$—O— or *—$CH_2CH(CH_2OH)O$— then $X^6$ is not N;
or a pharmaceutically acceptable salt thereof.

Unless specified otherwise, the term "compounds of the present invention" or "compound of the present invention" refers to compounds of formula (I), subformulae thereof and exemplified compounds, and salts thereof, as well as all stereoisomers (including diastereoisomers and enantiomers), rotamers, tautomers and isotopically labeled compounds (including deuterium substitutions), as well as inherently formed moieties.

Unless indicated otherwise, the expressions used in this invention have the following meanings:

As used herein, the term —$(CH_2)_{1-3}$— refers to a (in particular) straight hydrocarbon chain bi-radical consisting solely of carbon and hydrogen atoms, containing no unsaturation, having from one to three carbon atoms, and which is attached to the rest of the molecule at each end by a single bond. The end which is attached to the rest of the molecule at a particular location for such groups may be specified by the indicator symbols * or **. Groups incorporating analogous terms such as —$(CH_2)_2O$—, —$(CH_2)_{2-3}NH$—, —$(CH_2)_{3-4}NH(CH_2)_2$—, and —$(CH_2)_4NH$— are to be construed accordingly.

ENUMERATED EMBODIMENTS

Embodiment 1. A compound of the formula (I), or a pharmaceutically acceptable salt thereof, as described above.

Embodiment 2. A compound of the formula (I), or a pharmaceutically acceptable salt thereof, according to embodiment 1, wherein $R^1$ is H.

Embodiment 3. A compound of the formula (I), or a pharmaceutically acceptable salt thereof, according to embodiment 1 or 2, wherein $R^{1a}$ is F.

Embodiment 4. A compound of the formula (I), or a pharmaceutically acceptable salt thereof, according to any one of embodiments 1 to 3, wherein $R^2$ is H.

Embodiment 5. A compound of the formula (I), or a pharmaceutically acceptable salt thereof, according to any one of embodiments 1 to 4, wherein $R^{2a}$ is F.

Embodiment 6. A compound of formula (I), or a pharmaceutically acceptable salt thereof, according to any one of embodiments 1 to 5, wherein $R^6$ is H.

Embodiment 7. A compound of formula (I), or a pharmaceutically acceptable salt thereof, according to any one of embodiments 1 to 6, wherein $R^7$ is selected from F, —$CH_3$ and —$OCH_3$.

Embodiment 8. A compound of formula (I), or a pharmaceutically acceptable salt thereof, according to any one of embodiments 1 to 7, wherein $R^7$ is F.

Embodiment 9. A compound of formula (I), or a pharmaceutically acceptable salt thereof, according to any one of embodiments 1 to 7, wherein $R^7$ is —$CH_3$.

Embodiment 10. A compound of formula (I), or a pharmaceutically acceptable salt thereof, according to any one of embodiments 1 to 7, wherein $R^7$ is —$OCH_3$.

Embodiment 11. A compound of formula (I), or a pharmaceutically acceptable salt thereof, according to any one of embodiments 1 to 10, wherein $X^1$ is a group of formula (A):

(A)

Embodiment 12. A compound of formula (I), or a pharmaceutically acceptable salt thereof, according to embodiment 11, wherein *$X^{1a}$ is *—$(CH_2)_{1-3}$—.

Embodiment 13. A compound of formula (I), or a pharmaceutically acceptable salt thereof, according to embodiment 12, wherein *$X^{1a}$ is selected from *—$CH_2$— and *—$(CH_2)_2$—.

Embodiment 14. A compound of formula (I), or a pharmaceutically acceptable salt thereof, according to any one of embodiments 11 to 13, wherein $X^{2a}$ is selected from formula (C), (E), and (F):

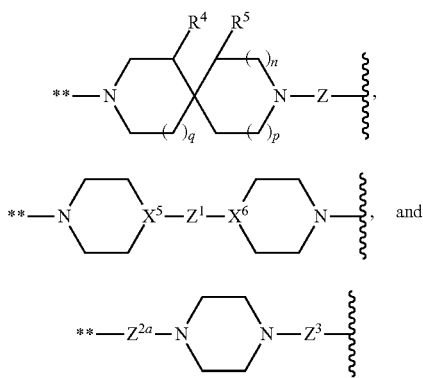

Embodiment 15. A compound of formula (I), or a pharmaceutically acceptable salt thereof, according to embodiment 14, wherein $X^{2a}$ is selected from formula (C) and (E):

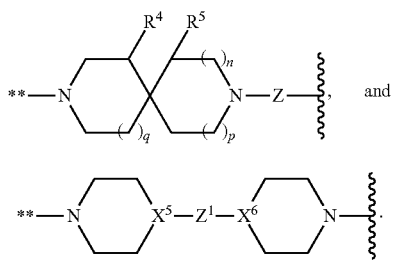

Embodiment 16. A compound of formula (I), or a pharmaceutically acceptable salt thereof, according to any one of embodiments 1 to 15, wherein $R^4$ is H.

Embodiment 17. A compound of formula (I), or a pharmaceutically acceptable salt thereof, according to any one of embodiments 1 to 16, wherein $R^5$ is H.

Embodiment 18. A compound of formula (I), or a pharmaceutically acceptable salt thereof, according to any one of embodiments 1 to 17, wherein q is 1.

Embodiment 19. A compound of formula (I), or a pharmaceutically acceptable salt thereof, according to any one of embodiments 1 to 18, wherein n and p are both 1.

Embodiment 20. A compound of formula (I), or a pharmaceutically acceptable salt thereof, according to any one of embodiments 1 to 19, wherein Z is absent.

Embodiment 21. A compound of formula (I), or a pharmaceutically acceptable salt thereof, according to any one of embodiments 1 to 20, wherein $X^5$ and $X^6$ are both CH.

Embodiment 22. A compound of formula (I), or a pharmaceutically acceptable salt thereof, according to any one of embodiments 1 to 20, wherein $X^5$ and $X^6$ are both N.

Embodiment 23. A compound of formula (I), or a pharmaceutically acceptable salt thereof, according to any one of embodiments 1 to 21, wherein $Z^1$ is *—O—.

Embodiment 24. A compound of formula (I), or a pharmaceutically acceptable salt thereof, according to embodiment 22, wherein $Z^1$ is *—(CH$_2$)$_2$—.

Embodiment 25. A compound of formula (I), or a pharmaceutically acceptable salt thereof, according to any one of embodiments 1 to 24, wherein $Z^{2a}$ is —NH(CH$_2$)$_4$—**.

Embodiment 26. A compound of formula (I), or a pharmaceutically acceptable salt thereof, according to embodiment 13, wherein $Z^{2a}$ is —NH(CH$_2$)$_4$—**.

Embodiment 27. A compound of formula (I), or a pharmaceutically acceptable salt thereof, according to any one of embodiments 1 to 26, wherein $Z^3$ is absent.

Embodiment 28. A compound of formula (I), or a pharmaceutically acceptable salt thereof, according to embodiment 1, wherein $Z^3$ is absent.

Embodiment 29. A compound of formula (Ia)

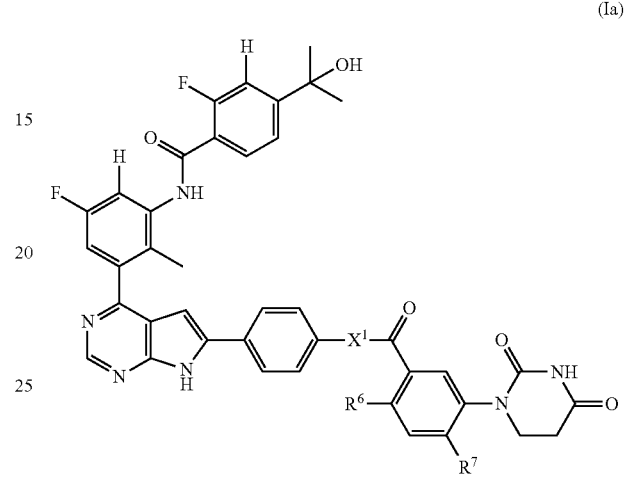

wherein, $R^6$ is H or F;

$R^7$ is selected from H, F, C, —CH$_3$, —OCH$_3$, and —OCH$_2$CH$_3$;

$X^1$ is a group of formula (A) or (B):

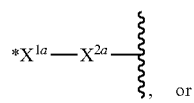

or

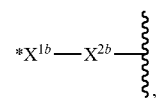

wherein,

*$X^{1a}$ is selected from *—(CH$_2$)$_{1-3}$—, and *—CH$_2$C(CH$_3$)$_2$—, wherein the * indicates the point of attachment of the $X^{1a}$ group to the phenyl ring in formula (Ia);

*$X^{1b}$ is selected from *—O—, *—OCH$_2$—, and *—CH$_2$O— wherein the * indicates the point of attachment of the $X^{1b}$ group to the phenyl ring in formula (Ia);

$X^{2a}$ is selected from formula (C), (D), (E), (F) and (G):

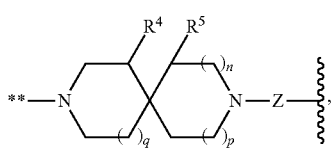

-continued

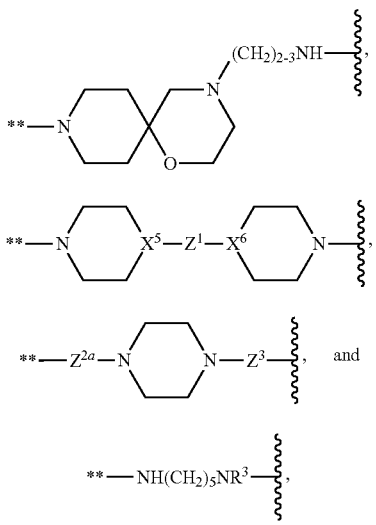

(D)

(E)

(F)

(G)

wherein ** indicates the point of attachment to $X^{1a}$;
$X^{2b}$ is selected from formula (E1) and (F1):

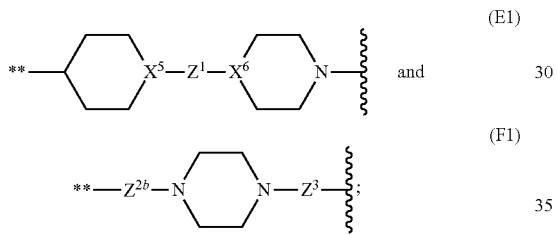

(E1)

(F1)

wherein ** indicates the point of attachment to $X^{1b}$;
$X^5$ is CH or N;
$X^6$ is CH or N:
$R^3$ is H or —$CH_3$;
$R^4$ is H or —$CH_2OH$;
$R^5$ is H or —$CH_2OH$;
Z is absent or *—$(CH_2)_{2-3}NH$—, wherein * indicates the point of attachment of Z to the N atom in formula (C);
$Z^1$ is selected from *—O—, *—C(O)—, *—$(CH_2)_{1-3}$—, *—$(CH_2)_2O$—, and *—$CH_2CH(CH_2OH)O$—, wherein * indicates the point of attachment of $Z^1$ to $X^5$ in formula (E) and formula (E1);
$Z^{2a}$ is absent or —$NH(CH_2)_4$—**;
$Z^{2b}$ is —$(CH_2)_{3-4}NH(CH_2)_2$—**;
$Z^3$ is absent or —$(CH_2)_4NH$—, wherein $Z^{2a}$ and $Z^3$ are not both at the same time absent; and wherein  in each of $Z^{2a}$, $Z^{2b}$ and $Z^3$ indicates the point of attachment to the respective N atoms in formulae (F) and (F1);
q is 0 or 1; and
n and p are independently 0 or 1; and
wherein (i) when $Z^1$ in formula (E) or formula (E1) is *—O—, then $X^5$ and $X^6$ are not N, and (ii) when $Z^1$ in formula (E) or formula (E1) is *—$(CH_2)_2$—O— or *—$CH_2CH(CH_2OH)O$—, then $X^6$ is not N;
or a pharmaceutically acceptable salt thereof.
Embodiment 30. A compound of formula (I) according to any one of embodiments 1 to 10 or formula (Ia) according to embodiment 29, or a pharmaceutically acceptable salt thereof, wherein, $X^1$ is selected from:

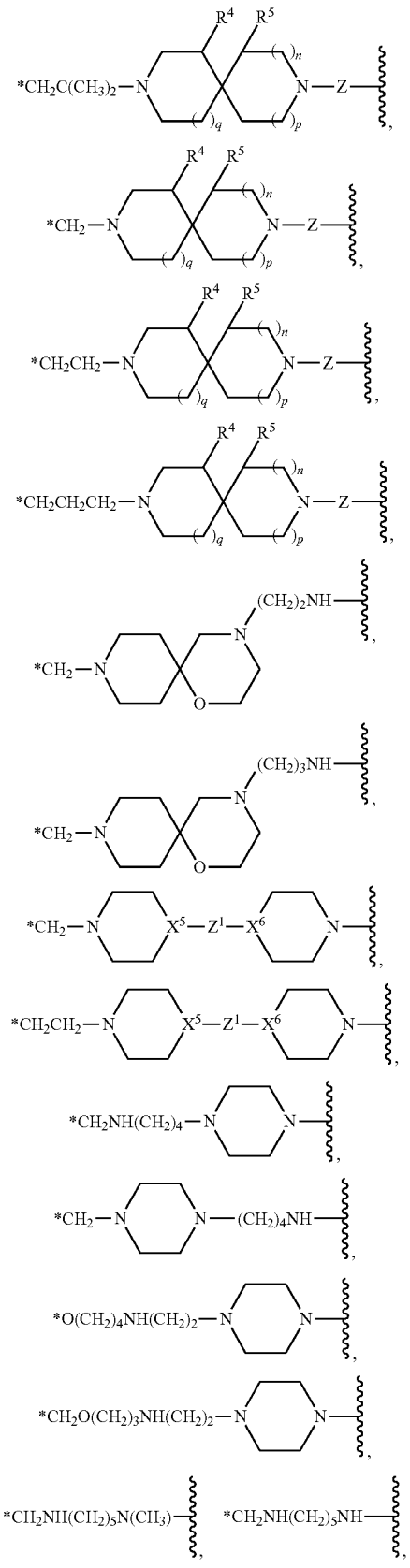

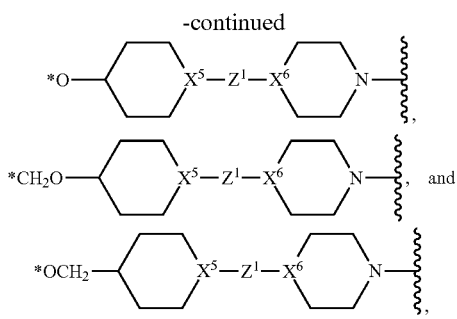

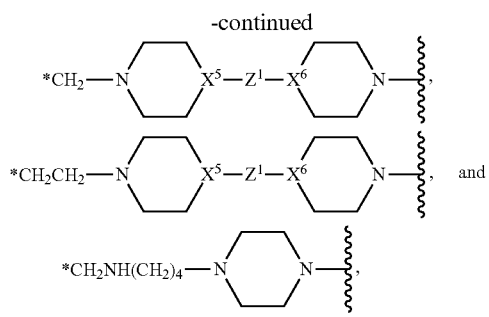

wherein * indicates the point of attachment to the phenyl ring in formula (I);
or a pharmaceutically acceptable salt thereof.

Embodiment 31. A compound of formula (Ia), or a pharmaceutically acceptable salt thereof, according to embodiment 29 or embodiment 30, wherein $R^4$ is H.

Embodiment 32. A compound of formula (Ia), or a pharmaceutically acceptable salt thereof, according to any one of embodiments 29 to 31, wherein $R^5$ is H.

Embodiment 33. A compound of formula (Ia), or a pharmaceutically acceptable salt thereof, according to any one of embodiments 29 to 32, wherein q is 1.

Embodiment 34. A compound of formula (Ia), or a pharmaceutically acceptable salt thereof, according to any one of embodiments 29 to 33, wherein n is 1.

Embodiment 35. A compound of formula (Ia), or a pharmaceutically acceptable salt thereof, according to any one of embodiments 29 to 34, wherein p is 1.

Embodiment 36. A compound of formula (Ia), or a pharmaceutically acceptable salt thereof, according to embodiment 29 to 35, wherein Z is absent.

Embodiment 37. A compound of formula (Ia), or a pharmaceutically acceptable salt thereof, according to any one of embodiments 29 to 36, wherein $X^5$ and $X^6$ are both CH.

Embodiment 38. A compound of formula (Ia), or a pharmaceutically acceptable salt thereof, according to any one of embodiments 29 to 36, wherein $X^5$ and $X^6$ are both N.

Embodiment 39. A compound of formula (Ia), or a pharmaceutically acceptable salt thereof, according to any one of embodiments 29 to 38, wherein $Z^1$ is selected from *—O— and *—$(CH_2)_{1-3}$—.

Embodiment 40. A compound of formula (Ia), or a pharmaceutically acceptable salt thereof, according to embodiment 39, wherein $Z^1$ is selected from *—O— and *—$(CH_2)_2$—.

Embodiment 41. A compound of formula (I) according to any one of embodiments 1 to 10, or formula (Ia) according to embodiment 29, or a pharmaceutically acceptable salt thereof, wherein,
$X^1$ is selected from:

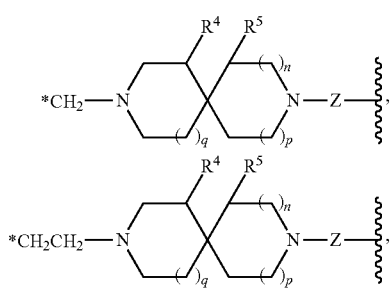

wherein * indicates the atom which is attached to the phenyl ring in formula (I) or formula (Ia).

Embodiment 42. A compound of formula (I) or (Ia), or a pharmaceutically acceptable salt thereof, according to embodiment 41, wherein,
$X^1$ is selected from:

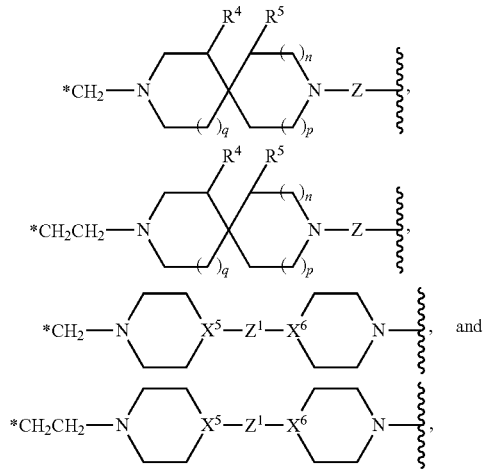

wherein * indicates the atom which is attached to the phenyl ring in formula (I) or (Ia).

Embodiment 43. A compound of formula (I) or (Ia), or a pharmaceutically acceptable salt thereof, according to embodiment 41 or 42, wherein $Z^1$ is —O— and $X^5$ and $X^6$ are both CH.

Embodiment 44. A compound of formula (I) or (Ia), or a pharmaceutically acceptable salt thereof, according to embodiment 41 or 42, wherein $Z^1$ is —$(CH_2)_2$— and $X^5$ and $X^6$ are both N.

Embodiment 45. A compound of formula (I) or (Ia), or a pharmaceutically acceptable salt thereof, according to any one of embodiments 41 to 44, wherein $R^4$ and $R^5$ are both H.

Embodiment 46. A compound of formula (I) or (Ia), or a pharmaceutically acceptable salt thereof, according to any one of embodiments 41 to 45, wherein n, p and q are each 1.

Embodiment 47. A compound of formula (I) or (Ia), or a pharmaceutically acceptable salt thereof, according to any one of embodiments 41 to 46, wherein Z is absent.

Embodiment 48. A compound of formula (I) or (Ia), or a pharmaceutically acceptable salt thereof, according to any one of embodiments 1 to 10, 29 and 30, wherein, $X^1$ is selected from:
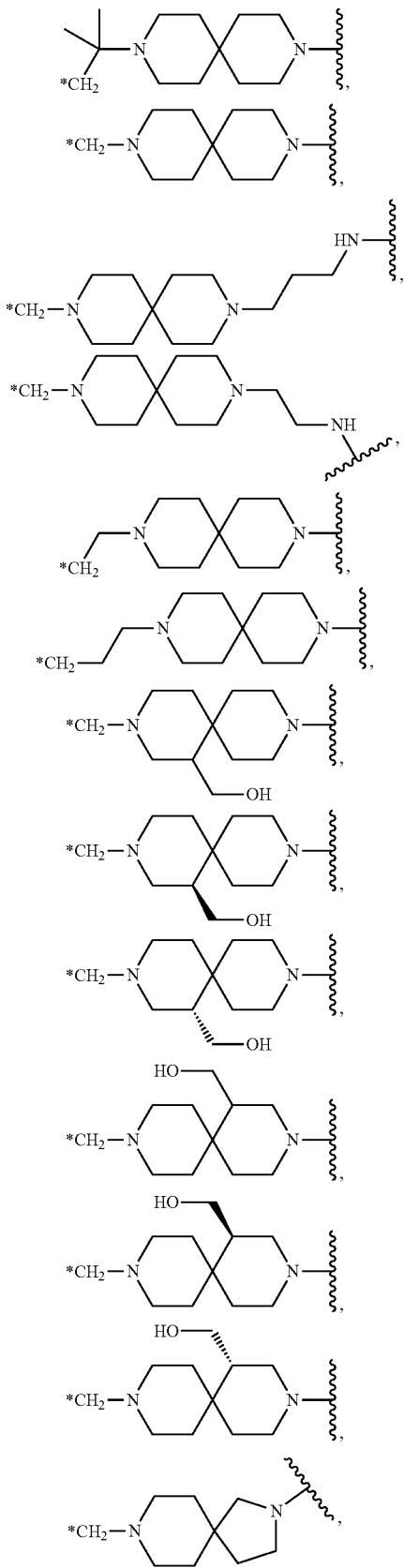
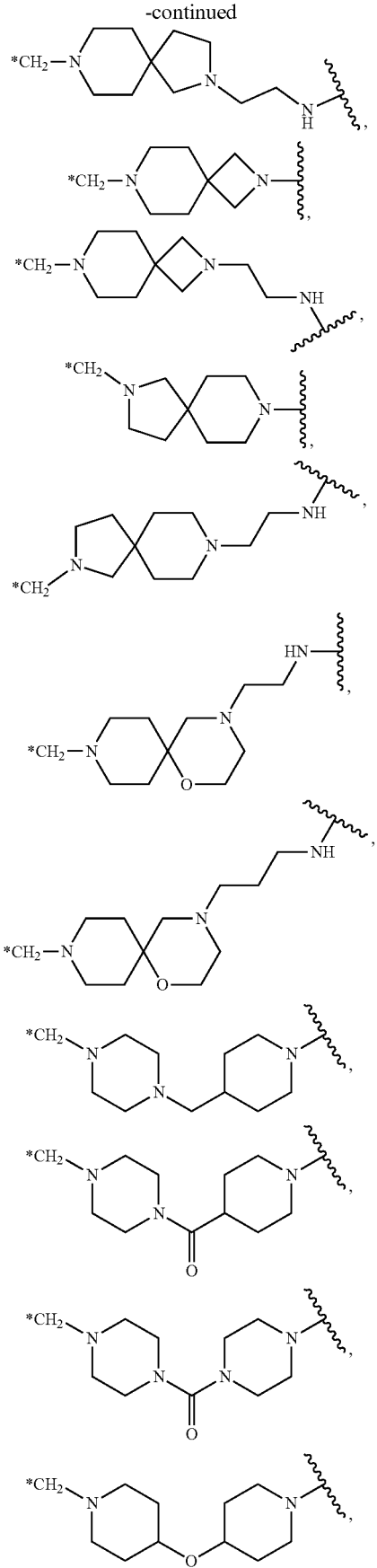

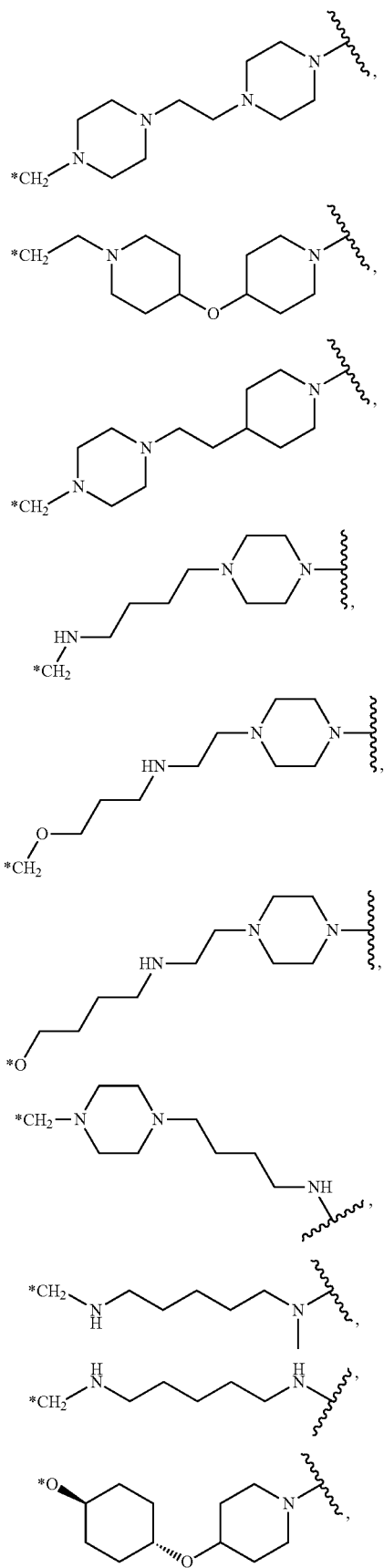
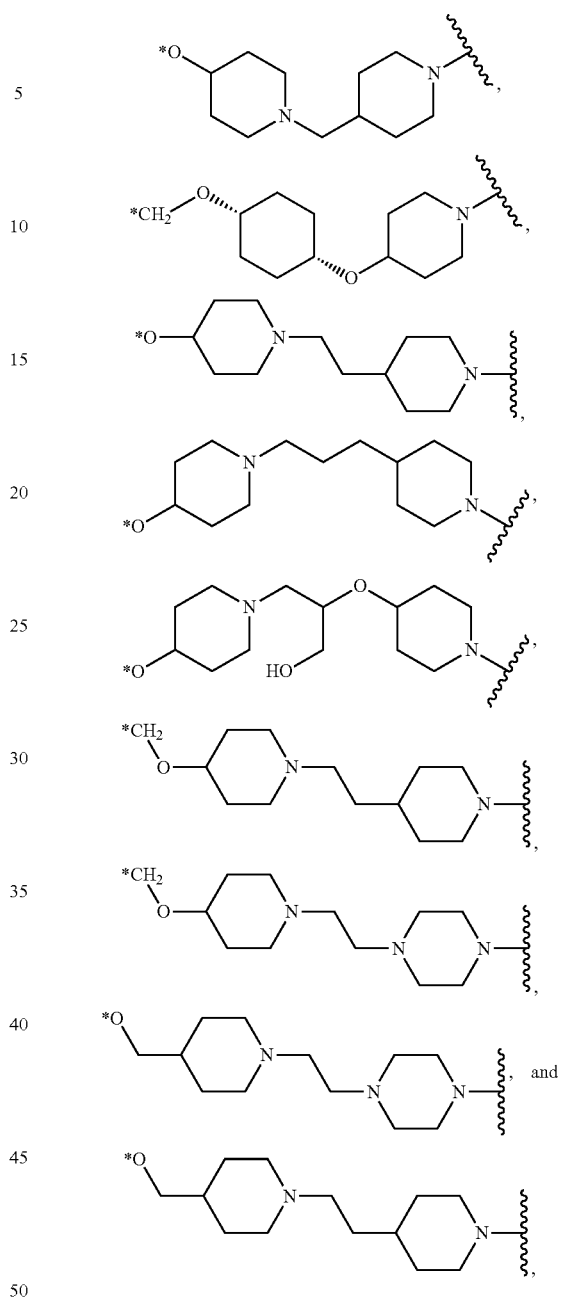
wherein * indicates the atom which is attached to the phenyl ring in formula (I) or (Ia).
Embodiment 49. A compound of formula (I) or (Ia), or a pharmaceutically acceptable salt thereof, according to embodiment 48, wherein, $X^1$ is selected from:
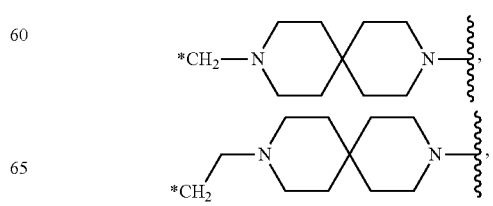

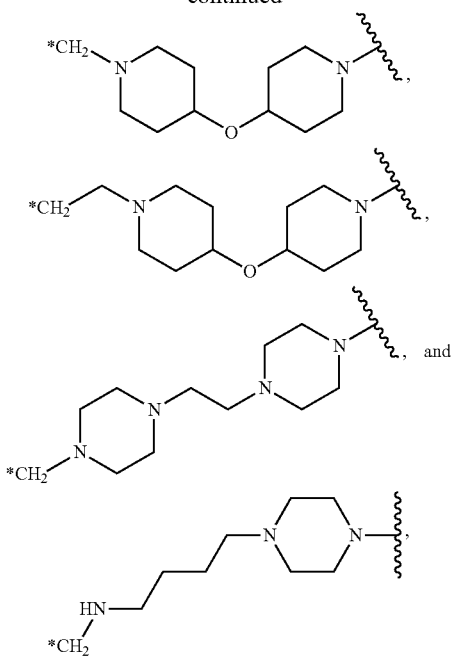

wherein * indicates the atom which is attached to the phenyl ring in formula (I) or (Ia).

Embodiment 50. A compound of formula (I) or (Ia), wherein the compound is rac-N-(3-(6-(4-((9-(3-(2,4-dioxotetrahydropyrimidin-1 (2H)-yl)-4-methoxybenzoyl)-7-(hydroxymethyl)-3,9-diazaspiro[5.5]undecan-3-yl)methyl)phenyl)-7H-pyrrolo[2,3-d]pyrimidin-4-yl)-5-fluoro-2-methylphenyl)-2-fluoro-4-(2-hydroxypropan-2-yl)benzamide, (R)—N-(3-(6-(4-((9-(3-(2,4-dioxotetrahydropyrimidin-1 (2H)-yl)-4-methoxybenzoyl)-7-(hydroxymethyl)-3,9-diazaspiro[5.5]undecan-3-yl)methyl)phenyl)-7H-pyrrolo[2,3-d]pyrimidin-4-yl)-5-fluoro-2-methylphenyl)-2-fluoro-4-(2-hydroxypropan-2-yl)benzamide, (S)—N-(3-(6-(4-((9-(3-(2,4-dioxotetrahydropyrimidin-1 (2H)-yl)-4-methoxybenzoyl)-7-(hydroxymethyl)-3,9-diazaspiro[5.5]undecan-3-yl)methyl)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-((9-(3-(2,4-dioxotetrahydropyrimidin-1(2H)-yl)-4-ethoxybenzoyl)-3,9-diazaspiro[5.5]undecan-3-yl)methyl)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-(2-(9-(3-(2,4-dioxotetrahydropyrimidin-1(2H)-yl)-4-methylbenzoyl)-3,9-diazaspiro[5.5]undecan-3-yl)ethyl)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-(((1-(2-(1-(3-(2,4-dioxotetrahydropyrimidin-1 (2H)-yl)-4-fluorobenzoyl)piperidin-4-yl)ethyl)piperidin-4-yl)oxy)methyl)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-((4-((1-(3-(2,4-dioxotetrahydropyrimidin-1 (2H)-yl)-4-methoxybenzoyl)piperidin-4-yl)methyl)piperazin-1-yl)methyl)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-((4-((1-(3-(2,4-dioxotetrahydropyrimidin-1 (2H)-yl)-4-methoxybenzoyl)piperidin-4-yl)oxy)piperidin-1-yl)methyl)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-((9-(3-(2,4-dioxotetrahydropyrimidin-1(2H)-yl)-4-methoxybenzoyl)-3,9-diazaspiro[5.5]undecan-3-yl)methyl)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-(2-(4-((1-(3-(2,4-dioxotetrahydropyrimidin-1 (2H)-yl)-4-methylbenzoyl)piperidin-4-yl)oxy)piperidin-1-yl)ethyl)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-(3-(9-(3-(2,4-dioxotetrahydropyrimidin-1(2H)-yl)-4-methoxybenzoyl)-3,9-diazaspiro[5.5]undecan-3-yl)propyl)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-(2-(9-(3-(2,4-dioxotetrahydropyrimidin-1(2H)-yl)benzoyl)-3,9-diazaspiro[5.5]undecan-3-yl)ethyl)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-(((1-(2-(1-(3-(2,4-dioxotetrahydropyrimidin-1 (2H)-yl)-4-methoxybenzoyl)piperidin-4-yl)ethyl)piperidin-4-yl)oxy)methyl)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-((9-(3-(2,4-dioxotetrahydropyrimidin-1(2H)-yl)-4-fluorobenzoyl)-3,9-diazaspiro[5.5]undecan-3-yl)methyl)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-((1-(3-(1-(3-(2,4-dioxotetrahydropyrimidin-1 (2H)-yl)-4-methoxybenzoyl)piperidin-4-yl)propyl)piperidin-4-yl)oxy)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-((4-(2-(4-(3-(2,4-dioxotetrahydropyrimidin-1 (2H)-yl)-4-methoxybenzoyl)piperazin-1-yl)ethyl)piperazin-1-yl)methyl)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-((4-(2-(1-(3-(2,4-dioxotetrahydropyrimidin-1 (2H)-yl)-4-methoxybenzoyl)piperidin-4-yl)ethyl)piperazin-1-yl)methyl)phenyl)-7H-pyrrolo[2,3-d]pyrimidin-4-yl)-5-fluoro-2-methylphenyl)-2-fluoro-4-(2-hydroxypropan-2-yl)benzamide, rac-N-(3-(6-(4-((1-(2-((1-(3-(2,4-dioxotetrahydropyrimidin-1(2H)-yl)-4-methoxybenzoyl)piperidin-4-yl)oxy)-3-hydroxypropyl)piperidin-4-yl)oxy)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-((1-((1-(3-(2,4-dioxotetrahydropyrimidin-1 (2H)-yl)-4-methoxybenzoyl)piperidin-4-yl)methyl)piperidin-4-yl)oxy)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-(2-(9-(3-(2,4-dioxotetrahydropyrimidin-1(2H)-yl)-4-methoxybenzoyl)-3,9-diazaspiro[5.5]undecan-3-yl)-2-methylpropyl)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-(((1-(2-(4-(3-(2,4-dioxotetrahydropyrimidin-1 (2H)-yl)-4-methoxybenzoyl)piperazin-1-yl)ethyl)piperidin-4-yl)oxy)methyl)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-((4-(4-(3-(2,4-dioxotetrahydropyrimidin-1(2H)-yl)-4-methoxybenzoyl)piperazine-1-carbonyl)piperazin-1-yl)methyl)phenyl)-7H-pyrrolo[2,3-d]pyrimidin-4-yl)-5-fluoro-2-methylphenyl)-2-fluoro-4-(2-hydroxypropan-2-yl)benzamide, rac-N-(3-(6-(4-((9-(3-(2,4-dioxotetrahydropyrimidin-1(2H)-yl)-4-methoxybenzoyl)-1-(hydroxymethyl)-3,9-diazaspiro[5.5]undecan-3-yl)methyl)phenyl)-7H-pyrrolo[2,3-d]pyrimidin-4-yl)-5-fluoro-2-methylphenyl)-2-fluoro-4-(2-hydroxypropan-2-yl)benzamide, (S)—N-(3-(6-(4-((9-(3-(2,4-dioxotetrahydropyrimidin-1(2H)-yl)-4-methoxybenzoyl)-1-(hydroxymethyl)-3,9-diazaspiro[5.5]undecan-3-yl)methyl)phenyl)-7H-pyrrolo[2,3-d]pyrimidin-4-yl)-5-fluoro-2-methylphenyl)-2-fluoro-4-(2-hydroxypropan-2-yl)benzamide, (R)—N-(3-(6-(4-((9-(3-(2,4-dioxotetrahydropyrimidin-1(2H)-yl)-4-methoxybenzoyl)-1-(hydroxymethyl)-3,9-diazaspiro[5.5]undecan-3-yl)methyl)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-((4-(4-(3-(2,4-dioxotetrahydropyrimidin-1(2H)-yl)-4-methoxybenzamido)butyl)piperazin-1-yl)methyl)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-((9-(3-(2,4-dioxotetrahydropyrimidin-1(2H)-yl)-4-methylbenzoyl)-3,9-diazaspiro[5.5]undecan-3-yl)methyl)phenyl)-7H-pyrrolo[2,3-d]pyrimidin-4-yl)-5-fluoro-2-methylphenyl)-2-fluoro-4-(2-hydroxypropan-2-yl)benzamide, 5-(2,4-dioxotetrahydropyrimidin-1(2H)-yl)-2-fluoro-N-(5-((4-(4-(5-fluoro-3-(2-fluoro-4-(2-hydroxypropan-2-yl)benzamido)-2-methylphenyl)-7H-pyrrolo[2,3-d]pyrimidin-6-yl)benzyl)amino)pentyl)-N,4-dimethylbenzamide, 5-(2,4-dioxotetrahydropyrimidin-1(2H)-yl)-2-fluoro-N-(5-((4-(4-(5-fluoro-3-(2-fluoro-4-(2-hydroxypropan-2-yl)benzamido)-2-methylphenyl)-7H-pyrrolo[2,3-d]pyrimidin-6-yl)benzyl)amino)pentyl)-4-methylbenzamide, 3-(2,4-dioxotetrahydropyrimidin-1(2H)-yl)-N-(5-((4-(4-(5-fluoro-3-(2-fluoro-4-(2-hydroxypropan-2-yl)benzamido)-2-methylphenyl)-7H-pyrrolo[2,3-d]pyrimidin-6-yl)benzyl)amino)pentyl)-N,4-dimethylbenzamide, N-(3-(6-(4-(2-(9-(3-(2,4-dioxotetrahydropyrimidin-1(2H)-yl)-4-methoxybenzoyl)-3,9-diazaspiro[5.5]undecan-3-yl)ethyl)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-((2-(3-(2,4-dioxotetrahydropyrimidin-1(2H)-yl)-4-methoxybenzoyl)-2,7-diazaspiro[3.5]nonan-7-yl)methyl)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-((4-(1-(3-(2,4-dioxotetrahydropyrimidin-1(2H)-yl)-4-methoxybenzoyl)piperidine-4-carbonyl)piperazin-1-yl)methyl)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-(2-(4-((1-(3-(2,4-dioxotetrahydropyrimidin-1(2H)-yl)-4-methoxybenzoyl)piperidin-4-yl)oxy)piperidin-1-yl)ethyl)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-((8-(2-(3-(2,4-dioxotetrahydropyrimidin-1(2H)-yl)-4-methoxybenzamido)ethyl)-2,8-diazaspiro[4.5]decan-2-yl)methyl)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-(4-((2-(4-(3-(2,4-dioxotetrahydropyrimidin-1(2H)-yl)-4-methoxybenzoyl)piperazin-1-yl)ethyl)amino)butoxy)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-((4-(2-(4-chloro-3-(2,4-dioxotetrahydropyrimidin-1(2H)-yl)benzamido)ethyl)-1-oxa-4,9-diazaspiro[5.5]undecan-9-yl)methyl)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-((1-(2-(1-(3-(2,4-dioxotetrahydropyrimidin-1(2H)-yl)-4-methoxybenzoyl)piperidin-4-yl)ethyl)piperidin-4-yl)oxy)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-((4-(2-(3-(2,4-dioxotetrahydropyrimidin-1(2H)-yl)-4-methoxybenzamido)ethyl)-1-oxa-4,9-diazaspiro[5.5]undecan-9-yl)methyl)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-(((4-(4-(3-(2,4-dioxotetrahydropyrimidin-1(2H)-yl)-4-methoxybenzoyl)piperazin-1-yl)butyl)amino)methyl)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-((((1s,4s)-4-((1-(3-(2,4-dioxotetrahydropyrimidin-1(2H)-yl)-4-methoxybenzoyl)piperidin-4-yl)oxy)cyclohexyl)oxy)methyl)phenyl)-7H-pyrrolo[2,3-d]pyrimidin-4-yl)-5-fluoro-2-methylphenyl)-2-fluoro-4-(2-hydroxypropan-2-yl)benzamide, 4-chloro-3-(2,4-dioxotetrahydropyrimidin-1(2H)-yl)-N-(5-((4-(4-(5-fluoro-3-(2-fluoro-4-(2-hydroxypropan-2-yl)benzamido)-2-methylphenyl)-7H-pyrrolo[2,3-d]pyrimidin-6-yl)benzyl)amino)pentyl)-N-methylbenzamide, N-(3-(6-(4-((1-(2-(1-(3-(2,4-dioxotetrahydropyrimidin-1(2H)-yl)-4-methoxybenzoyl)piperidin-4-yl)ethyl)piperidin-4-yl)methoxy)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-((9-(2-(3-(2,4-dioxotetrahydropyrimidin-1(2H)-yl)-4-methoxybenzamido)ethyl)-3,9-diazaspiro[5.5]undecan-3-yl)methyl)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-((3-((2-(4-(3-(2,4-dioxotetrahydropyrimidin-1(2H)-yl)-4-methoxybenzoyl)piperazin-1-yl)ethyl)amino)propoxy)methyl)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-(((1r,4r)-4-((1-(3-(2,4-dioxotetrahydropyrimidin-1(2H)-yl)-4-methoxybenzoyl)piperidin-4-yl)oxy)cyclohexyl)oxy)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-(2-(9-(3-(2,4-dioxotetrahydropyrimidin-1(2H)-yl)-4-fluorobenzoyl)-3,9-diazaspiro[5.5]undecan-3-yl)ethyl)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-((4-(3-(4-chloro-3-(2,4-dioxotetrahydropyrimidin-1(2H)-yl)benzamido)propyl)-1-oxa-4,9-diazaspiro[5.5]undecan-9-yl)methyl)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-((8-(3-(2,4-dioxotetrahydropyrimidin-1(2H)-yl)-4-methoxybenzoyl)-2,8-diazaspiro[4.5]decan-2-yl)methyl)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-((4-((1-(3-(2,4-dioxotetrahydropyrimidin-1(2H)-yl)-4-methylbenzoyl)piperidin-4-yl)oxy)piperidin-1-yl)methyl)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-((1-(2-(4-(3-(2,4-dioxotetrahydropyrimidin-1(2H)-yl)-4-methoxybenzoyl)piperazin-1-yl)ethyl)piperidin-4-yl)methoxy)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-((2-(2-(3-(2,4-dioxotetrahydropyrimidin-1(2H)-yl)-4-methoxybenzamido)ethyl)-2,7-diazaspiro[3.5]nonan-7-yl)methyl)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-((2-(2-(3-(2,4-dioxotetrahydropyrimidin-1(2H)-yl)-4-methoxybenzamido)ethyl)-2,8-diazaspiro[4.5]decan-8-yl)methyl)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-(((1s,4s)-4-((1-(3-(2,4-dioxotetrahydropyrimidin-1(2H)-yl)-4-methoxybenzoyl)piperidin-4-yl)oxy)cyclohexyl)oxy)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-((2-(3-(2,4-dioxotetrahydropyrimidin-1(2H)-yl)-4-methoxybenzoyl)-2,8-diazaspiro[4.5]decan-8-yl)methyl)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-((((1r,4r)-4-((1-(3-(2,4-dioxotetrahydropyrimidin-1(2H)-yl)-4-methoxybenzoyl)piperidin-4-yl)oxy)cyclohexyl)oxy)methyl)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-((9-(3-(4-chloro-3-(2,4-dioxotetrahydropyrimidin-1(2H)-yl)benzamido)propyl)-3,9-diazaspiro[5.5]undecan-3-yl)methyl)phenyl)-7H-pyrrolo[2,3-d]pyrimidin-4-yl)-5-fluoro-2-methylphenyl)-2-fluoro-4-(2-hydroxypropan-2-yl)benzamide, or N-(3-(6-(4-((1-(2-((1-(3-(2,4-dioxotetrahydropyrimidin-1(2H)-yl)-4-methoxybenzoyl)piperidin-4-yl)oxy)ethyl)piperidin-4-yl)oxy)phenyl)-7H-pyrrolo[2,3-d]pyrimidin-4-yl)-5-fluoro-2-methylphenyl)-2-fluoro-4-(2-hydroxypropan-2-yl)benzamide, or a pharmaceutically acceptable salt thereof.

Embodiment 51. A compound of formula (I) or (Ia), wherein the compound is

N-(3-(6-(4-((4-((1-(3-(2,4-dioxotetrahydropyrimidin-1(2H)-yl)-4-methoxybenzoyl)piperidin-4-yl)oxy)piperidin-1-yl)methyl)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-((9-(3-(2,4-dioxotetrahydropyrimidin-1(2H)-yl)-4-methoxybenzoyl)-3,9-diazaspiro[5.5]undecan-3-yl)methyl)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-(2-(4-((1-(3-(2,4-dioxotetrahydropyrimidin-1(2H)-yl)-4-methylbenzoyl)piperidin-4-yl)oxy)piperidin-1-yl)ethyl)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-((4-(2-(4-(3-(2,4-dioxotetrahydropyrimidin-1(2H)-yl)-4-methoxybenzoyl)piperazin-1-yl)ethyl)piperazin-1-yl)methyl)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-(2-(9-(3-(2,4-dioxotetrahydropyrimidin-1(2H)-yl)-4-methoxybenzoyl)-3,9-diazaspiro[5.5]undecan-3-yl)ethyl)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-(2-(4-((1-(3-(2,4-dioxotetrahydropyrimidin-1(2H)-yl)-4-methoxybenzoyl)piperidin-4-yl)oxy)piperidin-1-yl)ethyl)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-(((4-(4-(3-(2,4-dioxotetrahydropyrimidin-1(2H)-yl)-4-methoxybenzoyl)piperazin-1-yl)butyl)amino)methyl)phenyl)-7H-pyrrolo[2,3-d]pyrimidin-4-yl)-5-fluoro-2-methylphenyl)-2-fluoro-4-(2-hydroxypropan-2-yl)benzamide, and N-(3-(6-(4-(2-(9-(3-(2,4-dioxotetrahydropyrimidin-1(2H)-yl)-4-fluorobenzoyl)-3,9-diazaspiro[5.5]undecan-3-yl)ethyl)phenyl)-7H-pyrrolo[2,3-d]pyrimidin-4-yl)-5-fluoro-2-methylphenyl)-2-fluoro-4-(2-hydroxypropan-2-yl)benzamide, or a pharmaceutically acceptable salt thereof.

Embodiment 52. The compound N-(3-(6-(4-((4-((1-(3-(2,4-dioxotetrahydropyrimidin-1(2H)-yl)-4-methoxybenzoyl)piperidin-4-yl)oxy)piperidin-1-yl)methyl)phenyl)-7H-pyrrolo[2,3-d]pyrimidin-4-yl)-5-fluoro-2-methylphenyl)-2-fluoro-4-(2-hydroxypropan-2-yl)benzamide, or a pharmaceutically acceptable salt thereof.

Embodiment 53. The compound N-(3-(6-(4-((9-(3-(2,4-dioxotetrahydropyrimidin-1(2H)-yl)-4-methoxybenzoyl)-3,9-diazaspiro[5.5]undecan-3-yl)methyl)phenyl)-7H-pyrrolo[2,3-d]pyrimidin-4-yl)-5-fluoro-2-methylphenyl)-2-fluoro-4-(2-hydroxypropan-2-yl)benzamide, or a pharmaceutically acceptable salt thereof.

Embodiment 54. The compound N-(3-(6-(4-(2-(4-((1-(3-(2,4-dioxotetrahydropyrimidin-1(2H)-yl)-4-methylbenzoyl)piperidin-4-yl)oxy)piperidin-1-yl)ethyl)phenyl)-7H-pyrrolo[2,3-d]pyrimidin-4-yl)-5-fluoro-2-methylphenyl)-2-fluoro-4-(2-hydroxypropan-2-yl)benzamide, or a pharmaceutically acceptable salt thereof.

Embodiment 55. The compound N-(3-(6-(4-((4-(2-(4-(3-(2,4-dioxotetrahydropyrimidin-1(2H)-yl)-4-methoxybenzoyl)piperazin-1-yl)ethyl)piperazin-1-yl)methyl)phenyl)-7H-pyrrolo[2,3-d]pyrimidin-4-yl)-5-fluoro-2-methylphenyl)-2-fluoro-4-(2-hydroxypropan-2-yl)benzamide, or a pharmaceutically acceptable salt thereof.

Embodiment 56. The compound N-(3-(6-(4-(2-(9-(3-(2,4-dioxotetrahydropyrimidin-1(2H)-yl)-4-methoxybenzoyl)-3,9-diazaspiro[5.5]undecan-3-yl)ethyl)phenyl)-7H-pyrrolo[2,3-d]pyrimidin-4-yl)-5-fluoro-2-methylphenyl)-2-fluoro-4-(2-hydroxypropan-2-yl)benzamide, or a pharmaceutically acceptable salt thereof.

Embodiment 57. The compound N-(3-(6-(4-(2-(4-((1-(3-(2,4-dioxotetrahydropyrimidin-1(2H)-yl)-4-methoxybenzoyl)piperidin-4-yl)oxy)piperidin-1-yl)ethyl)phenyl)-7H-pyrrolo[2,3-d]pyrimidin-4-yl)-5-fluoro-2-methylphenyl)-2-fluoro-4-(2-hydroxypropan-2-yl)benzamide, or a pharmaceutically acceptable salt thereof.

Embodiment 58. The compound N-(3-(6-(4-(((4-(4-(3-(2,4-dioxotetrahydropyrimidin-1(2H)-yl)-4-methoxybenzoyl)

piperazin-1-yl)butyl)amino)methyl)phenyl)-7H-pyrrolo[2,3-d]pyrimidin-4-yl)-5-fluoro-2-methylphenyl)-2-fluoro-4-(2-hydroxypropan-2-yl)benzamide,
or a pharmaceutically acceptable salt thereof.

Embodiment 59. The compound N-(3-(6-(4-(2-(9-(3-(2,4-dioxotetrahydropyrimidin-1(2H)-yl)-4-fluorobenzoyl)-3,9-diazaspiro[5.5]undecan-3-yl)ethyl)phenyl)-7H-pyrrolo[2,3-d]pyrimidin-4-yl)-5-fluoro-2-methylphenyl)-2-fluoro-4-(2-hydroxypropan-2-yl)benzamide,
or a pharmaceutically acceptable salt thereof.

the compound contains a double bond, the substituent may be E or Z configuration. If the compound contains a disubstituted cycloalkyl, the cycloalkyl substituent may have a cis- or trans-configuration. All tautomeric forms are also intended to be included.

Compounds of formula (I) or (Ia) may occur in various tautomeric forms. All tautomeric forms of the compounds of formula (I) or (Ia) are embraced by the invention. For example, compounds of formula (I), may exist in tautomeric form according to formulae (I') and (I''), thus:

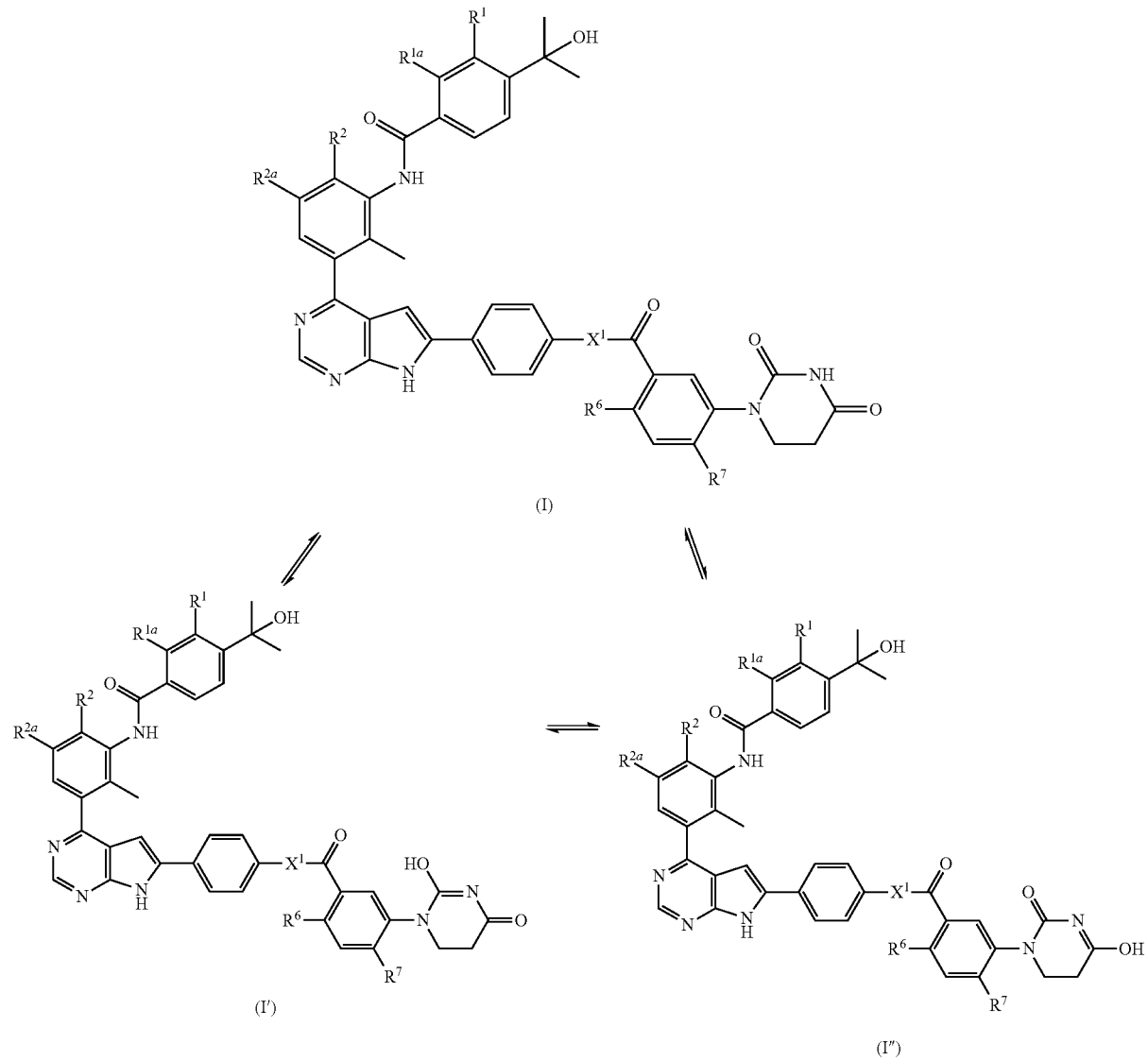

in which $R^1$, $R^{1a}$, $R^2$, $R^{2a}$, $X^1$, $R^6$, and $R^7$ are as defined according to formula (I) or (Ia).

As used herein, the terms "salt" or "salts" refers to an acid addition or base addition salt of a compound of the invention. "Salts" include in particular "pharmaceutically acceptable salts".

The term "pharmaceutically acceptable salts" refers to salts that retain the biological effectiveness and properties of the compounds of this invention and, which typically are not biologically or otherwise undesirable. The compounds of the Depending on the choice of the starting materials and procedures, the compounds can be present in the form of one of the possible stereoisomers or as mixtures thereof, for example as pure optical isomers, or as stereoisomer mixtures, such as racemates and diastereoisomer mixtures, depending on the number of asymmetric carbon atoms. The present invention is meant to include all such possible stereoisomers, including racemic mixtures, diastereomeric mixtures and optically pure forms. Optically active (R)- and (S)-stereoisomers may be prepared using chiral synthons or chiral reagents, or resolved using conventional techniques. If invention may be capable of forming acid and/or base salts by virtue of the presence of amino and/or carboxyl groups or groups similar thereto.

The pharmaceutically acceptable salts of the invention can be synthesized from a basic or acidic moiety, by conventional chemical methods. Generally, such salts can be prepared by reacting free acid forms of these compounds with a stoichiometric amount of the appropriate base or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, acetonitrile or tetrahydrofuran is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

When both a basic group and an acid group are present in the same molecule, the compounds of the invention may also form internal salts, e.g., zwitterionic molecules.

The compounds of the invention are particularly suited for forming acid addition salts by virtue that the compounds contain at least one basic group such as an amino group.

Pharmaceutically acceptable acid addition salts can be formed with inorganic acids and organic acids.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

In another aspect, the present invention provides compounds of the present invention in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate, trifenatate, trifluoroacetate or xinafoate salt form.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Isotopes that can be incorporated into compounds of the invention include, for example, isotopes of hydrogen.

In another aspect of the invention a compound of formula (I''') is provided:

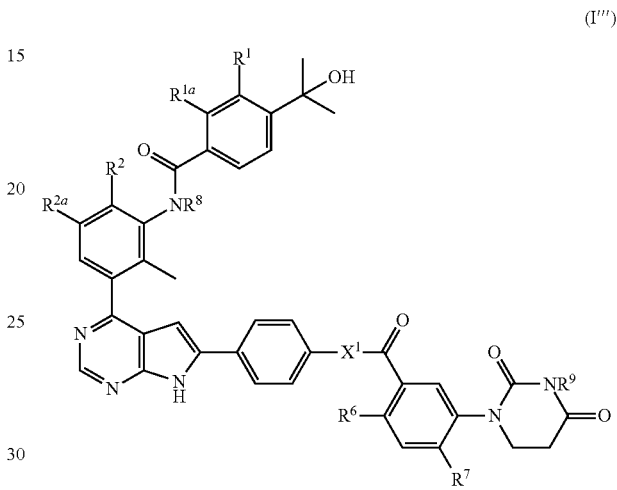

wherein $R^1$, $R^{1a}$, $R^2$, $R^{2a}$, $R^6$ are as defined as for formula (I) or (Ia), $R^7$ is $-C(R^{10})_3$, $-OC(R^{10})_3$ or $-OC(R^{10})_2C(R^{10})_3$, and $X^1$ is selected from:

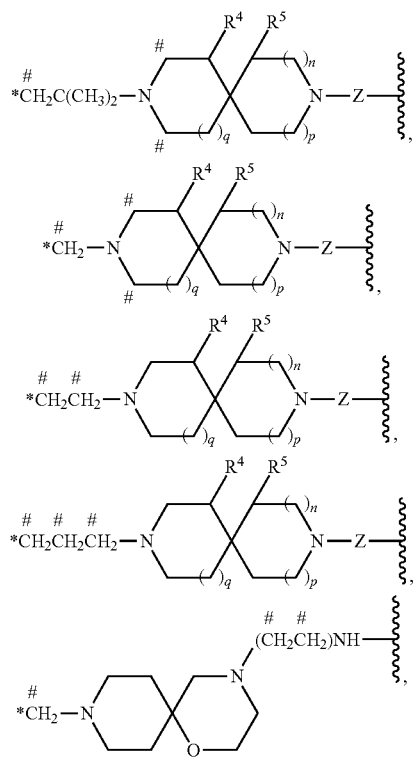

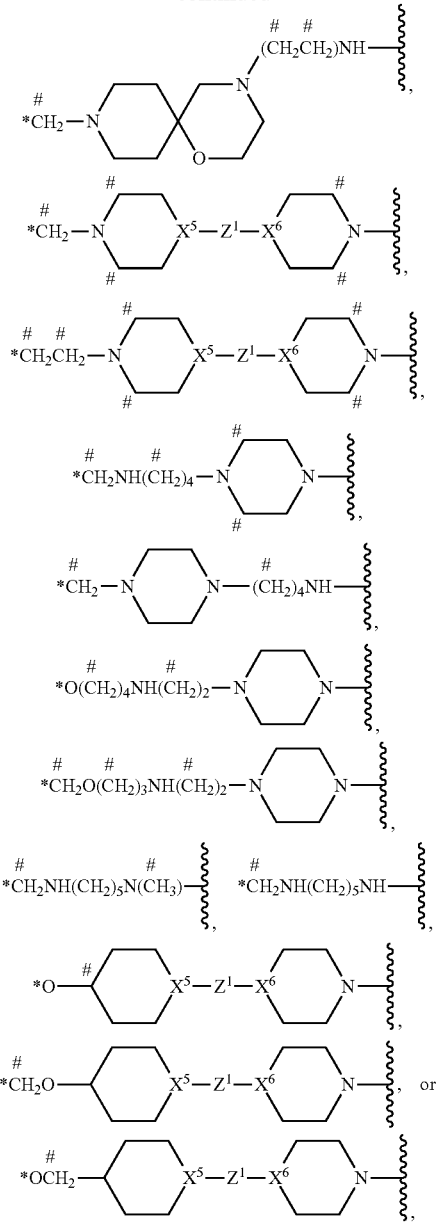

wherein each $R^8$, $R^9$, and $R^{10}$ is independently at each occurrence selected from H or deuterium and the symbol # indicates the positions shown to be substituted by H which may independently at each occurrence be substituted by H or deuterium.

Incorporation of certain isotopes, particularly deuterium (i.e., $^2$H or D) may afford certain therapeutic advantages resulting from greater metabolic stability, for example increased in vivo half-life or reduced dosage requirements or an improvement in therapeutic index or tolerability. It is understood that deuterium in this context is regarded as a substituent of a compound of formulae (I) and (Ia). The concentration of deuterium may be defined by the isotopic enrichment factor. The term "isotopic enrichment factor" as used herein means the ratio between the isotopic abundance and the natural abundance of a specified isotope. If a substituent in a compound of this invention is denoted as being deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). It should be understood that the term "isotopic enrichment factor" can be applied to any isotope in the same manner as described for deuterium.

Other examples of isotopes that can be incorporated into compounds of the invention include isotopes of hydrogen, carbon, nitrogen, oxygen, fluorine, and chlorine, such as $^3$H, $^{11}$C, $^{13}$C, $^{14}$C, $^{15}$N, $^{18}$F, $^{35}$S, $^{36}$Cl, and $^{125}$I respectively. Accordingly, it should be understood that the invention includes compounds that incorporate one or more of any of the aforementioned isotopes, including for example, radioactive isotopes, such as $^3$H and $^{14}$C, or those into which non-radioactive isotopes, such as $^2$H and $^{13}$C are present. Such isotopically labelled compounds are useful in metabolic studies (with $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. In particular, an $^{18}$F labeled compound may be particularly desirable for PET or SPECT studies. Isotopically-labeled compounds of formula (I) can generally be prepared by conventional techniques known to those skilled in the art or by processes analogous to those described in the accompanying Examples using an appropriate isotopically-labeled reagent in place of the non-labeled reagent previously employed.

As used herein, the term "pharmaceutical composition" refers to a compound of the invention, or a pharmaceutically acceptable salt thereof, together with at least one pharmaceutically acceptable carrier, in a form suitable for oral or parenteral administration.

As used herein, the term "pharmaceutically acceptable carrier" refers to a substance useful in the preparation or use of a pharmaceutical composition and includes, for example, suitable diluents, solvents, dispersion media, surfactants, antioxidants, preservatives, isotonic agents, buffering agents, emulsifiers, absorption delaying agents, salts, drug stabilizers, binders, excipients, disintegration agents, lubricants, wetting agents, sweetening agents, flavoring agents, dyes, and combinations thereof, as would be known to those skilled in the art (see, for example, Remington's Pharmaceutical Sciences, 18th Ed. Mack Printing Company, 1990, pp. 1289-1329).

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one embodiment, the term "a therapeutically effective amount" refers to the amount of the compound of the present invention that, when administered to a subject, is effective to (1) at least partially alleviate, prevent and/or ameliorate a condition, or a disorder or a disease (i) mediated by BTK, or (ii) associated with BTK activity, or (iii) characterized by activity (normal or abnormal) of BTK; or (2) reduce or inhibit the activity of BTK; or (3) reduce or inhibit the expression of BTK. These effects may be achieved for example by reducing the amount of BTK by degrading BTK. In another embodiment, the term "a therapeutically effective amount" refers to the amount of the compound of the present invention that, when administered to a cell, or a tissue, or a non-cellular biological material, or a medium, is effective to at least partially reduce or inhibit the activity of BTK; or at least partially reduce or inhibit the expression of BTK, for example by degrading BTK.

As used herein, the term "subject" refers to primates (e.g., humans, male or female), dogs, rabbits, guinea pigs, pigs, rats and mice. In certain embodiments, the subject is a primate. In an embodiment, the subject is a human.

As used herein, the term "inhibition" or "inhibiting" refers to the reduction or suppression of a given condition, symptom, or disorder, or disease, or a significant decrease in the baseline activity of a biological activity or process.

As used herein, the terms "degrades", "degrading", or "degradation" refers to the partial or full breakdown of a target protein, e.g. BTK, by the cellular proteasome system to an extent which reduces or eliminates the biological activity (especially aberrant activity) of BTK. Degradation may be achieved through mediation of an E3 ligase, in particular, E3-ligase complexes comprising the protein Cereblon. As used herein, the term "modulation of BTK activity" or "modulating BTK activity" means the alteration of, especially reduction, suppression or elimination, of BTK activity. This may be achieved by degrading BTK. The Amount of BTK degraded can be measured by comparing the amount of BTK remaining after treatment with a compound of the invention as compared to the initial amount or level of BTK present as measured prior to treatment with a compound of the invention. In an embodiment, at least about 30% of BTK is degraded compared to initial levels. In an embodiment, at least about 40% of BTK is degraded compared to initial levels. In an embodiment, at least about 50% of BTK is degraded compared to initial levels. In an embodiment, at least about 60% of BTK is degraded compared to initial levels. In an embodiment, at least about 70% of BTK is degraded compared to initial levels. In an embodiment, at least about 80% of BTK is degraded compared to initial levels. In an embodiment, at least about 90% of BTK is degraded compared to initial levels. In an embodiment, at least about 95% of BTK is degraded compared to initial levels. In an embodiment, over 95% of BTK is degraded compared to initial levels. In an embodiment, at least about 99% of BTK is degraded compared to initial levels.

In an embodiment, the BTK is degraded in an amount of from about 30% to about 99% compared to initial levels. In an embodiment, the BTK is degraded in an amount of from about 40% to about 99% compared to initial levels. In an embodiment, the BTK is degraded in an amount of from about 50% to about 99% compared to initial levels. In an embodiment, the BTK is degraded in an amount of from about 60% to about 99% compared to initial levels. In an embodiment, the BTK is degraded in an amount of from about 70% to about 99% compared to initial levels. In an embodiment, the BTK is degraded in an amount of from about 80% to about 99% compared to initial levels. In an embodiment, the BTK is degraded in an amount of from about 90% to about 99% compared to initial levels. In an embodiment, the BTK is degraded in an amount of from about 95% to about 99% compared to initial levels. In an embodiment, the BTK is degraded in an amount of from about 90% to about 95% compared to initial levels.

As used herein, the term "selectivity for BTK" means, for example, a compound of the invention degrades BTK in preference to, or to a greater extent than, another protein or proteins.

As used herein, the term "treat", "treating", or "treatment" of any disease or disorder refers to alleviating or ameliorating the disease or disorder (i.e., slowing or arresting the development of the disease or at least one of the clinical symptoms thereof); or alleviating or ameliorating at least one physical parameter or biomarker associated with the disease or disorder, including those which may not be discernible to the patient.

As used herein, the term "prevent", "preventing", or "prevention" of any disease or disorder refers to the prophylactic treatment of the disease or disorder; or delaying the onset or progression of the disease or disorder As used herein, a subject is "in need of" a treatment if such subject would benefit biologically, medically, or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as" or "for example") provided herein is intended merely to better illuminate the invention and does not pose a limitation on the scope of the invention otherwise claimed.

Any asymmetric atom (e.g., carbon or the like) of the compound(s) of the present invention can be present in racemic or enantiomerically enriched, for example the (R)-, (S)-, or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis-(Z)- or trans-(E)-form.

Accordingly, as used herein a compound of the present invention can be in the form of one of the possible stereoisomers, rotamers, atropisomers, tautomers or mixtures thereof, for example, as substantially pure geometric (cis or trans) stereoisomers, diastereomers, optical isomers (antipodes), racemates or mixtures thereof.

Any resulting mixtures of stereoisomers can be separated on the basis of the physicochemical differences of the constituents, into the pure or substantially pure geometric or optical isomers, diastereomers, racemates, for example, by chromatography and/or fractional crystallization.

Any resulting racemates of compounds of the present invention or of intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic compounds of the present invention or racemic intermediates can also be resolved by chiral chromatography, e.g., high pressure liquid chromatography (HPLC) using a chiral adsorbent.

The compounds of the present application can be prepared in a number of ways well known to those skilled in the art of organic synthesis using commercially available starting materials, compounds known in the literature, or from readily prepared intermediates, by employing standard synthetic methods and procedures either known to those skilled in the art, or which will be apparent to the skilled chemist in light of the teachings herein. For all examples, a potential alternative orthogonal protecting group strategy could be applied, following standard text book knowledge as described for example in *Protective Groups in Organic Synthesis*, 3$^{rd}$ edition, John Wiley & Sons: New York, 1999 or *Protecting Groups*, 3$^{rd}$ edition, Thieme, Stuttgart, 2004. Those skilled in the art will recognize if a stereocentre exists in the compounds disclosed herein.

Compounds of the invention can be synthesized according to the following schemes. The compounds may be assembled in various ways, building up the final molecules using related reaction procedures in a modular fashion which allows for different reaction orders. Several reaction types are of particular utility for making these compounds. All compounds of the invention contain an amide functionality which is generally formed by an amide coupling reaction between an amine and a carboxylic acid, using a coupling reagent (e.g. HATU or HBTU) and a base (e.g. DIPEA or NMM) in a solvent such as DMF or DMA. Alternatively the carboxylic acid may be first converted to its pentafluorophenol ester. This allows subsequent facile reaction with an amine in the presence of a base such as TEA in a solvent such as DMF to form the amide. Compounds of the invention containing a carbon-nitrogen bond can often be made using a reductive amination reaction starting from an amine and an aldehyde or ketone. Reaction occurs using conditions such as NaBH$_3$CN, ZnCl$_2$, and TEA in a solvent mixture such as THF and MeOH. Carbon-nitrogen bonds can also be formed by nucleophilic substitution reactions of an amine with a suitable reacting partner containing a leaving group, such as an alkyl halide or an alkyl mesylate generally in the presence of a base (such as TEA) in a solvent such as THF. Compounds containing an ether can also be made by nucleophilic substitution reactions, in this case by reacting an alcohol with a suitable partner containing a leaving group, such as a benzyl halide in the presence of a base (such as TEA) in a solvent such as THF. Another generally useful method to make compounds of the invention containing ethers is the Mitsunobu reaction. In this reaction a phenol and another alcohol are reacted together in the presence of a phosphine (such as triphenylphosphine) and an azodicarboxylate ester (such as diethylazodicarboxylate or diisopropylazodicarboxylate) in a solvent such as THF. Another reaction of high utility for the synthesis of compounds of the invention is the palladium (Pd) catalysed cross coupling reaction to link together two aromatic groups. Of particular utility is the Suzuki coupling reaction between an aromatic halide and an aromatic boronic acid or ester using a catalyst (e.g. PdCl$_2$(dppf) and a base (e.g. Na$_2$CO$_3$ or Cs$_2$CO$_3$) in a solvent mixture such as dioxane/water.

Specifically, compounds of formula (I) may be made as shown in Scheme 1 wherein R$^1$, R$^{1a}$, R$^2$, R$^{2a}$, X$^1$, R$^6$, R$^7$, X$^{1a}$, and X$^{2a}$ are as previously defined. M is defined as H or as a protecting group such as —SO$_2$Ph or —SEM and LG is defined as a leaving group such as mesylate (OMs).

Thus a compound of formula (I) can be made from a compound of formula (II) and a compound of formula (III) by an amide coupling formation between an amine and a carboxylic acid, using a coupling reagent (e.g. HATU) and a base (e.g. DIPEA or NMM) in a solvent such as DMF or DMA. Alternatively, a compound of formula (I) can be made by an amide coupling between an amine of formula (II) and the pentafluorophenyl ester of the acid (IIIa) by treating with TEA in a solvent such as DMF. A compound of formula (II) can be made from a compound of formula (IV). For compounds of formula (IV) where M is a protecting group such as —SO$_2$Ph, deprotection may be accomplished using a base (e.g. NaOH) in a solvent mixture (e.g. DMSO, THF and water); where M is a —SEM protecting group, deprotection using an acid such as TFA in a solvent such as DCM may be utilized and possibly combined with the subsequent amine deprotection step. Further deprotection of the t-butoxycarbonyl (Boc) group using an acid, (e.g. TFA) in a solvent such as DCM provides a compound of formula (II).

Scheme 1

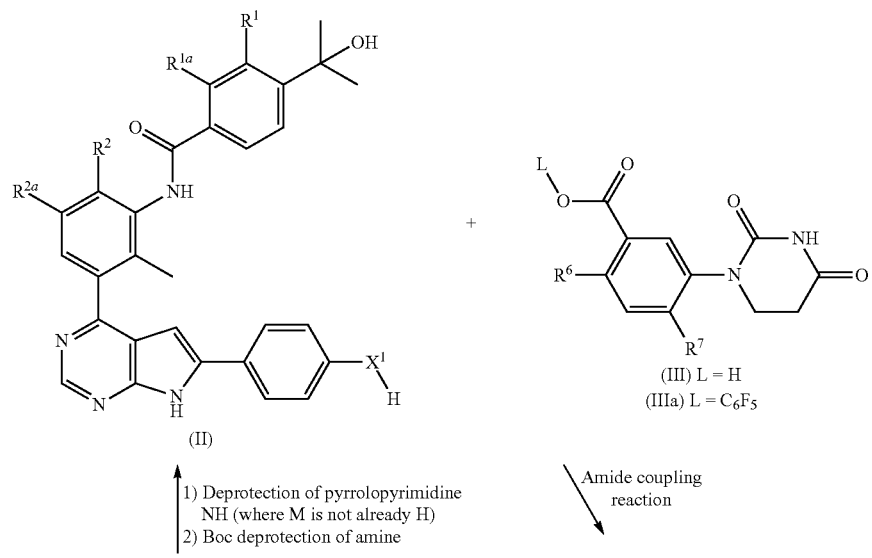

-continued

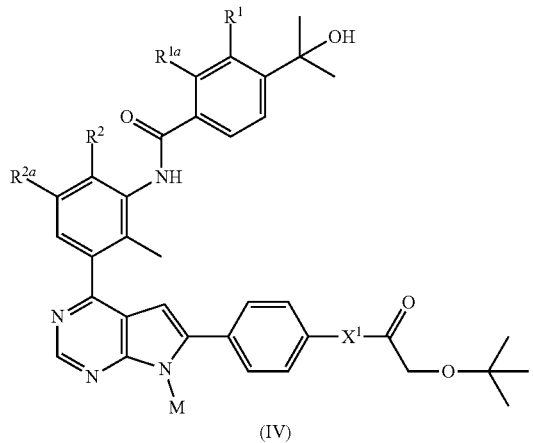

(IV)

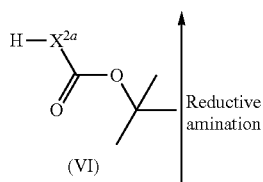

(VI) Reductive amination

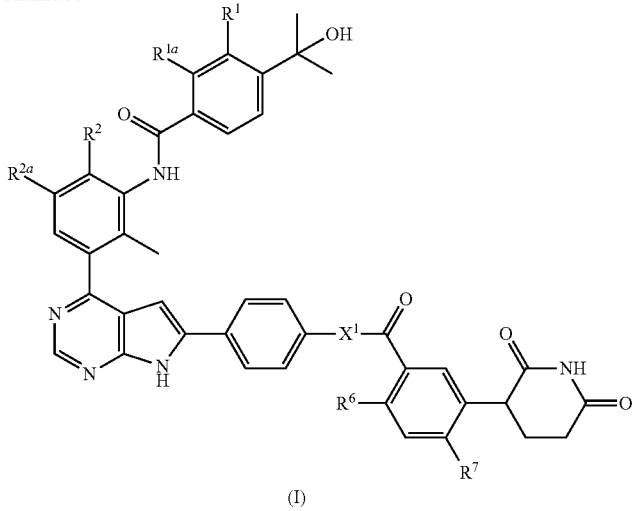

(I)

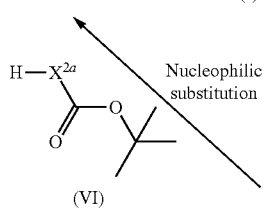

(VI) Nucleophilic substitution

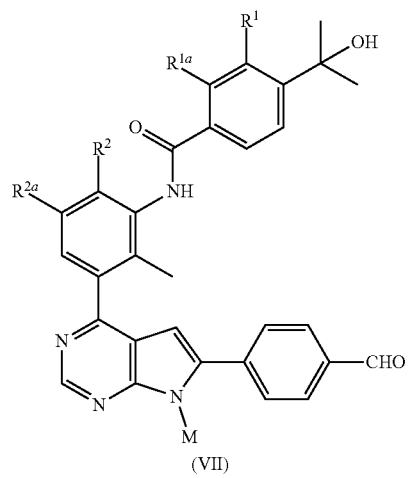

(VII)

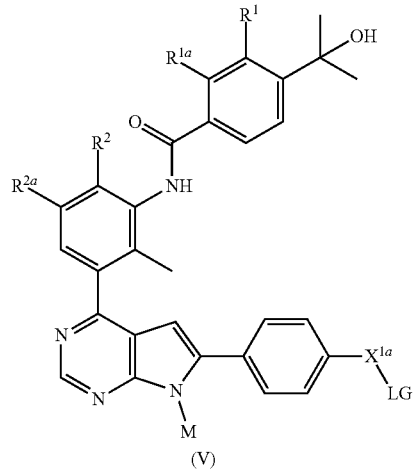

(V)

A compound of formula (IV) may be provided by reaction of a compound of formula (V) with a compound of formula (VI), for example in a nucleophilic substitution reaction, using a base (e.g. $K_2CO_3$) in a solvent mixture (e.g. DMF and ACN). A compound of formula (IV) may alternatively be provided by reaction of a compound of formula (VII) with a compound of formula (VI), for example in a reductive amination reaction, under conditions using $NaBH_3CN$, $ZnCl_2$, and TEA in a solvent mixture such as THF and MeOH.

Compounds of formula (V) can be made according to Scheme 2 wherein $R^1$, $R^{1a}$, $R^2$, $R^{2a}$, $X^{1a}$, M and LG are as previously defined. The group —B(OR$^x$)$_2$ defines a boronic acid or boronic ester functionality (including cyclic boronates e.g. boron pinacol esters). Thus, Pd-catalysed coupling, such as a Suzuki reaction between a compound of formula (VIII) and a compound of formula (IX) using a catalyst (e.g. PdCl$_2$(dppf) and a base (e.g. Cs$_2$CO$_3$) in a solvent mixture (e.g. dioxane/water) followed in a second step by conversion of the alcohol function connected to $X^{1a}$ into a leaving group LG, for example by mesylation using Ms$_2$O and TEA in a solvent such as THF provides compounds of formula (V). Compounds of formula (VIII) can be made by Pd-catalysed coupling, such as a Suzuki reaction between a compound of formula (X) and a compound of formula (XI) using a catalyst (e.g. PdCl$_2$(dppf) and a base (e.g. Cs$_2$CO$_3$) in a solvent mixture (e.g. dioxane/water).

Scheme 2

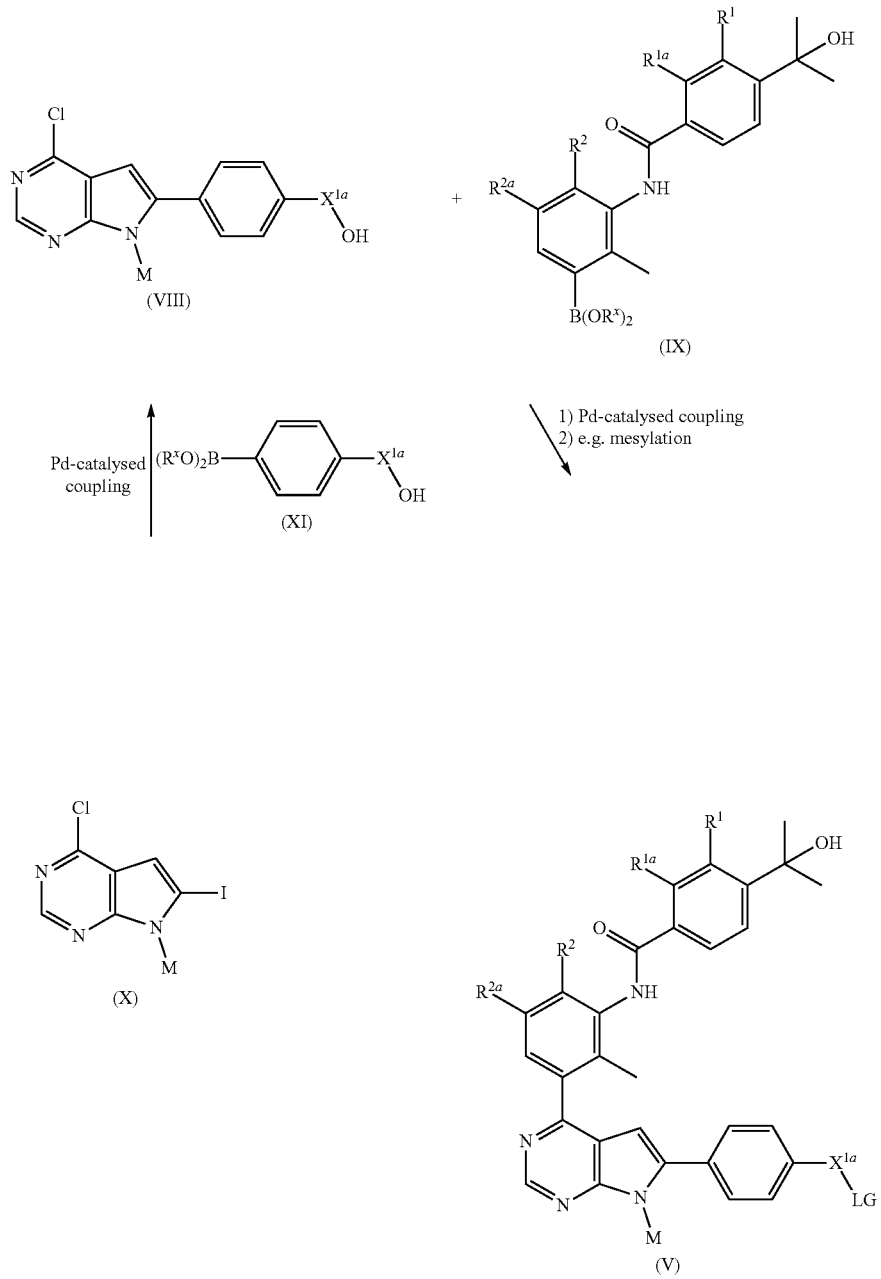

By analogy, compounds of formula (VII) can be made according to Scheme 3 wherein $R^1$, $R^{1a}$, $R^2$, $R^{2a}$, M, LG, and —B(OR$^x$)$_2$ are as previously defined.

Thus, Pd-catalysed coupling, such as a Suzuki reaction between a compound of formula (XII) and a compound of formula (IX) using a catalyst (e.g. PdCl$_2$(dppf)) and a base (e.g. Cs$_2$CO$_3$) in a solvent mixture (e.g. dioxane/water) provides compounds of formula (VII). Compounds of formula (XII) can also be made by Pd-catalysed coupling, such as a Suzuki reaction between a compound of formula (X) and a compound of formula (XIII) using a catalyst (e.g. PdCl$_2$(dppf)) and a base (e.g. Cs$_2$CO$_3$) in a solvent mixture (e.g. dioxane/water).

Scheme 3

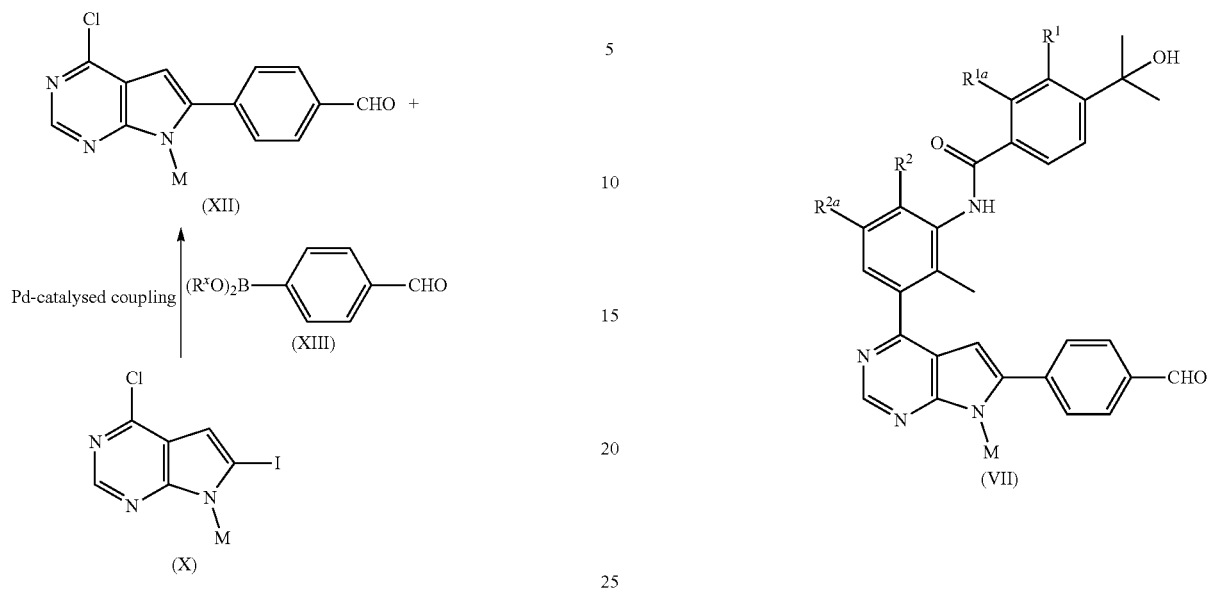

Compounds of formula (II) can also be made according to Scheme 4. Thus, reductive amination between compounds of formula (XIV) and (XV), for example, when M is H, using conditions such as NaBH$_3$CN, ZnCl$_2$ and TEA in a solvent mixture such as THF and MeOH followed by deprotection of the amine with an acid (e.g. TFA) in a solvent such as DCM gives a compound of formula (II). Compounds of formula (XIV) are made by a similar sequence starting from compounds of formula (VII), which can undergo reductive amination with N-(t-butoxycarbonyl) piperazine using conditions such as NaBH$_3$CN, ZnCl$_2$, and TEA in a solvent mixture such as THF and MeOH followed by deprotection of the amine with an acid (e.g. TFA) in a solvent such as DCM to provide (XIV).

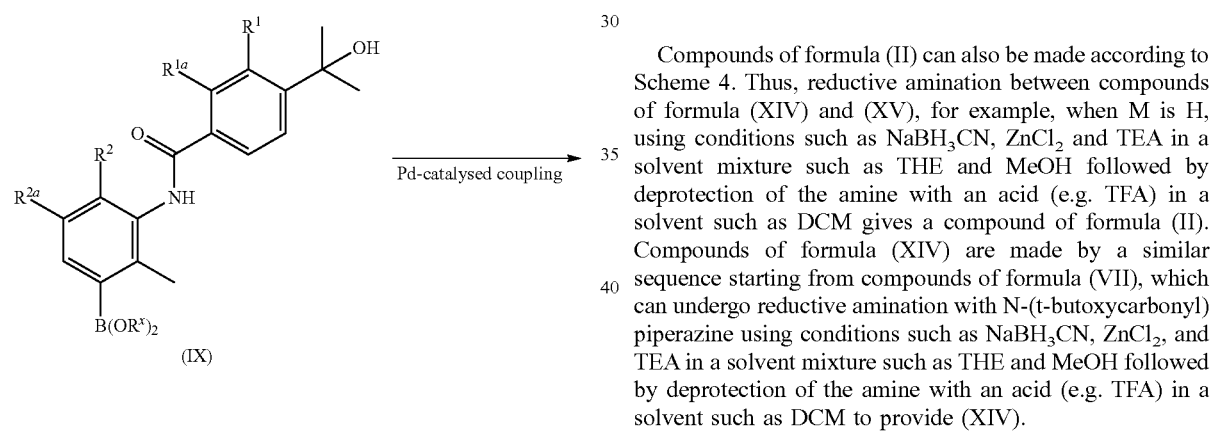

Scheme 4

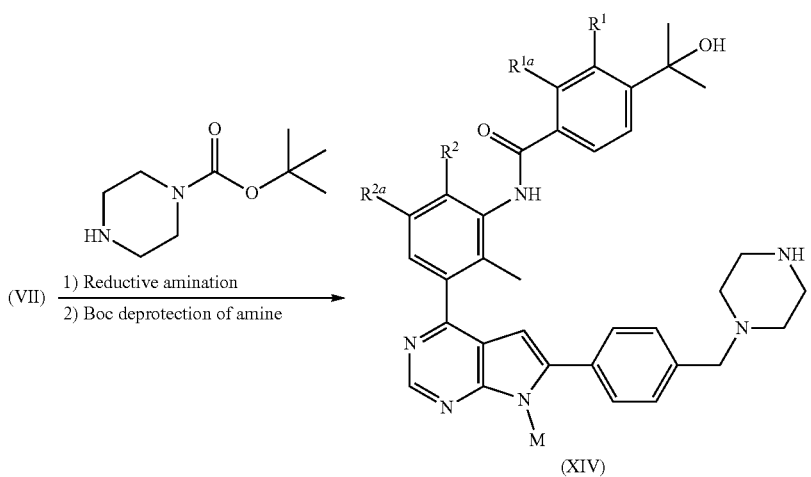

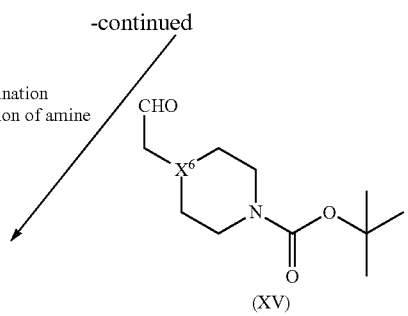

1) Reduction amination
2) Boc deprotection of amine (XV)

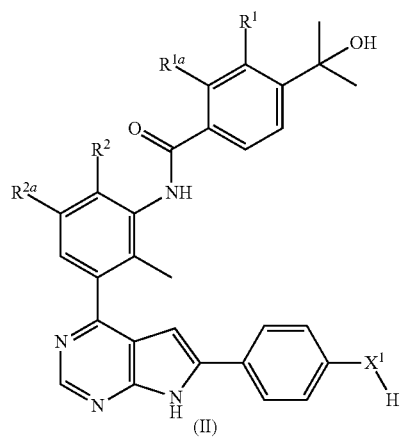

(II)

Compounds of formula (IV) can be made from a compound of formula (XVI), according to Scheme 5, by reacting with a compound of formula (IX) using a Pd-catalysed coupling, such as a Suzuki reaction using a catalyst (e.g. $PdCl_2(dppf)$ and a base (e.g. $Cs_2CO_3$) in a solvent mixture (e.g. dioxane/water). Compounds of formula (XVI) can in turn be made from compounds of formula (XVII), also by a Pd-catalysed coupling, such as a Suzuki reaction with a compound of formula (X) using a catalyst (e.g. $PdCl_2(dppf)$ and a base (e.g. $Cs_2CO_3$) in a solvent mixture (e.g. dioxane/water).

Scheme 5

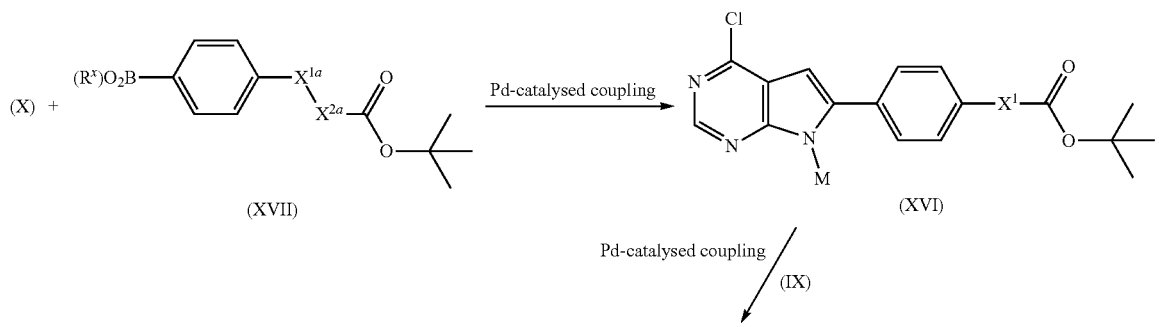

-continued

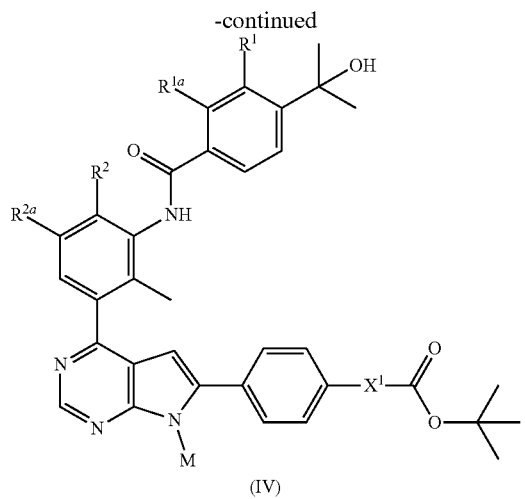

(IV)

Compounds of formula (XVII) can be made as shown in Scheme 6 by halogen-boron exchange reaction starting from compounds (XVIII) using a boronic ester dimer (e.g. bis(pinacolato)diboron), a Pd catalyst such as $PdCl_2(dpp)$ and a base such as KOAc in a solvent such as dioxane. Compounds (XVIII) where Hal denotes a halogen, can be accessed from compounds (XIX) and (VI) using a nucleophilic substitution reaction, for example when Hal and LG in formula (XIX) are both bromine using a base such as $K_2CO_3$ in a solvent such as acetonitrile.

Certain compounds of formula (XVII) can also be accessed from a compound of formula (XI) via a 2-step process, first converting the hydroxyl group to a leaving group, such as mesylate, followed by a nucleophilic substitution reaction with a compound of formula (VI). Compounds of type (XI) can be derived from compounds of type (XIXa) using a halogen boron exchange reaction.

A particular subset of compounds (XVIII), described by formula (XVIIIa) can be synthesized from a halophenyl acetic acid derivative (XX) and a compound of formula (VI) in a two-step procedure involving amide coupling reaction using a coupling reagent (e.g. HATU) and a base (e.g. DIPEA or NMM) in a solvent such as DMF or DMA, followed by addition of a Grignard reagent such as MeMgBr, in the presence of a catalyst (e.g. $ZrCl_4$) in a solvent such as THF. Compounds (XVIIIa) can be converted to compounds (XVII) by halogen-boron exchange in an analogous manner to the conversion described for compounds (XVIII).

Scheme 6

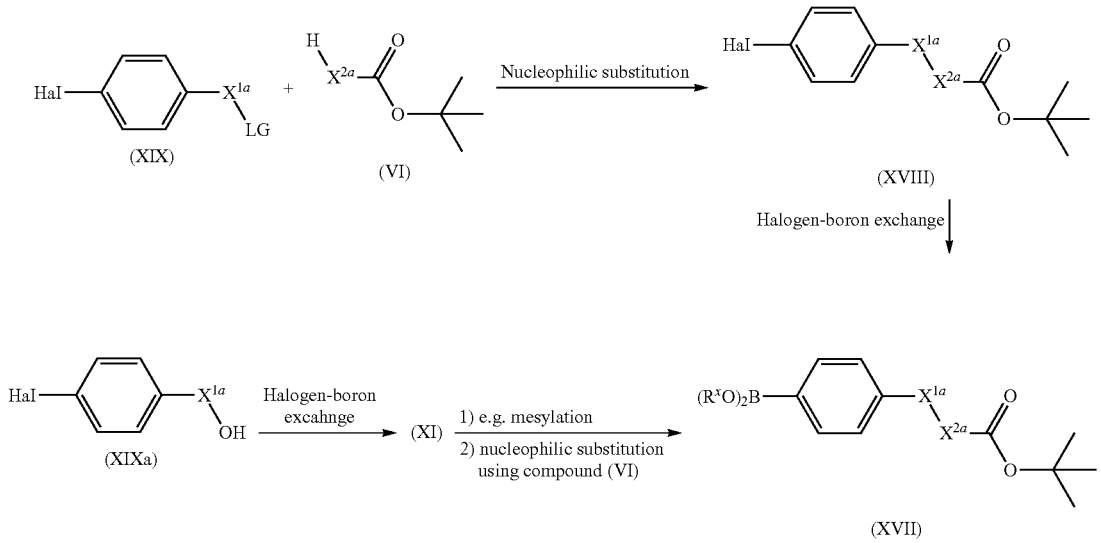

-continued

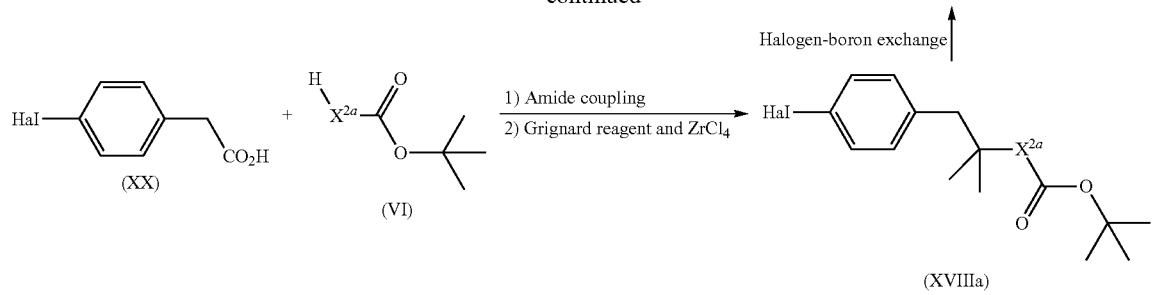

Compounds of formula (I) can be made according to Scheme 7 from compounds of formula (XXI) and compounds of formula (VIIa), a specific embodiment of compound type (VII) where M=H, using a reductive amination coupling using, for example, NaBH$_3$CN, ZnCl$_2$, and TEA in a solvent mixture such as THF and MeOH. Alternatively, compounds of formula (I) can be made by reaction of a compound of formula (Va), a specific embodiment of compound type (V) where M=H, with a compound of formula (XXI) in a nucleophilic substitution reaction using a base (e.g. K$_2$CO$_3$) in a solvent mixture (e.g. DMF and ACN).

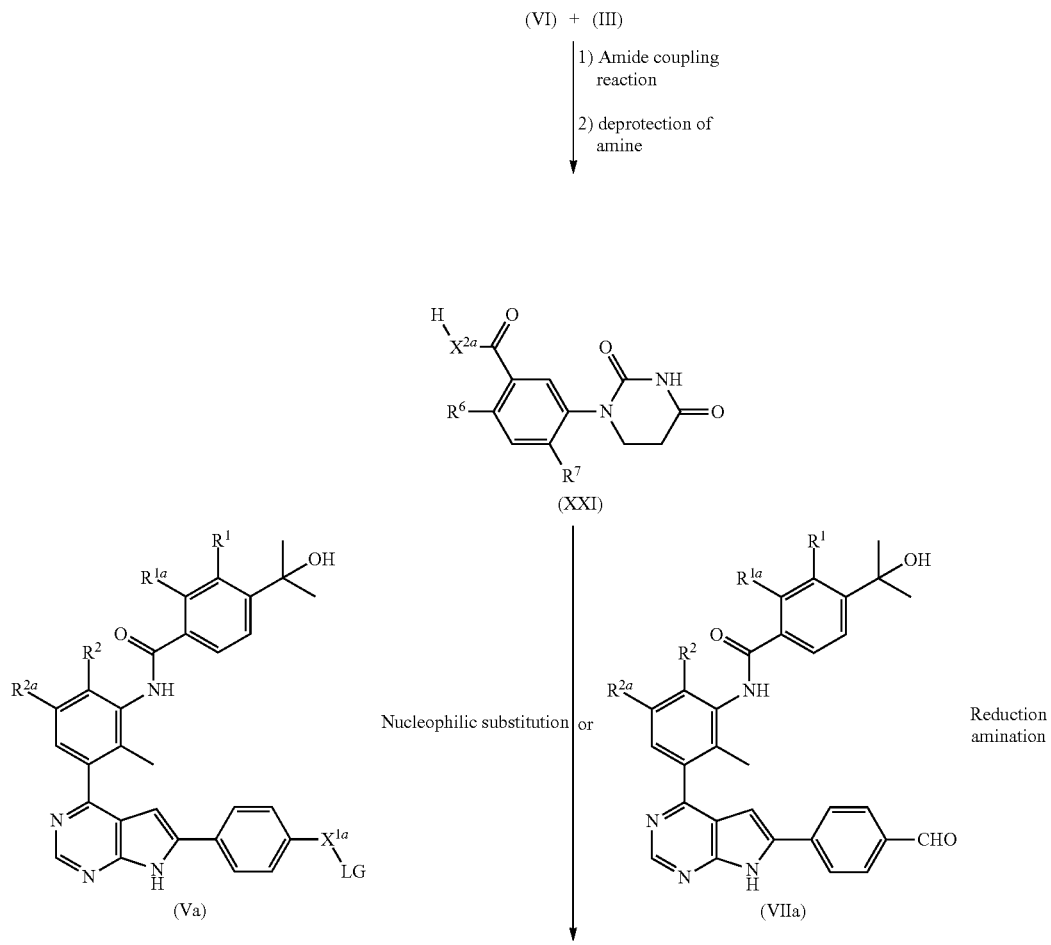

-continued

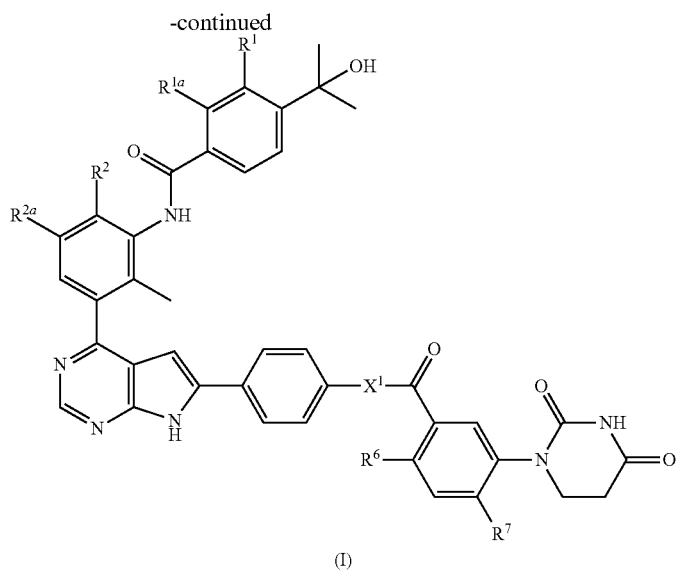

(I)

Compounds of formula (XXI) are synthesized from compounds of formula (VI) and compounds of formula (III) by an amide coupling reaction using a coupling reagent (e.g. HATU) and a base (e.g. DIPEA or NMM) in a solvent such as DMF or DMA, followed by deprotection of the t-butoxycarbonyl (Boc) group of the amine using an acid, (e.g. TFA) in a solvent such as DCM.

Compounds of formula (I) where Z is not absent can be made by reacting a compound of formula (XXII) with a compound of formula (XXIII), where Z, $R^1$, $R^{1a}$, $R^2$, $R^{2a}$, $X^{1a}$, $R^4$, $R^5$, $R^6$, $R^7$, n, p, and q are as previously defined, in a reductive amination coupling using for example NaBH$_3$CN, ZnCl$_2$, and TEA in a solvent mixture such as THF and MeOH. By analogy, compounds (XXIV) and (XXIII) may react under similar conditions to provide compounds of formula (I), according to Scheme 8.

Scheme 8

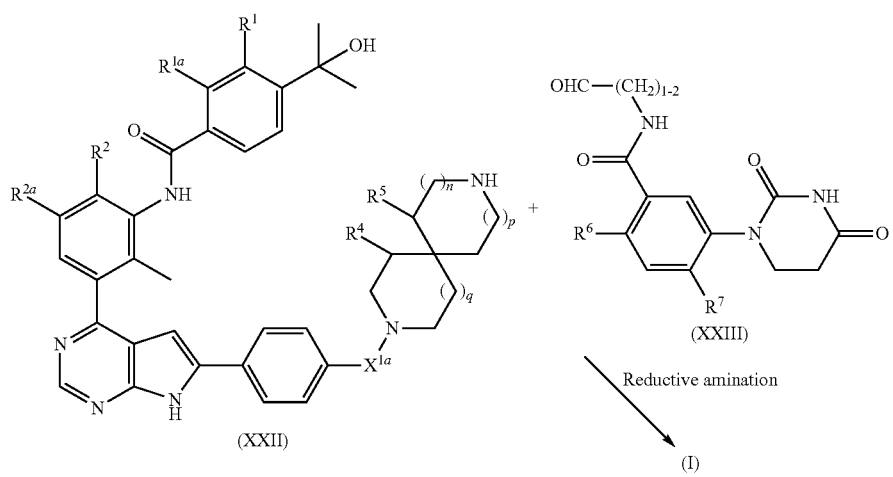

(XXIII) +

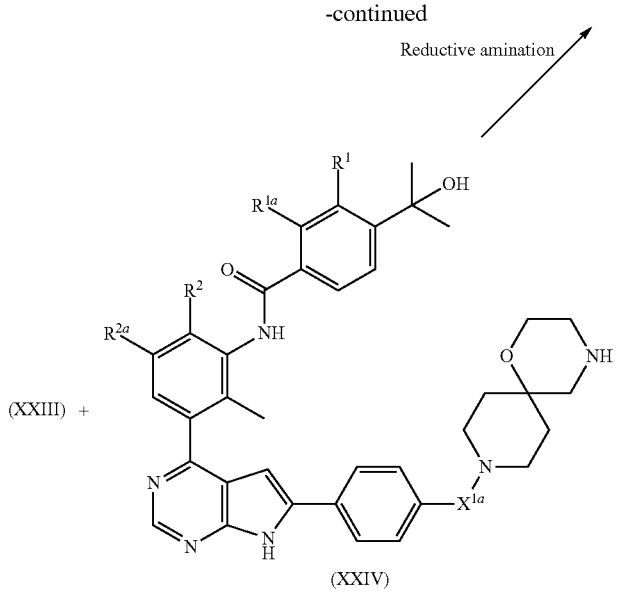

(XXIV)

Compounds of formula (XVI) can be synthesized according to Scheme 9 from a compound of formula (X) and compounds of formula (XXV) using a Pd-catalysed coupling, such as a Suzuki reaction, with a catalyst (e.g. PdCl$_2$(dppf) and a base (e.g. Cs$_2$CO$_3$) in a solvent mixture (e.g. dioxane/water).

Scheme 9

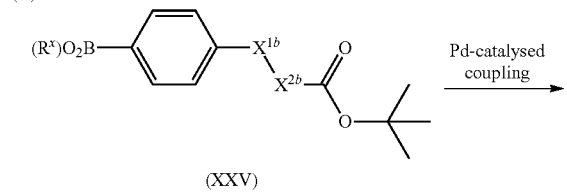

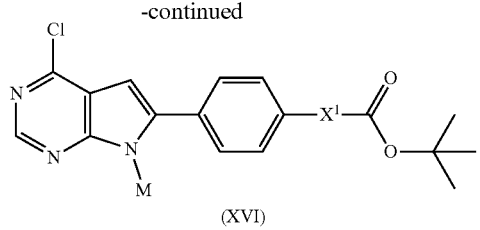

(XVI)

Compounds of formula (XXV) can be made using a variety of procedures under reaction conditions previously described. For example, in Scheme 10, starting from the common boronic acid/ester starting material (XXVIII), a Mitsunobu reaction using a compound of structure (XXIX) followed by deprotection provides an intermediate of formula (XXVI) which can then undergo a nucleophilic substitution reaction with compounds of formula (XXVII) to furnish compounds of formula (XXV). In some cases, the Mitsunobu reaction of (XXVIII) with a compound of formula (XXX) can directly provide (XXV).

Scheme 10

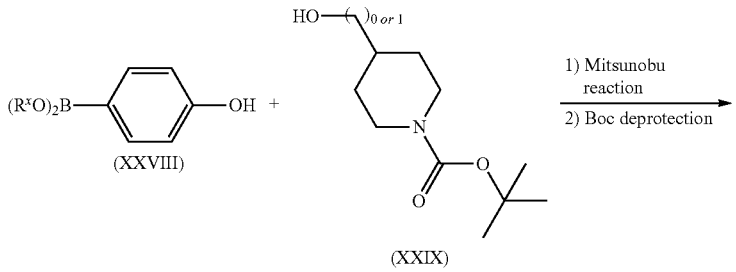

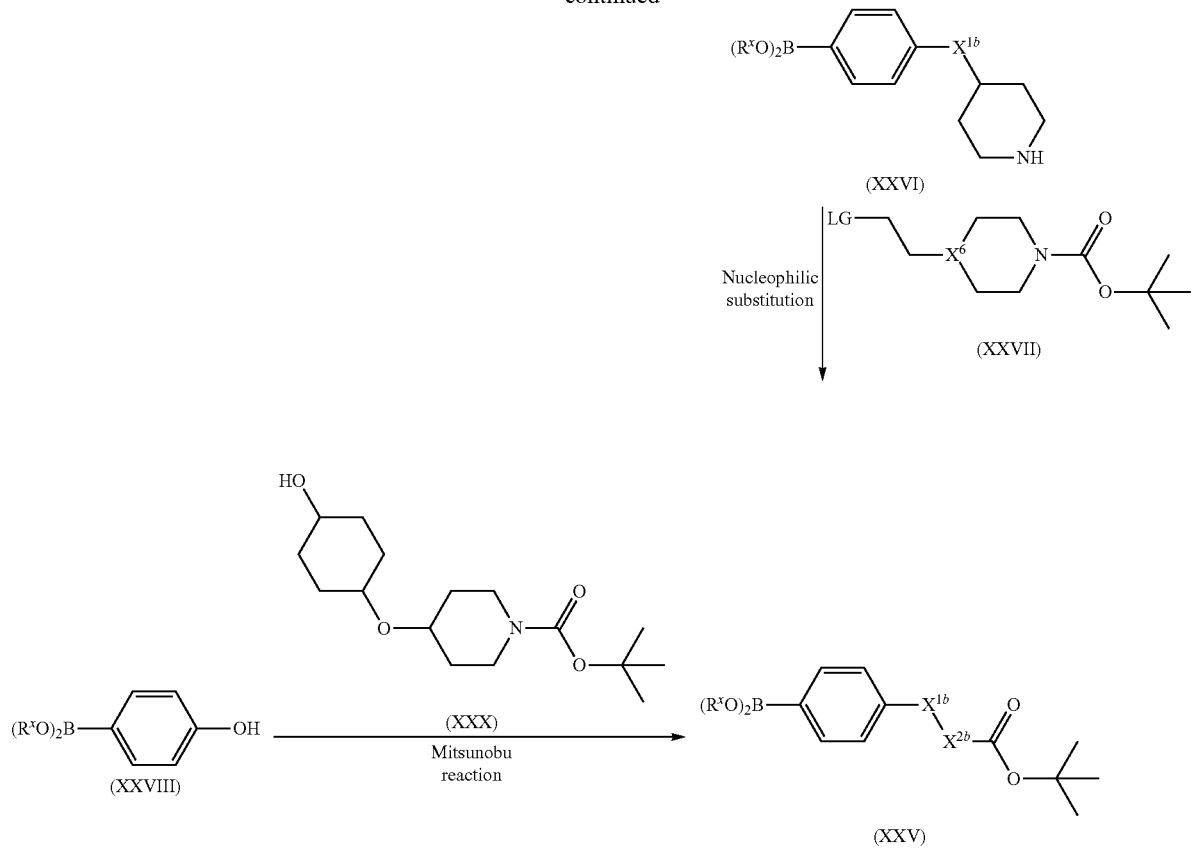

Compounds of formula (XXV) may also be synthesized from the common starting material 4-bromobenzyl bromide (XXXI). In these cases, as shown in Scheme 11, a nucleophilic substitution reaction with compound (XXX) using a base such as potassium t-butoxide in a solvent such as THF followed by halogen-boron exchange using conditions previously described can directly lead to (XXV). In other cases, a nucleophilic substitution reaction with compound (XXXII) followed by halogen-boron exchange and Boc-deprotection gives a new intermediate (XXXIII) which can be reacted in a further nucleophilic substitution reaction with compounds of type (XXVII) leading to (XXV) under similar reaction conditions to those previously described.

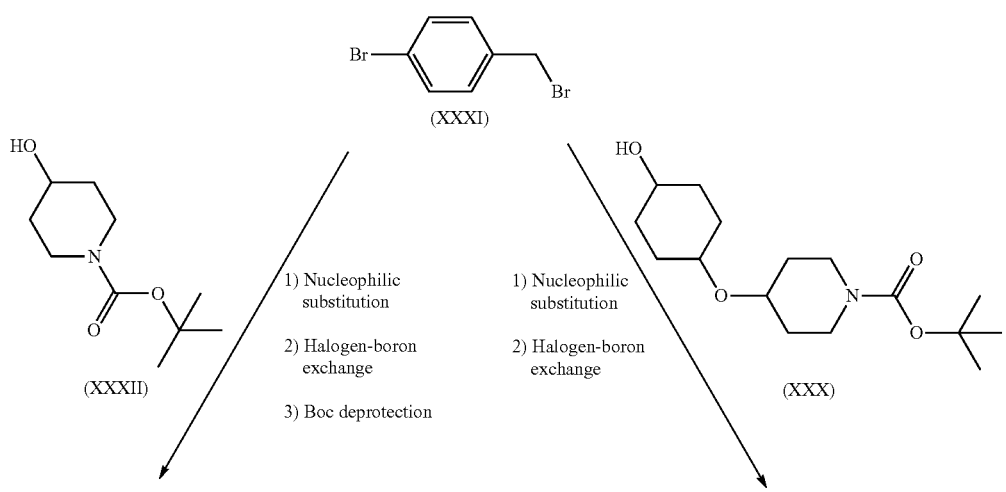

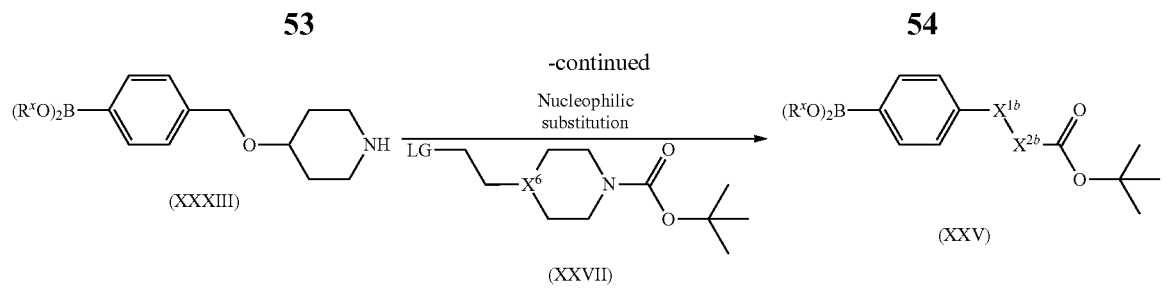

Well known to those skilled in the art, reaction sequence orders can often be changed while leading to similar compounds. Scheme 12 shows alternative methods for constructing compounds of formula (IV) using similar procedures to those already described. Thus, a Pd-catalysed coupling, such as a Suzuki reaction, using compounds (X) and (XXVIII) with a catalyst (e.g. PdCl$_2$(dppf) and a base (e.g. Cs$_2$CO$_3$) in a solvent mixture (e.g. dioxane/water) gives intermediate (XXXIV) which can undergo a Mitsunobu reaction with compound of formula (XXXII) to provide intermediate (XXXV). Compound (XXXV) can then undergo a further Suzuki coupling, this time with a compound of formula (IX) and subsequent deprotection sequence to give a compound of formula (XXXVI). Compounds of formula (XXXVI) can undergo reductive amination with a compound of formula (XXXVII) to give a compound of formula (IV).

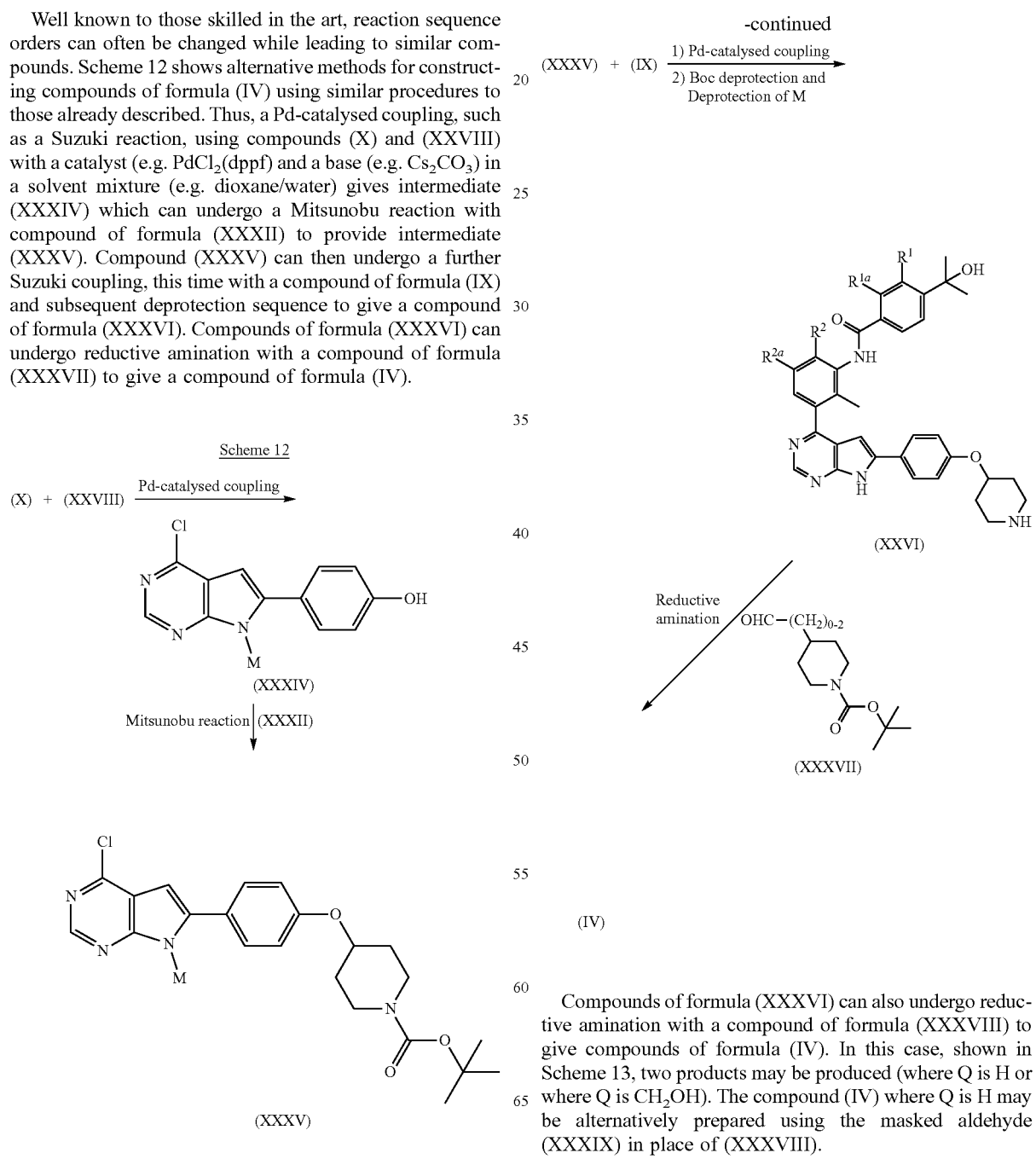

Compounds of formula (XXXVI) can also undergo reductive amination with a compound of formula (XXXVIII) to give compounds of formula (IV). In this case, shown in Scheme 13, two products may be produced (where Q is H or where Q is CH$_2$OH). The compound (IV) where Q is H may be alternatively prepared using the masked aldehyde (XXXIX) in place of (XXXVIII).

Scheme 13

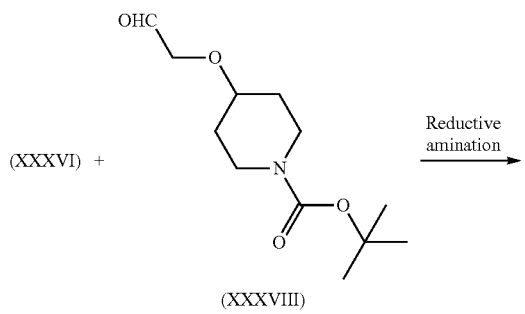

(XXXVI) +    (XXXVIII)

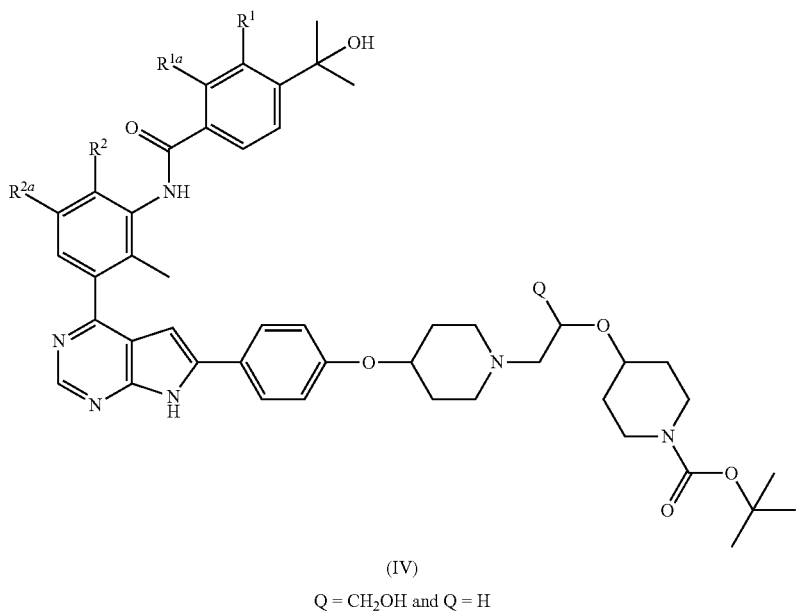

(IV)
Q = CH₂OH and Q = H

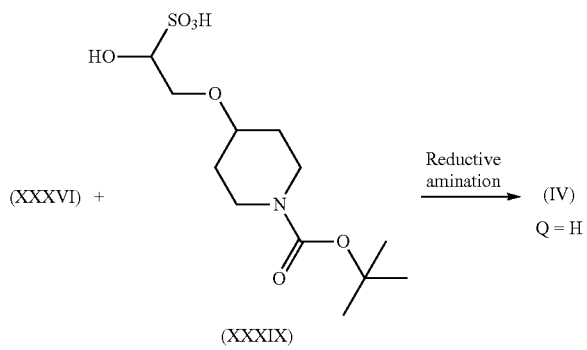

(XXXVI) +    (XXXIX)    → (IV) Q = H

Scheme 14 shows yet more approaches to provide compounds of formula (IV). Thus, intermediates of formula (XL) can be generated by, for example, a Mitsunobu reaction between compounds (XXVIII) and (XXIX). Alternatively, (XL) may be produced in two steps from a nucleophilic substitution between compounds of formula (XXXI) and (XXXII), followed by a halogen-boron exchange reaction. Reaction of intermediate (XL) in a Pd-catalysed coupling reaction with a compound of formula (X) gives a compound of formula (XLI) which may undergo a further Pd-catalysed coupling reaction with a compound of formula (IX) followed by deprotection to give a compound of formula (XLII). Compound (XLII) may undergo a reductive amination reaction with compounds of formula (XXXVII) to provide (IV).

Scheme 14
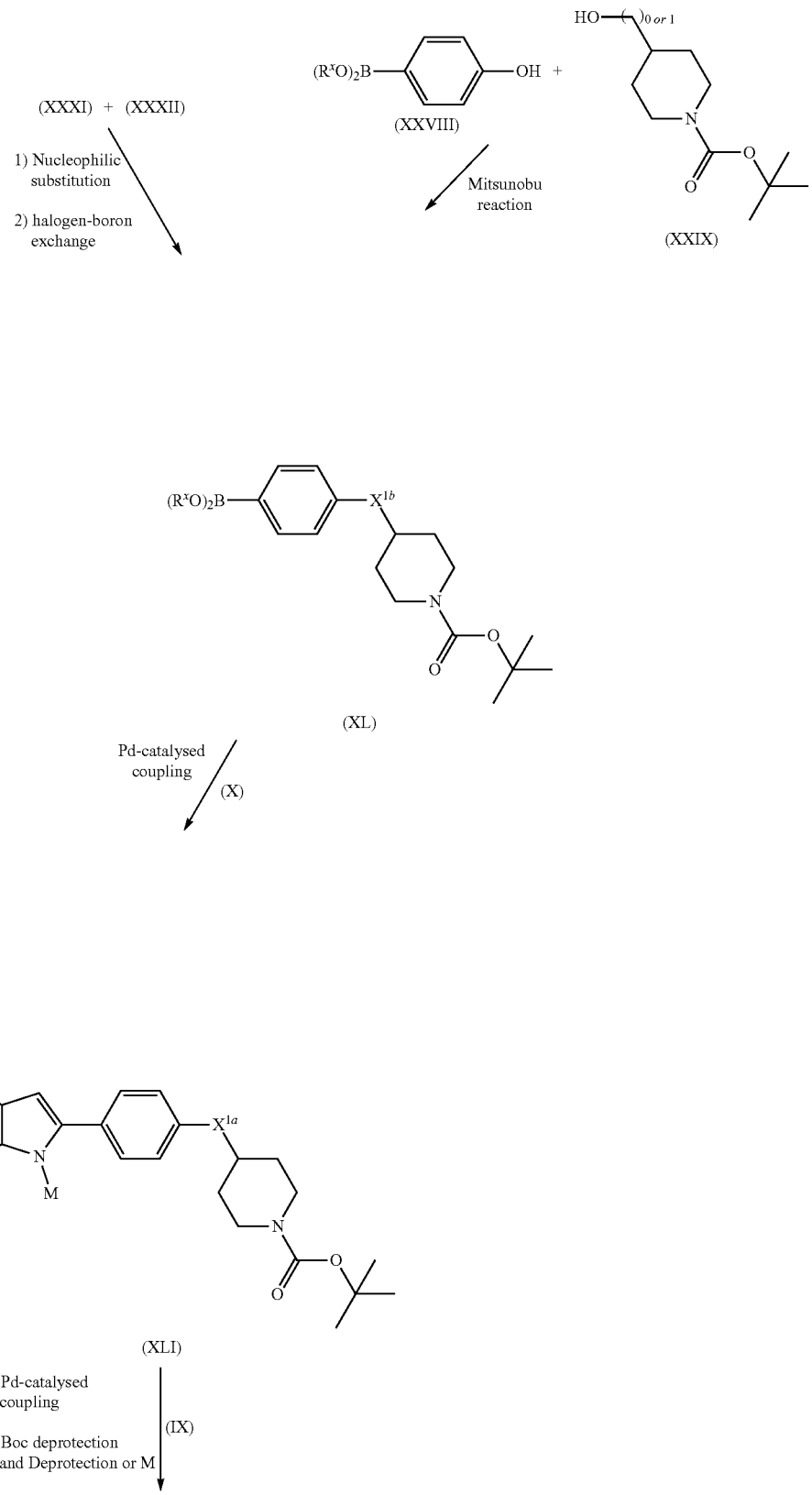

-continued

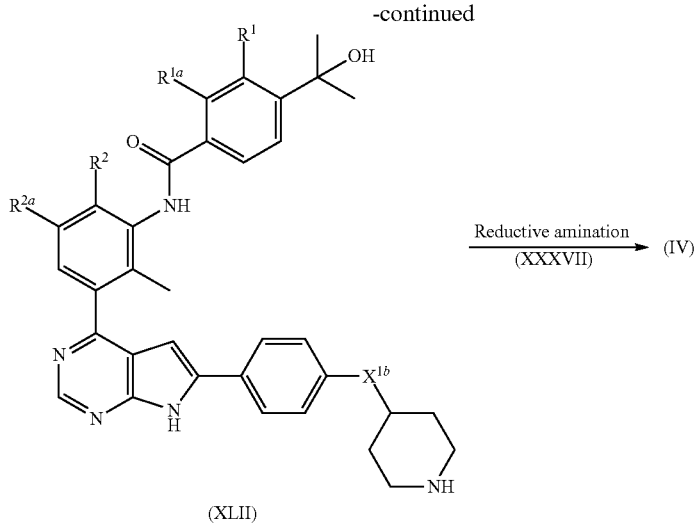

(XLII)

Compounds of formula (I) may be made as shown in Scheme 15 from an intermediate of formula (XLIV) which itself can be made by direct analogy to compound (XL) in Scheme 14. Thus intermediate (XLIV) is derived from either (XXVIII) or (XXXI) combined with (XLIII). Compound (XLIV) then undergoes two Pd-catalysed coupling reactions and a de-protection sequence to furnish (XLV). Compound (XLV) may be reacted with a compound of formula (XLVI) in a reductive amination reaction to furnish (I). Compound (XLVI) is made from compound of formula (III) using an amide coupling reaction with N-(2-hydroxyethyl)piperazine, followed by an oxidation reaction such as a Swern oxidation, using, for example, oxalyl chloride and DMSO, followed by addition of TEA in a solvent such as DCM.

Scheme 15

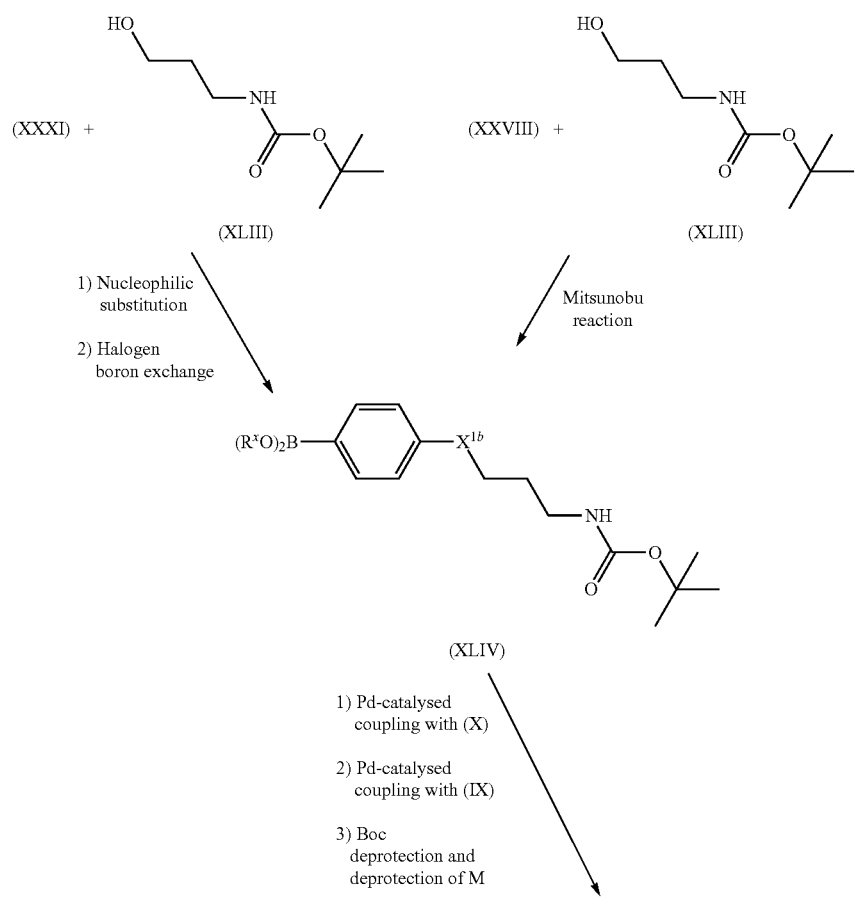

(III) + N-(2-hydroxyethyl)piperazine

1) Amide coupling
2) Oxidation

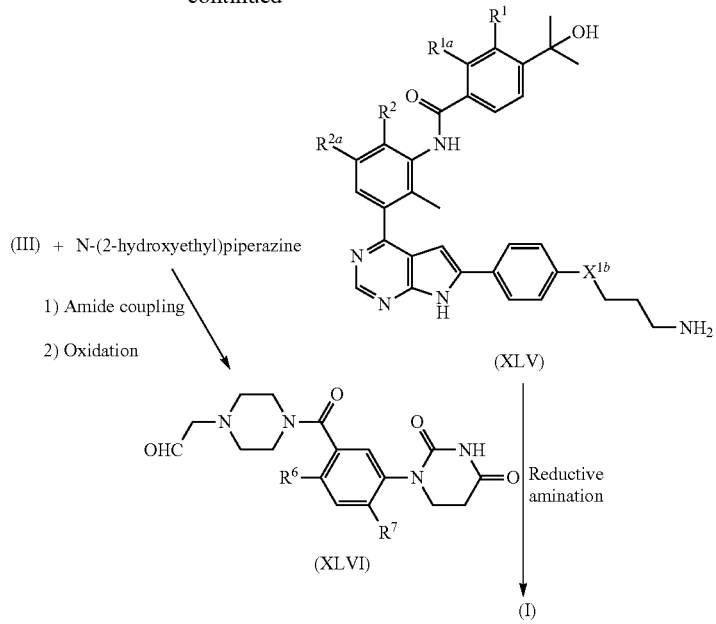
(XLV)

(XLVI)

Reductive amination (I)

Dihydrouracil molecules of formula (III) may be made by cyclisation of molecules of formula (XLVII) using urea in acetic acid heated to around 120° C. Compounds (XLVII) are in turn synthesized from the corresponding aniline derivatives (XLVIII) by heating in acrylic acid (Scheme 16), typically at temperatures around 100° C. A compound of formula (IIIa) may be synthesized from a compound of formula (III) by reaction with pentafluorophenyl-2,2,2-trifluoroacetate in the presence of a base such as DIPEA in a solvent such as DMF.

Scheme 16

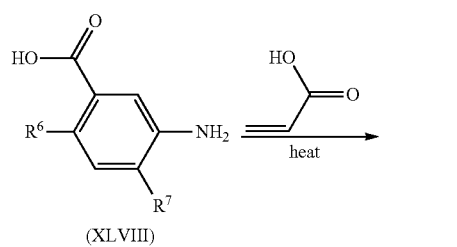
(XLVIII)

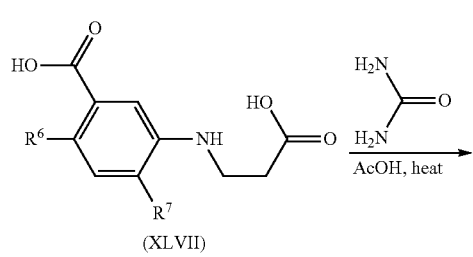
(XLVII)

(III)

DIPEA, DMF (IIIa)

Compounds of formula (IX) are made according to Scheme 17 using an amide coupling reaction between compounds of formula (XLIX) and (L), a coupling reagent (e.g. HATU) and a base (e.g. DIPEA or NMM) in a solvent such as DMF or DMA.

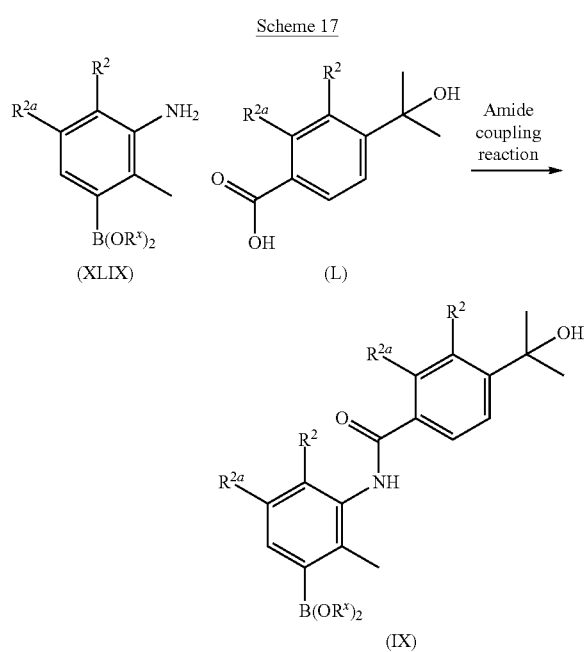

The specific preparation of intermediates and examples using the general methods described above is provided in detail in the experimental section.

In an additional embodiment, there is provided a compound according to Formula (III), or salt thereof,

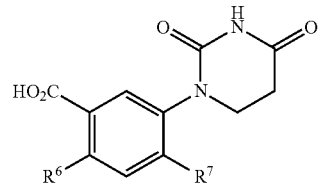

(III)

wherein $R^6$ is selected from H and F; and $R^7$ is selected from H, F, Cl, —CH$_3$, —OCH$_3$, and —OCH$_2$CH$_3$.

In another embodiment, there is provided a compound according to Formula (IIIa), or salt thereof,

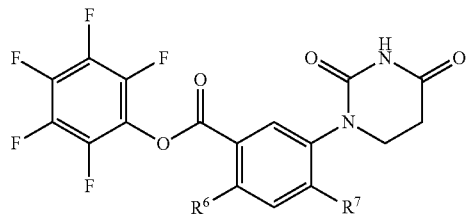

(IIIa)

wherein $R^6$ is selected from H and F; and $R^7$ is selected from H, F, Cl, —CH$_3$, —OCH$_3$, and —OCH$_2$CH$_3$.

In another embodiment, there is provided a compound according to Formula (XXIa), or salt thereof, (XXIa)

wherein $R^6$ is selected from H and F; and $R^7$ is selected from H, F, Cl, —CH$_3$, —OCH$_3$, and —OCH$_2$CH$_3$.

In an additional embodiment, there is provided a compound or salt thereof selected from the group consisting of:

3-(2,4-Dioxotetrahydropyrimidin-1(2H)-yl)-4-methoxybenzoic acid:

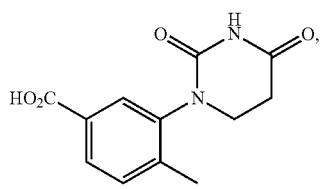 [SMILES: Cc1ccc(C(=O)O)cc1N1CCC(=O)NC1=O]

3-(2,4-Dioxotetrahydropyrimidin-1(2H)-yl)-4-methylbenzoic acid:

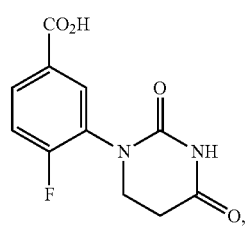 [SMILES: O=C1CCN(c2cc(C(=O)O)ccc2F)C(=O)N1]

3-(2,4-Dioxotetrahydropyrimidin-1(2H)-yl)-4-fluorobenzoic acid:

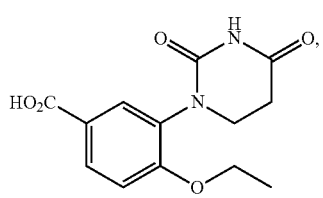 [SMILES: CCOc1ccc(C(=O)O)cc1N1CCC(=O)NC1=O]

3-(2,4-dioxotetrahydropyrimidin-1(2H)-yl)-4-ethoxybenzoic acid:

tert-butyl 9-(4-bromophenethyl)-3,9-diazaspiro[5.5]undecane-3-carboxylate:

5-(2,4-dioxotetrahydropyrimidin-1(2H)-yl)-2-fluoro-4-methylbenzoic acid:

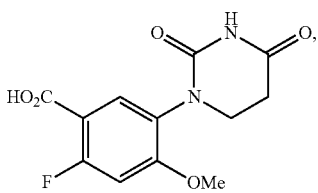

4-chloro-3-(2,4-dioxotetrahydropyrimidin-1(2H)-yl)benzoic acid:

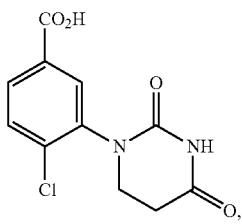 [SMILES: O=C1CCN(c2cc(C(=O)O)ccc2Cl)C(=O)N1]

pentafluorophenyl 3-(2,4-dioxotetrahydropyrimidin-1(2H)-yl)-4-methoxybenzoate:

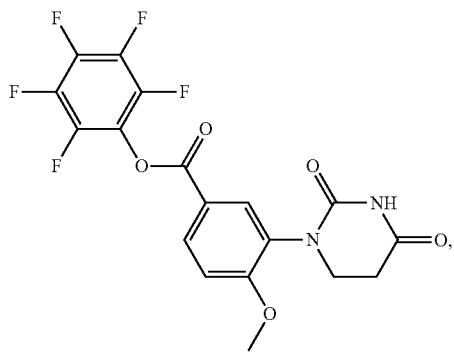 [SMILES: COc1ccc(C(=O)Oc2c(F)c(F)c(F)c(F)c2F)cc1N1CCC(=O)NC1=O]

and 1-(2-Methoxy-5-(3,9-diazaspiro[5.5]undecane-3-carbonyl)phenyl)dihydropyrimidine-2,4(1H,3H)-dione:

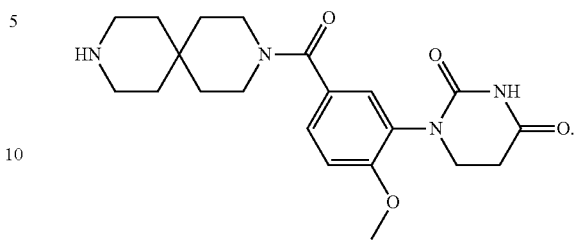

Compounds of these embodiments are useful in the preparation of compounds of the present invention.

The invention further includes any variant of the present processes, in which an intermediate obtainable at any stage thereof is used as starting material and the remaining steps are carried out, or in which the starting materials are formed in situ under the reaction conditions, or in which the reaction components are used in the form of their salts or optically pure material. Compounds of the present invention and intermediates can also be converted into each other according to methods generally known to those skilled in the art e.g. by reduction, oxidation and/or other functionalization of resulting compounds and/or by cleavage of any protecting group(s) optionally present or linker moieties, and of recovering the so obtainable compound.

In another aspect, the present invention provides a pharmaceutical composition comprising a compound of the present invention, or a pharmaceutically acceptable salt thereof, and a pharmaceutically acceptable carrier.

In another aspect, the present invention provides a pharmaceutical composition comprising a therapeutically effective amount of a compound of the present invention, or a pharmaceutically acceptable salt thereof, and a pharmaceutically acceptable carrier.

In a further embodiment, the composition comprises at least two pharmaceutically acceptable carriers, such as those described herein. The pharmaceutical composition can be formulated for particular routes of administration such as oral administration, parenteral administration (e.g. by injection, infusion, transdermal or topical administration), and rectal administration. Topical administration may also pertain to inhalation or intranasal application. The pharmaceutical compositions of the present invention can be made up in a solid form (including, without limitation, capsules, tablets, pills, granules, powders or suppositories), or in a liquid form (including, without limitation, solutions, suspensions or emulsions). Tablets may be either film coated or enteric coated according to methods known in the art.

Typically, the pharmaceutical compositions are tablets or gelatin capsules comprising the active ingredient together with one or more of:
a) diluents, e.g., lactose, dextrose, sucrose, mannitol, sorbitol, cellulose and/or glycine;
b) lubricants, e.g., silica, talcum, stearic acid, its magnesium or calcium salt and/or polyethyleneglycol; for tablets also
c) binders, e.g., magnesium aluminum silicate, starch paste, gelatin, tragacanth, methylcellulose, sodium carboxymethylcellulose and/or polyvinylpyrrolidone; if desired
d) disintegrants, e.g., starches, agar, alginic acid or its sodium salt, or effervescent mixtures; and
e) absorbents, colorants, flavors and sweeteners.

The compounds of formula (I) or (Ia), or pharmaceutical acceptable salts thereof, exhibit valuable pharmacological properties, for example, modulation of BTK activity, for example by acting as BTK degraders. This can be determined in vitro, for example, in cells by using engineered cell lines over-expressing BTK or BTK C481S mutant fusion proteins as described herein, for fluorescent readouts as well as in cell lines expressing endogenous BTK. The pharmacological usefulness of the compounds of the present invention can also be determined in vivo, for example, by administering compounds of the invention to animals, such as mice, bearing tumors such as TMD8 tumors and measuring the reduction of BTK in tumor tissue and reduction of tumor volume as a consequence of dosing the compound. The compounds of formula (I) or (Ia) may therefore be useful for the treatment of diseases mediated by BTK.

The compounds of formula (I) or (Ia) may be useful for research on diseases mediated by BTK, e.g. as tool compounds.

The compounds of the present invention, in free form or in pharmaceutically acceptable salt form, may be useful in the prevention or treatment of cancer, for example a cancer selected from solid tumor cancers and hematopoietic cancers.

Examples of solid tumor cancers include central nervous system cancer, brain cancer, breast cancer, head and neck cancer, lung cancer; esophageal and esophagogastric junction cancer, gastric cancer, colorectal cancer, rectal cancer, anal cancer, hepatobiliary cancer, pancreatic cancer, non-melanoma skin cancer, melanoma, renal cancer, prostate cancer, bladder cancer, uterine cancer, cervical cancer, ovarian cancer, bone cancer, neuroendocrine cancer, mesothelioma cancer, testicular cancer, thymoma and thymic carcinoma, and thyroid cancer.

Examples of hematopoietic cancers include B-cell neoplasms (including rare B-cell malignancies), Hodgkin lymphoma, non-Hodgkin lymphoma, post-transplant lymphoproliferative disorder, hairy cell leukemia, histiocytic and dendritic neoplasms.

Examples of B-cell neoplasms include chronic lymphocytic leukemia (CLL), mantle cell lymphoma (MCL), small lymphocytic lymphoma (SLL), Waldenstrom's macroglobulinemia, diffuse large B-cell lymphoma (DLBCL), follicular lymphoma, Burkitt lymphoma, Marginal Zone Lymphoma, immunoblastic large cell lymphoma, Richter Syndrome, and precursor B-lymphoblastic lymphoma, primary and secondary multiple myeloma, B-cell prolymphocytic leukemia, lymphoplasmacytic lymphoma, splenic marginal zone lymphoma, plasma cell myeloma, plasmacytoma, extranodal marginal zone B-cell lymphoma, nodal marginal zone B-cell lymphoma, mediastinal (thymic) large B-cell lymphoma, intravascular large B-cell lymphoma, primary effusion lymphoma, lymphomatoid granulomatosis, and acute lymphoblastic leukemia.

In a particular embodiment, the cancer is selected from chronic lymphocytic leukemia (CLL), diffuse large B-cell lymphoma (DLBCL), mantle cell lymphoma (MCL), small lymphocytic lymphoma (SLL), and Waldenström's macroglobulinemia.

In a further embodiment, the cancer is chronic lymphocytic leukemia (CLL).

In another embodiment, the cancer is diffuse large B-cell lymphoma (DLBCL).

The compounds of the present invention may have particular application in the treatment of subjects in which the cancer (e.g. CLL, DLBCL, MCL, SLL and Waldenström's macroglobulinemia) has acquired resistance to ibrutinib, for example in cancers in which resistance has arisen for example through mutation of cysteine-481 to serine (i.e. mutation C481S). Such subjects may have for example already been treated or are continuing to be treated with ibrutinib and where the subject has a reduced response or is no longer responding to treatment with ibrutinib. The compounds of the invention may therefore be beneficially used in the treatment of ibrutinib resistant cancer, especially ibrutinib resistant CLL, DLBCL, MCL, SLL and Waldenström's macroglobulinemia, in particular, ibrutinib resistant CLL.

In an another embodiment, the compounds of the present invention, in free form or in pharmaceutically acceptable salt form, may be useful in the prevention or treatment of autoimmune disorders, inflammatory disorders, allergic diseases, anaphylaxis, allergic asthma and airway diseases, and in transplantation. For example the compounds of the present invention, in free form or in pharmaceutically acceptable salt form, may be useful in the prevention or treatment of asthma; chronic obstructive pulmonary disease (COPD); transplant rejection; diseases in which antibody production, antigen presentation, cytokine production or lymphoid organogenesis are abnormal or are undesirable; rheumatoid arthritis; systemic onset juvenile idiopathic arthritis (SOJIA); gout; pemphigus vulgaris; idiopathic thrombocytopenic purpura; systemic lupus erythematosus; multiple sclerosiss; myasthenia gravis; Sjögren's syndrome; autoimmune hemolytic anemia; anti-neutrophil cytoplasmic antibodies (ANCA)-associated vasculitides; cryoglobulinemia; thrombotic thrombocytopenic purpura; chronic autoimmune urticarial; allergy (atopic dermatitis, contact dermatitis, allergic rhinitis); atherosclerosis; type 1 diabetes; type 2 diabetes; inflammatory bowel disease; ulcerative colitis; morbus Crohn; pancreatitis; glomerolunephritis; Goodpasture's syndrome; Hashimoto's thyroiditis; Grave's disease; antibody-mediated transplant rejection (AMR); graft versus host disease (GvHD); chronic graft versus host disease (cGvHD); B cell-mediated hyperacute; acute and chronic transplant rejection; thromboembolic disorders; myocardial infarct; angina pectoris; stroke; ischemic disorders; pulmonary embolism; polycythemia vera; essential thrombocythemia; and myelofibrosis with myeloid metaplasia.

In another embodiment, the compounds of the present invention, in free form or in pharmaceutically acceptable salt form, may be useful in the prevention or treatment of immunoglobulin Light Chain Amyloidosis (AL).

In a further aspect, the present invention provides the use of a compound of the invention, or a pharmaceutically acceptable salt thereof, in therapy. In an embodiment, the present invention provides the use of a compound of the invention, or a pharmaceutically acceptable salt thereof, in the prevention or treatment of diseases mediated by BTK. In another embodiment, the present invention provides the use of a compound of the invention, or a pharmaceutically acceptable salt thereof, in the prevention or treatment of cancer. In a further embodiment, the cancer is a hematopoietic cancer. In a further embodiment the hematopoietic cancer is chronic lymphocytic leukemia (CLL), diffuse large B-cell lymphoma (DLBCL), mantle cell lymphoma (MCL), small lymphocytic lymphoma (SLL), and Waldenström's macroglobulinemia, especially CLL or DLBCL.

In an embodiment, the compound is N-(3-(6-(4-((4-((1-(3-(2,4-dioxotetrahydropyrimidin-1(2H)-yl)-4-methoxybenzoyl)piperidin-4-yl)oxy)piperidin-1-yl)methyl)phenyl)-7H-pyrrolo[2,3-d]pyrimidin-4-yl)-5-fluoro-2-methylphenyl)-2-fluoro-4-(2-hydroxypropan-2-yl) benzamide, or a pharmaceutically acceptable salt thereof.

In an embodiment, the compound is N-(3-(6-(4-((9-(3-(2,4-dioxotetrahydropyrimidin-1(2H)-yl)-4-methoxybenzoyl)-3,9-diazaspiro[5.5]undecan-3-yl)methyl)phenyl)-7H-pyrrolo[2,3-d]pyrimidin-4-yl)-5-fluoro-2-methylphenyl)-2-fluoro-4-(2-hydroxypropan-2-yl)benzamide, or a pharmaceutically acceptable salt thereof.

In an embodiment, the compound is N-(3-(6-(4-(2-(4-((1-(3-(2,4-dioxotetrahydropyrimidin-1(2H)-yl)-4-methylbenzoyl)piperidin-4-yl)oxy)piperidin-1-yl)ethyl)phenyl)-7H-pyrrolo[2,3-d]pyrimidin-4-yl)-5-fluoro-2-methylphenyl)-2-fluoro-4-(2-hydroxypropan-2-yl)benzamide, or a pharmaceutically acceptable salt thereof.

In an embodiment, the compound is N-(3-(6-(4-((4-(2-(4-(3-(2,4-dioxotetrahydropyrimidin-1(2H)-yl)-4-methoxybenzoyl)piperazin-1-yl)ethyl)piperazin-1-yl)methyl)phenyl)-7H-pyrrolo[2,3-d]pyrimidin-4-yl)-5-fluoro-2-methylphenyl)-2-fluoro-4-(2-hydroxypropan-2-yl)benzamide, or a pharmaceutically acceptable salt thereof.

In an embodiment, the compound is N-(3-(6-(4-(2-(9-(3-(2,4-dioxotetrahydropyrimidin-1(2H)-yl)-4-methoxybenzoyl)-3,9-diazaspiro[5.5]undecan-3-yl)ethyl)phenyl)-7H-pyrrolo[2,3-d]pyrimidin-4-yl)-5-fluoro-2-methylphenyl)-2-fluoro-4-(2-hydroxypropan-2-yl)benzamide, or a pharmaceutically acceptable salt thereof.

In an embodiment, the compound is N-(3-(6-(4-(2-(4-((1-(3-(2,4-dioxotetrahydropyrimidin-1(2H)-yl)-4-methoxybenzoyl)piperidin-4-yl)oxy)piperidin-1-yl)ethyl)phenyl)-7H-pyrrolo[2,3-d]pyrimidin-4-yl)-5-fluoro-2-methylphenyl)-2-fluoro-4-(2-hydroxypropan-2-yl)benzamide, or a pharmaceutically acceptable salt thereof.

In an embodiment, the compound is N-(3-(6-(4-(((4-(4-(3-(2,4-dioxotetrahydropyrimidin-1(2H)-yl)-4-methoxybenzoyl)piperazin-1-yl)butyl)amino)methyl)phenyl)-7H-pyrrolo[2,3-d]pyrimidin-4-yl)-5-fluoro-2-methylphenyl)-2-fluoro-4-(2-hydroxypropan-2-yl)benzamide, or a pharmaceutically acceptable salt thereof.

In an embodiment, the compound is N-(3-(6-(4-(2-(9-(3-(2,4-dioxotetrahydropyrimidin-1(2H)-yl)-4-fluorobenzoyl)-3,9-diazaspiro[5.5]undecan-3-yl)ethyl)phenyl)-7H-pyrrolo[2,3-d]pyrimidin-4-yl)-5-fluoro-2-methylphenyl)-2-fluoro-4-(2-hydroxypropan-2-yl)benzamide, or a pharmaceutically acceptable salt thereof.

In a further aspect, the present invention provides a method of treating a disease mediated by BTK comprising administering to a patient in need thereof a therapeutically acceptable amount of a compound of the invention, or a pharmaceutically acceptable salt thereof. In an embodiment, the present invention provides a method of treating cancer comprising administering to a patient in need thereof a therapeutically acceptable amount of a compound of the invention, or a pharmaceutically acceptable salt thereof. In a further embodiment, the cancer is a hematopoietic cancer. In a further embodiment the hematopoietic cancer is chronic lymphocytic leukemia (CLL), diffuse large B-cell lymphoma (DLBCL), mantle cell lymphoma (MCL), small lymphocytic lymphoma (SLL), and Waldenström's macroglobulinemia, especially CLL or DLBCL.

In an embodiment, the compound is N-(3-(6-(4-((4-((1-(3-(2,4-dioxotetrahydropyrimidin-1(2H)-yl)-4-methoxybenzoyl)piperidin-4-yl)oxy)piperidin-1-yl)methyl)phenyl)-7H-pyrrolo[2,3-d]pyrimidin-4-yl)-5-fluoro-2-methylphenyl)-2-fluoro-4-(2-hydroxypropan-2-yl)benzamide, or a pharmaceutically acceptable salt thereof.

In an embodiment, the compound is N-(3-(6-(4-((9-(3-(2,4-dioxotetrahydropyrimidin-1(2H)-yl)-4-methoxybenzoyl)-3,9-diazaspiro[5.5]undecan-3-yl)methyl)phenyl)-7H-pyrrolo[2,3-d]pyrimidin-4-yl)-5-fluoro-2-methylphenyl)-2-fluoro-4-(2-hydroxypropan-2-yl)benzamide, or a pharmaceutically acceptable salt thereof.

In an embodiment, the compound is N-(3-(6-(4-(2-(4-((1-(3-(2,4-dioxotetrahydropyrimidin-1(2H)-yl)-4-methylbenzoyl)piperidin-4-yl)oxy)piperidin-1-yl)ethyl)phenyl)-7H-pyrrolo[2,3-d]pyrimidin-4-yl)-5-fluoro-2-methylphenyl)-2-fluoro-4-(2-hydroxypropan-2-yl)benzamide, or a pharmaceutically acceptable salt thereof.

In an embodiment, the compound is N-(3-(6-(4-((4-(2-(4-(3-(2,4-dioxotetrahydropyrimidin-1(2H)-yl)-4-methoxybenzoyl)piperazin-1-yl)ethyl)piperazin-1-yl)methyl)phenyl)-7H-pyrrolo[2,3-d]pyrimidin-4-yl)-5-fluoro-2-methylphenyl)-2-fluoro-4-(2-hydroxypropan-2-yl)benzamide, or a pharmaceutically acceptable salt thereof.

In an embodiment, the compound is N-(3-(6-(4-(2-(9-(3-(2,4-dioxotetrahydropyrimidin-1(2H)-yl)-4-methoxybenzoyl)-3,9-diazaspiro[5.5]undecan-3-yl)ethyl)phenyl)-7H-pyrrolo[2,3-d]pyrimidin-4-yl)-5-fluoro-2-methylphenyl)-2-fluoro-4-(2-hydroxypropan-2-yl)benzamide, or a pharmaceutically acceptable salt thereof.

In an embodiment, the compound is N-(3-(6-(4-(2-(4-((1-(3-(2,4-dioxotetrahydropyrimidin-1(2H)-yl)-4-methoxybenzoyl)piperidin-4-yl)oxy)piperidin-1-yl)ethyl)phenyl)-7H-pyrrolo[2,3-d]pyrimidin-4-yl)-5-fluoro-2-methylphenyl)-2-fluoro-4-(2-hydroxypropan-2-yl)benzamide, or a pharmaceutically acceptable salt thereof.

In an embodiment, the compound is N-(3-(6-(4-(((4-(4-(3-(2,4-dioxotetrahydropyrimidin-1(2H)-yl)-4-methoxybenzoyl)piperazin-1-yl)butyl)amino)methyl)phenyl)-7H-pyrrolo[2,3-d]pyrimidin-4-yl)-5-fluoro-2-methylphenyl)-2-fluoro-4-(2-hydroxypropan-2-yl)benzamide, or a pharmaceutically acceptable salt thereof.

In an embodiment, the compound is N-(3-(6-(4-(2-(9-(3-(2,4-dioxotetrahydropyrimidin-1(2H)-yl)-4-fluorobenzoyl)-3,9-diazaspiro[5.5]undecan-3-yl)ethyl)phenyl)-7H-pyrrolo[2,3-d]pyrimidin-4-yl)-5-fluoro-2-methylphenyl)-2-fluoro-4-(2-hydroxypropan-2-yl)benzamide, or a pharmaceutically acceptable salt thereof.

In a further aspect, the present invention provides the use of a compound of the invention, or a pharmaceutically acceptable salt thereof, for the manufacture of a medicament. In an embodiment, the present invention provides the use of a compound of the invention, or a pharmaceutically acceptable salt thereof, for the manufacture of a medicament, for the prevention or treatment of a disease mediated by BTK. In an embodiment, the present invention provides the use of a compound of the invention, or a pharmaceutically acceptable salt thereof, for the manufacture of a medicament, for the prevention or treatment of cancer. In a further embodiment, the cancer is a hematopoietic cancer. In a further embodiment the hematopoietic cancer is chronic lymphocytic leukemia (CLL), diffuse large B-cell lymphoma (DLBCL), mantle cell lymphoma (MCL), small lymphocytic lymphoma (SLL), and Waldenström's macroglobulinemia, especially CLL or DLBCL.

In an embodiment, the compound is N-(3-(6-(4-((4-((1-(3-(2,4-dioxotetrahydropyrimidin-1(2H)-yl)-4-methoxybenzoyl)piperidin-4-yl)oxy)piperidin-1-yl)methyl)phenyl)-7H-pyrrolo[2,3-d]pyrimidin-4-yl)-5-fluoro-2-methylphenyl)-2-fluoro-4-(2-hydroxypropan-2-yl)benzamide, or a pharmaceutically acceptable salt thereof.

In an embodiment, the compound is N-(3-(6-(4-((9-(3-(2,4-dioxotetrahydropyrimidin-1(2H)-yl)-4-methoxybenzoyl)-3,9-diazaspiro[5.5]undecan-3-yl)methyl)phenyl)-7H-pyrrolo[2,3-d]pyrimidin-4-yl)-5-fluoro-2-methylphenyl)-2-fluoro-4-(2-hydroxypropan-2-yl)benzamide, or a pharmaceutically acceptable salt thereof.

In an embodiment, the compound is N-(3-(6-(4-(2-(4-((1-(3-(2,4-dioxotetrahydropyrimidin-1(2H)-yl)-4-methylbenzoyl)piperidin-4-yl)oxy)piperidin-1-yl)ethyl)phenyl)-7H-pyrrolo[2,3-d]pyrimidin-4-yl)-5-fluoro-2-methylphenyl)-2-fluoro-4-(2-hydroxypropan-2-yl)benzamide, or a pharmaceutically acceptable salt thereof.

In an embodiment, the compound is N-(3-(6-(4-((4-(2-(4-(3-(2,4-dioxotetrahydropyrimidin-1(2H)-yl)-4-methoxybenzoyl)piperazin-1-yl)ethyl)piperazin-1-yl)methyl)phenyl)-7H-pyrrolo[2,3-d]pyrimidin-4-yl)-5-fluoro-2-methylphenyl)-2-fluoro-4-(2-hydroxypropan-2-yl)benzamide, or a pharmaceutically acceptable salt thereof.

In an embodiment, the compound is N-(3-(6-(4-(2-(9-(3-(2,4-dioxotetrahydropyrimidin-1(2H)-yl)-4-methoxybenzoyl)-3,9-diazaspiro[5.5]undecan-3-yl)ethyl)phenyl)-7H-pyrrolo[2,3-d]pyrimidin-4-yl)-5-fluoro-2-methylphenyl)-2-fluoro-4-(2-hydroxypropan-2-yl)benzamide, or a pharmaceutically acceptable salt thereof.

In an embodiment, the compound is N-(3-(6-(4-(2-(4-((1-(3-(2,4-dioxotetrahydropyrimidin-1(2H)-yl)-4-methoxybenzoyl)piperidin-4-yl)oxy)piperidin-1-yl)ethyl)phenyl)-7H-pyrrolo[2,3-d]pyrimidin-4-yl)-5-fluoro-2-methylphenyl)-2-fluoro-4-(2-hydroxypropan-2-yl)benzamide, or a pharmaceutically acceptable salt thereof.

In an embodiment, the compound is N-(3-(6-(4-(((4-(4-(3-(2,4-dioxotetrahydropyrimidin-1(2H)-yl)-4-methoxybenzoyl)piperazin-1-yl)butyl)amino)methyl)phenyl)-7H-pyrrolo[2,3-d]pyrimidin-4-yl)-5-fluoro-2-methylphenyl)-2-fluoro-4-(2-hydroxypropan-2-yl)benzamide, or a pharmaceutically acceptable salt thereof.

In an embodiment, the compound is N-(3-(6-(4-(2-(9-(3-(2,4-dioxotetrahydropyrimidin-1(2H)-yl)-4-fluorobenzoyl)-3,9-diazaspiro[5.5]undecan-3-yl)ethyl)phenyl)-7H-pyrrolo[2,3-d]pyrimidin-4-yl)-5-fluoro-2-methylphenyl)-2-fluoro-4-(2-hydroxypropan-2-yl)benzamide, or a pharmaceutically acceptable salt thereof.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about $10^{-6}$ molar and $10^{-10}$ molar concentrations. A therapeutically effective amount in vivo may range depending on the route of administration, between about 0.1-500 mg/kg, or between about 1-100 mg/kg.

A compound of the present invention may be administered either simultaneously with, or before or after, one or more other therapeutic agent. A compound of the present invention may be administered separately, by the same or different route of administration, or together in the same pharmaceutical composition as the other agents. A therapeutic agent is, for example, a chemical compound, peptide, antibody, antibody fragment or nucleic acid, which is therapeutically active or enhances the therapeutic activity when administered to a patient in combination with a compound of the present invention.

In one embodiment, the invention provides a product comprising a compound of the present invention and at least one other therapeutic agent as a combined preparation for simultaneous, separate or sequential use in therapy. In one embodiment, the therapy is the treatment of a disease or condition mediated by BTK. In another embodiment, the therapy is the treatment of a cancer described herein. Products provided as a combined preparation include a composition comprising the compound of the present invention and the other therapeutic agent(s) together in the same pharmaceutical composition, or the compound of the present invention and the other therapeutic agent(s) in separate form, e.g. in the form of a kit.

In one embodiment, the invention provides a pharmaceutical composition comprising a compound of the present invention and another therapeutic agent(s). In another embodiment, the invention provides a pharmaceutical composition comprising a therapeutically effective amount of a compound of the present invention and another therapeutic agent(s).

Optionally, the pharmaceutical composition may comprise a pharmaceutically acceptable carrier, as described above.

In one embodiment, the invention provides a kit comprising two or more separate pharmaceutical compositions, at least one of which contains a compound of the present invention. In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the present invention and the other therapeutic agent may be manufactured and/or formulated by the same or different manufacturers. Moreover, the compound of the present invention and the other therapeutic may be brought together into a combination therapy: (i) prior to release of the combination product to physicians (e.g. in the case of a kit comprising the compound of the present invention and the other therapeutic agent); (ii) by the physician themselves (or under the guidance of the physician) shortly before administration; (iii) in the patient themselves, e.g. during sequential administration of the compound of the present invention and the other therapeutic agent.

Accordingly, the invention also provides the use of another therapeutic agent for treating a disease or condition mediated by BTK, wherein the other therapeutic agent is administered with a compound of the present invention.

The invention also provides a compound of the present invention for use in a method of treating a disease or condition mediated by BTK, wherein the compound of the present invention is administered with another therapeutic agent.

The invention also provides another therapeutic agent for use in a method of treating a disease or condition mediated by BTK, wherein the other therapeutic agent is administered with a compound of the present invention.

The invention also provides the use of a compound of the present invention for treating a disease or condition mediated by BTK, wherein the patient has previously (e.g. within 24 hours) been treated with another therapeutic agent.

The invention also provides the use of another therapeutic agent for treating a disease or condition mediated by BTK, wherein the patient has previously (e.g. within 24 hours) been treated with a compound of the present invention.

The invention also provides the use of another therapeutic agent for treating cancer wherein the other therapeutic agent is administered with a compound of the present invention.

The invention also provides a compound of the present invention for use in a method of treating cancer, wherein the compound of the present invention is administered with another therapeutic agent.

The invention also provides another therapeutic agent for use in a method of treating cancer, wherein the other therapeutic agent is administered with a compound of the present invention.

The invention also provides the use of a compound of the present invention for treating cancer, wherein the patient has previously (e.g. within 24 hours) been treated with another therapeutic agent.

The invention also provides the use of another therapeutic agent for treating cancer, wherein the patient has previously (e.g. within 24 hours) been treated with a compound of the present invention.

In one embodiment, the other therapeutic agent is selected from:

Apoptosis modulators, Anti-CD20 antibodies, Anti-CD22 antibodies, PI3K inhibitors, Tyrosine kinase inhibitors, Immune checkpoint agents, CART therapeutic agents, Immunomodulators, bispecific antibodies targeting CD20 and CD3, antibody-drug conjugates (ADC), Proteasome inhibitors, epigenetic modifiers, Anti-CD38 mAb, Anti-SLAMF7 agent, XPO1 inhibitors and other agents such as chemotherapeutic agents.

In an embodiment the apoptosis modulators are selected from Bcl2 inhibitors (such as Antimycin, obatoclax, venetoclax (Venclexta®), ethyl-2-amino-6-cyclopentyl-4-(1-cyano-2-ethoxy-2-oxoethyl)-4H-chromone-3-carboxylate (HA14-1), oblimersen (G3139, Genasense®), Bak BH3 peptide, (−)-Gossypol (AT-101, BL-193), Navitoclax (ABT-263)), Mcl1 inhibitors (such as AMG176, S63845, AZD5991, MIK665), and MDM2/p53 inhibitors (such as NVP-HDM201, NVP-CGM-097, ALRN-6924, idasanutlin, AMG232, and DS-3032B).

In an embodiment the Anti-CD20 antibodies are selected from Rituximab, obinutuzumab, ofatumumab, ocrelizumab, and ublituximab.

In an embodiment the Anti-CD22 antibodies are selected from Inotuzumab, epratuzumab, bectumomab, and moxetumomab.

In an embodiment the PI3K inhibitors are selected from duvelisib, umbralisib tosylate, INCB050465, apilimod mesylate (LAM-002), copanlisib hydrochloride (Aliqopa®), tenalisib, pictilisib (GDC 0941), sonolisib (PX866), pilaralisib (SAR 245408 or XL 147), alpelisib (BYL719), and leniolisib (CDZ173).

In an embodiment the Tyrosine kinase inhibitors are selected from BTK inhibitors (such as ibrutinib, acalabrutinib, zanubrutinib (BGB-3111), tirabrutinib (ONO-4059), ARQ531, CC-292 (AVL-292), CT-1530, DTRMWXHS-12, GDC-0853, M7583, and vecabrutinib (SNS-062), SYK inhibitors (such as entospletinib (GS9973), fostamatinib, and HMPL-523, the SYK/JAK inhibitor cerdulatinib (PRT062070), SYK/FLT inhibitors such as TAK-659, FLT3 inhibitors such as FF-10101, the FLT3/BTK inhibitor (CG806), JAK inhibitors (such as itacitanib, INCB052793, BMS911543, fedratinib, WP-1066, NS-018, and ruxolitinib (Jakavi®)), Erlotinib hydrochloride (Tarceva®), Linifanib (ABT869), Sunitinib malate (Sutent®), Bosutinib (Bosulif®), Dasatinib (Sprycel®), Pazopanib (Votrient®), Sorafenib (Nexavar®), Zactima (ZD6474), Imatinib or Imatinib mesylate (Gilvec® and Gleevec®), and tozasertib (VX680 or MK-0457).

In an embodiment the Immune checkpoint agent is an Anti-PD-1 agent, anti-PD-L1 agent selected from Pembrolizumab, nivolumab, tislelizumab, atezolizumab, ipilimumab, cemiplimab, TLR4 agonist, CCR4 mAb mogamulizumab and CD47 mAb fusion protein (TTI-621).

In an embodiment the CART therapy is selected from CD19, BCMA CART, CD20, CD79b, CD22, CD30.

In an embodiment the immunomodulators are selected from lenalidomide (Revlimid®), thalidomide (Thalomid®), avadomide (CC-122), and pomalidomide (Actimid®, Imnovid®, Pomalyst®).

In an embodiment the bispecific antibody targeting CD20 and CD3 is selected from REGN-1979, XmAb-13676, BTCT-4465-A, CD20-TCB, and 8RG-6026.

In an embodiment the ADC is selected from CD79 ADC polatuzumab vedotin, CD30 ADC brentuximab vedotin, CD25 ADC camidanlumab tesirine, and CD19 ADC loncastuximab tesirine.

In an embodiment the proteasome inhibitors are selected from Bortezomib (Velcade®), carfilzomib (Kyprolis®), marizomib (NPI-0052), ixazomib citrate (MLN-9708, Ninlaro®), delanzomib (CEP-18770), and oprozomib (ONX-0912).

In an embodiment the epigenetic modifiers such as HDAC and DNA methylation inhibitors are selected from Vorinostat (Zolinza®), Romidepsin (Istodax®), azacitidine (Mylosar®, Vidaza®), Pyroxamide, Spiruchostatin A, Mylproin (Valproic acid), Entinostat, and guadecitabine.

In an embodiment the Anti-CD38 mAb is selected from Daratumumab and Isatuximab.

In an embodiment the Anti-SLAMF7 agent is Elotuzumab.

In an embodiment the XPO1 inhibitors are selected from Selinexor and Eltanexor.

In an embodiment other agents, such as general chemotherapeutic agents, which may be combined with a compound of the invention are selected from anastrozole (Arimidex®), bendamustine (Treanda®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), epirubicin (Ellence®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), nab-paclitaxel (Abraxane®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban), vincristine (Oncovin®), and vinorelbine (Navelbine®), ROR mAb cirmtuzumab, Dual PI3K/HDAC inhibitor (CUDC-907), Bet inhibitors (INCB357643), ALK inhibitors (crizotinib), EZH1/2 inhibitors (DS-3201b), MAPK inhibitors, Aplidin, Plitidepsin (eEF1A2 inhibitor), Wnt inhibitors, radiopharmaceuticals, idiotype vaccines, Pegfilgrastim (Neulasta®), citoplurikin (IRX-2).

In a further embodiment, the other therapeutic agent is selected from:
venetoclax, oblimersen, navitoclax, MIK665, NVP-HDM201, Rituximab, obinutuzumab, ofatumumab, ocrelizumab, ublituximab, Inotuzumab, epratuzumab, bectumomab, moxetumomab, duvelisib, umbralisib tosylate, INCB050465, leniolisib (CDZ173), apilimod mesylate (LAM-002), copanlisib hydrochloride, tenalisib, pictilisib, alpelisib, ibrutinib, acalabrutinib, zanubrutinib (BGB-3111), tirabrutinib (ONO-4059), ARQ531, CC-292 (AVL-292), CT-1530, DTRMWXHS-12, GDC-0853, M7583, vecabrutinib (SNS-062), entospletinib, (GS9973), fostamatinib, HMPL-523, cerdulatinib (PRT062070), (TAK-659), FF-10101, FLT3/BTK inhibitor (CG806), itacitanib, INCB052793, BMS911543, fedratinib, WP-1066, NS-018, ruxolitinib (Jakavi®), Pembrolizumab, nivolumab, tislelizumab, atezolizumab, ipilimumab, cemiplimab, TLR4 agonist, CCR4 mAb mogamulizumab, CD47 mAb fusion protein (TTI-621), CD19, BCMA CART, CD20, CD79b, CD22, CD30, lenalidomide, thalidomide, avadomide, pomalidomide, XmAb-13676, CD79 ADC polatuzumab vedotin, CD30 ADC brentuximab vedotin, CD25 ADC camidanlumab tesirine, CD19 ADC loncastuximab tesirine, Carfilzomib, Bortezomib, Ixazomib, marizomib, oprozomib, Azacitidine, Romidepsin, Vorinostat, guadecitabine, Daratumumab, Isatuximab, Elotuzumab, Selinexor, Eltanexor, Fludarabine, carmustine, cyclophosphamide, chlorambucil, bendamustine, melphalan, cladribine, dacarbazine, pentostatin, vincristine, etoposide, epirubicin, doxorubicin, anthracyclines and antifolate agents.

In a further embodiment, the other therapeutic agent is selected from a Bcl2 inhibitor and a BTK inhibitor.

In a further embodiment, the other therapeutic agent is selected from venetoclax, ibrutinib, and acalabrutinib.

Specific individual combinations which may provide particular treatment benefits include a compound selected from:

N-(3-(6-(4-((4-((1-(3-(2,4-dioxotetrahydropyrimidin-1 (2H)-yl)-4-methoxybenzoyl)piperidin-4-yl)oxy)piperidin-1-yl)methyl)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-((9-(3-(2,4-dioxotetrahydropyrimidin-1(2H)-yl)-4-methoxybenzoyl)-3,9-diazaspiro[5.5]undecan-3-yl) methyl)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-(2-(4-((1-(3-(2,4-dioxotetrahydropyrimidin-1 (2H)-yl)-4-methylbenzoyl)piperidin-4-yl)oxy)piperidin-1-yl)ethyl)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-((4-(2-(4-(3-(2,4-dioxotetrahydropyrimidin-1 (2H)-yl)-4-methoxybenzoyl)piperazin-1-yl)ethyl)piperazin-1-yl)methyl)phenyl)-7H-pyrrolo[2,3-d]pyrimidin-4- yl)-5-fluoro-2-methylphenyl)-2-fluoro-4-(2-hydroxypropan-2-yl)benzamide,

N-(3-(6-(4-(2-(9-(3-(2,4-dioxotetrahydropyrimidin-1(2H)-yl)-4-methoxybenzoyl)-3,9-diazaspiro[5.5]undecan-3-yl)ethyl)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-(2-(4-((1-(3-(2,4-dioxotetrahydropyrimidin-1(2H)-yl)-4-methoxybenzoyl)piperidin-4-yl)oxy)piperidin-1-yl)ethyl)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-(((4-(4-(3-(2,4-dioxotetrahydropyrimidin-1(2H)-yl)-4-methoxybenzoyl)piperazin-1-yl)butyl)amino)methyl)phenyl)-7H-pyrrolo[2,3-d]pyrimidin-4-yl)-5-fluoro-2-methylphenyl)-2-fluoro-4-(2-hydroxypropan-2-yl)benzamide, and N-(3-(6-(4-(2-(9-(3-(2,4-dioxotetrahydropyrimidin-1(2H)-yl)-4-fluorobenzoyl)-3,9-diazaspiro[5.5]undecan-3-yl)ethyl)phenyl)-7H-pyrrolo[2,3-d]pyrimidin-4-yl)-5-fluoro-2-methylphenyl)-2-fluoro-4-(2-hydroxypropan-2-yl)benzamide, or a pharmaceutically acceptable salt thereof, in combination with venetoclax.

Further specific individual combinations which may provide particular treatment benefits include a compound selected from:

N-(3-(6-(4-((4-((1-(3-(2,4-dioxotetrahydropyrimidin-1(2H)-yl)-4-methoxybenzoyl)piperidin-4-yl)oxy)piperidin-1-yl)methyl)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-((9-(3-(2,4-dioxotetrahydropyrimidin-1(2H)-yl)-4-methoxybenzoyl)-3,9-diazaspiro[5.5]undecan-3-yl)methyl)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-(2-(4-((1-(3-(2,4-dioxotetrahydropyrimidin-1(2H)-yl)-4-methylbenzoyl)piperidin-4-yl)oxy)piperidin-1-yl)ethyl)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-((4-(2-(4-(3-(2,4-dioxotetrahydropyrimidin-1(2H)-yl)-4-methoxybenzoyl)piperazin-1-yl)ethyl)piperazin-1-yl)methyl)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-(2-(9-(3-(2,4-dioxotetrahydropyrimidin-1(2H)-yl)-4-methoxybenzoyl)-3,9-diazaspiro[5.5]undecan-3-yl)ethyl)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-(2-(4-((1-(3-(2,4-dioxotetrahydropyrimidin-1(2H)-yl)-4-methoxybenzoyl)piperidin-4-yl)oxy)piperidin-1-yl)ethyl)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-(((4-(4-(3-(2,4-dioxotetrahydropyrimidin-1(2H)-yl)-4-methoxybenzoyl)piperazin-1-yl)butyl)amino)methyl)phenyl)-7H-pyrrolo[2,3-d]pyrimidin-4-yl)-5-fluoro-2-methylphenyl)-2-fluoro-4-(2-hydroxypropan-2-yl)benzamide, and N-(3-(6-(4-(2-(9-(3-(2,4-dioxotetrahydropyrimidin-1(2H)-yl)-4-fluorobenzoyl)-3,9-diazaspiro[5.5]undecan-3-yl)ethyl)phenyl)-7H-pyrrolo[2,3-d]pyrimidin-4-yl)-5-fluoro-2-methylphenyl)-2-fluoro-4-(2-hydroxypropan-2-yl)benzamide, or a pharmaceutically acceptable salt thereof, in combination with ibrutinib.

Yet further specific individual combinations which may provide particular treatment benefits include a compound selected from N-(3-(6-(4-((4-((1-(3-(2,4-dioxotetrahydropyrimidin-1(2H)-yl)-4-methoxybenzoyl)piperidin-4-yl)oxy)piperidin-1-yl)methyl)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-((9-(3-(2,4-dioxotetrahydropyrimidin-1(2H)-yl)-4-methoxybenzoyl)-3,9-diazaspiro[5.5]undecan-3-yl)methyl)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-(2-(4-((1-(3-(2,4-dioxotetrahydropyrimidin-1(2H)-yl)-4-methylbenzoyl)piperidin-4-yl)oxy)piperidin-1-yl)ethyl)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-((4-(2-(4-(3-(2,4-dioxotetrahydropyrimidin-1(2H)-yl)-4-methoxybenzoyl)piperazin-1-yl)ethyl)piperazin-1-yl)methyl)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-(2-(9-(3-(2,4-dioxotetrahydropyrimidin-1(2H)-yl)-4-methoxybenzoyl)-3,9-diazaspiro[5.5]undecan-3-yl)ethyl)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-(2-(4-((1-(3-(2,4-dioxotetrahydropyrimidin-1(2H)-yl)-4-methoxybenzoyl)piperidin-4-yl)oxy)piperidin-1-yl)ethyl)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-(((4-(4-(3-(2,4-dioxotetrahydropyrimidin-1(2H)-yl)-4-methoxybenzoyl)piperazin-1-yl)butyl)amino)methyl)phenyl)-7H-pyrrolo[2,3-d]pyrimidin-4-yl)-5-fluoro-2-methylphenyl)-2-fluoro-4-(2-hydroxypropan-2-yl)benzamide, and N-(3-(6-(4-(2-(9-(3-(2,4-dioxotetrahydropyrimidin-1(2H)-yl)-4-fluorobenzoyl)-3,9-diazaspiro[5.5]undecan-3-yl)ethyl)phenyl)-7H-pyrrolo[2,3-d]pyrimidin-4-yl)-5-fluoro-2-methylphenyl)-2-fluoro-4-(2-hydroxypropan-2-yl)benzamide, or a pharmaceutically acceptable salt thereof, in combination with acalabrutinib.

These combinations may be provided as a pharmaceutical composition comprising an afore-mentioned compound of the present invention, or pharmaceutically acceptable salt thereof, and venetoclax, ibrutinib or acalabrutinib.

Alternatively these combinations may be provided as a combined preparation of an afore-mentioned compound of the present invention, or pharmaceutically acceptable salt thereof, for simultaneous, separate or sequential use with venetoclax, ibrutinib or acalabrutinib in therapy.

These combinations, especially with ibrutinib, may be particularly effective in the treatment of hematopoietic cancers, in particular CLL and DLBCL.

The activity of a compound of the invention can be assessed by the following in vitro methods described herein.

Compounds of the present invention can be prepared as described in the following Examples.

Examples

The following examples illustrate the invention and are not to be construed as being limitations thereon. Temperatures are given in degrees Celsius. Abbreviations used are those conventional in the art and listed below.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art. Further, the compounds of the present invention can be produced by organic synthesis methods known to one of ordinary skill in the art as shown in the following examples.

Abbreviations

ACN acetonitrile
OAc acetate
AcOH acetic acid
aq. aqueous
BISPIN bis(pinacolato)diboron
BOC tert-butoxycarbonyl
br broad
CHX cyclohexane
d doublet
DCM dichloromethane
dd doublet of doublets
DEA diethylamine
DEAD diethyl azodicarboxylate
DIAD diisopropyl azodicarboxylate
DIPEA diisopropylethylamine
DMA N,N-dimethylacetamide
DMEM Dulbecco's Modified Eagle's medium
DMF N,N-dimethylformamide
DMSO dimethylsulfoxide
e.g. for example
eq. equivalent
ESI electrospray ionization
$Et_2O$ diethyl ether
EtOAc ethyl acetate
EtOH ethanol
FCS fetal calf serum
h hour(s)
HATU 1-[bis(dimethylamino)methylene]-1H-1,2,3-triazolo[4,5-b]pyridinium 3-oxid hexafluorophosphate
HBTU 2-(1H-benzotriazol-1-yl)-1,1,3,3-tetramethyluronium hexafluorophosphate
HPLC high pressure liquid chromatography
HV high vacuum
iPrOH isopropanol
LC-MS liquid chromatography and mass spectrometry
m multiplet
m/z mass to charge ratio
MeOH methanol
mg milligram
min minute
ml milliliter
mmol millimole
MS mass spectrometry
$Ms_2O$ methanesulfonic anhydride
$NaBH(OAc)_3$ sodium triacetoxyborohydride
$NaBH_3CN$ sodium cyanoborohydride
NaPyr. Sodiumpyruvate
NEAA none essential amino acid
NMM N-methylmorpholine
NMP N-methyl-2-pyrrolidone
NMR nuclear magnetic resonance
PBS phosphate buffered saline
PG protecting group
$Pd(PPh_3)_4$ tetrakis(triphenylphosphine)palladium
$PdCl_2(dppf)$ [1,1'-bis(diphenylphosphino)ferrocene]palladium dichloride
$PdCl_2(dppf\text{-}CH_2Cl_2$ [1,1'-bis(diphenylphosphino)ferrocene]palladium dichloride-dichloromethane adduct
$PdCl_2(PPh_3)_2$ bis(triphenylphosphine)palladium dichloride
ppm parts per million
rac racemic
RM reaction mixture
Rt retention time
RT room temperature
s singlet
sat. saturated
SFC supercritical fluid chromatography
t triplet
TBME tert-butyl methyl ether
TBTU O-(benzotriazol-1-yl)-N,N,N',N'-tetramethyluronium tetrafluoroborate
TEA triethylamine
TFA trifluoroaceticacid
THF tetrahydrofuran Analytical Methods
General Conditions:
NMR:
NMR spectra were recorded on Bruker AVANCE 400 MHz, 500 MHz or 600 MHz NMR spectrometers using ICON-NMR, under TopSpin program control. Spectra were measured at 298 K, unless indicated otherwise, and were referenced relative to known solvent resonances.
LC-MS:
Mass spectra were acquired on LC-MS, SFC-MS, or GC-MS systems using electrospray, chemical and electron impact ionization methods from a range of instruments of the following configurations: Waters Acquity UPLC/SQD system, using a photodiode array detector and a single quadrupole mass detector or Agilent 1200 systems with G 6110 series Mass Spectrometer. $[M+H]^+$ refers to the protonated molecular ion of the chemical species.

Method A:
Column: Waters Acquity HSS T3 1.8 μm 2.1×50 mm or 2.1×100 mm
Column temperature: 60° C.
Eluents: A: aq. formic acid (0.05%)+aq. ammonium acetate (3.75 mM) B: ACN containing formic acid (0.04%)
Flow rate: 1.0 ml/min
Gradient: 5% to 98% B in 1.4 min Method B:
Column: Waters Acquity HSS T3 1.8 μm 2.1×50 mm or 2.1×100 mm
Column temperature: 60° C.
Eluents: A: aq. formic acid (0.05%)+aq. ammonium acetate (3.75 mM) B: ACN containing formic acid (0.04%)
Flow rate: 0.8 ml/min
Gradient: 5% to 98% B in 9.4 min Method C:
Column: Waters Acquity HSS T3 1.8 μm 2.1×50 mm or 2.1×100 mm
Column temperature: 50° C.
Eluents: A: aq. formic acid (0.05%)+aq. ammonium acetate (3.75 mM) B: ACN containing formic acid (0.04%)
Flow rate: 1.2 ml/min
Gradient: 2% to 98% B in 1.4 min Method D:
Column: SunFire C18, 4.6×50 mm, 3.5 μm
Column temperature: 50° C.
Eluents: A: aq. TFA (0.01%) B: acetonitrile containing TFA (0.01%)
Flow rate: 2.0 ml/min
Gradient: 5% to 95% B in 1.4 min Method E:
Column: SunFire C18, 4.6×50 mm, 3.5 µm
Column temperature: 50° C.
Eluents: A: aq. TFA (0.01%) B: acetonitrile containing TFA (0.01%)
Flow rate: 2.0 ml/min
Gradient: 5% to 95% B in 1.2 min, 95% B for 1.3 min
Method F:
Column: Phenomenex, 3.0×30 mm, 5 µm
Column temperature; 50° C.
Eluents: A: aq. ammonium hydrogen carbonate (10 mM) B: acetonitrile
Flow rate: 1.5 ml/min
Gradient: 5% to 95% B in 1.5 min, 95% B for 0.7 min
Method G:
Column: XBridge C18, 4.6×50 mm, 3.5 µm
Column temperature: 40° C.
Eluents: A: aq. ammonium hydrogen carbonate (10 mM) B: acetonitrile
Flow rate: 2.0 ml/min
Gradient: 5% to 95% B in 1.5 min
Method H:
Column: XBridge C18, 4.6×50 mm, 3.5 µm
Column temperature: 50° C.
Eluents: A: aq. ammonium hydrogen carbonate (10 mM) B: acetonitrile
Flow rate: 1.8 ml/min
Gradient: 5% to 95% B in 1.5 min, 95% B for 1.5 min
Method I:
Column: SunFire C18, 3×30 mm, 2.5 µm
Column temperature: 50° C.
Eluents: A: aq. TFA (0.01%) B: acetonitrile containing TFA (0.01%)
Flow rate: 1.5 ml/min
Gradient: 5% to 95% B in 1.5 min
Method J:
Column: XBridge C18, 4.6×50 mm, 3.5 µm
Column temperature: 40° C.
Eluents: A: aq. ammonium hydrogen carbonate (10 mM) B: acetonitrile
Flow rate: 1.8 ml/min
Gradient: 5% to 95% B in 1.4 min, 95% B for 1.6 min
Chiral Analytical HPLC Methods:
Method K:
Instrument: Agilent 1200 system
Column: Chiralpak ID Sum 4.6×250 mm
Column temperature: RT
Eluents: Hept:DCM:MeOH (40:35:25)+DEA (0.1%)
Flow rate: 1.0 mL/min
Gradient: isocratic
Detection: UV at 254 nm
Preparative Chromatography Methods
Normal and reverse phase flash chromatography purifications have been performed on a CombiFlash Rf200 or Rf+ system. Alternatively, chromatography purifications on reverse phase have been performed on an Interchim Puriflash 4250 system or a Biotage system. Supercritical fluid chromatography (SFC) separations have been performed using a Waters preparative SFC-100-MS system with either a Waters 2998 photodiode array detector or a Waters MS single quadrupole detection using MeOH as modifier. Generally, the back pressure was 120 bar, the flow 100 g $CO_2$/min and the column temperature 40° C. Reverse phase HPLC purifications have been performed on a Waters HPLC preparative system with either a Waters 2998 photodiode array detector or a Waters MS single quadrupole detection.

Achiral Preparative HPLC Methods:
Method L:
Instrument: Gilson GX-281
Column: SunFire C18
Column temperature: RT
Mobile phase: ACN in water containing TFA (0.1%)
Flow: 40 ml/min
Detection: UV @ 254 nm
Chiral Preparative Chromatography Methods:
Method M:
Instrument: Gilson Trilution I HPLC System
Column: ChiralPak ID, 5 µM, 250×20 mm
Column temperature: RT
Mobile phase: heptane/DCM/MeOH (40:35:25) containing DEA (0.05%)
Flow: 10 ml/min
Detection: UV @ 254 nm
Materials Used for Solid Phase Extraction:
The following solid phase extraction (SPE) cartridges were used according to manufacturers notice to generate the corresponding free base from different salts:
PL-HCO3 MP SPE cartridges were purchased from Agilent StratosPhere—Ref: PL-HCO3 MP-resin, 1.8 mmol/g, 100 A, 150-300 µm, 500 mg, 6 ml.
SCX cartridges were purchased from Agilent—Ref.: HF Mega DE-SCX, 2 g, 12 ml.

Synthesis of Intermediates

Intermediate 1

4-(4-Chloro-7H-pyrrolo[2,3-d]pyrimidin-6-yl)benzaldehyde

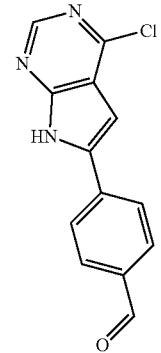 [SMILES: O=Cc1ccc(-c2cc3c(Cl)ncnc3[nH]2)cc1]

Step 1: (4-(4-chloro-7H-pyrrolo[2,3-d]pyrimidin-6-yl)phenyl)methanol

To a suspension of ethyl 4-(4-chloro-7H-pyrrolo[2,3-d]pyrimidin-6-yl)benzoate (which may be prepared according to the procedure described in published U.S. Pat. No. 6,140,332, column 45, example 30) (10.2 g, 33.8 mmol) in THF (100 ml) under argon was slowly added a solution of lithium aluminum hydride (1 M) in THF (50.7 ml, 50.7 mmol) between 0 and 5° C. During the addition the RM was diluted with THF (5 ml). After the addition, the RM was stirred at 0° C. for 10 min and was then allowed to warm to RT. After stirring 3 h at RT, the RM was quenched at 0° C. using a mixture of water and an aq. solution of NaOH (15%). The mixture was filtered through Hyflo®, the solids were washed with THF and the combined filtrates were concentrated to afford the title compound (9.32 g).

Method A: Rt=0.78 min; [M+H]⁺=260.1.

Step 2: 4-(4-chloro-7H-pyrrolo[2,3-d]pyrimidin-6-yl)benzaldehyde

A suspension of (4-(4-chloro-7H-pyrrolo[2,3-d]pyrimidin-6-yl)phenyl)methanol (9.32 g, 32.7 mmol) and manganese dioxide (28.4 g, 327 mmol) in THF (250 ml) was stirred at RT overnight. Additional manganese dioxide (8.52 g, 98 mmol) was added to the RM and stirring was continued at RT for another night. The RM was filtered through Hyflo® and the solids were washed with THF. The combined filtrates were concentrated, rediluted with THF, filtered through Hyflo® again and concentrated to afford the title compound as a solid (5.68 g).

Method A: Rt=0.88 min; [M+H]⁺=258.1.

Intermediate 2

2-Fluoro-N-(5-fluoro-2-methyl-3-(4,4,5,5-tetramethyl-1,3,2-dioxaborolan-2-yl)phenyl)-4-(2-hydroxypropan-2-yl)benzamide

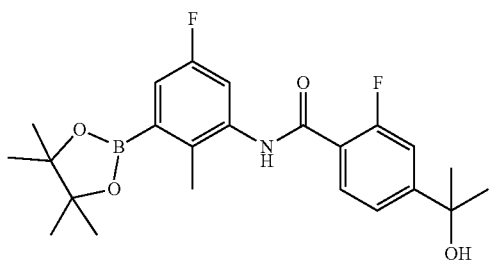 [SMILES: Cc1c(NC(=O)c2ccc(C(C)(C)O)cc2F)cc(F)cc1B1OC(C)(C)C(C)(C)O1]

A mixture of 2-fluoro-4-(2-hydroxypropan-2-yl)benzoic acid (6.35 g, 32.0 mmol), HATU (17.06 g, 44.9 mmol) and DIPEA (16.79 ml, 96 mmol) in DMF (100 ml) was stirred at RT for 30 min. Then, 5-fluoro-2-methyl-3-(4,4,5,5-tetramethyl-1,3,2-dioxaborolan-2-yl)aniline (can be prepared according to the procedure described in published patent application WO2013/008095 A1, page 37, intermediate 5) (8.47 g, 32.0 mmol) was added and the RM was stirred at 50° C. overnight. The RM was diluted with EtOAc and the organic phase was washed with a sat. aq. solution of NaHCO₃ and brine. The combined aqueous phases were extracted again with EtOAc and the combined organic phases were dried over Na₂SO₄, filtered, concentrated and purified by chromatography on silica gel eluting with MeOH in DCM (from 0 to 10%). The resulting solid was triturated with Et₂O, filtered, the solids were washed with diisopropylether and dried to afford the title compound as a solid (9.28 g).

Method A: Rt=1.28 min, [M+H]⁺=432.3.

Note: An alternative preparation of intermediate 2 is described in WO2013/008095 A1, page 81, intermediate 35.

Intermediate 3

2-Fluoro-N-(5-fluoro-3-(6-(4-formylphenyl)-7H-pyrrolo[2,3-d]pyrimidin-4-yl)-2-methylphenyl)-4-(2-hydroxypropan-2-yl)benzamide

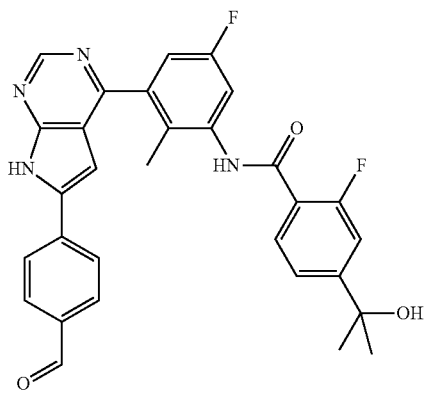 [SMILES: Cc1c(NC(=O)c2ccc(C(C)(C)O)cc2F)cc(F)cc1-c1ncnc2[nH]c(-c3ccc(C=O)cc3)cc12]

A suspension of 4-(4-chloro-7H-pyrrolo[2,3-d]pyrimidin-6-yl)benzaldehyde (intermediate 1, 150 mg, 0.553 mmol), 2-fluoro-N-(5-fluoro-2-methyl-3-(4,4,5,5-tetramethyl-1,3,2-dioxaborolan-2-yl)phenyl)-4-(2-hydroxypropan-2-yl)benzamide (intermediate 2, 328 mg, 0.608 mmol), an aq. solution of Na₂CO₃ (2 M) (0.553 ml, 1.106 mmol) and PdCl₂(PPh₃)₂ (19.41 mg, 0.028 mmol) in 1-propanol (4 ml) was heated at 140° C. using microwave irradiation for 15 min. The suspension was filtered and the solids were washed with 1-propanol, water and 1-propanol. The remaining solid was dried to afford the title compound as a solid (178 mg).

Method A: Rt=0.99 min; [M+H]⁺=527.2.

Intermediate 4 rac-2-Fluoro-N-(5-fluoro-3-(6-(4-((7-(hydroxymethyl)-3,9-diazaspiro[5.5]undecan-3-yl)methyl)phenyl)-7H-pyrrolo[2,3-d]pyrimidin-4-yl)-2-methylphenyl)-4-(2-hydroxypropan-2-yl)benzamide

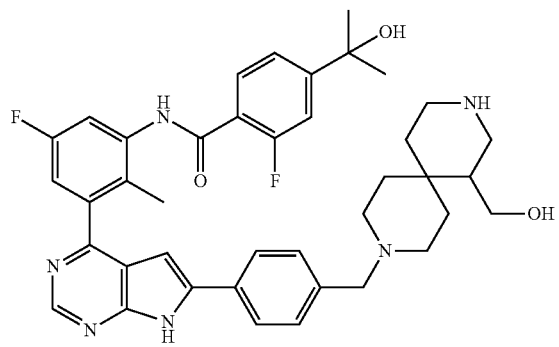 [SMILES: Cc1c(NC(=O)c2ccc(C(C)(C)O)cc2F)cc(F)cc1-c1ncnc2[nH]c(-c3ccc(CN4CCC5(CCNCC5CO)CC4)cc3)cc12]

Step 1: rac-tert-butyl 9-(4-(4-(5-fluoro-3-(2-fluoro-4-(2-hydroxypropan-2-yl)benzamido)-2-methylphenyl)-7H-pyrrolo[2,3-d]pyrimidin-6-yl)benzyl)-1-(hydroxymethyl)-3,9-diazaspiro[5.5]undecane-3-carboxylate To a mixture of 2-fluoro-N-(5-fluoro-3-(6-(4-formylphenyl)-7H-pyrrolo[2,3-d]pyrimidin-4-yl)-2-methylphenyl)-4-

(2-hydroxypropan-2-yl)benzamide (intermediate 3, 300 mg, 0.570 mmol), rac-tert-butyl 1-(hydroxymethyl)-3,9-diazaspiro[5.5]undecane-3-carboxylate (219 mg, 0.684 mmol) and TEA (0.119 ml, 0.855 mmol) in THF (3 ml) was added a solution of ZnCl$_2$ (0.5 M) in THF (1.197 ml, 0.598 mmol). The resulting RM was stirred under argon at RT for 3 h, then solid NaBH$_3$CN (71.6 mg, 1.140 mmol) was added. The RM was stirred at RT overnight, then diluted with DCM and washed with water and brine. The organic phase was dried over MgSO$_4$, concentrated and purified by chromatography on silica gel eluting with MeOH in DCM (from 0 to 20%) to afford the title compound as a solid (273 mg).

Method A: Rt=0.87 min; [M+H]$^+$=795.6.

Step 2: rac-2-fluoro-N-(5-fluoro-3-(6-(4-((7-(hydroxymethyl)-3,9-diazaspiro[5.5]undecan-3-yl)methyl)phenyl)-7H-pyrrolo[2,3-d]pyrimidin-4-yl)-2-methylphenyl)-4-(2-hydroxypropan-2-yl)benzamide A solution of rac-tert-butyl 9-(4-(4-(5-fluoro-3-(2-fluoro-4-(2-hydroxypropan-2-yl)benzamido)-2-methylphenyl)-7H-pyrrolo[2,3-d]pyrimidin-6-yl)benzyl)-1-(hydroxymethyl)-3,9-diazaspiro[5.5]undecane-3-carboxylate (273 mg, 0.343 mmol) and TFA (0.794 ml, 10.30 mmol) in DCM (3 ml) was stirred at RT for 2 h, concentrated and dried to afford the title compound as a solid TFA salt (288 mg).

Method A: Rt=0.63 min; [M+H]$^+$=695.5.

Intermediate 5

3-(2,4-Dioxotetrahydropyrimidin-1(2H)-yl)-4-methoxybenzoic Acid

3-Amino-4-methoxybenzoic acid (5.0 g, 29.3 mmol) was suspended in acrylic acid (8.05 ml, 117 mmol) and the resulting suspension was stirred at 100° C. for 3 h and the RM was allowed to cool to RT. AcOH (33 ml) was added and the stirred suspension was heated at 100° C. for 10 min., then urea (11.00 g, 183 mmol) was added and the RM was stirred at 120° C. overnight. The solution was added into an ice cold mixture of water and concentrated aqueous HCl (37%). After stirring, the resulting suspension was stored overnight in the fridge at 5° C., then filtered and the solids were washed with water and dried to afford a solid. The solid was triturated in an aq. solution of HCl (0.05 M), filtered and the solids were washed with TBME and dried at 40° C. under reduced pressure to afford the title compound as a solid (6.29 g).

Method A: Rt=0.48 min; [M+H]$^+$=265.2.

Intermediate 6

N-(3-(6-(4-(3,9-Diazaspiro[5.5]undecan-3-ylmethyl)phenyl)-7H-pyrrolo[2,3-d]pyrimidin-4-yl)-5-fluoro-2-methylphenyl)-2-fluoro-4-(2-hydroxypropan-2-yl)benzamide

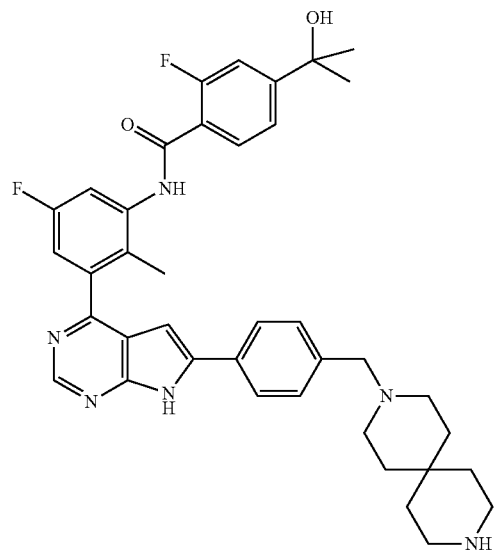 [SMILES: Cc1c(NC(=O)c2ccc(C(C)(C)O)cc2F)cc(F)cc1-c1ncnc2[nH]c(-c3ccc(CN4CCC5(CCNCC5)CC4)cc3)cc12]

Step 1: tert-butyl 9-(4-(4-(5-fluoro-3-(2-fluoro-4-(2-hydroxypropan-2-yl)benzamido)-2-methylphenyl)-7H-pyrrolo[2,3-d]pyrimidin-6-yl)benzyl)-3,9-diazaspiro[5.5]undecane-3-carboxylate A mixture of 2-fluoro-N-(5-fluoro-3-(6-(4-formylphenyl)-7H-pyrrolo[2,3-d]pyrimidin-4-yl)-2-methylphenyl)-4-(2-hydroxypropan-2-yl)benzamide (intermediate 3, 510 mg, 0.969 mmol), tert-butyl 3,9-diazaspiro[5.5]undecane-3-carboxylate (271 mg, 1.065 mmol), TEA (0.135 ml, 0.969 mmol) and a solution of ZnCl$_2$ (0.5 M) in THF (2.325 ml, 1.162 mmol) was stirred in MeOH (10 ml) at RT for 6 h. Solid NaBH$_3$CN (67.0 mg, 1.065 mmol) was added and the RM was stirred at RT overnight. The RM was diluted with EtOAc and the organic phase was washed with a sat. aq. solution of NaHCO$_3$ and brine, dried over Na$_2$SO$_4$, concentrated and purified by chromatography on silica gel eluting with MeOH in DCM (from 0 to 50%) to afford the title compound as a solid (550 mg).

Method A: Rt=4.60 min; [M+H]$^+$=765.4.

Step 2: N-(3-(6-(4-(3,9-diazaspiro[5.5]undecan-3-ylmethyl)phenyl)-7H-pyrrolo[2,3-d]pyrimidin-4-yl)-5-fluoro-2-methylphenyl)-2-fluoro-4-(2-hydroxypropan-2-yl)benzamide To a solution of tert-butyl 9-(4-(4-(5-fluoro-3-(2-fluoro-4-(2-hydroxypropan-2-yl)benzamido)-2-methylphenyl)-7H-pyrrolo[2,3-d]pyrimidin-6-yl)benzyl)-3,9-diazaspiro[5.5]undecane-3-carboxylate (0.55 g, 0.683 mmol) in DCM (40 ml) was added TFA (1.053 ml, 13.66 mmol) at RT. The resulting RM was stirred at RT overnight, evaporated, redissolved in a mixture of ACN and water, and freeze-dried yielding the title compound as a solid TFA salt (0.76 g).

Method B: Rt=2.84 min; [M+H]$^+$=665.6.

Intermediate 7

4-Chloro-6-iodo-7-(phenylsulfonyl)-7H-pyrrolo[2,3-d]pyrimidine

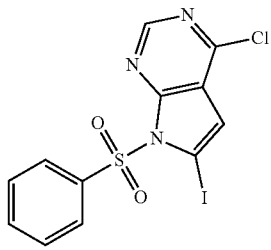 [SMILES: O=S(=O)(c1ccccc1)n1c(I)cc2c(Cl)ncnc21]

Step 1: 4-chloro-7-(phenylsulfonyl)-7H-pyrrolo[2,3-d]pyrimidine

In a flame-dried flask placed under argon, NaH (60%) in mineral oil (1.563 g, 39.1 mmol) was suspended in DMF (60 ml) and the mixture was cooled to 0° C. A solution of 4-chloro-7H-pyrrolo[2,3-d]pyrimidine (4 g, 26.0 mmol) in DMF (20 ml) was slowly added over 10 min. and the RM was stirred for 10 min. until hydrogen evolution ceased. Benzenesulfonyl chloride (3.36 ml, 26.0 mmol) was added and the RM was stirred for 1 h at RT. Water was added and the resulting precipitate was filtered and the solids were dried to afford the title compound as a solid (7.418 g).
Method C: Rt=1.01 min; [M+H]$^+$=294.1.

Step 2: 4-chloro-6-iodo-7-(phenylsulfonyl)-7H-pyrrolo[2,3-d]pyrimidine

To a stirred solution of 4-chloro-7-(phenylsulfonyl)-7H-pyrrolo[2,3-d]pyrimidine in dry THE (80 ml) under argon atmosphere at −78° C., was added a solution of lithium diisopropylamide mono-tetrahydrofuran (1.5 M) in CHX (5.22 ml, 7.83 mmol) over 15 min. After 1 h, a solution of iodine (1.987 g, 7.83 mmol) in THE (20 ml) was added dropwise over 15 min at −78° C. The resulting solution was stirred for 3 h at −78° C. Water (2 ml) was added and the mixture was allowed to warm to RT. The mixture was diluted with DCM, the organic phase was washed with brine, dried over Na$_2$SO$_4$ and evaporated to dryness. The resulting solid was triturated with ACN, filtered and dried to afford the title compound as a solid (1.513 g).
Method C: Rt=1.12 min; [M+H]$^+$=419.9.

Intermediate 8

3-(2,4-Dioxotetrahydropyrimidin-1(2H)-yl)-4-methylbenzoic Acid

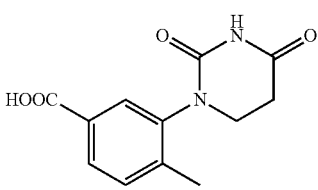 [SMILES: Cc1ccc(C(=O)O)cc1N1CCC(=O)NC1=O]

Step 1: 3-((2-carboxyethyl)amino)-4-methylbenzoic Acid

A suspension of 3-amino-4-methylbenzoic acid (15.12 g, 100 mmol) in toluene (25 ml) was heated to reflux. Acrylic acid (27.5 ml, 400 mmol) and toluene (10 ml) was added, the mixture started to become a homogeneous solution and the RM was stirred at 100° C. for 3 h and was then allowed to cooled to RT. The separating solid was collected by filtration, the solids were washed with toluene and dried to afford the title compound as a solid (17.87 g).
Method A: Rt=0.61 min; [M+H]$^+$=224.1.

Step 2: 3-(2,4-dioxotetrahydropyrimidin-1(2H)-yl)-4-methylbenzoic Acid

A suspension of 3-((2-carboxyethyl)amino)-4-methylbenzoic acid (893 mg, 4 mmol) and urea (601 mg, 10 mmol) in AcOH (12 ml) was stirred at 120° C. overnight. The RM was cooled to RT, poured onto crushed ice and the resulting mixture was acidified with an aq. solution of HCl (1 M) to pH 0. The solids were collected by filtration, washed with cold water, and dried to afford the title compound as a solid (661 mg).
Method A: Rt=0.51 min; [M+H]$^+$=249.1.

Intermediate 9

3-(2,4-Dioxotetrahydropyrimidin-1(2H)-yl)-4-fluorobenzoic Acid

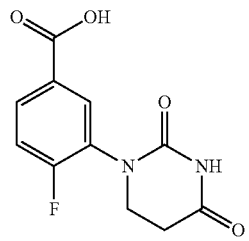 [SMILES: O=C1CCN(c2cc(C(=O)O)ccc2F)C(=O)N1]

Step 1: 3-(2-carboxyethylamino)-4-fluorobenzoic Acid

To a mixture of 3-amino-4-fluorobenzoic acid (9.3 g, 60 mmol) and acrylic acid (13.0 g, 180 mmol) at 25° C. were added AcOH (40 ml) and concentrated H$_2$SO$_4$ (0.5 ml). The mixture was stirred at 100° C. for 5.5 h. The crude mixture containing the title compound (13.6 g) was directly used for the next step without further purification.
Method D: Rt=1.298 min; [M+H]$^+$=228.

Step 2: 3-(2,4-dioxotetrahydropyrimidin-1(2H)-yl)-4-fluorobenzoic Acid

AcOH (60 ml) and urea (18.0 g, 300.0 mmol) were added to the crude mixture of 3-(2-carboxyethylamino)-4-fluorobenzoic acid (13.6 g, 60.0 mmol) and the resulting RM was stirred at 120° C. for 26 h and evaporated. Ice and water were added, followed by a concentrated aq. solution of HCl (37%). The resulting mixture was filtered, the filtrate was saturated with solid NaCl and placed at 15° C. for 20 h. The precipitate was collected and dried, yielding a first crop (5 g). The filtrate was evaporated, the residue was diluted with H₂O and the resulting mixture was placed at 15° C. for 20 h. The precipitate was filtered and dried yielding a second crop (4 g). To the combined crops (9 g) was added AcOH and the mixture was sonicated for 10 min. TBME was added, the TBME phase was decanted and this was repeated one more time. The residue was evaporated, AcOH and TBME were added and the mixture was sonicated. Additional TBME was added, the TBME phase was decanted and this was repeated one more time. TBME was added, the mixture was placed at 15° C. for 20 h and the TBME phase was decanted. The mixture was evaporated to dryness, an aq. solution of HCl (0.001 M) was added, the mixture was filtered and the solids were washed with an aq. solution of HCl (0.001 M), ACN and dried to afford the title compound as a solid (4.0 g).

Method D: Rt=1.164 min; [M+H]⁺=253.1.

¹H NMR (500 MHz, DMSO-d₆) δ 13.16 (br s, 1H), 10.54 (s, 1H), 8.02 (dd, J=7.4, 2.0 Hz, 1H), 7.93 (ddd, J=8.3, 4.7, 2.1 Hz, 1H), 7.44 (dd, J=9.8, 8.9 Hz, 1H), 3.77 (t, J=6.6 Hz, 2H), 2.74 (t, J=6.6 Hz, 2H).

Intermediate 10

Tert-butyl 4-(piperidin-4-yloxy)piperidine-1-carboxylate

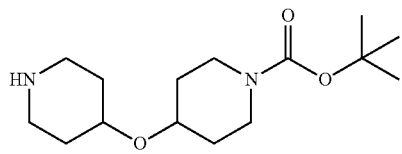 [SMILES: CC(C)(C)OC(=O)N1CCC(OC2CCNCC2)CC1]

Step 1: tert-butyl 4-(pyridin-4-yloxy)piperidine-1-carboxylate

To a 500 ml round bottom flask were added pyridin-4-ol (5 g, 52.6 mmol), THF (200 ml), tert-butyl 4-hydroxypiperidine-1-carboxylate (13.3 g, 65.8 mmol), and triphenylphosphine (18 g, 68.4 mmol). DEAD (12 g, 68.4 mmol) was added dropwise at RT and after the addition the RM was stirred at RT for 3 h. The RM was concentrated and purified by chromatography on silica gel eluting with methanol in DCM (1:30) yielding the title compound as a solid (10 g).

Method E: Rt=1.35 min; MS m/z [M+H]⁺ 279.

Step 2: tert-butyl 4-(piperidin-4-yloxy)piperidine-1-carboxylate

To a 500 ml round bottom flask, purged and maintained under inert atmosphere, were added tert-butyl 4-(pyridin-4-yloxy)piperidine-1-carboxylate (2 g, 7.2 mmol), EtOH (100 ml), AcOH (5 ml) and Pd/C (10%) (0.4 g). The RM was stirred at 80° C. for 16 h under an atmosphere of hydrogen (4 MPa). The mixture was filtered through Celite®, the filtrate was concentrated and purified by chromatography on silica gel eluting with MeOH in DCM (1:10) yielding the title compound as an oil (0.5 g).

Method D: Rt=1.32 min; MS m/z [M+H]⁺ 285.3.

Intermediate 11

N-(3-(6-(4-(3,9-Diazaspiro[5.5]undecan-3-ylmethyl) phenyl)-7H-pyrrolo[2,3-d]pyrimidin-4-yl)-5-fluoro-2-methylphenyl)-2-fluoro-4-(2-hydroxypropan-2-yl) benzamide

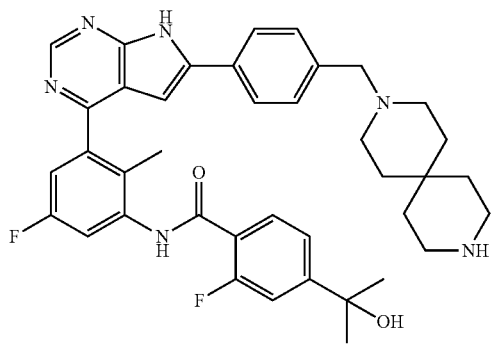 [SMILES: Cc1c(NC(=O)c2ccc(C(C)(C)O)cc2F)cc(F)cc1-c1ncnc2[nH]c(-c3ccc(CN4CCC5(CCNCC5)CC4)cc3)cc12]

Step 1: tert-butyl 9-(4-(4-(5-fluoro-3-(2-fluoro-4-(2-hydroxypropan-2-yl)benzamido)-2-methylphenyl)-7H-pyrrolo[2,3-d]pyrimidin-6-yl)benzyl)-3,9-diazaspiro[5.5]undecane-3-carboxylate To a 25 ml round bottom flask was added tert-butyl 3,9-diazaspiro[5.5]undecane-3-carboxylate (118 mg, 0.450 mmol), TEA (0.100 ml, 0.717 mmol), 2-fluoro-N-(5-fluoro-3-(6-(4-formylphenyl)-7H-pyrrolo[2,3-d]pyrimidin-4-yl)-2-methylphenyl)-4-(2-hydroxypropan-2-yl)benzamide (intermediate 3, 220 mg, 0.409 mmol) and MeOH (4 ml). A solution of ZnCl₂ (0.5M) in THF (1 ml, 0.500 mmol) was added and the resulting RM was stirred at RT overnight. Solid NaBH₃CN (30 mg, 0.477 mmol) was added and the RM was stirred at RT for 5 h, evaporated and the residue was purified by chromatography on silica gel eluting with MeOH in DCM (from 0 to 50%) to afford the title compound as a solid (354 mg).

Method A: Rt=0.96 min; [M+H]⁺=765.4.

Step 2: N-(3-(6-(4-(3,9-diazaspiro[5.5]undecan-3-ylmethyl)phenyl)-7H-pyrrolo[2,3-d]pyrimidin-4-yl)-5-fluoro-2-methylphenyl)-2-fluoro-4-(2-hydroxypropan-2-yl)benzamide To a solution of tert-butyl 9-(4-(4-(5-fluoro-3-(2-fluoro-4-(2-hydroxypropan-2-yl)benzamido)-2-methylphenyl)-7H-pyrrolo[2,3-d]pyrimidin-6-yl)benzyl)-3,9-diazaspiro[5.5] undecane-3-carboxylate (354 mg, 0.407 mmol) in MeOH (2 ml) was added a solution of HCl (4 M) in 1,4-dioxane (2 ml, 8.00 mmol) and the RM was stirred at RT for 1 h. The RM was concentrated, co-evaporated with DCM and dried to give the title compound as a solid HCl salt (340 mg).

Method A: Rt=0.65 min; [M+H]⁺=665.5.

Intermediate 12

2-(4-(4-Chloro-7H-pyrrolo[2,3-d]pyrimidin-6-yl)phenyl)ethanol

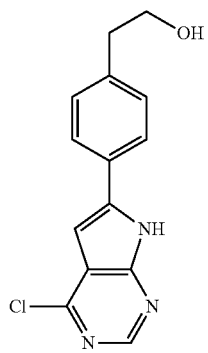 [SMILES: OCCc1ccc(-c2cc3c(Cl)ncnc3[nH]2)cc1]

A 100 ml round bottom flask containing a mixture of 4-chloro-6-iodo-7H-pyrrolo[2,3-d]pyrimidine (1.2 g, 4.29 mmol), 4-(2-hydroxyethyl)phenylboronic acid (750 mg, 4.29 mmol), an aq. solution of $Na_2CO_3$ (2.0 M) (4.72 ml, 9.45 mmol), $PdCl_2(PPh_3)_2$ (154 mg, 0.215 mmol) and 1-propanol (36 ml) was purged with $N_2$ at RT and then stirred at 105° C. overnight. The mixture was concentrated to dryness and purified by chromatography on silica gel eluting with EtOAc in CHX (from 40 to 100%) to give the title compound as a solid (762 mg).

Method A: Rt=0.82 min; $[M+H]^+$=274.0.

Intermediate 13

4-(4-(5-Fluoro-3-(2-fluoro-4-(2-hydroxypropan-2-yl)benzamido)-2-methylphenyl)-7H-pyrrolo[2,3-d]pyrimidin-6-yl)phenethyl methanesulfonate

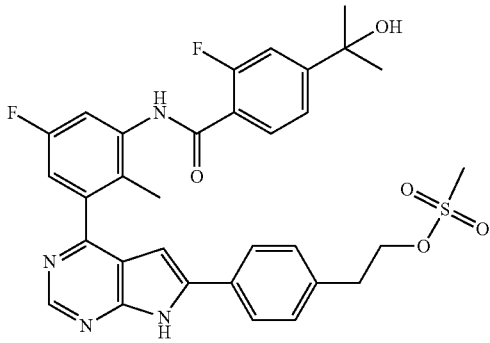 [SMILES: Cc1c(NC(=O)c2ccc(C(C)(C)O)cc2F)cc(F)cc1-c1ncnc2[nH]c(-c3ccc(CCOS(C)(=O)=O)cc3)cc12]

Step 1: 2-fluoro-N-(5-fluoro-3-(6-(4-(2-hydroxyethyl)phenyl)-7H-pyrrolo[2,3-d]pyrimidin-4-yl)-2-methylphenyl)-4-(2-hydroxypropan-2-yl)benzamide At RT, 2-(4-(4-chloro-7H-pyrrolo[2,3-d]pyrimidin-6-yl)phenyl)ethanol (intermediate 12, 888 mg, 2.60 mmol) and 2-fluoro-N-(5-fluoro-2-methyl-3-(4,4,5,5-tetramethyl-1,3,2-dioxaborolan-2-yl)phenyl)-4-(2-hydroxypropan-2-yl)benzamide (intermediate 2, 1567 mg, 3.63 mmol) were suspended in a mixture of 1-propanol (12 ml) and an aqueous solution of $Na_2CO_3$ (2.0 M) (2.60 ml, 5.19 mmol). Argon was passed through the RM for 2 min and $PdCl_2(PPh_3)_2$ (91 mg, 0.130 mmol) was added. The mixture was heated at 140° C. for 20 min. using microwave radiation. The RM was diluted with EtOAc, water and brine, the phases were separated and the organic phase was dried over $MgSO_4$ and adsorbed and dried on Isolute® HM-N. Purification by chromatography on silica gel eluting with MeOH in DCM (from 0 to 20%) afforded the title compound as a solid (863 mg).

Method A: Rt=0.92 min; $[M+H]^+$=543.3.

Step 2: 4-(4-(5-fluoro-3-(2-fluoro-4-(2-hydroxypropan-2-yl)benzamido)-2-methylphenyl)-7H-pyrrolo[2,3-d]pyrimidin-6-yl)phenethyl methanesulfonate At RT and under argon, 2-fluoro-N-(5-fluoro-3-(6-(4-(2-hydroxyethyl)phenyl)-7H-pyrrolo[2,3-d]pyrimidin-4-yl)-2-methylphenyl)-4-(2-hydroxypropan-2-yl)benzamide (89 mg, 0.164 mmol) was dissolved in dry THF (2 ml) and TEA (0.114 ml, 0.820 mmol) and the mixture was cooled to 0° C. $Ms_2O$ (57.1 mg, 0.328 mmol) was added and the RM was stirred at 0° C. for 30 min., quenched with ice water, DCM was added and the phases were separated. The aqueous phase was extracted with DCM and the combined organic phases were dried over $MgSO_4$. Evaporation afforded the title compound as a solid (94 mg).

Method A: Rt=1.01 min; $[M+H]^+$=621.2.

Intermediate 14

Tert-butyl 4-((4-(4-chloro-7H-pyrrolo[2,3-d]pyrimidin-6-yl)benzyl)oxy)piperidine-1-carboxylate

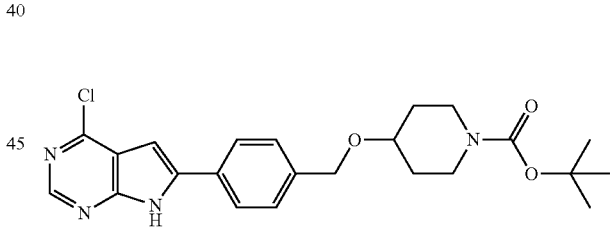

To a suspension of 4-chloro-6-iodo-7H-pyrrolo[2,3-d]pyrimidine (848 mg, 3.03 mmol) and (4-(((1-(tert-butoxycarbonyl)piperidin-4-yl)oxy)methyl)phenyl)boronic acid (1.068 g, 3.19 mmol) in 1-propanol (20 ml) under argon was added $PdCl_2(PPh_3)_2$ (106 mg, 0.152 mmol), followed by an aqueous solution of $Na_2CO_3$ (2.0 M) (3.03 ml, 6.07 mmol). The RM was stirred at 100° C. overnight and was then diluted with EtOAc. The organic phase was separated, washed with water and brine and dried over $MgSO_4$. After evaporation the residue was purified by chromatography on silica gel eluting with EtOAc in CHX (from 0 to 100%) to afford the title compound (844 mg).

Method A: Rt=1.29 min; $[M+H]^+$=443.3.

Intermediate 15

4-Chloro-6-iodo-7-((2-(trimethylsilyl)ethoxy)methyl)-7H-pyrrolo[2,3-d]pyrimidine

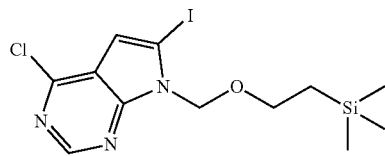 [SMILES: C[Si](C)(C)CCOCn1c(I)cc2c(Cl)ncnc21]

To a solution of 4-chloro-6-iodo-7H-pyrrolo[2,3-d]pyrimidine (10 g, 35.8 mmol) in DMF (120 ml) at 0° C. was added portionwise NaH (60%) in mineral oil (1.7 g, 42.5 mmol) under argon. The resulting suspension was stirred at 0° C. for 30 min., 2-(trimethylsilyl)ethoxymethyl chloride (7.5 ml, 42.3 mmol) was added and the RM was allowed to warm to RT for over 1 h. The RM was then poured carefully into ice water and extracted with $Et_2O$. The combined organic phases were washed with brine and evaporated. The residue was diluted with ACN and the resulting mixture was filtered to give of the title compound as a solid (8.052 g). The filtrate was concentrated, triturated in cold MeOH and filtered to give a second crop of the title compound as a solid (3.120 g).

Method A: Rt=1.48 min; [M+H]$^+$=410.1.

Intermediate 16

2-Fluoro-N-(5-fluoro-2-methyl-3-(6-(4-(piperidin-4-yloxy)phenyl)-7H-pyrrolo[2,3-d]pyrimidin-4-yl)phenyl)-4-(2-hydroxypropan-2-yl)benzamide

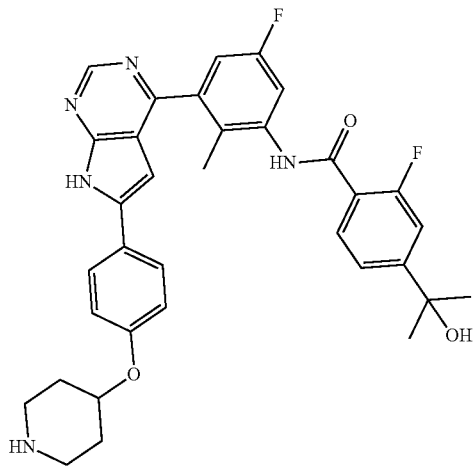 [SMILES: Cc1c(NC(=O)c2ccc(C(C)(C)O)cc2F)cc(F)cc1-c1ncnc2[nH]c(-c3ccc(OC4CCNCC4)cc3)cc12]

Step 1: 4-(4-chloro-7-((2-(trimethylsilyl)ethoxy)methyl)-7H-pyrrolo[2,3-d]pyrimidin-6-yl)phenol A solution of 4-chloro-6-iodo-7-((2-(trimethylsilyl)ethoxy)methyl)-7H-pyrrolo[2,3-d]pyrimidine (intermediate 15, 1333 mg, 3.254 mmol), $Cs_2CO_3$ (2.651 g, 11.33 mmol) and 4-hydroxyphenylboronic acid (840 mg, 2.67 mmol) in a mixture of 1,4-dioxane (15 ml) and water (15 ml) was degassed with argon. $PdCl_2$(dppf-$CH_2Cl_2$ adduct (266 mg, 0.325 mmol) was added and the RM was stirred at 100° C. for 1.5 h. The RM was filtered over Hyflo® and the solids were washed with MeOH. The combined filtrates were concentrated and partitioned between EtOAc and water. The phases were separated, the organic phase was washed with brine, dried over $MgSO_4$ and evaporated to afford the title compound as a solid (575 mg).

Method A: Rt=1.30 min; [M+H]$^+$=376.

Step 2: 2-fluoro-N-(5-fluoro-3-(6-(4-hydroxyphenyl)-7-((2-(trimethylsilyl)ethoxy)methyl)-7H-pyrrolo[2,3-d]pyrimidin-4-yl)-2-methylphenyl)-4-(2-hydroxypropan-2-yl)benzamide A solution of 4-(4-chloro-7-((2-(trimethylsilyl)ethoxy)methyl)-7H-pyrrolo[2,3-d]pyrimidin-6-yl)phenol (1635 mg, 2.044 mmol), $K_2CO_3$ (1119 mg, 8.1 mmol), and 2-fluoro-N-(5-fluoro-2-methyl-3-(4,4,5,5-tetramethyl-1,3,2-dioxaborolan-2-yl)phenyl)-4-(2-hydroxypropan-2-yl)benzamide (intermediate 2, 1811 mg, 4.2 mmol) in a mixture of 1,4-dioxane (10 ml) and water (10 ml) was degassed with argon. $PdCl_2$(dpp) (238 mg, 0.325 mmol) was added and the RM was stirred at 100° C. for 1.5 h. The RM was filtered over Hyflo® and the solids were washed with MeOH. The combined filtrates were concentrated and partitioned between EtOAc and water. The phases were separated, the organic phase was washed with brine, dried over $MgSO_4$, evaporated and purified by chromatography on silica gel eluting with MeOH in DCM (from 0 to 7.5%) yielding the title compound as a solid (1.214 g).

Method A: Rt=1.35 min; [M+H]+=645.3.

Step 3: tert-butyl 4-(4-(4-(5-fluoro-3-(2-fluoro-4-(2-hydroxypropan-2-yl)benzamido)-2-methylphenyl)-7-((2-(trimethylsilyl)ethoxy)methyl)-7H-pyrrolo[2,3-d]pyrimidin-6-yl)phenoxy)piperidine-1-carboxylate To a solution of 2-fluoro-N-(5-fluoro-3-(6-(4-hydroxyphenyl)-7-((2-(trimethylsilyl)ethoxy)methyl)-7H-pyrrolo[2,3-d]pyrimidin-4-yl)-2-methylphenyl)-4-(2-hydroxypropan-2-yl)benzamide (749 mg, 0.999 mmol), 1-Boc-4-hydroxypiperidine (221 mg, 1.099 mmol) and triphenylphosphine (365 mg, 1.392 mmol) in THF (10 ml) was added drop by drop a solution of DEAD (40%) in toluene (0.550 ml, 1.390 mmol) under argon at RT. The resulting RM was stirred at RT overnight. Additional 1-Boc-4-hydroxypiperidine (79 mg, 0.393 mmol) was added, the RM was stirred at RT for 2 h and the solvent was removed. The residue was purified by chromatography on a Redisep® C18 column eluting with ACN in an aq. solution of TFA (0.1%) (from 2 to 100%) affording the title compound as a solid (421 mg).

Method A: Rt=1.64 min; [M+H]$^+$=828.5.

Step 4: 2-fluoro-N-(5-fluoro-2-methyl-3-(6-(4-(piperidin-4-yloxy)phenyl)-7-((2-(trimethylsilyl)ethoxy)methyl)-7H-pyrrolo[2,3-d]pyrimidin-4-yl)phenyl)-4-(2-hydroxypropan-2-yl)benzamide A solution of tert-butyl 4-(4-(4-(5-fluoro-3-(2-fluoro-4-(2-hydroxypropan-2-yl)benzamido)-2-methylphenyl)-7-((2-(trimethylsilyl)ethoxy)methyl)-7H-pyrrolo[2,3-d]pyrimidin-6-yl)phenoxy)piperidine-1-carboxylate (416.6 mg, 0.503 mmol) and TFA (1 ml, 12.98 mmol) in DCM (5 ml) was stirred at RT for 2 h, concentrated and purified by reversed phase chromatography on a Redisep® C18 column eluting with ACN in an aq. solution of TFA (0.1%) (from 2 to 100%) affording the title compound as a solid TFA salt (101 mg).

Method A: Rt=0.77 min; [M+H]⁺=598.4.

Intermediate 17

2-Fluoro-N-(5-fluoro-2-methyl-3-(6-(4-(piperazin-1-ylmethyl)phenyl)-7H-pyrrolo[2,3-d]pyrimidin-4-yl)phenyl)-4-(2-hydroxypropan-2-yl)benzamide

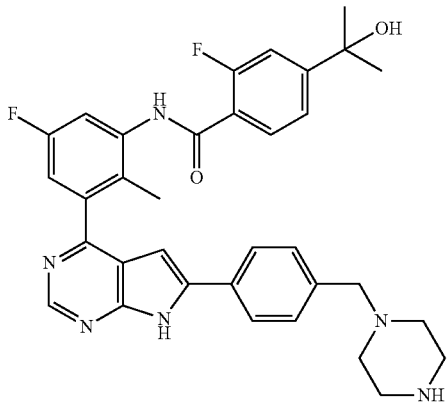 [SMILES: Cc1c(NC(=O)c2ccc(C(C)(C)O)cc2F)cc(F)cc1-c1ncnc2[nH]c(-c3ccc(CN4CCNCC4)cc3)cc12]

Step 1: tert-butyl 4-(4-(4-(5-fluoro-3-(2-fluoro-4-(2-hydroxypropan-2-yl)benzamido)-2-methylphenyl)-7H-pyrrolo[2,3-d]pyrimidin-6-yl)benzyl)piperazine-1-carboxylate 1-Boc-piperazine (95 mg, 0.500 mmol), TEA (0.100 ml, 0.717 mmol) and 2-fluoro-N-(5-fluoro-3-(6-(4-formylphenyl)-7H-pyrrolo[2,3-d]pyrimidin-4-yl)-2-methylphenyl)-4-(2-hydroxypropan-2-yl)benzamide (intermediate 3, 250 mg, 0.465 mmol) were dissolved in MeOH (4 ml) at RT. A solution of ZnCl₂ (0.5 M) in THF (1 ml, 0.500 mmol) was added and the resulting mixture was stirred at RT for 3 days. Solid NaBH₃CN (32 mg, 0.509 mmol) was added, the RM was stirred at RT overnight, the solvent was removed and the residue was purified by reversed phase chromatography on a Redisep® C18 column eluting with ACN in an aq. solution of TFA (0.1%) (from 2 to 100%) to afford the title compound as a solid TFA salt (370 mg).

Method A: Rt=0.94 min; [M+H]⁺=697.5.

Step 2: 2-fluoro-N-(5-fluoro-2-methyl-3-(6-(4-(piperazin-1-ylmethyl)phenyl)-7H-pyrrolo[2,3-d]pyrimidin-4-yl)phenyl)-4-(2-hydroxypropan-2-yl)benzamide To a solution of tert-butyl 4-(4-(4-(5-fluoro-3-(2-fluoro-4-(2-hydroxypropan-2-yl)benzamido)-2-methylphenyl)-7H-pyrrolo[2,3-d]pyrimidin-6-yl)benzyl)piperazine-1-carboxylate (360 mg, 0.431 mmol) in MeOH (2 ml) was added a solution of HCl (4 M) in 1,4-dioxane (2 ml, 8.00 mmol) and the RM was stirred at RT for 4 h. The RM was concentrated and dried to afford the title compound as a solid HCl salt (281 mg).

Method A: Rt=0.76 min; [M+H]⁺=597.5.

Intermediate 18

2-Fluoro-N-(5-fluoro-2-methyl-3-(6-(4-(piperazin-1-ylmethyl)phenyl)-7H-pyrrolo[2,3-d]pyrimidin-4-yl)phenyl)-4-(2-hydroxypropan-2-yl)benzamide

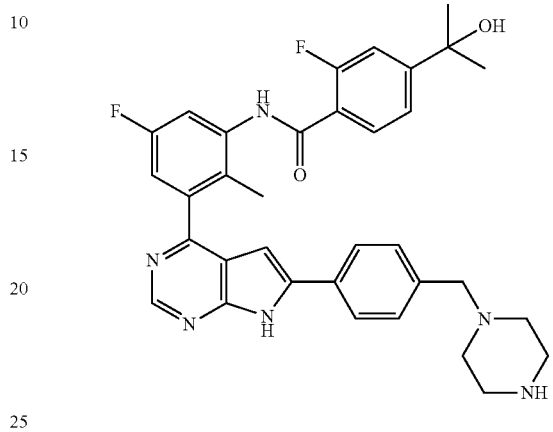

Step 1: tert-butyl 4-(4-(4-(5-fluoro-3-(2-fluoro-4-(2-hydroxypropan-2-yl)benzamido)-2-methylphenyl)-7H-pyrrolo[2,3-d]pyrimidin-6-yl)benzyl)piperazine-1-carboxylate 1-Boc-piperazine (170 mg, 0.912 mmol), TEA (0.300 ml, 2.152 mmol) and 2-fluoro-N-(5-fluoro-3-(6-(4-formylphenyl)-7H-pyrrolo[2,3-d]pyrimidin-4-yl)-2-methylphenyl)-4-(2-hydroxypropan-2-yl)benzamide (intermediate 3, (400 mg, 0.760 mmol) were dissolved in MeOH (6 ml) at RT. A solution of ZnCl₂ (0.7 M) in THF (1.2 ml, 0.840 mmol) was added and the resulting mixture was stirred at RT for 5 h. Solid NaBH₃CN (50 mg, 0.796 mmol) was added, the RM was stirred at RT for 3 days, the solvent was evaporated and the residue was purified by reversed phase chromatography on a Redisep® C18 column eluting with ACN in an aq. solution of TFA (0.1%) (from 2 to 100%) to afford the title compound as a solid TFA salt (328 mg).

Method A: Rt=0.94 min; [M+H]⁺=697.5.

Step 2: 2-fluoro-N-(5-fluoro-2-methyl-3-(6-(4-(piperazin-1-ylmethyl)phenyl)-7H-pyrrolo[2,3-d]pyrimidin-4-yl)phenyl)-4-(2-hydroxypropan-2-yl)benzamide To a solution of tert-butyl 4-(4-(4-(5-fluoro-3-(2-fluoro-4-(2-hydroxypropan-2-yl)benzamido)-2-methylphenyl)-7H-pyrrolo[2,3-d]pyrimidin-6-yl)benzyl)piperazine-1-carboxylate (328 mg, 0.360 mmol) in MeOH (2.0 ml) was added a solution of HCl (4 M) in 1,4-dioxane (2 ml, 8.00 mmol) and the RM was stirred at RT for 4 h. The RM was concentrated and the residue was purified by reversed phase chromatography on a Redisep® C18 column eluting with ACN in an aq. solution of TFA (0.1%) (from 2 to 100%) to afford the title compound as a solid TFA salt (278 mg).

Method A: Rt=0.74 min; [M+H]⁺=597.4.

Intermediate 19

Tert-butyl 4-(2-oxoethoxy)piperidine-1-carboxylate

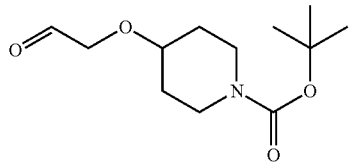 [SMILES: CC(C)(C)OC(=O)N1CCC(OCC=O)CC1]

Step 1: tert-butyl 4-(allyloxy)piperidine-1-carboxylate

NaH (60%) in mineral oil (964 mg, 24.10 mmol) was added portionwise to a solution of 1-Boc-4-hydroxypiperidine (1000 mg, 4.82 mmol) in anhydrous THF (45 ml) under argon at RT and stirring was continued for 30 minutes. Allyl bromide (0.500 ml, 5.78 mmol) was added dropwise and the RM was stirred at RT for 40 hours and was then quenched with ice water. The mixture was extracted with EtOAc, the combined organic phases were dried over $Na_2SO_4$, concentrated and purified by chromatography on silica gel eluting with EtOAc in CHX (from 0 to 20%) to afford the title compound as a colorless liquid (1130 mg).
Method A: Rt=1.13 min, $[M-tBu+H]^+$=186.1.

Step 2: tert-butyl 4-(2-oxoethoxy)piperidine-1-carboxylate

A solution of tert-butyl 4-(allyloxy)piperidine-1-carboxylate (1120 mg, 4.64 mmol) in anhydrous DCM (40 ml) was cooled to −78° C. and ozone was bubbled through the RM for 70 min. The RM was allowed to warm to RT and polymer bound triphenylphosphine (5 g, 16.00 mmol) was added. The RM was stirred at RT for 30 min., filtered over Celite® and the solids were washed with DCM. The combined filtrates were evaporated to dryness yielding the title compound as a colorless oil (1147 mg) which was used without further purification.

Intermediate 20 rac-1-(5-(7-(Hydroxymethyl)-3,9-diazaspiro[5.5]undecane-3-carbonyl)-2-methoxyphenyl)dihydropyrimidine-2,4(1H,3H)-dione

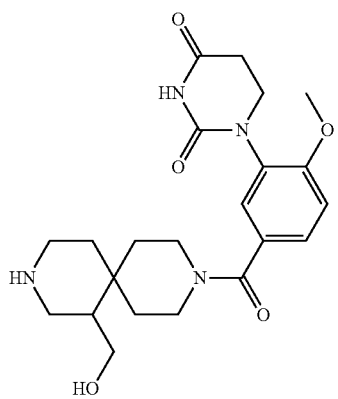 [SMILES: COc1ccc(C(=O)N2CCC3(CCNCC3CO)CC2)cc1N1CCC(=O)NC1=O]

Step 1: rac-tert-butyl 9-(3-(2,4-dioxotetrahydropyrimidin-1(2H)-yl)-4-methoxybenzoyl)-1-(hydroxymethyl)-3,9-diazaspiro[5.5]undecane-3-carboxylate To a solution of rac-tert-butyl 1-(hydroxymethyl)-3,9-diazaspiro[5.5]undecane-3-carboxylate (200 mg, 0.703 mmol), 3-(2,4-dioxotetrahydropyrimidin-1(2H)-yl)-4-methoxybenzoic acid (intermediate 5, 204 mg, 0.774 mmol) and NMM (0.387 ml, 3.52 mmol) in DMF (3 ml) was added HATU (401 mg, 1.055 mmol), the RM was stirred at RT for 2 h and then poured into water and filtered. The filtrate was extracted with DCM, the combined organic phases were washed with brine, dried over $MgSO_4$, evaporated and purified by chromatography on silica gel eluting with MeOH in DCM (from 0 to 20%) to afford the title compound as a solid (241 mg).
Method A: Rt=0.77 min $[M+H]^+$=531.3.

Step 2: rac-1-(5-(7-(hydroxymethyl)-3,9-diazaspiro[5.5]undecane-3-carbonyl)-2-methoxyphenyl)dihydropyrimidine-2,4(1H,3H)-dione A solution of rac-tert-butyl 9-(3-(2,4-dioxotetrahydropyrimidin-1(2H)-yl)-4-methoxybenzoyl)-1-(hydroxymethyl)-3,9-diazaspiro[5.5]undecane-3-carboxylate (241 mg, 0.454 mmol) and TFA (1.050 ml, 13.63 mmol) in DCM (4 ml) was stirred at RT for 2 h, concentrated and the residue was purified by reversed phase chromatography on a Redisep® C18 column eluting with ACN in an aq. solution of TFA (0.1%) to afford the title compound as a solid TFA salt (228 mg).
Method A: Rt=0.38 min; $[M+H]^+$=431.2.

Intermediate 21

1-(2-Methoxy-5-(3,9-diazaspiro[5.5]undecane-3-carbonyl)phenyl)dihydropyrimidine-2,4(1H,3H)-dione

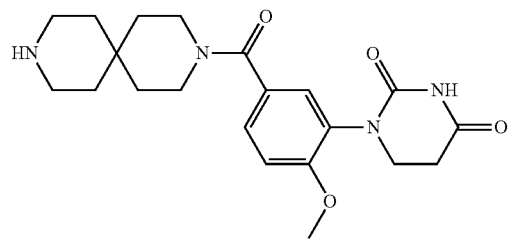 [SMILES: COc1ccc(C(=O)N2CCC3(CCNCC3)CC2)cc1N1CCC(=O)NC1=O]

Step 1: tert-butyl 9-(3-(2,4-dioxotetrahydropyrimidin-1(2H)-yl)-4-methoxybenzoyl)-3,9-diazaspiro[5.5]undecane-3-carboxylate To a solution of tert-butyl 3,9-diazaspiro[5.5]undecane-3-carboxylate (432 mg, 1.698 mmol) and NMM (0.392 ml, 3.57 mmol) at RT under argon in DMF (4 ml) was added 3-(2,4-dioxotetrahydropyrimidin-1(2H)-yl)-4-methoxybenzoic acid (intermediate 5, 471 mg, 1.783 mmol), followed by HATU (743 mg, 1.953 mmol). The RM was stirred at RT for 2.5 h and a saturated aq. solution of $NaHCO_3$ was added. EtOAc was added and both phases were separated. The aqueous phase was extracted with EtOAc and the combined organic phases were washed with water and brine, dried over MgSO$_4$ and concentrated to afford the title compound as a solid (900 mg).

Method A: Rt=0.91 min; [M+H]$^+$=501.4.

Step 2: 1-(2-methoxy-5-(3,9-diazaspiro[5.5]undecane-3-carbonyl)phenyl)dihydropyrimidine-2,4(1H,3H)-dione To a solution of tert-butyl 9-(3-(2,4-dioxotetrahydropyrimidin-1(2H)-yl)-4-methoxybenzoyl)-3,9-diazaspiro[5.5]undecane-3-carboxylate (805 mg, 1.415 mmol) in DCM (19 ml) was added TFA (3.27 ml, 42.5 mmol). The RM was stirred at RT for 1 h, concentrated and the residue was purified by reversed phase chromatography on a Redisep® C18 column eluting with ACN in an aq. solution of TFA (0.1%) (from 5 to 100%) to afford the title compound as a solid TFA salt (767 mg).

Method A: Rt=0.40 min: [M+H]$^+$=401.3.

Intermediate 22

5-(2,4-Dioxotetrahydropyrimidin-1(2H)-yl)-2-fluoro-4-methylbenzoic Acid

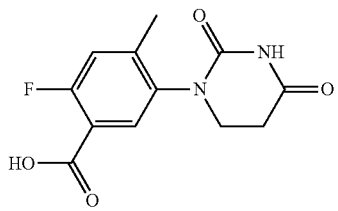 [SMILES: Cc1cc(F)c(C(=O)O)cc1N1CCC(=O)NC1=O]

Step 1: 5-amino-2-fluoro-4-methylbenzoic Acid

To a stirred solution of methyl 5-amino-2-fluoro-4-methylbenzoate (250 mg, 1.365 mmol) in THF (5.4 ml) at RT was added a solution of lithium hydroxide monohydrate (128 mg, 3.02 mmol) in water (1.35 ml). The resulting RM was stirred at RT overnight. The RM was concentrated, rediluted with water (5 ml) and an aq. solution of HCl (2 M) (1.5 ml) was added until the mixture reached a pH of 4. The mixture was cooled in an ice-water bath, filtered, the solids were washed with water and Et$_2$O and the solids were dried to afford the title compound as a solid (217 mg).

Method A: Rt=0.46 min; [M+H]$^+$=170.1.

Step 2: 5-((2-carboxyethyl)amino)-2-fluoro-4-methylbenzoic Acid

A mixture of 5-amino-2-fluoro-4-methylbenzoic acid (216 mg, 1.277 mmol) and acrylic acid (0.354 ml, 5.11 mmol) in toluene (0.5 ml) was flushed with N$_2$ and stirred at 100° C. for 3.5 h. The RM was concentrated to afford the title compound as a solid (352 mg).

Method A: Rt=0.58 min; [M+H]$^+$=242.1.

Step 3: 5-(2,4-dioxotetrahydropyrimidin-1(2H)-yl)-2-fluoro-4-methylbenzoic Acid

A mixture of 5-((2-carboxyethyl)amino)-2-fluoro-4-methylbenzoic acid (350 mg, 1.277 mmol) and urea (460 mg, 7.66 mmol) in AcOH (1 ml) was stirred at 120° C. overnight and cooled to RT. The resulting oil was diluted with water (1-2 ml) and the mixture was poured onto crushed ice. An aq. solution of HCl (1 M) was added and stirring was continued until all the ice has melted. The resulting mixture was filtered and the solids were washed with ACN and dried to afford the title compound as a solid (250 mg).

Method A: Rt=0.48 min; [M+H]$^+$=267.1

Intermediate 23

Pentafluorophenyl 3-(2,4-dioxotetrahydropyrimidin-1(2H)-yl)-4-methoxybenzoate

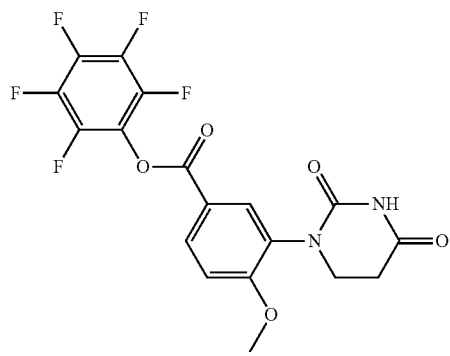 [SMILES: COc1ccc(C(=O)Oc2c(F)c(F)c(F)c(F)c2F)cc1N1CCC(=O)NC1=O]

To a 250 ml round bottom flask were added 3-(2,4-dioxotetrahydropyrimidin-1(2H)-yl)-4-methoxybenzoic acid (intermediate 5, 28 g, 106 mmol), pentafluorophenyl 2,2,2-trifluoroacetate (36 g, 127 mmol) and DMF (50 ml). DIPEA (76 ml, 424 mmol) was added at 0° C., the RM was stirred at RT for 2 h and diluted with water. The mixture was extracted with EtOAc, the combined organic phases were washed with brine, dried over Na$_2$SO$_4$, filtered and concentrated. The residue was purified by chromatography on silica gel eluting with EtOAc in petroleum ether (from 10 to 30%) to afford the title compound as a solid (40 g).

Method H: Rt=1.51 min, [M+H]$^+$=432.

Intermediate 24

Tert-butyl 9-(4-(4-chloro-7-(phenylsulfonyl)-7H-pyrrolo[2,3-d]pyrimidin-6-yl)phenethyl)-3,9-diazaspiro[5.5]undecane-3-carboxylate

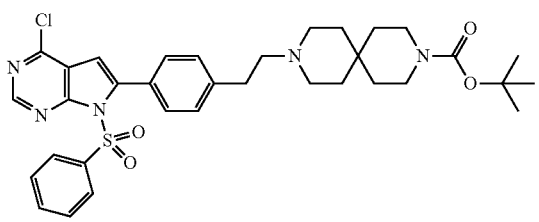 [SMILES: CC(C)(C)OC(=O)N1CCC2(CCN(CCc3ccc(-c4cc5c(Cl)ncnc5n4S(=O)(=O)c4ccccc4)cc3)CC2)CC1]

Step 1: 2-(4-(4,4,5,5-tetramethyl-1,3,2-dioxaborolan-2-yl)phenyl)ethan-1-ol

A mixture of 2-(4-bromophenyl)ethan-1-ol (60 g, 300 mmol), BISPIN (84 g, 330 mmol), KOAc (90 g, 900 mmol) and PdCl$_2$(dppf) (6.6 g, 9 mmol) in 1,4-dioxane (600 ml) was stirred under N$_2$ at 85° C. for 16 h. The RM was cooled to RT, filtered, the filtrate was concentrated and the residue purified by chromatography on silica gel eluting with EtOAc in petroleum ether (from 0 to 30%) to afford of the title compound as an oil (100 g).

Method J: Rt=1.87 min, [M+NH$_4$]$^+$=266.

Step 2: 4-(4,4,5,5-tetramethyl-1,3,2-dioxaborolan-2-yl)phenethyl Methanesulfonate A mixture of 2-(4-(4,4,5,5-tetramethyl-1,3,2-dioxaborolan-2-yl)phenyl)ethan-1-ol (100 g, 300 mmol) and TEA (240 g, 2400 mmol) in DCM (1300 ml) was stirred at 0° C. for 20 min. A solution of MsCl (136 g, 1200 mmol) in DCM (200 ml) was added drop by drop and the RM was stirred at RT for 16 h and water was added. The phases were separated, the organic phase was dried over Na$_2$SO$_4$, concentrated and the residue purified by chromatography on silica gel eluting with EtOAc in DCM (from 0 to 50%) to afford the title compound as an oil (87 g).

Method E: Rt=1.92 min, [M+H]$^+$=327.

Step 3: tert-butyl 9-(4-(4,4,5,5-tetramethyl-1,3,2-dioxaborolan-2-yl)phenethyl)-3,9-diazaspiro[5.5]undecane-3-carboxylate A mixture of tert-butyl 3,9-diazaspiro[5.5]undecane-3-carboxylate (34 g, 133 mmol), 4-(4,4,5,5-tetramethyl-1,3,2-dioxaborolan-2-yl)phenethyl methanesulfonate (86 g, 172 mmol), K$_2$CO$_3$ (47 g, 345 mmol) and KI (2.3 g, 13.8 mmol) in ACN (1000 ml) was stirred at 60° C. for 16 h. The RM was filtered, the filtrate was concentrated and the residue purified by chromatography on silica gel eluting with MeOH in DCM (from 0 to 10%) to afford of the title compound as a solid (49 g).

Method I: Rt=1.47 min, [M+H]$^+$=485.

Step 4: tert-butyl 9-(4-(4-chloro-7-(phenylsulfonyl)-7H-pyrrolo[2,3-d]pyrimidin-6-yl)phenethyl)-3,9-diazaspiro[5.5]undecane-3-carboxylate A mixture of tert-butyl 9-(4-(4,4,5,5-tetramethyl-1,3,2-dioxaborolan-2-yl)phenethyl)-3,9-diazaspiro[5.5]undecane-3-carboxylate (38 g, 79 mmol), 4-chloro-6-iodo-7-(phenylsulfonyl)-7H-pyrrolo[2,3-d]pyrimidine (intermediate 7, 37 g, 88 mmol), K$_2$CO$_3$ (22 g, 160 mmol) and PdCl$_2$(dpp) (5.8 g, 8 mmol) in a mixture of 1,4-dioxane and water (5:1) (480 ml) was stirred under N$_2$ at 80° C. for 16 h. The RM was poured into EtOAc, the organic phase was separated and washed with water, dried over Na$_2$SO$_4$, filtered, concentrated and the residue was purified by chromatography on silica gel eluting with MeOH in DCM (from 0 to 10%) to afford the title compound as a solid (34 g).

Method I: Rt=1.99 min, [M+H]$^+$=650.

Synthesis of Final Compounds

Compound 1 rac-N-(3-(6-(4-(((9-(3-(2,4-Dioxotetrahydropyrimidin-1(2H)-yl)-4-methoxybenzoyl)-7-(hydroxymethyl)-3,9-diazaspiro[5.5]undecan-3-yl)methyl)phenyl)-7H-pyrrolo[2,3-d]pyrimidin-4-yl)-5-fluoro-2-methylphenyl)-2-fluoro-4-(2-hydroxypropan-2-yl)benzamide

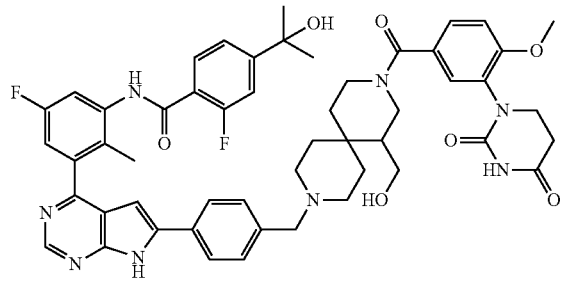 [SMILES: COc1ccc(C(=O)N2CCC3(CCN(Cc4ccc(-c5cc6c(-c7cc(F)cc(NC(=O)c8ccc(C(C)(C)O)cc8F)c7C)ncnc6[nH]5)cc4)CC3)C(CO)C2)cc1N1CCC(=O)NC1=O]

To a mixture of rac-2-fluoro-N-(5-fluoro-3-(6-(4-(((7-(hydroxymethyl)-3,9-diazaspiro[5.5]undecan-3-yl)methyl)phenyl)-7H-pyrrolo[2,3-d]pyrimidin-4-yl)-2-methylphenyl)-4-(2-hydroxypropan-2-yl)benzamide (intermediate 4, 100 mg, 0.108 mmol) and 3-(2,4-dioxotetrahydropyrimidin-1(2H)-yl)-4-methoxybenzoic acid (intermediate 5, 31.5 mg, 0.119 mmol) were added HATU (61.8 mg, 0.163 mmol) and NMM (0.060 ml, 0.542 mmol). The RM was stirred for 2 h at RT, the solution was poured into water, filtered and the solids were dried and purified by reversed phase chromatography on a Redisep® C18 column eluting with ACN in an aq. solution of TA (0.1%) (from 10 to 100%) to afford the title compound as a solid TFA salt. The solid was dissolved in MeOH, filtered through a SCX cartridge and the combined filtrates were concentrated to afford the title compound (19.6 mg).

Method B: Rt=3.41 min; [M+H]$^+$=941.6.

$^1$H NMR (400 MHz, DMSO-d$_6$) δ 12.53 (s, 1H), 9.92 (s, 1H), 9.62 (d, J=3.1 Hz, 1H), 8.85 (s, 1H), 7.99 (s, 2H), 7.8-7.6 (m, 2H), 7.50-7.25 (m, 6H), 7.25-7.05 (m, 2H), 6.81 (s, 1H), 3.86 (s, 4H), 3.75-3.6 (s, 6H), 3.29 (s, 3H), 2.69 (t, J=6.7 Hz, 4H), 2.19 (s, 4H), 2.1-1.6 (m, 2H), 1.6-1.4 (m, 11H), 1.4-1.25 (m, 3H).

Compound 2 and Compound 3

(R)—N-(3-(6-(4-((9-(3-(2,4-Dioxotetrahydropyrimidin-1(2H)-yl)-4-methoxybenzoyl)-7-(hydroxymethyl)-3,9-diazaspiro[5.5]undecan-3-yl)methyl)phenyl)-7H-pyrrolo[2,3-d]pyrimidin-4-yl)-5-fluoro-2-methylphenyl)-2-fluoro-4-(2-hydroxypropan-2-yl)benzamide and (S)—N-(3-(6-(4-((9-(3-(2,4-Dioxotetrahydropyrimidin-1(2H)-yl)-4-methoxybenzoyl)-7-(hydroxymethyl)-3,9-diazaspiro[5.5]undecan-3-yl)methyl)phenyl)-7H-pyrrolo[2,3-d]pyrimidin-4-yl)-5-fluoro-2-methylphenyl)-2-fluoro-4-(2-hydroxypropan-2-yl)benzamide

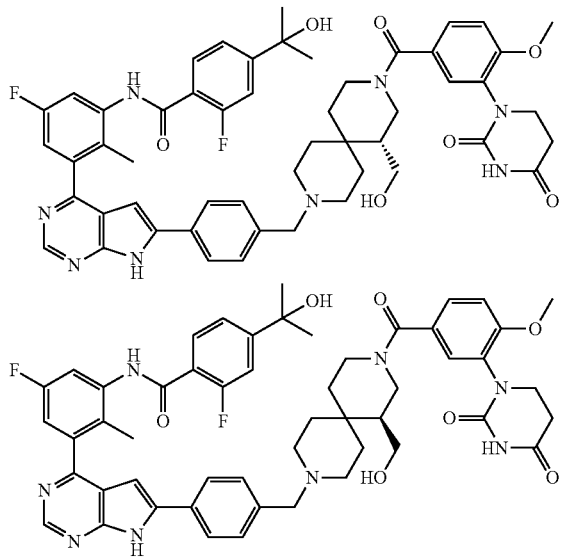

Chiral separation of rac-N-(3-(6-(4-((9-(3-(2,4-dioxotetrahydropyrimidin-1(2H)-yl)-4-methoxybenzoyl)-7-(hydroxymethyl)-3,9-diazaspiro[5.5]undecan-3-yl)methyl)phenyl)-7H-pyrrolo[2,3-d]pyrimidin-4-yl)-5-fluoro-2-methylphenyl)-2-fluoro-4-(2-hydroxypropan-2-yl)benzamide (7.7 mg, 7.9 µmol) using HPLC on a Chiralpak ID column (5 µm, 250×20 mm) eluting with a mixture of heptane, DCM and MeOH (40:35:25) containing DEA (0.05%) at a flow rate of 10 ml/min (Method M) afforded the title compounds as single enantiomers in the following order:

first eluting enantiomer: 1.2 mg
Method K: Rt=29.5 min
Method B: Rt=3.44 min; [M+H]$^+$=941.5
$^1$H NMR (400 MHz, DMSO-d$_6$) is in accordance with the NMR for the racemate reported above second eluting enantiomer: 2.0 mg
Method K: Rt=37.5 min
Method B: Rt=3.46 min; [M+H]$^+$=941.4
$^1$H NMR (400 MHz, DMSO-d$_6$) is in accordance with the NMR for the racemate reported above

Compound 4

N-(3-(6-(4-((9-(3-(2,4-Dioxotetrahydropyrimidin-1(2H)-yl)-4-ethoxybenzoyl)-3,9-diazaspiro[5.5]undecan-3-yl)methyl)phenyl)-7H-pyrrolo[2,3-d]pyrimidin-4-yl)-5-fluoro-2-methylphenyl)-2-fluoro-4-(2-hydroxypropan-2-yl)benzamide

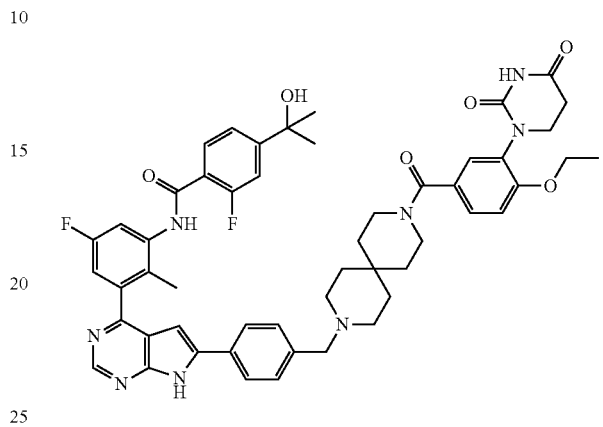

Step 1: 3-(2,4-dioxotetrahydropyrimidin-1(2H)-yl)-4-ethoxybenzoic Acid

3-Amino-4-ethoxybenzoic acid (2.7 g, 14.90 mmol) was suspended in acrylic acid (4.09 ml, 59.6 mmol) and the RM was stirred at 110° C. for 1 h. Urea (5.37 g, 89 mmol) and AcOH (18 ml) were added and the RM was stirred at 130° C. for 2 h. The RM was quenched with water, acidified with an aq. concentrated solution of HCl (37%) and extracted with EtOAc. The organic phases were combined and evaporated. Water was added, the mixture was filtered and the solids were washed with water and EtOAc yielding the title compound as a solid (1.1 g).
Method A: Rt=0.56 min; [M+H]$^+$=279.1.

Step 2: N-(3-(6-(4-((9-(3-(2,4-dioxotetrahydropyrimidin-1(2H)-yl)-4-ethoxybenzoyl)-3,9-diazaspiro[5.5]undecan-3-yl)methyl)phenyl)-7H-pyrrolo[2,3-d]pyrimidin-4-yl)-5-fluoro-2-methylphenyl)-2-fluoro-4-(2-hydroxypropan-2-yl)benzamide TBTU (38.4 mg, 0.119 mmol) was added to a solution of 3-(2,4-dioxotetrahydropyrimidin-1(2H)-yl)-4-ethoxybenzoic acid (33.2 mg, 0.119 mmol) in DMF (0.5 ml), followed by 2,4,6-collidine (0.2 ml, 1.508 mmol). The RM was stirred for 15 min at RT. N-(3-(6-(4-(3,9-diazaspiro[5.5]undecan-3-ylmethyl)phenyl)-7H-pyrrolo[2,3-d]pyrimidin-4-yl)-5-fluoro-2-methylphenyl)-2-fluoro-4-(2-hydroxypropan-2-yl)benzamide (intermediate 6, 60 mg, 0.060 mmol) was added and the RM was stirred for 3 days at RT. The RM was diluted with DMF (2 ml) and purified by HPLC on a SunFire C18 column eluting with ACN in an aq. solution of TFA (0.1%) (linear gradient from 5 to 100%) (Method L) to afford the title compound as a solid TFA salt (32.8 mg).
Method B: Rt=3.74 min; [M+H]$^+$=925.3.
$^1$H NMR (400 MHz, methanol-d$_4$) δ 8.91 (s, 1H), 8.06 (d, J=8.1 Hz, 2H), 7.90 (t, J=7.9 Hz, 1H), 7.74-7.68 (m, 1H), 7.66 (d, J=8.1 Hz, 2H), 7.52-7.37 (m, 4H), 7.25 (dd, J=8.5, 2.7 Hz, 1H), 7.19 (d, J=8.5 Hz, 1H), 7.00 (s, 1H), 4.41 (s, 2H), 4.19 (q, J=7.0 Hz, 2H), 3.8-3.5 (m, 6H), 3.45-3.15 (m, 4H), 2.82 (t, J=6.7 Hz, 2H), 2.23 (s, 3H), 2.07 (m, 2H), 1.9-1.4 (m, 6H), 1.58 (s, 6H), 1.45 (t, J=7.0 Hz, 3H).

Compound 5

N-(3-(6-(4-(2-(9-(3-(2,4-Dioxotetrahydropyrimidin-1(2H)-yl)-4-methylbenzoyl)-3,9-diazaspiro[5.5]undecan-3-yl)ethyl)phenyl)-7H-pyrrolo[2,3-d]pyrimidin-4-yl)-5-fluoro-2-methylphenyl)-2-fluoro-4-(2-hydroxypropan-2-yl)benzamide

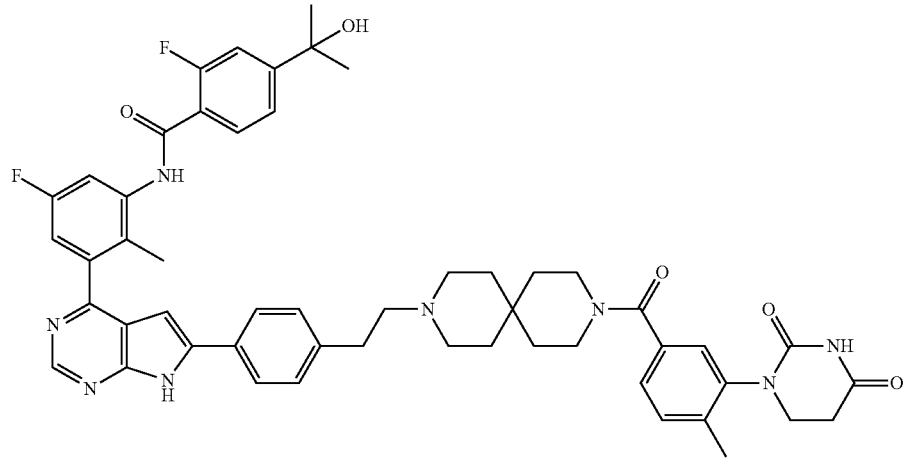 [SMILES: Cc1ccc(C(=O)N2CCC3(CCN(CCc4ccc(-c5cc6c(-c7cc(F)cc(NC(=O)c8ccc(C(C)(C)O)cc8F)c7C)ncnc6[nH]5)cc4)CC3)CC2)cc1N1CCC(=O)NC1=O]

Step 1: tert-butyl 9-(4-bromophenethyl)-3,9-diazaspiro[5.5]undecane-3-carboxylate To a 250 ml round bottom flask were added tert-butyl 3,9-diazaspiro[5.5]undecane-3-carboxylate (5 g, 19.7 mmol), K$_2$CO$_3$ (4.07 g, 29.5 mmol) and 1-bromo-4-(2-bromoethyl)benzene (5.2 g, 17.6 mmol) in ACN (50 ml). The RM was stirred at RT for 16 h under N$_2$. The RM was concentrated, diluted with water and extracted with DCM. The combined organic phases were concentrated and purified by chromatography on silica gel eluting with MeOH in DCM (1:100) yielding the title compound as a solid (4.8 g).
Method F: Rt=1.91 min; MS m/z [M+H]$^+$ 438.1.

Step 2: tert-butyl 9-(4-(4,4,5,5-tetramethyl-1,3,2-dioxaborolan-2-yl)phenethyl)-3,9-diazaspiro[5.5]undecane-3-carboxylate To a 250 ml round bottom flask were added tert-butyl 9-(4-bromophenethyl)-3,9-diazaspiro[5.5]undecane-3-carboxylate (4.8 g, 11 mmol), BISPIN (3.4 g, 13.2 mmol), KOAc (2.2 g, 22 mmol), PdCl$_2$(dpp) (0.8 g, 1.1 mmol) and DMSO (60 ml). The RM was stirred at 80° C. for 16 h and was then diluted with water. The mixture was extracted with EtOAc and the combined organic phases were washed with water and brine, concentrated and purified by chromatography on silica gel eluting with EtOAc in petroleum ether (from 0 to 100%) yielding the title compound as a solid (4.0 g).
Method E: Rt=1.67 min; MS m/z [M+H]$^+$ 485.

Step 3: tert-butyl 9-(4-(4-chloro-7-(phenylsulfonyl)-7H-pyrrolo[2,3-d]pyrimidin-6-yl)phenethyl)-3,9-diazaspiro[5.5]undecane-3-carboxylate To a 25 ml round bottom flask were added tert-butyl 9-(4-(4,4,5,5-tetramethyl-1,3,2-dioxaborolan-2-yl)phenethyl)-3,9-diazaspiro[5.5]undecane-3-carboxylate (889 mg, 1.83 mmol), 4-chloro-6-iodo-7-(phenylsulfonyl)-7H-pyrrolo[2,3-d]pyrimidine (intermediate 7, 700 mg, 1.67 mmol), Na$_2$CO$_3$ (354 mg, 3.34 mmol) and PdCl$_2$(dpp) (124 mg, 0.17 mmol). ACN (10 ml) and water (2 ml) were added and the RM was stirred at 80° C. for 16 h under N. The RM was diluted with EtOAc, the mixture was filtered, the filtrate was concentrated and purified by chromatography on silica gel eluting with EtOAc in petroleum ether (from 0 to 100%) yielding the title compound as an oil (600 mg).

Method F: Rt=1.85 min; MS m/z [M+H]$^+$ 650.

Step 4: tert-butyl 9-(4-(4-(5-fluoro-3-(2-fluoro-4-(2-hydroxypropan-2-yl)benzamido)-2-methylphenyl)-7-(phenylsulfonyl)-7H-pyrrolo[2,3-d]pyrimidin-6-yl)phenethyl)-3,9-diazaspiro[5.5]undecane-3-carboxylate To a 25 ml round bottom flask were added tert-butyl 9-(4-(4-chloro-7-(phenylsulfonyl)-7H-pyrrolo[2,3-d]pyrimidin-6-yl)phenethyl)-3,9-diazaspiro[5.5]undecane-3-carboxylate (400 mg, 0.62 mmol), 2-fluoro-N-(5-fluoro-2-methyl-3-(4,4,5,5-tetramethyl-1,3,2-dioxaborolan-2-yl)phenyl)-4-(2-hydroxypropan-2-yl)benzamide (intermediate 2, 265 mg, 0.62 mmol), Na$_2$CO$_3$ (130 mg, 1.23 mmol) and PdCl$_2$(dppf) (44 mg, 0.06 mmol). ACN (10 ml) and water (2 ml) were added and the RM was stirred at 80° C. for 16 h under N$_2$. The RM was diluted with EtOAc, the mixture was filtered, the filtrate concentrated and purified by chromatography on silica gel eluting with EtOAc in petroleum ether (from 0 to 100%) yielding the title compound as a solid (200 mg).
Method E: Rt=1.74 min; MS m/z [M+H]$^+$ 919.

Step 5: tert-butyl 9-(4-(4-(5-fluoro-3-(2-fluoro-4-(2-hydroxypropan-2-yl)benzamido)-2-methylphenyl)-7H-pyrrolo[2,3-d]pyrimidin-6-yl)phenethyl)-3,9-diazaspiro[5.5]undecane-3-carboxylate To a 10 ml round bottom flask was added tert-butyl 9-(4-(4-(5-fluoro-3-(2-fluoro-4-(2-hydroxypropan-2-yl)benzamido)-2-methylphenyl)-7-(phenylsulfonyl)-7H-pyrrolo[2,3-d]pyrimidin-6-yl)phenethyl)-3,9-diazaspiro[5.5]undecane-3-carboxylate (200 mg, 0.22 mmol) and DMSO (2 ml). A solution of NaOH (35 mg, 0.87 mmol) in water (1 ml)

was added at RT, the RM was stirred at RT for 1 h and was diluted with EtOAc. The phases were separated and the organic phase was washed with water and brine, dried, and concentrated yielding the title compound as a solid (170 mg).

Method E: Rt=1.64 min; MS m/z [M+H]+ 779.

Step 6: N-(3-(6-(4-(2-(3,9-diazaspiro[5.5]undecan-3-yl)ethyl)phenyl)-7H-pyrrolo[2,3-d]pyrimidin-4-yl)-5-fluoro-2-methylphenyl)-2-fluoro-4-(2-hydroxypropan-2-yl)benzamide To a 10 ml round bottom flask was added tert-butyl 9-(4-(4-(5-fluoro-3-(2-fluoro-4-(2-hydroxypropan-2-yl)

benzamido)-2-methylphenyl)-7H-pyrrolo[2,3-d]pyrimidin-6-yl)phenethyl)-3,9-diazaspiro[5.5]undecane-3-carboxylate (160 mg, 0.21 mmol), EtOH (2 ml) and DCM (0.5 ml). A solution of HCl (4 M) in 1,4-dioxane (1.5 ml, 6 mmol) was added at 0° C. The RM was allowed to warm to RT and stirring was continued for 2 h. The RM was concentrated yielding the title compound as a solid HCl salt (130 mg).

Method E: Rt=1.45 min; MS m/z [M+H]+ 679.

Step 7: N-(3-(6-(4-(2-(9-(3-(2,4-dioxotetrahydropyrimidin-1(2H)-yl)-4-methylbenzoyl)-3,9-diazaspiro[5.5]undecan-3-yl)ethyl)phenyl)-7H-pyrrolo[2,3-d]pyrimidin-4-yl)-5-fluoro-2-methylphenyl)-2-fluoro-4-(2-hydroxypropan-2-yl)benzamide To a 10 ml round bottom flask were added N-(3-(6-(4-(2-(3,9-diazaspiro[5.5]undecan-3-yl)ethyl)phenyl)-7H-pyrrolo[2,3-d]pyrimidin-4-yl)-5-fluoro-2-methylphenyl)-2-fluoro-4-(2-hydroxypropan-2-yl)benzamide hydrochloride (100 mg, 0.13 mmol), 3-(2,4-dioxotetrahydropyrimidin-1 (2H)-yl)-4-methylbenzoic acid (intermediate 8, 33 mg, 0.13 mmol), HATU (59 mg, 0.16 mmol) and DIPEA (34 mg, 0.27 mmol) in DMF (2 ml). The RM was stirred at RT for 2 h and the mixture was purified by preparative HPLC on a XBridge C18 column eluting with ACN in an aq. solution of ammonium hydrogencarbonate (10 mM), yielding the title compound as a solid (40 mg).

Method G: Rt=1.92 min; MS m/z [M+H]+ 909.

1H NMR (500 MHz, DMSO-d6) δ 12.72 (br. s, 1H), 10.37 (br. s, 1H), 9.93 (br. s, 1H), 8.80 (s, 1H), 7.89 (d, J=8.1 Hz, 2H), 7.73 (t, J=7.9 Hz, 1H), 7.7-7.6 (m, 1H), 7.5-7.4 (m, 2H), 7.4-7.3 (m, 4H), 7.3-7.2 (m, 2H), 6.77 (s, 1H), 5.4-5.3 (m, 1H), 3.9-3.8 (m, 1H), 3.6-3.5 (m, 3H), 2.9-2.7 (m, 4H), 2.6-2.5 (m, 2H), 2.4-2.3 (m, 4H), 2.21 (s, 3H), 2.17 (s, 3H), 1.7-1.3 (m, 16H).

Compound 6

N-(3-(6-(4-(((1-(2-(1-(3-(2,4-dioxotetrahydropyrimidin-1(2H)-yl)-4-fluorobenzoyl)piperidin-4-yl)ethyl)piperidin-4-yl)oxy)methyl)phenyl)-7H-pyrrolo[2,3-d]pyrimidin-4-yl)-5-fluoro-2-methylphenyl)-2-fluoro-4-(2-hydroxypropan-2-yl)benzamide

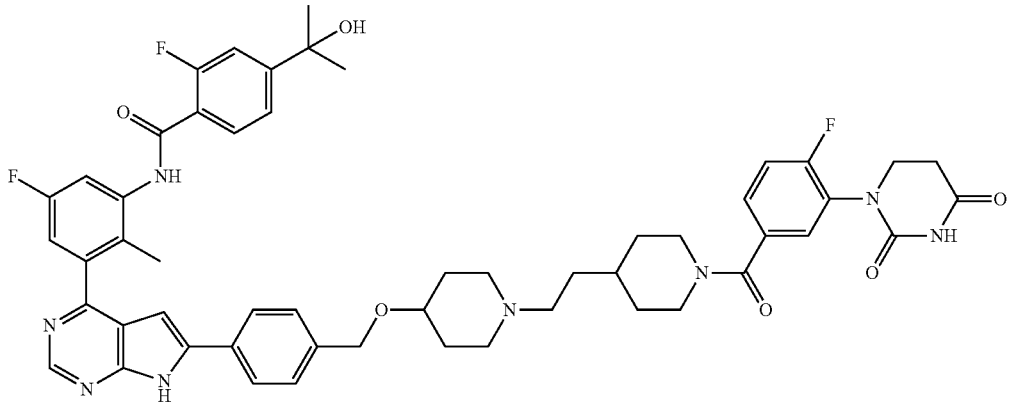 [SMILES: Cc1c(NC(=O)c2ccc(C(C)(C)O)cc2F)cc(F)cc1-c1ncnc2[nH]c(-c3ccc(COC4CCN(CCC5CCN(C(=O)c6ccc(F)c(N7CCC(=O)NC7=O)c6)CC5)CC4)cc3)cc12]

Step 1: tert-butyl 4-(4-bromobenzyloxy)piperidine-1-carboxylate

To a suspension of NaH (60%) in mineral oil (1.17 g, 29.25 mmol) in DMF (30 ml) at 5° C. was added dropwise a solution of tert-butyl 4-hydroxypiperidine-1-carboxylate (4.03 g, 20.0 mmol) in DMF (15 ml) at 5° C. The RM was stirred at 5° C. for 1 h, then 1-bromo-4-(bromomethyl)benzene (7.0 g, 28.0 mmol) was added at 5° C. The RM was allowed to warm to RT and stirring was continued for 18 h. Ice cold water (250 ml) was added, the mixture was extracted with a mixture of EtOAc and petroleum ether (2:1), the combined organic phases were dried on MgSO4, concentrated and purified by chromatography on silica gel eluting with EtOAc in petroleum ether (from 0 to 20%) yielding the title compound as an oil (6.1 g).

Method H: Rt=2.301 min, [M−100+H]+=270.

Step 2: tert-butyl 4-(4-(4,4,5,5-tetramethyl-1,3,2-dioxaborolan-2-yl)benzyloxy)piperidine-1-carboxylate To a mixture of tert-butyl-4-(4-bromobenzyloxy)piperidine-1-carboxylate (2.0 g, 5.4 mmol), BISPIN (2.7 g, 10.8 mmol), KOAc (1.59 g, 16.2 mmol), and PdCl2(dpp) (630 mg, 0.86 mmol) placed under inert atmosphere was added 1,4-dioxane (45 ml) and the RM was stirred at 85° C. for 18 h under N2. The RM was evaporated and purified by chromatography on silica gel eluting with EtOAc in petroleum ether (from 0 to 20%) yielding the title compound as a solid (2.1 g).

Method F: Rt=1.698 min, [M−100+H]+=318.

Step 3: 4-(4-(4,4,5,5-tetramethyl-1,3, 2-dioxaborolan-2-yl)benzyloxy) piperidine To a solution of tert-butyl-4-(4-(4,4,5,5-tetramethyl-1,3,2-dioxaborolan-2-yl)benzyloxy) piperidine-1-carboxylate (2.1 g, 5.0 mmol) in DCM (10 ml) at 5° C. was slowly added a solution of HCl (4 M) in 1,4-dioxane (5 ml, 20 mmol). The RM was allowed to warm to 30° C. and stirring was continued for 2 h. The RM was concentrated, the residue was triturated in a mixture of petroleum ether and TBME (2:1), filtered and the solids were dried to afford the title compound as a solid HCl salt (1.2 g).
Method E: Rt=1.743 min, [M+H]$^+$=318.2.

Step 4: tert-butyl 4-(2-(methylsulfonyloxy)ethyl)piperidine-1-carboxylate

To a mixture of tert-butyl-4-(2-hydroxyethyl)piperidine-1-carboxylate (2 g, 8.72 mmol) and TEA (1.77 g, 17.44 mmol) in DCM (50 ml) was added dropwise methanesulfonyl chloride (1.2 g, 10.47 mmol) and the RM was stirred at RT for 16 h. The RM was diluted with DCM (100 ml), washed with water and brine, dried over Na$_2$SO$_4$ and concentrated to give the title compound as a solid (2.6 g).
$^1$H NMR (500 MHz, DMSO-d$_6$) δ 4.24 (t, J=6.3 Hz, 2H), 3.91 (d, J=9.9 Hz, 2H), 3.17 (s, 3H), 2.68 (s, 2H), 1.71-1.48 (m, 5H), 1.39 (s, 9H), 1.07-0.94 (m, 2H).

Step 5: tert-butyl 4-(2-(4-(4-(4,4,5,5-tetramethyl-1,3,2-dioxaborolan-2-yl)benzyloxy)piperidin-1-yl)ethyl)piperidine-1-carboxylate To a mixture of 4-(4-(4,4,5,5-tetramethyl-1,3,2-dioxaborolan-2-yl)benzyloxy)piperidine (700 mg, 1.98 mmol), tert-butyl-4-(2-(methylsulfonyloxy)ethyl)piperidine-1-carboxylate (913 mg, 2.97 mmol), K$_2$CO$_3$ (821 mg, 5.94 mmol) and NaI (445 mg, 1.5 mmol) under inert atmosphere was added ACN (20 ml) and the RM was stirred at RT for 16 h under N$_2$. The RM was then diluted with EtOAc (100 ml), filtered and the filtrate was concentrated to afford the title compound as a solid (1 g).
Method I: Rt=1.527 min; [M+H]$^+$=529.

Step 6: tert-butyl 4-(2-(4-(4-(4-chloro-7-(phenylsulfonyl)-7H-pyrrolo [2, 3-d] pyrimidin-6-yl) benzyloxy) piperidin-1-yl) ethyl) piperidine-1-carboxylate To a mixture of tert-butyl-4-(2-(4-(4-(4,4,5,5-tetramethyl-1,3,2-dioxaborolan-2-yl)benzyloxy)piperidin-1-yl)ethyl)piperidine-1-carboxylate (472 mg, 0.89 mmol), 4-chloro-6-iodo-7-(phenylsulfonyl)-7H-pyrrolo[2,3-d]pyrimidine (intermediate 7, 250 mg, 0.60 mmol), Na$_2$CO$_3$ (126 mg, 1.19 mmol) and PdCl$_2$(dpp) (49 mg, 0.06 mmol) under inert atmosphere was added ACN (5 ml) and water (1 ml) and the RM was stirred at 80° C. for 16 h. The RM was diluted with EtOAc (100 ml), filtered, the filtrate was concentrated and purified by chromatography on silica gel eluting with MeOH in DCM (from 0 to 15%) yielding the title compound as an oil (500 mg).
Method I: Rt=1.553 min; [M+H]$^+$=694.

Step 7: tert-butyl 4-(2-(4-(4-(4-(5-fluoro-3-(2-fluoro-4-(2-hydroxypropan-2-yl)benzamido)-2-methylphenyl)-7-(phenylsulfonyl)-7H-pyrrolo[2,3-d]pyrimidin-6-yl)benzyloxy)piperidin-1-yl)ethyl)piperidine-1-carboxylate To a mixture of 2-fluoro-N-(5-fluoro-2-methyl-3-(4,4,5,5-tetramethyl-1,3,2-dioxaborolan-2-yl)phenyl)-4-(2-hydroxypropan-2-yl)benzamide (intermediate 2, 149 mg, 1.2 mmol), tert-butyl-4-(2-(4-(4-(4-chloro-7-(phenylsulfonyl)-7H-pyrrolo[2,3-d]pyrimidin-6-yl)benzyloxy)piperidin-1-yl)ethyl)piperidine-1-carboxylate (200 mg, 1 mmol), Na$_2$CO$_3$ (92 mg, 0.86 mmol) and PdCl$_2$(dppf) (24 mg, 0.03 mmol) under inert atmosphere was added ACN (5 ml) and water (1 ml) and the RM was stirred at 80° C. for 16 h under N$_2$. The RM was then diluted with EtOAc (100 ml), filtered, the filtrate was concentrated and purified by chromatography on silica gel eluting with methanol in DCM (from 0 to 15%) yielding the title compound as an oil (260 mg).
Method G: Rt=2.875 min, [M+H]$^+$=694.

Step 8: tert-butyl 4-(2-(4-(4-(4-(5-fluoro-3-(2-fluoro-4-(2-hydroxypropan-2-yl)benzamido)-2-methylphenyl)-7H-pyrrolo[2,3-d]pyrimidin-6-yl)benzyloxy)piperidin-1-yl)ethyl)piperidine-1-carboxylate To a solution of tert-butyl-4-(2-(4-(4-(4-(5-fluoro-3-(2-fluoro-4-(2-hydroxypropan-2-yl)benzamido)-2-methylphenyl)-7-(phenylsulfonyl)-7H-pyrrolo[2,3-d]pyrimidin-6-yl)benzyloxy)piperidin-1-yl)ethyl)piperidine-1-carboxylate (200 mg, 0.21 mmol) in DMSO (2 ml) was slowly added a solution of NaOH (33 mg, 0.83 mmol) in water (1 ml) at RT. The RM was stirred at RT for 2 h and the mixture was purified by reverse phase HPLC on a XBridge C18 column eluting with ACN in an aq. solution of ammonium hydrogencarbonate (0.1%) (from 5 to 95%), yielding the title compound as a solid (150 mg).
Method J: Rt=2.419 min, [M+H]$^+$=823.

Step 9: 2-fluoro-N-(5-fluoro-2-methyl-3-(6-(4-((1-(2-(piperidin-4-yl)ethyl)piperidin-4-yloxy)methyl)phenyl)-7H-pyrrolo[2,3-d]pyrimidin-4-yl)phenyl)-4-(2-hydroxypropan-2-yl)benzamide A solution of tert-butyl 4-(2-(4-(4-(4-(5-fluoro-3-(2-fluoro-4-(2-hydroxypropan-2-yl)benzamido)-2-methylphenyl)-7H-pyrrolo[2,3-d]pyrimidin-6-yl)benzyloxy)piperidin-1-yl)ethyl)piperidine-1-carboxylate (150 mg, 0.16 mmol) in DCM (4 ml) was cooled at 0° C. A solution of HCl (6 M) in 1,4-dioxane (1 ml, 6 mmol) was slowly added. The RM was allowed to warm to RT and stirring was continued for 2 h. The RM was concentrated to afford the title compound as a solid HCl salt (115 mg).
Method I: Rt=1.142 min, [M+H]$^+$=723.

Step 10: N-(3-(6-(4-(((1-(2-(1-(3-(2,4-dioxotetrahydropyrimidin-1(2H)-yl)-4-fluorobenzoyl) piperidin-4-yl)ethyl)piperidin-4-yl)oxy)methyl)phenyl)-7H-pyrrolo[2,3-d]pyrimidin-4-yl)-5-fluoro-2-methylphenyl)-2-fluoro-4-(2-hydroxypropan-2-yl)benzamide A mixture of 2-fluoro-N-(5-fluoro-2-methyl-3-(6-(4-((1-(2-(piperidin-4-yl)ethyl)piperidin-4-yloxy)methyl)phenyl)-7H-pyrrolo[2,3-d]pyrimidin-4-yl)phenyl)-4-(2-hydroxypropan-2-yl)benzamide (80 mg, 0.11 mmol), 3-(2,4-dioxotetrahydropyrimidin-1(2H)-yl)-4-fluorobenzoic acid (intermediate 9, 31 mg, 0.12 mmol), HATU (50 mg, 0.13 mmol), DIPEA (29 mg, 0.22 mmol) and DMF (2 ml) was stirred at RT for 2 h. The mixture was purified by reverse phase HPLC on a XBridge C18 column (21.2×250 mm, 10 μm) eluting with ACN in an aq. solution of ammonium hydrogencarbonate (0.1%) (from 5 to 95%), affording the title compound as a solid (53 mg).

Method D: Rt=1.319 min, [M+H]+=957.

¹H NMR (500 MHz, DMSO-d₆) δ 12.77 (s, 1H), 9.94 (s, 1H), 8.85 (s, 1H), 7.96 (d, J=8.2 Hz, 2H), 7.73 (t, J=8.0 Hz, 1H), 7.67-7.65 (dd, J=9.2 Hz, 1H), 7.49 (dd, J=7.6 Hz, 1H), 7.44-7.36 (m, 6H), 7.24 (dd, J=8.3, 2.6 Hz, 1H), 6.84 (s, 1H), 5.30 (s, 1H), 4.53 (s, 2H), 3.75 (t, J=6.6 Hz, 2H), 3.41-3.36 (m, 2H), 2.99-2.93 (m, 1H), 2.77-2.61 (m, 4H), 2.49-2.35 (m, 2H), 2.28-2.24 (m, 2H), 2.18 (s, 3H), 2.04-1.93 (m, 3H), 1.92-1.79 (m, 2H), 1.88-1.85 (m, 2H), 1.75-1.46 (m, 3H), 1.45 (s, 6H), 1.39-1.31 (m, 2H), 1.13-1.04 (m, 2H).

Compound 7

N-(3-(6-(4-((4-((1-(3-(2,4-Dioxotetrahydropyrimidin-1(2H)-yl)-4-methoxybenzoyl)piperidin-4-yl)methyl)piperazin-1-yl)methyl)phenyl)-7H-pyrrolo[2,3-d]pyrimidin-4-yl)-5-fluoro-2-methylphenyl)-2-fluoro-4-(2-hydroxypropan-2-yl)benzamide

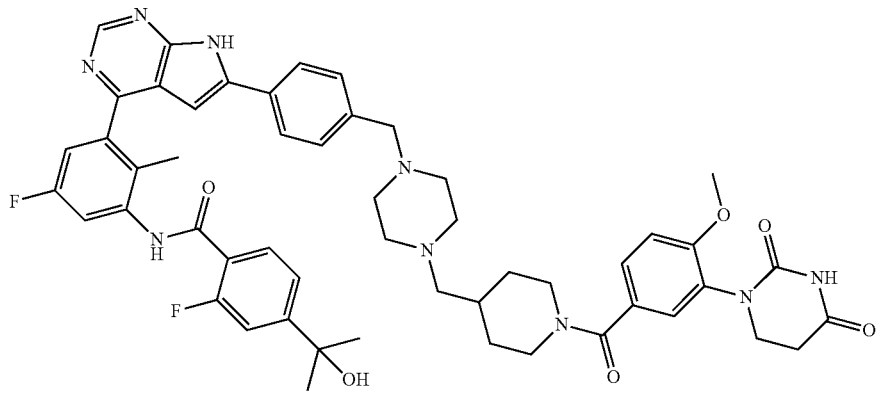 [SMILES: COc1ccc(C(=O)N2CCC(CN3CCN(Cc4ccc(-c5cc6c(-c7cc(F)cc(NC(=O)c8ccc(C(C)(C)O)cc8F)c7C)ncnc6[nH]5)cc4)CC3)CC2)cc1N1CCC(=O)NC1=O]

Step 1: tert-butyl 4-(piperazin-1-ylmethyl)piperidine-1-carboxylate

To a 100 ml round bottom flask was added tert-butyl 4-(bromomethyl)piperidine-1-carboxylate (1.0 g, 3.59 mmol), piperazine (3.1 g, 31.95 mmol) and ACN (20 ml). The RM was stirred at 80° C. for 16 h. The mixture was concentrated and the residue was purified by chromatography on silica gel eluting with MeOH in DCM (from 0 to 10%) to afford the title compound as a solid (400 mg).

Method G: Rt=1.56 min; MS m/z [M+H]+ 284.

Step 2: tert-butyl 4-((4-(4-(4-(5-fluoro-3-(2-fluoro-4-(2-hydroxypropan-2-yl)benzamido)-2-methylphenyl)-7H-pyrrolo[2,3-d]pyrimidin-6-yl)benzyl)piperazin-1-yl)methyl) piperidine-1-carboxylate To a 25 ml round bottom flask was added tert-butyl 4-(piperazin-1-ylmethyl)piperidine-1-carboxylate (400 mg, 1.41 mmol), K₂CO₃ (585 mg, 4.23 mmol), and DMSO (5 ml) and the RM was stirred at RT for 30 min. A solution of ZnCl₂ (1.0 M) in THF (1.55 ml, 1.55 mmol) and 2-fluoro-N-(5-fluoro-3-(6-(4-formylphenyl)-7H-pyrrolo[2,3-d]pyrimidin-4-yl)-2-methylphenyl)-4-(2-hydroxypropan-2-yl)benzamide (intermediate 3, 743 mg, 1.41 mmol) were added. The RM was stirred at RT for 30 min., solid NaBH₃CN (266 mg, 4.23 mmol) and MeOH (5 ml) were added and the RM was stirred at RT for 16 h. The mixture was concentrated and the residue was purified by chromatography on an Agela C18 column (spherical 20-35 μm, 100 Å, 120 g) eluting with ACN in an aq. solution of ammonium hydrogencarbonate (10 mM) yielding the title compound as a solid (500 mg).

Method G: Rt=2.44 min; MS m/z [M+H]+ 794.

Step 3: 2-fluoro-N-(5-fluoro-2-methyl-3-(6-(4-((4-(piperidin-4-ylmethyl)piperazin-1-yl)methyl)phenyl)-7H-pyrrolo[2,3-d]pyrimidin-4-yl)phenyl)-4-(2-hydroxypropan-2-yl)benzamide Hydrochloride To a 25 ml round bottom flask was added tert-butyl 4-((4-(4-(4-(5-fluoro-3-(2-fluoro-4-(2-hydroxypropan-2-yl)benzamido)-2-methylphenyl)-7H-pyrrolo[2,3-d]pyrimidin-6-yl)benzyl)piperazin-1-yl)methyl)piperidine-1-carboxylate (150 mg, 0.19 mmol) in DCM (3 ml). A solution of HCl (4 M) in 1,4-dioxane (3.0 ml, 12.0 mmol) was slowly added. The RM was stirred at RT for 3 h, concentrated and the residue was directly used for the next step without further purification. The title compound was obtained as a solid HCl salt (138 mg).

Method G: Rt=1.98 min; MS m/z [M+H]+ 694.

Step 4: N-(3-(6-(4-((4-((1-(3-(2,4-dioxotetrahydropyrimidin-1(2H)-yl)-4-methoxybenzoyl)piperidin-4-yl)methyl)piperazin-1-yl)methyl)phenyl)-7H-pyrrolo[2,3-d]pyrimidin-4-yl)-5-fluoro-2-methylphenyl)-2-fluoro-4-(2-hydroxypropan-2-yl)benzamide To a 25 ml round bottom flask were added 2-fluoro-N-(5-fluoro-2-methyl-3-(6-(4-((4-(piperidin-4-ylmethyl)piperazin-1-yl)methyl)phenyl)-7H-pyrrolo[2,3-d]pyrimidin-4-yl)phenyl)-4-(2-hydroxypropan-2-yl)benzamide hydrochloride (138 mg, 0.19 mmol), 3-(2,4-dioxotetrahydropyrimidin-1 (2H)-yl)-4-methoxybenzoic acid (intermediate 5, 55 mg, 0.21 mmol), DIPEA (123 mg, 0.95 mmol) and DMF (3 ml). Then HATU (86 mg, 0.23 mmol) was added and the RM was stirred at RT for 2 h. The mixture was concentrated and the residue was purified by preparative HPLC on a XBridge C18 column (21.2*250 mm, 10 μm) eluting with ACN in an aq. solution of ammonium hydrogencarbonate (10 mM), yielding the title compound as a solid (65 mg).

Method J: Rt=1.76 min; MS m/z [M+H]+ 940.

¹H NMR (500 MHz, DMSO-d₆) δ 12.77 (s, 1H), 10.34 (s, 1H), 9.96 (s, 1H), 8.84 (s, 1H), 7.94 (d, J=8.2 Hz, 2H), 7.81-7.58 (m, 2H), 7.46-7.33 (m, 5H), 7.31 (d, J=2.1 Hz, 1H), 7.24 (dd, J=8.8, 2.7 Hz, 1H), 7.15 (dd, J=8.6 Hz, 2.6 Hz, 1H), 6.83 (s, 1H), 5.31 (s, 1H), 3.84 (s, 3H), 3.59 (t, J=6.6 Hz, 2H), 3.49 (s, 2H), 3.20-2.70 (m, 4H), 2.68 (m, 2H), 2.48-2.36 (m, 8H), 2.22-2.10 (m, 5H), 1.82-1.61 (m, 3H), 1.45 (s, 6H), 1.04 (m, 2H).

Compound 8

N-(3-(6-(4-((4-((1-(3-(2,4-dioxotetrahydropyrimidin-1(2H)-yl)-4-methoxybenzoyl)piperidin-4-yl)oxy)piperidin-1-yl)methyl)phenyl)-7H-pyrrolo[2,3-d]pyrimidin-4-yl)-5-fluoro-2-methylphenyl)-2-fluoro-4-(2-hydroxypropan-2-yl)benzamide

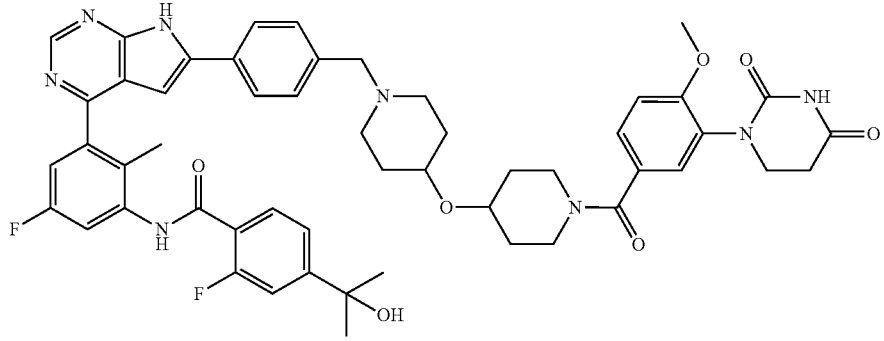 [SMILES: COc1ccc(C(=O)N2CCC(OC3CCN(Cc4ccc(-c5cc6c(-c7cc(F)cc(NC(=O)c8ccc(C(C)(C)O)cc8F)c7C)ncnc6[nH]5)cc4)CC3)CC2)cc1N1CCC(=O)NC1=O]

Step 1: tert-butyl 4-(1-(4-(4-(5-fluoro-3-(2-fluoro-4-(2-hydroxypropan-2-yl)benzamido)-2-methylphenyl)-7H-pyrrolo[2,3-d]pyrimidin-6-yl)benzyl)piperidin-4-yloxy)piperidine-1-carboxylate To a 100 ml round bottom flask was added 2-fluoro-N-(5-fluoro-3-(6-(4-formylphenyl)-7H-pyrrolo[2,3-d]pyrimidin-4-yl)-2-methylphenyl)-4-(2-hydroxypropan-2-yl)benzamide (intermediate 3, 4.35 g, 8.26 mmol) and tert-butyl 4-(piperidin-4-yloxy)piperidine-1-carboxylate (intermediate 10, 2.35 g, 9.09 mmol) and DMSO (30 ml). A solution of $ZnCl_2$ (1 M) in THF (9.1 ml, 9.1 mmol) was added and the mixture was stirred at RT for 45 min. Solid $NaBH_3CN$ (1.56 g, 24.8 mmol) was added and the mixture was stirred at RT for 30 minutes. MeOH (20 ml) was added and stirring was continued for 16 h. The mixture was concentrated and the residue was purified by chromatography on an Agela C18 column (spherical 20-35 μm, 100 Å, 120 g) eluting with ACN in an aq. solution of ammonium hydrogen carbonate (10 mM), yielding the title compound as a solid (4.0 g).
Method E: Rt=1.58 min; MS m/z [M+H]+ 795.

Step 2: 2-fluoro-N-(5-fluoro-2-methyl-3-(6-(4-((4-(piperidin-4-yloxy)piperidin-1-yl)methyl)phenyl)-7H-pyrrolo[2,3-d]pyrimidin-4-yl)phenyl)-4-(2-hydroxypropan-2-yl)benzamide To a 50 ml round bottom flask was added tert-butyl 4-(1-(4-(4-(5-fluoro-3-(2-fluoro-4-(2-hydroxypropan-2-yl)benzamido)-2-methylphenyl)-7H-pyrrolo[2,3-d]pyrimidin-6-yl)benzyl)piperidin-4-yloxy)piperidine-1-carboxylate (4.5 g, 5.66 mmol), 1,4-dioxane (20 ml) and MeOH (2 ml). A solution of HCl (4 M) in 1,4-dioxane (4 ml, 16 mmol) was slowly added. The mixture was stirred at RT for 1 h and then concentrated to obtain the title compound as a solid HCl salt (5.0 g). This material was used in next step without further purification.
Method F: Rt=1.27 min; MS m/z [M+H]+ 695.

Step 3: N-(3-(6-(4-((4-(1-(3-(2,4-dioxotetrahydropyrimidin-1(2H)-yl)-4-methoxybenzoyl)piperidin-4-yloxy)piperidin-1-yl)methyl)phenyl)-7H-pyrrolo[2,3-d]pyrimidin-4-yl)-5-fluoro-2-methylphenyl)-2-fluoro-4-(2-hydroxypropan-2-yl)benzamide To a 100 ml round bottom flask was added 3-(2,4-dioxotetrahydropyrimidin-1(2H)-yl)-4-methoxybenzoic acid (intermediate 5, 1.6 g, 6.23 mmol), DMF (25 ml) and HATU (2.58 g, 6.79 mmol). The RM was stirred at RT for 0.5 h. 2-Fluoro-N-(5-fluoro-2-methyl-3-(6-(4-((4-(piperidin-4-yloxy)piperidin-1-yl)methyl)phenyl)-7H-pyrrolo[2,3-d]pyrimidin-4-yl)phenyl)-4-(2-hydroxypropan-2-yl)benzamide hydrochloride (5 g, 6.84 mmol) and DIPEA (2.19 g, 16.98 mmol) were added, the mixture was stirred at RT for 3 h and the mixture was purified by chromatography on an Agela C18 column (spherical 20-35 μm, 100 Å, 120 g) eluting with ACN in an aq. solution of ammonium hydrogencarbonate (10 mM), yielding the title compound as a solid (4.17 g).
Method J: Rt=1.78 min; MS m/z [M+H]+ 941.
$^1$H NMR (500 MHz, DMSO-$d_6$) δ 12.77 (s, 1H), 10.34 (s, 1H), 9.95 (s, 1H), 8.85 (s, 1H), 7.94 (d, J=7.5 Hz, 2H), 7.73 (t, J=7.9 Hz, 1H), 7.66 (d, J=9.1 Hz, 1H), 7.47-7.31 (m, 6H), 7.24 (dd, J=8.8, 2.7 Hz, 1H), 7.15 (d, J=8.6 Hz, 1H), 6.83 (s, 1H), 5.31 (s, 1H), 3.84 (s, 3H), 3.74-3.38 (m, 8H), 3.20 (t, J=9.7 Hz, 2H), 2.68-2.57 (m, 4H), 2.18 (s, 3H), 2.18-2.05 (m, 2H), 1.84-1.74 (m, 4H), 1.49-1.40 (m, 10H).

Compound 9

N-(3-(6-(4-((9-(3-(2,4-Dioxotetrahydropyrimidin-1(2H)-yl)-4-methoxybenzoyl)-3,9-diazaspiro[5.5]undecan-3-yl)methyl)phenyl)-7H-pyrrolo[2,3-d]pyrimidin-4-yl)-5-fluoro-2-methylphenyl)-2-fluoro-4-(2-hydroxypropan-2-yl)benzamide

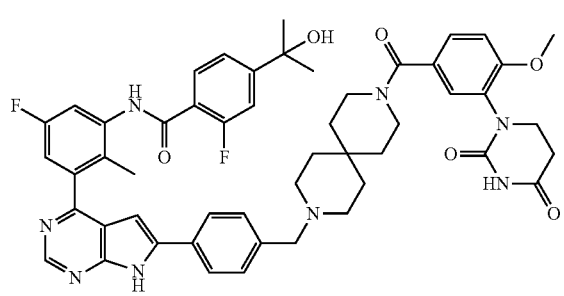 [SMILES: COc1ccc(C(=O)N2CCC3(CCN(Cc4ccc(-c5cc6c(-c7cc(F)cc(NC(=O)c8ccc(C(C)(C)O)cc8F)c7C)ncnc6[nH]5)cc4)CC3)CC2)cc1N1CCC(=O)NC1=O]

To a solution of N-(3-(6-(4-(3,9-diazaspiro[5.5]undecan-3-ylmethyl)phenyl)-7H-pyrrolo[2,3-d]pyrimidin-4-yl)-5-fluoro-2-methylphenyl)-2-fluoro-4-(2-hydroxypropan-2-yl)benzamide (intermediate 11, 50 mg, 0.068 mmol), 3-(2,4-dioxotetrahydropyrimidin-1(2H)-yl)-4-methoxybenzoic acid (intermediate 5, 17.91 mg, 0.068 mmol) and HBTU (30.8 mg, 0.081 mmol) in DMF (3 ml) was added DIPEA (0.071 ml, 0.407 mmol). The RM was stirred for 2 h at RT under argon, water was added and the resulting suspension was filtered, the solids were washed with water, dried and purified by SFC on a Princeton PPU column (250×30 mm, 100 A, 5 μm) eluting with MeOH in CO₂ (from 30 to 45%) to afford the title compound (15 mg).

Method B: Rt=3.67 min, [M+H]+=911.6.

¹H NMR (400 MHz, DMSO-d₆) δ 12.74 (s, 1H), 10.31 (s, 1H), 9.93 (d, J=2.6 Hz, 1H), 8.85 (s, 1H), 7.94 (d, J=8.2 Hz, 2H), 7.74 (t, J=7.9 Hz, 1H), 7.66 (m, 1H), 7.47-7.34 (m, 5H), 7.32 (d, J=2.1 Hz, 1H), 7.24 (dd, J=8.8, 2.8 Hz, 1H), 7.15 (d, J=8.6 Hz, 1H), 6.82 (s, 1H), 5.29 (s, 1H), 3.85 (s, 3H), 3.60 (t, J=6.6 Hz, 2H), 3.55-3.25 (m, 6H), 2.68 (t, J=6.4 Hz, 2H), 2.42-2.28 (m, 4H), 2.18 (s, 3H), 1.6-1.35 (m, 8H), 1.46 (s, 6H).

Compound 10

N-(3-(6-(4-(2-(4-((1-(3-(2,4-Dioxotetrahydropyrimidin-1(2H)-yl)-4-methylbenzoyl)piperidin-4-yl)oxy)piperidin-1-yl)ethyl)phenyl)-7H-pyrrolo[2,3-d]pyrimidin-4-yl)-5-fluoro-2-methylphenyl)-2-fluoro-4-(2-hydroxypropan-2-yl)benzamide Step 1: tert-butyl 4-((1-(4-(4-(5-fluoro-3-(2-fluoro-4-(2-hydroxypropan-2-yl)benzamido)-2-methylphenyl)-7H-pyrrolo[2,3-d]pyrimidin-6-yl)phenethyl)piperidin-4-yl)oxy)piperidine-1-carboxylate To a mixture of 4-(4-(5-fluoro-3-(2-fluoro-4-(2-hydroxypropan-2-yl)benzamido)-2-methylphenyl)-7H-pyrrolo[2,3-d]pyrimidin-6-yl)phenethyl methanesulfonate (intermediate 13, 334 mg, 0.538 mmol) and tert-butyl 4-(piperidin-4-yloxy)piperidine-1-carboxylate (intermediate 10, 306 mg, 1.076 mmol) in a mixture of ACN and DMF (4:1) (13.5 ml) at RT flushed with N₂ was added K₂CO₃ (446 mg, 3.23 mmol). The resulting RM was stirred at 50° C. for 3 days. The RM was cooled under stirring in an ice-water bath and slowly acidified with TFA until the mixture reached a pH between 3 and 4. The resulting mixture was allowed to warm to RT, partially concentrated, adsorbed on Isolute® and purified by reverse phase chromatography on a Redisep® C18 column eluting with ACN in an aq. solution of TFA (0.1%) to afford the title compound as a TFA salt (225 mg).

Method A: Rt=0.99 min; [M+H]+=809.6.

Step 2: 2-fluoro-N-(5-fluoro-2-methyl-3-(6-(4-(2-(4-(piperidin-4-yloxy)piperidin-1-yl)ethyl)phenyl)-7H-pyrrolo[2,3-d]pyrimidin-4-yl)phenyl)-4-(2-hydroxypropan-2-yl)benzamide To a solution of tert-butyl 4-((1-(4-(4-(5-fluoro-3-(2-fluoro-4-(2-hydroxypropan-2-yl)benzamido)-2-methylphenyl)-7H-pyrrolo[2,3-d]pyrimidin-6-yl)phenethyl)piperidin-4-yl)oxy)piperidine-1-carboxylate (223 mg, 0.194 mmol) in DCM (3.7 ml) at RT was added TFA (0.447 ml, 5.81 mmol). The resulting solution was stirred at RT for 1 h, diluted with a mixture of DCM and ACN, concentrated and dried to afford a resin. The resin was redissolved in a mixture of ACN and water and freeze dried to afford the title compound as a solid TFA salt (225 mg).

Method A: Rt=0.67 min; [M+H]+=709.5.

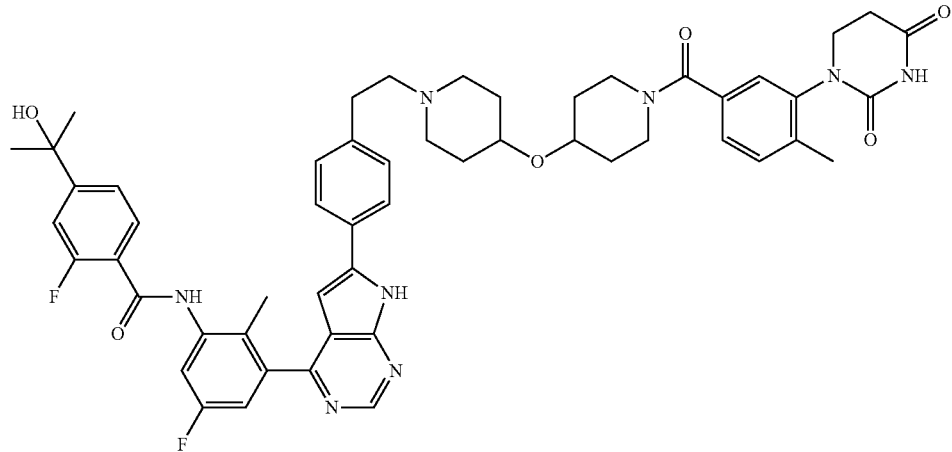 [SMILES: Cc1ccc(C(=O)N2CCC(OC3CCN(CCc4ccc(-c5cc6c(-c7cc(F)cc(NC(=O)c8ccc(C(C)(C)O)cc8F)c7C)ncnc6[nH]5)cc4)CC3)CC2)cc1N1CCC(=O)NC1=O]

Step 3: N-(3-(6-(4-(2-(4-((1-(3-(2,4-dioxotetrahydropyrimidin-1(2H)-yl)-4-methylbenzoyl)piperidin-4-yl)oxy)piperidin-1-yl)ethyl)phenyl)-7H-pyrrolo[2,3-d]pyrimidin-4-yl)-5-fluoro-2-methylphenyl)-2-fluoro-4-(2-hydroxypropan-2-yl)benzamide To a mixture of 2-fluoro-N-(5-fluoro-2-methyl-3-(6-(4-(2-(4-(piperidin-4-yloxy)piperidin-1-yl)ethyl)phenyl)-7H-pyrrolo[2,3-d]pyrimidin-4-yl)phenyl)-4-(2-hydroxypropan-2-yl)benzamide (120 mg, 0.114 mmol), 3-(2,4-dioxotetrahydropyrimidin-1(2H)-yl)-4-methylbenzoic acid (intermediate 8, 29.8 mg, 0.120 mmol) and HBTU (46.4 mg, 0.120 mmol) in dry DMF (2.25 ml) flushed with N₂ was slowly added DIPEA (140 μl, 0.799 mmol). The resulting solution was stirred at RT for 1.5 h, then diluted with ACN, adsorbed on Isolute® and purified by reverse phase chromatography on a Redisep® C18 column eluting with ACN in an aq. solution of TFA (0.1%) (from 10 to 100%) to afford, after filtration of the fractions containing the pure target compound through PL-HCO₃ MP SPE cartridges and freeze drying, the title compound as a solid (66 mg).

Method B: Rt=3.85 min, [M+H]⁺=939.6.

$^1$H NMR (400 MHz, DMSO-d$_6$) δ 12.70 (s, 1H), 10.36 (s, 1H), 9.91 (s, 1H), 8.76 (s, 1H), 7.89 (d, J=8.07 Hz, 2H), 7.73 (t, J=7.89 Hz, 1H), 7.63 (d, J=9.05 Hz, 1H), 7.37-7.46 (m, 2H), 7.31-7.36 (m, 2H), 7.16-7.31 (m, 4H), 6.73 (s, 1H), 5.29 (s, 1H), 3.96 (m, 1H), 3.81 (m, 1H), 3.68 (m, 1H), 3.38-3.59 (m, 3H), 3.20 (m, 2H), 2.69-2.83 (m, 6H), 2.52-2.55 (m, 2H), 2.21 (s, 3H), 2.17 (s, 3H), 2.11 (t, J=10.15 Hz, 2H), 1.62-1.94 (m, 4H), 1.32-1.51 (m, 10H).

Compound 11

N-(3-(6-(4-(3-(9-(3-(2,4-Dioxotetrahydropyrimidin-1(2H)-yl)-4-methoxybenzoyl)-3,9-diazaspiro[5.5]undecan-3-yl)propyl)phenyl)-7H-pyrrolo[2,3-d]pyrimidin-4-yl)-5-fluoro-2-methylphenyl)-2-fluoro-4-(2-hydroxypropan-2-yl)benzamide

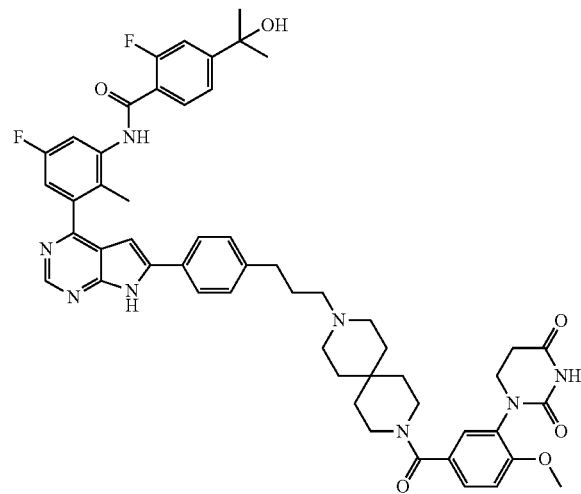 [SMILES: COc1ccc(C(=O)N2CCC3(CCN(CCCc4ccc(-c5cc6c(-c7cc(F)cc(NC(=O)c8ccc(C(C)(C)O)cc8F)c7C)ncnc6[nH]5)cc4)CC3)CC2)cc1N1CCC(=O)NC1=O]

Step 1: 3-(4-(4-chloro-7H-pyrrolo[2,3-d]pyrimidin-6-yl)phenyl)propan-1-ol 4-(3-Hydroxypropyl)benzeneboronic acid (2.511 g, 13.95 mmol) and 4-chloro-6-iodo-7H-pyrrolo[2,3-d]pyrimidine (3.44 g, 12.31 mmol) were dissolved in 1-propanol (100 ml) at RT and an aq. solution of Na₂CO₃ (2 M) (13.54 ml, 27.1 mmol) was added. Argon was bubbled through the mixture for 5 min and PdCl₂(PPh₃)₂ (0.432 g, 0.615 mmol) was added. The RM was stirred at 105° C. for 22 h and then allowed to cool to RT overnight. The solvent was removed and the residue was sonicated in a mixture of water and THF (3:2). The mixture was filtered, the solids were washed with water and dried to afford the title compound as a solid (2.4 g).

Method A: Rt=0.86 min; [M+H]⁺=288.2.

Step 2: 2-fluoro-N-(5-fluoro-3-(6-(4-(3-hydroxypropyl)phenyl)-7H-pyrrolo[2,3-d]pyrimidin-4-yl)-2-methylphenyl)-4-(2-hydroxypropan-2-yl)benzamide 3-(4-(4-Chloro-7H-pyrrolo[2,3-d]pyrimidin-6-yl)phenyl)propan-1-ol (1.5 g, 4.85 mmol) and 2-fluoro-N-(5-fluoro-2-methyl-3-(4,4,5,5-tetramethyl-1,3,2-dioxaborolan-2-yl)phenyl)-4-(2-hydroxypropan-2-yl)benzamide (intermediate 2, 2.1 g, 4.87 mmol) were suspended in 1-propanol (36 ml) at RT and an aq. solution of Na₂CO₃ (2 M) (5.1 ml, 10.20 mmol) was added. Argon was bubbled through the mixture for 1 min and PdCl₂(PPh₃)₂ (0.180 g, 0.256 mmol) was added. The RM was heated at 140° C. for 20 min. using microwave radiation. The RM was diluted with EtOAc and filtered over Hyflo®. The filtrate was evaporated, rediluted with a mixture of THF and H₂O (1:1) and extracted with EtOAc. The combined organic phases were dried over MgSO₄ and evaporated. The residue was triturated in a mixture of DCM and MeOH, filtered, the solids were washed with DCM and dried to afford the title compound as a solid (1.696 g).

Method A: Rt=0.95 min; [M+H]⁺=557.4.

Step 3: 3-(4-(4-(5-fluoro-3-(2-fluoro-4-(2-hydroxypropan-2-yl)benzamido)-2-methylphenyl)-7H-pyrrolo[2,3-d]pyrimidin-6-yl)phenyl)propyl methanesulfonate 2-Fluoro-N-(5-fluoro-3-(6-(4-(3-hydroxypropyl)phenyl)-7H-pyrrolo[2,3-d]pyrimidin-4-yl)-2-methylphenyl)-4-(2-hydroxypropan-2-yl)benzamide (1032 mg, 1.539 mmol) was dissolved in dry THF (16 ml) at RT under argon and TEA (0.858 ml, 6.16 mmol) was added. The mixture was cooled to 0° C., Ms₂O (536 mg, 3.08 mmol) was added and the RM was stirred at 0° C. for 40 min. The RM was quenched with ice water, extracted with DCM, the combined organic phases were dried over MgSO₄ and concentrated to afford the title compound as a solid (1.33 g).

Method A: Rt=1.03 min; [M+H]⁺=635.3.

Step 4: Tert-butyl 9-(3-(4-(4-(5-fluoro-3-(2-fluoro-4-(2-hydroxypropan-2-yl)benzamido)-2-methylphenyl)-7H-pyrrolo[2,3-d]pyrimidin-6-yl)phenyl)propyl)-3,9-diazaspiro[5.5]undecane-3-carboxylate 3-(4-(4-(5-Fluoro-3-(2-fluoro-4-(2-hydroxypropan-2-yl)benzamido)-2-methylphenyl)-7H-pyrrolo[2,3-d]pyrimidin-6-yl)phenyl)propyl methanesulfonate (0.977 g, 1.539 mmol) was dissolved in a mixture of dry DMF (4 ml) and ACN (16 ml) at RT under argon. K₂CO₃ (1.063 g, 7.70 mmol) and 3,9-diaza-spiro[5.5]undecane-3-carboxylic acid tert-butyl ester (0.783 g, 3.08 mmol) were added and the RM was stirred at 60° C. for 13.5 h. The mixture was evaporated to dryness, the resulting residue was taken up in a mixture of EtOAc and water and the phases were separated. The aq. layer was extracted with EtOAc and the combined organic phases were washed with an aq. solution of lithium bromide, a mixture of brine and water (1:1) and with brine, dried over MgSO₄, concentrated and dried to afford the title compound as a solid (1.76 g).

Method A: Rt=1.00 min; [M+H]⁺=793.5.

Step 5: N-(3-(6-(4-(3-(3,9-diazaspiro[5.5]undecan-3-yl)propyl)phenyl)-7H-pyrrolo[2,3-d]pyrimidin-4-yl)-5-fluoro-2-methylphenyl)-2-fluoro-4-(2-hydroxypropan-2-yl)benzamide A solution of tert-butyl 9-(3-(4-(4-(5-fluoro-3-(2-fluoro-4-(2-hydroxypropan-2-yl)benzamido)-2-methylphenyl)-7H-pyrrolo[2,3-d]pyrimidin-6-yl)phenyl)propyl)-3,9-diazaspiro[5.5]undecane-3-carboxylate (1.545 g, 1.539 mmol) in DCM (10 ml) and TFA (4 ml, 51.9 mmol) was stirred for 30 min at RT, the mixture was evaporated and adsorbed on Isolute® HM-N and purified by reverse phase chromatography on a Redisep® C18 column eluting with ACN in an aq. solution of TFA (0.1%) (from 5 to 100%) to afford the title compound as a solid TFA salt (1.337 g).
Method A: Rt=0.75 min; [M+H]⁺=693.5.

Step 6: N-(3-(6-(4-(3-(9-(3-(2,4-dioxotetrahydropyrimidin-1(2H)-yl)-4-methoxybenzoyl)-3,9-diazaspiro[5.5]undecan-3-yl)propyl)phenyl)-7H-pyrrolo[2,3-d]pyrimidin-4-yl)-5-fluoro-2-methylphenyl)-2-fluoro-4-(2-hydroxypropan-2-yl)benzamide N-(3-(6-(4-(3-(3,9-Diazaspiro[5.5]undecan-3-yl)propyl)phenyl)-7H-pyrrolo[2,3-d]pyrimidin-4-yl)-5-fluoro-2-methylphenyl)-2-fluoro-4-(2-hydroxypropan-2-yl)benzamide trifluoroacetate (200 mg, 0.193 mmol) was dissolved in dry DMF (3 ml) at RT under argon, DIPEA (0.270 ml, 1.546 mmol) and 3-(2,4-dioxotetrahydropyrimidin-1(2H)-yl)-4-methoxybenzoic acid (intermediate 5, 58 mg, 0.220 mmol) were added, followed by HBTU (86 mg, 0.227 mmol). The RM was stirred for 20 min at RT, diluted with ACN, adsorbed and dried on Isolute® HM-N and purified by reverse phase chromatography on a Redisep® C18 column eluting with ACN in an aq. solution of TFA (0.1%) (from 5 to 100%) to afford the compound as a TFA salt. Filtration over PL-HCO3 MP SPE cartridges followed by freeze drying afforded the title compound as a solid TFA salt (100 mg).
¹H NMR (400 MHz, DMSO-d₆) δ 12.76 (s, 1H), 10.33 (s, 1H), 9.95 (s, 1H), 9.0-9.25 (m, 1H), 8.85 (s, 1H), 7.95 (d, J=8.1 Hz, 2H), 7.73 (t, J=7.9 Hz, 1H), 7.65 (d, J=10.0 Hz, 1H), 7.48-7.28 (m, 6H), 7.25-7.21 (m, 1H), 7.16 (d, J=8.6 Hz, 1H), 6.84 (s, 1H), 5.30 (s, 1H), 3.84 (s, 3H), 3.6-3.3 (m, 7H), 3.2-2.9 (m, 4H), 2.75-2.6 (m, 4H), 2.17 (s, 3H), 2.1-1.9 (m, 2H), 1.9-1.8 (m, 2H), 1.7-1.25 (m, 12H).
Method B: Rt=3.91 min [M+H]⁺=939.7.

Compound 12

N-(3-(6-(4-(2-(9-(3-(2,4-Dioxotetrahydropyrimidin-1(2H)-yl)benzoyl)-3,9-diazaspiro[5.5]undecan-3-yl)ethyl)phenyl)-7H-pyrrolo[2,3-d]pyrimidin-4-yl)-5-fluoro-2-methylphenyl)-2-fluoro-4-(2-hydroxypropan-2-yl)benzamide Step 1: tert-butyl 9-(4-bromophenethyl)-3,9-diazaspiro[5.5]undecane-3-carboxylate To a 250 ml round bottom flask were added tert-butyl 3,9-diazaspiro[5.5]undecane-3-carboxylate (5 g, 19.7 mmol), K₂CO₃ (4.07 g, 29.5 mmol) and 1-bromo-4-(2-bromoethyl)benzene (5.2 g, 17.6 mmol) in ACN (50 ml). The RM was stirred at RT for 16 h under N₂, concentrated and rediluted in a mixture of water and DCM. The phases were separated, the aq. phase was extracted with DCM, the combined organic phases were concentrated and purified by chromatography on silica gel eluting with MeOH in DCM (1:100) yielding the title compound as a solid (4.8 g).
Method F: Rt=1.91 min; MS m/z [M+H]⁺ 438.1.

Step 2: tert-butyl 9-(4-(4,4,5,5-tetramethyl-1,3,2-dioxaborolan-2-yl)phenethyl)-3,9-diazaspiro[5.5]undecane-3-carboxylate To a 250 ml round bottom flask were added tert-butyl 9-(4-bromophenethyl)-3,9-diazaspiro[5.5]undecane-3-carboxylate (4.8 g, 11 mmol), BISPIN (3.4 g, 13.2 mmol), KOAc (2.2 g, 22 mmol), PdCl₂(dpp) (0.8 g, 1.1 mmol) and DMSO (60 ml). The RM was stirred at 80° C. for 16 h, diluted with water and extracted with EtOAc. The combined organic phases were washed with water and brine, concentrated and purified by chromatography on silica gel eluting with EtOAc in petroleum ether (from 0 to 100%) yielding the title compound as a solid (4.0 g).
Method E: Rt=1.67 min; MS m/z [M+H]⁺ 485.

Step 3: tert-butyl 9-(4-(4-chloro-7-(phenylsulfonyl)-7H-pyrrolo[2,3-d]pyrimidin-6-yl)phenethyl)-3,9-diazaspiro[5.5]undecane-3-carboxylate To a 25 ml round bottom flask were added tert-butyl 9-(4-(4,4,5,5-tetramethyl-1,3,2-dioxaborolan-2-yl)phenethyl)-3,9-diazaspiro[5.5]undecane-3-carboxylate (889 mg, 1.83 mmol), 4-chloro-6-iodo-7-(phenylsulfonyl)-7H-pyrrolo[2,3-d]pyrimidine (intermediate 7, 700 mg, 1.67 mmol), Na₂CO₃ (354 mg, 3.34 mmol) and PdCl₂(dpp) (124 mg, 0.17 mmol). ACN (10 ml) and water (2 ml) were added and the RM was stirred at 80° C. for 16 h under N₂. The RM was diluted with EtOAc, filtered, the filtrate was concentrated and purified by chromatography on silica gel eluting with

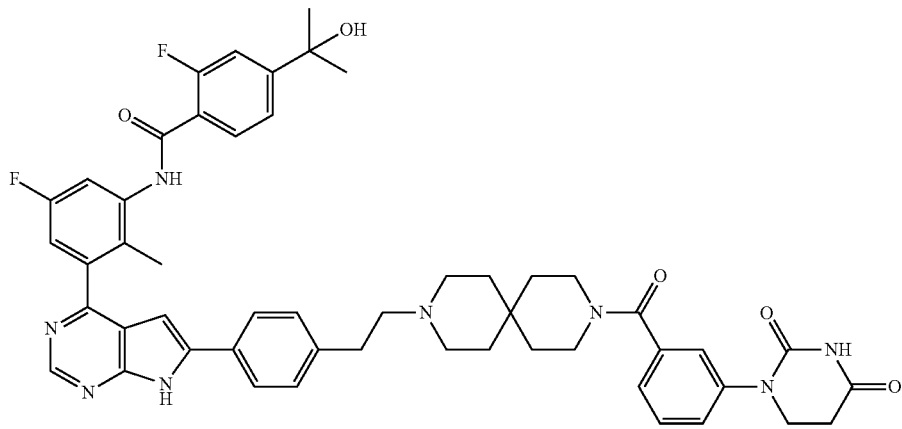 [SMILES: Cc1c(NC(=O)c2ccc(C(C)(C)O)cc2F)cc(F)cc1-c1ncnc2[nH]c(-c3ccc(CCN4CCC5(CC4)CCN(C(=O)c4cccc(N6CCC(=O)NC6=O)c4)CC5)cc3)cc12]

EtOAc in petroleum ether (from 0 to 100%) yielding the title compound as an oil (600 mg).

Method F: Rt=1.85 min: MS m/z [M+H]$^+$ 650.

Step 4: tert-butyl 9-(4-(4-(5-fluoro-3-(2-fluoro-4-(2-hydroxypropan-2-yl)benzamido)-2-methylphenyl)-7-(phenylsulfonyl)-7H-pyrrolo[2,3-d]pyrimidin-6-yl)phenethyl)-3,9-diazaspiro[5.5]undecane-3-carboxylate To a 25 ml round bottom flask were added tert-butyl 9-(4-(4-chloro-7-(phenylsulfonyl)-7H-pyrrolo[2,3-d]pyrimidin-6-yl)phenethyl)-3,9-diazaspiro[5.5]undecane-3-carboxylate (400 mg, 0.62 mmol), 2-fluoro-N-(5-fluoro-2-methyl-3-(4,4,5,5-tetramethyl-1,3,2-dioxaborolan-2-yl)phenyl)-4-(2-hydroxypropan-2-yl)benzamide (intermediate 2, 265 mg, 0.62 mmol), Na$_2$CO$_3$ (130 mg, 1.23 mmol) and PdCl$_2$(dppf) (44 mg, 0.06 mmol). ACN (10 ml) and water (2 ml) were added and the RM was stirred at 80° C. for 16 h under N$_2$. The RM was diluted with EtOAc, filtered, the filtrate was concentrated and purified by chromatography on silica gel eluting with EtOAc in petroleum ether (from 0 to 100%) yielding the title compound as a solid (200 mg).

Method E: Rt=1.74 min; MS m/z [M+H]$^+$ 919.

Step 5: tert-butyl 9-(4-(4-(5-fluoro-3-(2-fluoro-4-(2-hydroxypropan-2-yl)benzamido)-2-methylphenyl)-7H-pyrrolo[2,3-d]pyrimidin-6-yl)phenethyl)-3,9-diazaspiro[5.5]undecane-3-carboxylate To a 10 ml round bottom flask were added tert-butyl 9-(4-(4-(5-fluoro-3-(2-fluoro-4-(2-hydroxypropan-2-yl)benzamido)-2-methylphenyl)-7-(phenylsulfonyl)-7H-pyrrolo[2,3-d]pyrimidin-6-yl)phenethyl)-3,9-diazaspiro[5.5]undecane-3-carboxylate (200 mg, 0.22 mmol) and DMSO (2 ml). A solution of NaOH (35 mg, 0.87 mmol) in water (1 ml) was added at RT, the RM was stirred for 1 h and then diluted with EtOAc. The phases were separated and the organic phase was washed with water and brine, dried and concentrated yielding the title compound as a solid (170 mg).

Method E: Rt=1.64 min; MS m/z [M+H]$^+$ 779.

Step 6: N-(3-(6-(4-(2-(3,9-diazaspiro[5.5]undecan-3-yl)ethyl)phenyl)-7H-pyrrolo[2,3-d]pyrimidin-4-yl)-5-fluoro-2-methylphenyl)-2-fluoro-4-(2-hydroxypropan-2-yl)benzamide To a 10 ml round bottom flask was added tert-butyl 9-(4-(4-(5-fluoro-3-(2-fluoro-4-(2-hydroxypropan-2-yl)benzamido)-2-methylphenyl)-7H-pyrrolo[2,3-d]pyrimidin-6-yl)phenethyl)-3,9-diazaspiro[5.5]undecane-3-carboxylate (160 mg, 0.21 mmol), EtOH (2 ml) and DCM (0.5 ml). A solution of HCl (6 N) in 1,4-dioxane (1.5 ml, 6 mmol) was added at 0° C., the RM was allowed to warm to RT and stirring was continued for 2 h. The RM was concentrated to afford the title compound as a solid HCl salt (130 mg).

Method E: Rt=1.45 min; MS m/z [M+H]$^+$ 679.

Step 7: 3-(2-carboxyethylamino)benzoic Acid

To a 500 ml round bottom flask were added 3-aminobenzoic acid (10 g, 72.92 mmol), acrylic acid (6.83 g, 94.79 mmol) and toluene (200 ml) and the RM was stirred at 120° C. for 48 h, allowed to cool to RT and filtered. The solids were washed with toluene and dried to obtain the title compound as a solid (14.0 g).

Method D: Rt=1.19 min; MS m/z [M+H]$^+$ 210.

Step 8: 3-(2,4-dioxotetrahydropyrimidin-1(2H)-yl)benzoic Acid

To a 50 ml round bottom flask were added 3-(2-carboxyethylamino)benzoic acid (2 g, 9.56 mmol), AcOH (25 ml) and urea (1.72 g, 28.68 mmol) and the RM was stirred at 120° C. for 16 h. The solvent was evaporated, water (20 ml) was added, the mixture was filtered and the solids were washed with water and dried to obtain a solid. The solid was redissolved in DMF, the mixture was stirred at RT for 2 h, filtered and the solids were washed with water and dried to afford the title compound as a solid (800 mg).

Method D: Rt=1.13 min; MS m/z [M+H]$^+$ 235.

$^1$H NMR (500 MHz, DMSO-d$_6$) δ 13.12 (s, 1H), 10.46 (s, 1H), 7.89 (s, 1H), 7.80 (d, J=7.6 Hz, 1H), 7.59 (d, J=8.6 Hz, 1H), 7.53 (t, J=7.8 Hz, 1H), 3.84 (t, J=6.6 Hz, 2H), 2.73 (t, J=6.6 Hz, 2H).

Step 9: N-(3-(6-(4-(2-(9-(3-(2,4-dioxotetrahydropyrimidin-1(2H)-yl)benzoyl)-3,9-diazaspiro[5.5]undecan-3-yl)ethyl)phenyl)-7H-pyrrolo[2,3-d]pyrimidin-4-yl)-5-fluoro-2-methylphenyl)-2-fluoro-4-(2-hydroxypropan-2-yl)benzamide To a 25 ml round bottom flask, containing a solution of N-(3-(6-(4-(2-(3,9-diazaspiro[5.5]undecan-3-yl)ethyl)phenyl)-7H-pyrrolo[2,3-d]pyrimidin-4-yl)-5-fluoro-2-methylphenyl)-2-fluoro-4-(2-hydroxypropan-2-yl)benzamide (137 mg, 0.182 mmol) and 3-(2,4-dioxotetrahydropyrimidin-1(2H)-yl)benzoic acid (43 mg, 0.182 mmol) in DMF (2.5 ml), were added DIPEA (141 mg, 1.09 mmol) and HATU (73 mg, 0.191 mmol) at 5° C. The RM was stirred at 25° C. for 1 h, filtered, the filtrate was concentrated and purified by preparative HPLC on a XBridge C18 column (250×21.2 mm, 10 μm) eluting with ACN in an aq. solution of ammonium hydrogen carbonate (10 mM), yielding the title compound as a solid (50 mg).

Method G: Rt=2.003 min, MS m/z [M+H]$^+$ 895.

$^1$H NMR (500 MHz, DMSO-d$_6$) δ 12.72 (s, 1H), 10.42 (s, 1H), 9.94 (s, 1H), 8.83 (s, 1H), 7.89 (d, J=8.1 Hz, 2H), 7.73 (t, J=7.6 Hz, 1H), 7.65 (d, J=10.7 Hz, 1H), 7.50-7.35 (m, 5H), 7.31 (d, J=8.2 Hz, 2H), 7.25-7.20 (m, 2H), 6.79 (s, 1H), 5.30 (s, 1H), 3.82 (t, J=6.7 Hz, 2H), 3.65-3.50 (m, 2H), 2.76 (t, J=7.6 Hz, 2H), 2.71 (t, J=6.6 Hz, 2H), 2.60-2.50 (m, 2H), 2.45-2.35 (m, 6H), 2.17 (s, 3H), 1.55-1.45 (m, 6H), 1.45 (s, 6H), 1.40-1.30 (m, 2H).

Compound 13

N-(3-(6-(4-(((1-(2-(1-(3-(2,4-Dioxotetrahydropyrimidin-1(2H)-yl)-4-methoxybenzoyl)piperidin-4-yl)ethyl)piperidin-4-yl)oxy)methyl)phenyl)-7H-pyrrolo[2,3-d]pyrimidin-4-yl)-5-fluoro-2-methylphenyl)-2-fluoro-4-(2-hydroxypropan-2-yl)benzamide

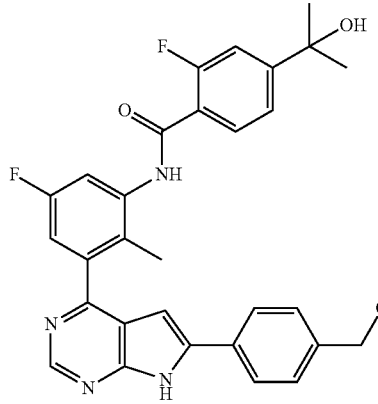
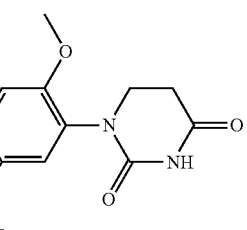

Step 1: tert-butyl 4-((4-(4-(5-fluoro-3-(2-fluoro-4-(2-hydroxypropan-2-yl)benzamido)-2-methylphenyl)-7H-pyrrolo[2,3-d]pyrimidin-6-yl)benzyl)oxy)piperidine-1-carboxylate To a mixture of tert-butyl 4-((4-(4-chloro-7H-pyrrolo[2,3-d]pyrimidin-6-yl)benzyl)oxy)piperidine-1-carboxylate (intermediate 14, 560 mg, 1.264 mmol), 2-fluoro-N-(5-fluoro-2-methyl-3-(4,4,5,5-tetramethyl-1,3,2-dioxaborolan-2-yl)phenyl)-4-(2-hydroxypropan-2-yl)benzamide (intermediate 2, 709 mg, 1.0644 mmol) and an aq. solution of $Na_2CO_3$ (2 M) (1.26 ml, 2.53 mmol) in 1-propanol (10 ml) was added $PdCl_2(PPh_3)_2$ (89 mg, 0.126 mmol). The resulting RM was heated at 140° C. using microwave radiation for 15 min. The mixture was filtered over Hyflo®, the filtrate was concentrated and purified by chromatography on silica eluting with EtOAc in CHX (from 0 to 95%) affording the title compound as a solid (526 mg).

Method A: Rt=1.29 min; $[M+H]^+$=712.5.

Step 2: 2-fluoro-N-(5-fluoro-2-methyl-3-(6-(4-((piperidin-4-yloxy)methyl)phenyl)-7H-pyrrolo[2,3-d]pyrimidin-4-yl)phenyl)-4-(2-hydroxypropan-2-yl)benzamide Tert-butyl 4-((4-(4-(5-fluoro-3-(2-fluoro-4-(2-hydroxypropan-2-yl)benzamido)-2-methylphenyl)-7H-pyrrolo[2,3-d]pyrimidin-6-yl)benzyl)oxy)piperidine-1-carboxylate (526 mg, 0.739 mmol) was dissolved in dry DCM (4 ml), TFA (1.708 ml, 22.17 mmol) was added and the resulting mixture was stirred for 2 h at RT. The RM was evaporated to dryness to afford the title compound as a TFA salt and as an oil (536 mg).

Method A: Rt=0.79 min; $[M+H]^+$=612.5.

Step 3: tert-butyl 4-(2-(4-((4-(4-(5-fluoro-3-(2-fluoro-4-(2-hydroxypropan-2-yl)benzamido)-2-methylphenyl)-7H-pyrrolo[2,3-d]pyrimidin-6-yl)benzyl)oxy)piperidin-1-yl)ethyl)piperidine-1-carboxylate To a mixture of 2-fluoro-N-(5-fluoro-2-methyl-3-(6-(4-((piperidin-4-yloxy)methyl)phenyl)-7H-pyrrolo[2,3-d]pyrimidin-4-yl)phenyl)-4-(2-hydroxypropan-2-yl)benzamide (536 mg, 0.739 mmol), tert-butyl (2-oxoethyl)carbamate (201 mg, 0.886 mmol) and TEA (0.309 ml, 2.216 mmol) in MeOH (5 ml) was added a solution of $ZnCl_2$ (0.5 M) in THF (1.625 ml, 0.812 mmol) and the RM was stirred at RT under argon for 3 h. Solid $NaBH_3CN$ (20.06 mg, 0.319 mmol) was added and the RM was stirred at RT overnight. The RM was diluted with EtOAc and the aq. phase was washed with an aq. solution of $NaHCO_3$ and brine. The organic phase was dried over $MgSO_4$, absorbed and dried on Isolute® and purified by reverse phase chromatography on a Redisep® C18 column eluting with ACN in an aq. solution of TFA (0.1%) to afford the title compound as a solid TFA salt (400 mg).

Method B: Rt=4.90 min; $[M+H]^+$=823.6.

Step 4: 2-fluoro-N-(5-fluoro-2-methyl-3-(6-(4-(((1-(2-(piperidin-4-yl)ethyl)piperidin-4-yl)oxy)methyl)phenyl)-7H-pyrrolo[2,3-d]pyrimidin-4-yl)phenyl)-4-(2-hydroxypropan-2-yl)benzamide A solution of tert-butyl 4-(2-(4-((4-(4-(5-fluoro-3-(2-fluoro-4-(2-hydroxypropan-2-yl)benzamido)-2-methylphenyl)-7H-pyrrolo[2,3-d]pyrimidin-6-yl)benzyl)oxy)piperidin-1-yl)ethyl)piperidine-1-carboxylate (400 mg, 0.427 mmol) in DCM (10 ml) and TFA (0.987 ml, 12.81 mmol) was stirred for 2 h at RT under argon. The RM was concentrated to afford the title compound as a solid TFA salt (500 mg).

Method A: Rt=0.70 min; $[M+H]^+$=723.6.

Step 5: N-(3-(6-(4-(((1-(2-(1-(3-(2,4-dioxotetrahydropyrimidin-1(2H)-yl)-4-methoxybenzoyl)piperidin-4-yl)ethyl)piperidin-4-yl)oxy)methyl)phenyl)-7H-pyrrolo[2,3-d]pyrimidin-4-yl)-5-fluoro-2-methylphenyl)-2-fluoro-4-(2-hydroxypropan-2-yl)benzamide To a solution of 2-fluoro-N-(5-fluoro-2-methyl-3-(6-(4-(((1-(2-(piperidin-4-yl)ethyl)piperidin-4-yl)oxy)methyl)

phenyl)-7H-pyrrolo[2,3-d]pyrimidin-4-yl)phenyl)-4-(2-hydroxypropan-2-yl)benzamide trifluoroacetate (120 mg, 0.102 mmol), 3-(2,4-dioxotetrahydropyrimidin-1(2H)-yl)-4-methoxybenzoic acid (intermediate 5, 27.0 mg, 0.102 mmol) and HBTU (46.5 mg, 0.123 mmol) in DMF (3 ml) was added DIPEA (0.107 ml, 0.613 mmol) and the RM was stirred for 2 h at RT under argon. Water was added and the resulting white precipitate was filtered, washed with water, dried and purified by SFC on a Reprospher PEI column (250×30 mm, 100 A, 5 μm) eluting with MeOH in $CO_2$ (from 22 to 55%), followed by a purification by reverse phase HPLC on a XBridge C18 OBD column (100×30 mm, 5 μm) eluting with ACN in an aq. solution of TFA (0.1%) (from 18 to 48%) to afford, after filtration through PL-HCO3 MP SPE cartridges and freeze drying, the title compound as a solid (35.9 mg).

Method B: Rt=4.11 min; [M+H]$^+$=970.5.

$^1$H NMR (400 MHz, DMSO-$d_6$) δ 12.73 (s, 1H), 10.35 (s, 1H), 9.95 (s, 1H), 8.79 (s, 1H), 7.98 (d, J=8.0 Hz, 2H), 7.80-7.56 (m, 2H), 7.52-7.12 (m, 9H), 6.79 (s, 1H), 5.32 (s, 1H), 4.54 (s, 2H), 4.35 (m, 1H), 3.85 (s, 3H), 3.61 (t, J=6.7 Hz, 2H), 3.10-2.60 (m, 6H), 2.28 (t, J=7.4 Hz, 2H), 2.19 (s, 3H), 2.02 (t, J=10.6 Hz, 2H), 1.95-1.82 (m, 2H), 1.69 (m, 2H), 1.47 (m, 10H), 1.39 (m, 2H), 1.10 (m, 2H).

Compound 14

N-(3-(6-(4-((9-(3-(2,4-Dioxotetrahydropyrimidin-1 (2H)-yl)-4-fluorobenzoyl)-3,9-diazaspiro[5.5]undecan-3-yl)methyl)phenyl)-7H-pyrrolo[2,3-d]pyrimidin-4-yl)-5-fluoro-2-methylphenyl)-2-fluoro-4-(2-hydroxypropan-2-yl)benzamide To a solution of 3-(2,4-dioxotetrahydropyrimidin-1(2H)-yl)-4-fluorobenzoic acid (intermediate 9, 8.89 mg, 0.035 mmol) in DMA (0.5 ml) at RT was added HATU (15.46 mg, 0.041 mmol) followed by DIPEA (0.047 ml, 0.271 mmol). After 15 min, N-(3-(6-(4-(3,9-diazaspiro[5.5]undecan-3-yl-methyl)phenyl)-7H-pyrrolo[2,3-d]pyrimidin-4-yl)-5-fluoro-2-methylphenyl)-2-fluoro-4-(2-hydroxypropan-2-yl)benzamide (intermediate 6, 31 mg, 0.027 mmol) was added and the RM was stirred at RT overnight. The RM was diluted with EtOAc, the organic phase was washed with an aq. solution of $NaHCO_3$ and brine, dried over $Na_2SO_4$, concentrated, and purified by reverse phase HPLC on a Reprosil® C18 column eluting with ACN in an aq. solution of TFA (0.1%) (from 10 to 100%). Fractions containing the pure compound were combined, basified with an aq. solution of $NaHCO_3$ and extracted with EtOAc. The combined organic phases were dried over $Na_2SO_4$, concentrated, and the residue was dissolved in a mixture of water and ACN and freeze-dried to afford the title compound as a solid (18.5 mg).

Method B: Rt=3.64 min, [M+H]$^+$=899.8.

$^1$H NMR (600 MHz, DMSO-$d_6$) δ 12.79 (s, 1H), 10.55 (s, 1H), 9.98 (s, 1H), 8.87 (s, 1H), 8.08-7.90 (m, 2H), 7.74 (t, J=7.8 Hz, 1H), 7.67 (d, J=10.9 Hz, 1H), 7.51 (d, J=6.6 Hz, 1H), 7.46-7.35 (m, 6H), 7.25 (dd, J=8.7, 2.6 Hz, 1H), 6.85 (br. s, 1H), 5.32 (s, 1H), 3.76 (t, J=6.6 Hz, 2H), 3.67-3.44 (m, 4H), 3.42-3.32 (m, 2H), 2.73 (t, J=6.6 Hz, 2H), 2.55-2.51 (m, 2H), 2.42-2.31 (m, 2H), 2.18 (s, 3H), 1.57-1.35 (m, 8H), 1.46 (s, 6H).

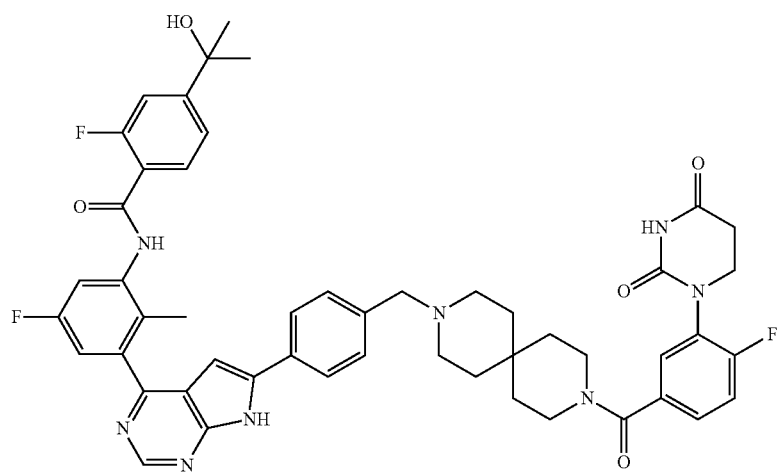 [SMILES: Cc1c(NC(=O)c2ccc(C(C)(C)O)cc2F)cc(F)cc1-c1ncnc2[nH]c(-c3ccc(CN4CCC5(CC4)CCN(C(=O)c4ccc(F)c(N6CCC(=O)NC6=O)c4)CC5)cc3)cc12]

Compound 15

N-(3-(6-(4-((1-(3-(1-(3-(2,4-Dioxotetrahydropyrimidin-1(2H)-yl)-4-methoxybenzoyl)piperidin-4-yl)propyl)piperidin-4-yl)oxy)phenyl)-7H-pyrrolo[2,3-d]pyrimidin-4-yl)-5-fluoro-2-methylphenyl)-2-fluoro-4-(2-hydroxypropan-2-yl)benzamide

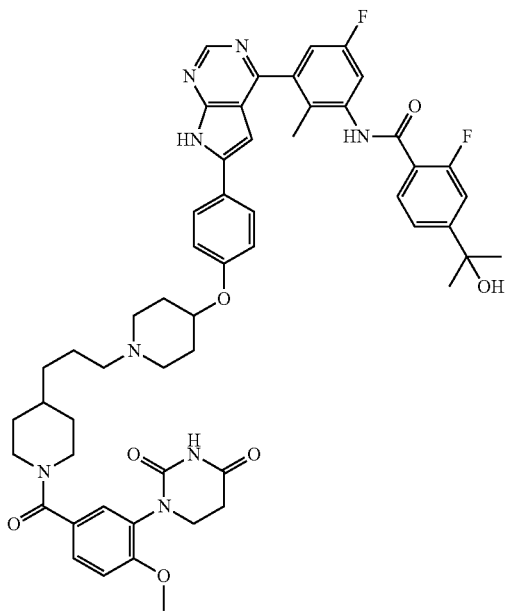 [SMILES: COc1ccc(C(=O)N2CCC(CCCN3CCC(Oc4ccc(-c5cc6c(-c7cc(F)cc(NC(=O)c8ccc(C(C)(C)O)cc8F)c7C)ncnc6[nH]5)cc4)CC3)CC2)cc1N1CCC(=O)NC1=O]

Step 1: tert-butyl 4-(3-(4-(4-(4-(5-fluoro-3-(2-fluoro-4-(2-hydroxypropan-2-yl)benzamido)-2-methylphenyl)-7H-pyrrolo[2,3-d]pyrimidin-6-yl)phenoxy)piperidin-1-yl)propyl)piperidine-1-carboxylate 2-Fluoro-N-(5-fluoro-2-methyl-3-(6-(4-(piperidin-4-yloxy)phenyl)-7H-pyrrolo[2,3-d]pyrimidin-4-yl)phenyl)-4-(2-hydroxypropan-2-yl)benzamide (intermediate 16, 101 mg, 0.142 mmol), TEA (0.060 ml, 0.430 mmol) and tert-butyl 4-(3-oxopropyl)piperidine-1-carboxylate (45 mg, 0.186 mmol) were dissolved in MeOH (1.5 ml) at RT. A solution of ZnCl$_2$ (0.7 M) in THF (0.250 ml, 0.175 mmol) was added and the RM was stirred at RT overnight under argon. Solid NaBH$_3$CN (11 mg, 0.175 mmol) was added and the RM was stirred at RT overnight. The solvent was removed and the resulting residue was used without further purification directly for the next step (134 mg).
Method A: Rt=1.05 min; [M+H]$^+$=823.5.

Step 2: 2-fluoro-N-(5-fluoro-2-methyl-3-(6-(4-((1-(3-(piperidin-4-yl)propyl)piperidin-4-yl)oxy)phenyl)-7H-pyrrolo[2,3-d]pyrimidin-4-yl)phenyl)-4-(2-hydroxypropan-2-yl)benzamide A solution of crude tert-butyl 4-(3-(4-(4-(4-(5-fluoro-3-(2-fluoro-4-(2-hydroxypropan-2-yl)benzamido)-2-methylphenyl)-7H-pyrrolo[2,3-d]pyrimidin-6-yl)phenoxy)piperidin-1-yl)propyl)piperidine-1-carboxylate (117 mg, 0.142 mmol) in DCM (1.5 ml) and TFA (0.150 ml, 1.947 mmol) was stirred for 2.5 h at RT, the solvent was removed and the residue was purified by reverse phase chromatography on a Redisep® C18 column eluting with ACN in an aq. solution of TFA (0.1%) (from 2 to 100%) to afford the title compound as a solid TFA salt (135 mg).
Method A: Rt=0.72 min; [M+H]$^+$=723.6.

Step 3: N-(3-(6-(4-((1-(3-(1-(3-(2,4-dioxotetrahydropyrimidin-1(2H)-yl)-4-methoxybenzoyl)piperidin-4-yl)propyl)piperidin-4-yl)oxy)phenyl)-7H-pyrrolo[2,3-d]pyrimidin-4-yl)-5-fluoro-2-methylphenyl)-2-fluoro-4-(2-hydroxypropan-2-yl)benzamide To a solution of 3-(2,4-dioxotetrahydropyrimidin-1(2H)-yl)-4-methoxybenzoic acid (intermediate 5.45 mg, 0.170 mmol) in DMF (1 ml) was added NMM (0.050 ml, 0.455 mmol), followed by HATU (65 mg, 0.170 mmol). After stirring the RM for 30 min, a solution of 2-fluoro-N-(5-fluoro-2-methyl-3-(6-(4-((1-(3-(piperidin-4-yl)propyl)piperidin-4-yl)oxy)phenyl)-7H-pyrrolo[2,3-d]pyrimidin-4-yl)phenyl)-4-(2-hydroxypropan-2-yl)benzamide trifluoroacetate (0.142 mmol) and NMM (0.050 ml, 0.455 mmol) in DMF (0.5 ml) was added drop by drop and the RM was stirred at RT for 2.5 h. The mixture was concentrated and purified by reverse phase chromatography on a Redisep® C18 column eluting with ACN in an aq. solution of NH$_4$HCO$_3$ (0.1%) (from 2 to 100%) to afford the title compound as a solid (93 mg).
Method B: Rt=3.99 min, [M+H]$^+$=969.7.
$^1$H NMR (400 MHz, DMSO-d$_6$) δ 12.64 (s, 1H), 10.31 (s, 1H), 9.92 (s, 1H), 8.80 (s, 1H), 7.89 (d, J=8.3 Hz, 2H), 7.72 (t, J=7.9 Hz, 1H), 7.68-7.57 (m, 1H), 7.47-7.26 (m, 4H), 7.26-7.18 (m, 1H), 7.13 (d, J=8.5 Hz, 1H), 7.02 (d, J=8.4 Hz, 2H), 6.70 (s, 1H), 5.29 (s, 1H), 4.45 (m, 1H), 3.82 (s, 3H), 3.58 (t, J=6.8 Hz, 2H), 3.00-2.63 (m, 6H), 2.21 (m, 7H), 1.93 (m, 2H), 1.63 (m, 4H), 1.44 (m, 10H), 1.22 (m, 3H), 1.15-0.97 (m, 2H).

Compound 16

N-(3-(6-(4-((4-(2-(4-(3-(2,4-Dioxotetrahydropyrimidin-1(2H)-yl)-4-methoxybenzoyl)piperazin-1-yl)ethyl)piperazin-1-yl)methyl)phenyl)-7H-pyrrolo[2,3-d]pyrimidin-4-yl)-5-fluoro-2-methylphenyl)-2-fluoro-4-(2-hydroxypropan-2-yl)benzamide

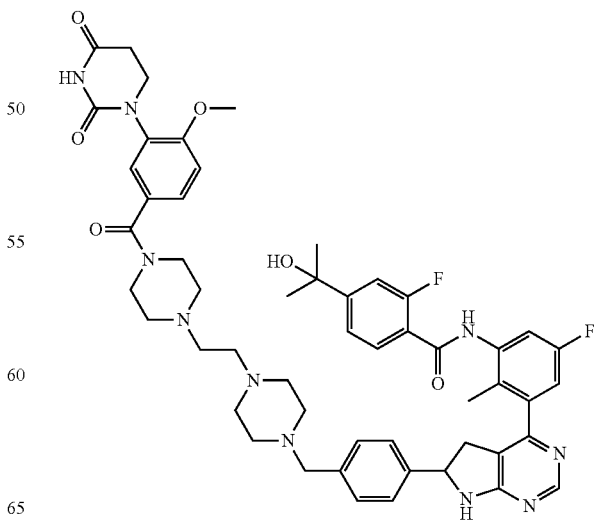

Step 1: tert-butyl 4-(2-oxoethyl)piperazine-1-carboxylate

To a stirred solution of oxalyl chloride (0.380 ml, 4.25 mmol) in anhydrous DCM (10 ml) at −78° C. was added DMSO (0.538 ml, 7.58 mmol). The RM was stirred for 30 min. followed by the addition of 1-Boc-4-(2-hydroxyethyl)piperazine (500 mg, 2.106 mmol) in DCM (10 ml). After stirring the RM at −78° C. for 30 minutes, TEA (2.4 ml, 17.22 mmol) was added and stirring was continued for 1.5 h while allowing the RM to warm to RT. The RM was quenched by addition of a sat. aq. solution of NaHCO$_3$ and was then extracted with DCM. The combined organic phases were dried over Na$_2$SO$_4$, evaporated to dryness and the residue was purified by chromatography on silica eluting with a mixture of EtOAc and MeOH (4:1) in EtOAc (from 0 to 30%) to afford the title compound as a solid (371 mg).

$^1$H NMR (400 MHz, DMSO-d$_6$) δ 9.57 (d, J=1.5 Hz, 1H), 3.31 (dd, J=10.0, 5.0 Hz, 4H), 3.18 (d, J=1.5 Hz, 2H), 2.38 (t, J=5.1 Hz, 4H), 1.38 (s, 9H).

Step 2: tert-butyl 4-(2-(4-(4-(4-(5-fluoro-3-(2-fluoro-4-(2-hydroxypropan-2-yl)benzamido)-2-methylphenyl)-7H-pyrrolo[2,3-d]pyrimidin-6-yl)benzyl)piperazin-1-yl)ethyl)piperazine-1-carboxylate 2-Fluoro-N-(5-fluoro-2-methyl-3-(6-(4-(piperazin-1-ylmethyl)phenyl)-7H-pyrrolo[2,3-d]pyrimidin-4-yl)phenyl)-4-(2-hydroxypropan-2-yl)benzamide hydrochloride (intermediate 17, 265 mg, 0.384 mmol), TEA (0.200 ml, 1.435 mmol) and tert-butyl 4-(2-oxoethyl)piperazine-1-carboxylate (96 mg, 0.399 mmol) were dissolved in MeOH (2 ml) at RT. A solution of ZnCl$_2$ (0.5 M) in THF (0.850 ml, 0.425 mmol) was added and the RM was stirred for 7 h at RT. Solid NaBH$_3$CN (27 mg, 0.430 mmol) was added and the RM was stirred at RT overnight, concentrated and the residue purified by reverse phase chromatography on a Redisep® C18 column eluting with ACN in an aq. solution of TFA (0.1%) to afford the title compound as a solid TFA salt (259 mg).

Method D: Rt=0.58 min; [M+H]$^+$=809.6.

Step 3: 2-fluoro-N-(5-fluoro-2-methyl-3-(6-(4-((4-(2-(piperazin-1-yl)ethyl)piperazin-1-yl)methyl)phenyl)-7H-pyrrolo[2,3-d]pyrimidin-4-yl)phenyl)-4-(2-hydroxypropan-2-yl)benzamide To a solution of tert-butyl 4-(2-(4-(4-(4-(5-fluoro-3-(2-fluoro-4-(2-hydroxypropan-2-yl)benzamido)-2-methylphenyl)-7H-pyrrolo[2,3-d]pyrimidin-6-yl)benzyl)piperazin-1-yl)ethyl)piperazine-1-carboxylate (259 mg, 0.109 mmol) in MeOH (2 ml) was added a solution of HCl (4 M) in 1,4-dioxane (2 ml, 8.00 mmol) and the RM was stirred for 1 h at RT, concentrated and the residue purified by reverse phase chromatography on a Redisep® C18 column eluting with ACN in an aq. solution of TFA (0.1%) (from 2 to 100%) to afford the title compound as a solid TFA salt (91 mg).

Method A: Rt=0.65 min; [M+H]$^+$=709.6.

Step 4: N-(3-(6-(4-((4-(2-(4-(3-(2,4-dioxotetrahydropyrimidin-1(2H)-yl)-4-methoxybenzoyl)piperazin-1-yl)ethyl)piperazin-1-yl)methyl)phenyl)-7H-pyrrolo[2,3-d]pyrimidin-4-yl)-5-fluoro-2-methylphenyl)-2-fluoro-4-(2-hydroxypropan-2-yl)benzamide 3-(2,4-Dioxotetrahydropyrimidin-1(2H)-yl)-4-methoxybenzoic acid (intermediate 5, 20 mg, 0.074 mmol) was dissolved in DMF (0.5 ml) at RT, NMM (0.050 ml, 0.455 mmol) and HATU (30 mg, 0.077 mmol) were added and the RM was stirred for 30 min. at RT. A solution of 2-fluoro-N-(5-fluoro-2-methyl-3-(6-(4-((4-(2-(piperazin-1-yl)ethyl)piperazin-1-yl)methyl)phenyl)-7H-pyrrolo[2,3-d]pyrimidin-4-yl)phenyl)-4-(2-hydroxypropan-2-yl)benzamide trifluoroacetate (91 mg, 0.059 mmol) and NMM (0.050 ml, 0.455 mmol) in DMF (0.5 ml) was added drop by drop and the RM was stirred for 2.5 h at RT. The mixture was concentrated and purified by reverse phase chromatography on a Redisep® C18 column eluting with ACN in an aq. solution of TFA (0.1%) (from 2 to 100%) to afford, after filtration over a PL-HCO3 MP SPE cartridge, freeze drying and an additional purification by SFC on a Torus 2PIC column (250×30 mm, 130 A, 5 μm) eluting with MeOH in CO$_2$ (from 22 to 52%), the title compound as a solid (34 mg).

Method B: Rt=3.07 min, [M+H]$^+$=955.5.

$^1$H NMR (400 MHz, DMSO-d$_6$) δ 12.75 (s, 1H), 10.31 (s, 1H), 9.92 (s, 1H), 8.83 (s, 1H), 7.92 (m, 2H), 7.68 (m, 2H), 7.36 (m, 6H), 7.19 (m, 2H), 6.81 (s, 1H), 5.28 (s, 1H), 3.82 (s, 3H), 3.75-2.85 (m, 14H), 2.64 (m, 8H), 2.16 (m, 6H), 1.44 (m, 6H).

Compound 17

N-(3-(6-(4-((4-(2-(1-(3-(2,4-Dioxotetrahydropyrimidin-1(2H)-yl)-4-methoxybenzoyl)piperidin-4-yl)ethyl)piperazin-1-yl)methyl)phenyl)-7H-pyrrolo[2,3-d]pyrimidin-4-yl)-5-fluoro-2-methylphenyl)-2-fluoro-4-(2-hydroxypropan-2-yl)benzamide

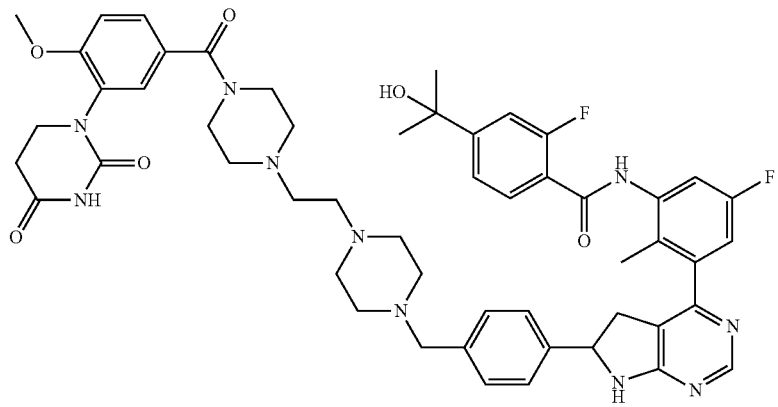 [SMILES: COc1ccc(C(=O)N2CCN(CCN3CCN(Cc4ccc(C5Cc6c(ncnc6-c6cc(F)cc(NC(=O)c7ccc(C(C)(C)O)cc7F)c6C)N5)cc4)CC3)CC2)cc1N1CCC(=O)NC1=O]

Step 1: tert-butyl 4-(2-(4-(4-(4-(5-fluoro-3-(2-fluoro-4-(2-hydroxypropan-2-yl)benzamido)-2-methylphenyl)-7H-pyrrolo[2,3-d]pyrimidin-6-yl)benzyl)piperazin-1-yl)ethyl)piperidine-1-carboxylate 2-Fluoro-N-(5-fluoro-2-methyl-3-(6-(4-(piperazin-1-ylmethyl)phenyl)-7H-pyrrolo[2,3-d]pyrimidin-4-yl)phenyl)-4-(2-hydroxypropan-2-yl)benzamide trifluoroacetate (intermediate 18, 200 mg, 0.228 mmol), TEA (0.100 ml, 0.717 mmol) and N-Boc-4-piperidineacetaldehyde (70 mg, 0.293 mmol) were dissolved in MeOH (2 ml) at RT, a solution of $ZnCl_2$ (0.7 M) in THF (0.370 ml, 0.259 mmol) was added and the RM was stirred at RT for 5 h under argon. Solid $NaBH_3CN$ (16 mg, 0.255 mmol) was added and the RM was stirred at RT overnight, the solvent was removed and the residue purified by reverse phase chromatography on a Redisep® C18 column eluting with ACN in an aq. solution of TFA (0.1%) (from 2 to 100%) to afford the title compound as a solid TFA salt (236 mg).

Method A: Rt=0.96 min; [M+H]⁺=808.5.

Step 2: 2-fluoro-N-(5-fluoro-2-methyl-3-(6-(4-((4-(2-(piperidin-4-yl)ethyl)piperazin-1-yl)methyl)phenyl)-7H-pyrrolo[2,3-d]pyrimidin-4-yl)phenyl)-4-(2-hydroxypropan-2-yl)benzamide To a solution of tert-butyl 4-(2-(4-(4-(4-(5-fluoro-3-(2-fluoro-4-(2-hydroxypropan-2-yl)benzamido)-2-methylphenyl)-7H-pyrrolo[2,3-d]pyrimidin-6-yl)benzyl)piperazin-1-yl)ethyl)piperidine-1-carboxylate (230 mg, 0.249 mmol) in MeOH (2 ml) was added a solution of HCl (4 M) in 1,4-dioxane (1.5 ml, 6.00 mmol) and the RM was stirred at RT for 2 h. The RM was concentrated to afford the title compound as a solid HCl salt (234 mg).

Method A: Rt=0.68 min; [M+H]⁺=708.5.

Step 3: N-(3-(6-(4-((4-(2-(1-(3-(2,4-dioxotetrahydropyrimidin-1(2H)-yl)-4-methoxybenzoyl)piperidin-4-yl)ethyl)piperazin-1-yl)methyl)phenyl)-7H-pyrrolo[2,3-d]pyrimidin-4-yl)-5-fluoro-2-methylphenyl)-2-fluoro-4-(2-hydroxypropan-2-yl)benzamide 3-(2,4-Dioxotetrahydropyrimidin-1(2H)-yl)-4-methoxybenzoic acid (intermediate 5, 41 mg, 0.155 mmol) was dissolved in DMF (1 ml), NMM (0.050 ml, 0.455 mmol) and HATU (58 mg, 0.153 mmol) were added and the RM was stirred at RT for 30 min. A solution of 2-fluoro-N-(5-fluoro-2-methyl-3-(6-(4-((4-(2-(piperidin-4-yl)ethyl)piperazin-1-yl)methyl)phenyl)-7H-pyrrolo[2,3-d]pyrimidin-4-yl)phenyl)-4-(2-hydroxypropan-2-yl)benzamide hydrochloride (100 mg, 0.122 mmol) and NMM (0.050 ml, 0.455 mmol) in DMF (0.5 ml) was added drop by drop and the RM was stirred at RT overnight. The mixture was concentrated and purified by reverse phase chromatography on a Redisep® C18 column eluting with ACN in an aq. solution of $NH_4HCO_3$ (0.1%) to afford the title compound as a solid (78 mg).

Method B: Rt=3.77 min; [M+H]⁺=954.5.

¹H NMR (400 MHz, DMSO-d₆) δ 12.76 (s, 1H), 10.32 (s, 1H), 9.94 (s, 1H), 8.85 (s, 1H), 7.94 (d, J=7.6 Hz, 2H), 7.82-7.60 (m, 2H), 7.53-7.06 (m, 8H), 6.83 (s, 1H), 5.30 (s, 1H), 3.83 (s, 3H), 3.53 (m, 4H), 3.00-2.3 (m, 16H), 2.17 (s, 3H), 1.91-0.91 (m, 13H).

Compound 18 rac-N-(3-(6-(4-((1-(2-((1-(3-(2,4-Dioxotetrahydropyrimidin-1(2H)-yl)-4-methoxybenzoyl)piperidin-4-yl)oxy)-3-hydroxypropyl)piperidin-4-yl)oxy)phenyl)-7H-pyrrolo[2,3-d]pyrimidin-4-yl)-5-fluoro-2-methylphenyl)-2-fluoro-4-(2-hydroxypropan-2-yl)benzamide

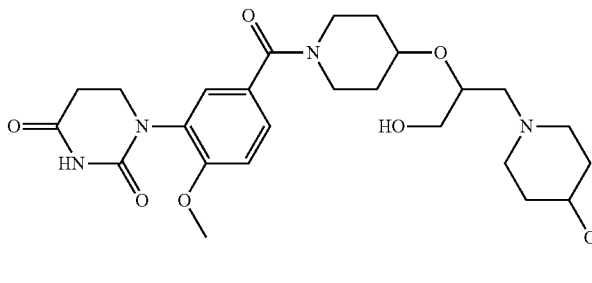
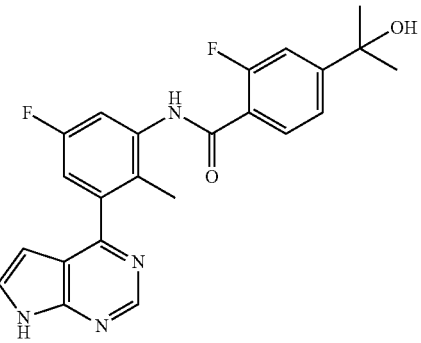

Step 1: rac-tert-butyl 4-((1-(4-(4-(4-(5-fluoro-3-(2-fluoro-4-(2-hydroxypropan-2-yl)benzamido)-2-methylphenyl)-7H-pyrrolo[2,3-d]pyrimidin-6-yl)phenoxy)piperidin-1-yl)-3-hydroxypropan-2-yl)oxy)piperidine-1-carboxylate 2-Fluoro-N-(5-fluoro-2-methyl-3-(6-(4-(piperidin-4-yloxy)phenyl)-7H-pyrrolo[2,3-d]pyrimidin-4-yl)phenyl)-4-(2-hydroxypropan-2-yl)benzamide trifluoroacetate (intermediate 16, 124 mg, 0.171 mmol), TEA (0.100 ml, 0.717 mmol) and tert-butyl 4-(2-oxoethoxy)piperidine-1-carboxylate (intermediate 19, 60 mg, 0.222 mmol) were dissolved in MeOH (2 ml) at RT, a solution of $ZnCl_2$ (0.7 M) in THF (0.300 ml, 0.210 mmol) was added and the RM was stirred at RT overnight under argon. Solid $NaBH_3CN$ (13 mg, 0.207 mmol) was added, the RM was stirred at RT overnight, concentrated and the residue purified by reverse phase chromatography on a Redisep® C18 column eluting with ACN in an aq. solution of TFA (0.1%) (from 2 to 100%) to afford the title compound as a solid TFA salt (78 mg).

Method A: Rt=0.94 min; [M+H]⁺=855.5.

Step 2: rac-2-fluoro-N-(5-fluoro-3-(6-(4-((1-(3-hydroxy-2-(piperidin-4-yloxy)propyl)piperidin-4-yl)oxy)phenyl)-7H-pyrrolo[2,3-d]pyrimidin-4-yl)-2-methylphenyl)-4-(2-hydroxypropan-2-yl)benzamide A solution of rac-tert-butyl 4-((1-(4-(4-(4-(5-fluoro-3-(2-fluoro-4-(2-hydroxypropan-2-yl)benzamido)-2-methylphenyl)-7H-pyrrolo[2,3-d]pyrimidin-6-yl)phenoxy)piperidin-1-yl)-3-hydroxypropan-2-yl)oxy)piperidine-1-carboxylate trifluoroacetate (75 mg, 0.079 mmol) in DCM (1 ml) and TFA (0.100 ml, 1.3 mmol) was stirred for 2 h at RT, concentrated and the residue was purified by reverse phase chromatography on a Redisep® C18 column eluting with ACN in an aq. solution of TFA (0.1%) (from 2 to 100%) to afford the title compound as a solid TFA salt (67 mg).

Method A: Rt=0.67 min; [M+H]+=755.5.

Step 3: rac-N-(3-(6-(4-((1-(2-((1-(3-(2,4-dioxotetrahydropyrimidin-1(2H)-yl)-4-methoxybenzoyl)piperidin-4-yl)oxy)-3-hydroxypropyl)piperidin-4-yl)oxy)phenyl)-7H-pyrrolo[2,3-d]pyrimidin-4-yl)-5-fluoro-2-methylphenyl)-2-fluoro-4-(2-hydroxypropan-2-yl)benzamide To a solution of 3-(2,4-dioxotetrahydropyrimidin-1(2H)-yl)-4-methoxybenzoic acid (intermediate 5.20 mg, 0.076 mmol) in DMF (0.5 ml) was added NMM (0.050 ml, 0.455 mmol) and HATU (30 mg, 0.079 mmol) and the RM was stirred at RT for 30 min. A solution of rac-2-fluoro-N-(5-fluoro-3-(6-(4-((1-(3-hydroxy-2-(piperidin-4-yloxy)propyl)piperidin-4-yl)oxy)phenyl)-7H-pyrrolo[2,3-d]pyrimidin-4-yl)-2-methylphenyl)-4-(2-hydroxypropan-2-yl)benzamide (65 mg, 0.065 mmol) and NMM (0.050 ml, 0.455 mmol) in DMF (0.5 ml) was added drop by drop and the RM was stirred at RT for 2 h. The solvent was removed and the residue purified by reverse phase chromatography on a Redisep® C18 column eluting with ACN in an aq. solution of NH$_4$HCO$_3$ (0.1%), to afford, after an additional purification by SFC on a Torus 2PIC column (250×30 mm, 130 A, 5 μm) eluting with MeOH in CO$_2$ (from 22 to 55%), the title compound as a solid (30 mg).

Method B: Rt=3.77 min; [M+H]+=1001.6.

$^1$H NMR (600 MHz, DMSO-d$_6$) δ 13.99 (s, 1H), 10.31 (s, 1H), 10.08 (s, 1H), 9.22 (s, 1H), 8.04 (m, 2H), 7.86 (d, J=9.9 Hz, 1H), 7.72 (t, J=7.8 Hz, 1H), 7.44-7.38 (m, 3H), 7.36 (m, 1H), 7.32 (s, 1H), 7.15 (m, 4H), 4.75-4.35 (m, 1H), 3.94 (m, 1H), 3.82 (m, 4H), 3.75-3.50 (m, 6H), 3.50-3.32 (m, 2H), 3.32-3.07 (m, 5H), 2.66 (t, J=6.8 Hz, 2H), 2.28 (m, 1H), 2.19 (s, 3H), 2.14-2.01 (m, 2H), 2.00-1.77 (m, 3H), 1.63-1.45 (m, 3H), 1.44 (s, 6H).

Compound 19

N-(3-(6-(4-((1-(((1-(3-(2,4-Dioxotetrahydropyrimidin-1(2H)-yl)-4-methoxybenzoyl)piperidin-4-yl)methyl)piperidin-4-yl)oxy)phenyl)-7H-pyrrolo[2,3-d]pyrimidin-4-yl)-5-fluoro-2-methylphenyl)-2-fluoro-4-(2-hydroxypropan-2-yl)benzamide

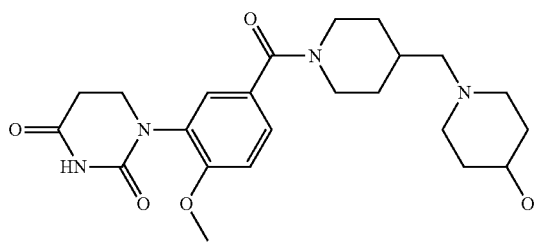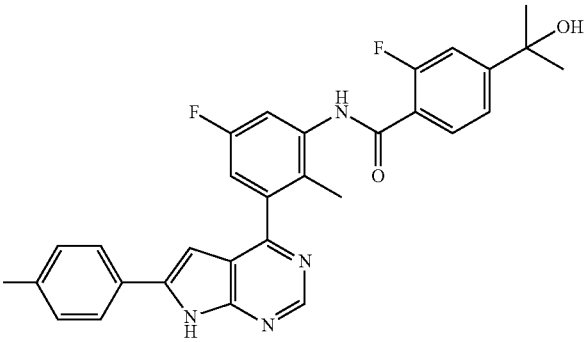

Step 1: tert-butyl 4-((4-(4-(4-(5-fluoro-3-(2-fluoro-4-(2-hydroxypropan-2-yl)benzamido)-2-methylphenyl)-7H-pyrrolo[2,3-d]pyrimidin-6-yl)phenoxy)piperidin-1-yl)methyl)piperidine-1-carboxylate 2-Fluoro-N-(5-fluoro-2-methyl-3-(6-(4-(piperidin-4-yloxy)phenyl)-7H-pyrrolo[2,3-d]pyrimidin-4-yl)phenyl)-4-(2-hydroxypropan-2-yl)benzamide trifluoroacetate (intermediate 16, 127 mg, 0.170 mmol), TEA (0.075 ml, 0.538 mmol) and 1-Boc-piperidine4-carboxaldehyde (40 mg, 0.182 mmol) were dissolved in MeOH (2 ml) at RT, a solution of ZnCl$_2$ (0.7 M) in THF (0.300 ml, 0.210 mmol) was added and the RM was stirred at RT under argon for 7 h. Solid NaBH$_3$CN (13 mg, 0.207 mmol) was added, the RM was stirred at RT for 4 days, the solvent was removed and the residue was purified by reverse phase chromatography on a Redisep® C18 column eluting with ACN in an aq. solution of TFA (0.1%) (from 2 to 100%) to afford the title compound as a solid TFA salt (174 mg).

Method D: Rt=0.75 min; [M+H]+=795.5.

Step 2: 2-fluoro-N-(5-fluoro-2-methyl-3-(6-(4-((1-(piperidin-4-ylmethyl)piperidin-4-yl)oxy)phenyl)-7H-pyrrolo[2,3-d]pyrimidin-4-yl)phenyl)-4-(2-hydroxypropan-2-yl)benzamide A solution of tert-butyl 4-((4-(4-(4-(5-fluoro-3-(2-fluoro-4-(2-hydroxypropan-2-yl)benzamido)-2-methylphenyl)-7H-pyrrolo[2,3-d]pyrimidin-6-yl)phenoxy)piperidin-1-yl)methyl)piperidine-1-carboxylate trifluoroacetate (170 mg, 0.190 mmol) in DCM (2 ml) and TFA (0.100 ml, 1.298 mmol) was stirred at RT for 1 h and the RM was concentrated to afford the title compound as a solid TFA salt (202 mg).

Method D: Rt=0.52 min; [M+H]+=695.6.

Step 3: N-(3-(6-(4-((1-((1-(3-(2,4-dioxotetrahydro-pyrimidin-1(2H)-yl)-4-methoxybenzoyl)piperidin-4-yl)methyl)piperidin-4-yl)oxy)phenyl)-7H-pyrrolo[2,3-d]pyrimidin-4-yl)-5-fluoro-2-methylphenyl)-2-fluoro-4-(2-hydroxypropan-2-yl)benzamide To a solution of 3-(2,4-dioxotetrahydropyrimidin-1(2H)-yl)-4-methoxybenzoic acid (intermediate 5, 60 mg, 0.227 mmol) in DMF (1 ml) at RT was added NMM (0.050 ml, 0.455 mmol) and HATU (87 mg, 0.042 mmol) and the RM was stirred at RT for 30 min. A solution of 2-fluoro-N-(5-fluoro-2-methyl-3-(6-(4-((1-(piperidin-4-ylmethyl)piperidin-4-yl)oxy)phenyl)-7H-pyrrolo[2,3-d]pyrimidin-4-yl)phenyl)-4-(2-hydroxypropan-2-yl)benzamide trifluoroacetate (0.190 mmol) and NMM (0.050 ml, 0.455 mmol) in DMF (1 ml) was added drop by drop and the RM was stirred at RT for 2.5 h. The solvent was removed and the residue was purified by reverse phase chromatography on a Redisep® C18 column eluting with ACN in an aq. solution of NH$_4$HCO$_3$ (0.1%) (from 2 to 100%) to afford, after an additional purification by reverse phase HPLC on a XBridge column (50×250 mm, 5 µm) eluting with ACN in an aq. solution of NH$_4$OH (0.1%) (from 30 to 65%), the title compound as a solid (47 mg).

Method B: Rt=3.95 min; [M+H]$^+$=941.8.

$^1$H NMR (600 MHz, DMSO-d$_6$) δ 12.69 (s, 1H), 10.36 (s, 1H), 9.97 (s, 1H), 8.83 (s, 1H), 7.92 (d, J=8.4 Hz, 2H), 7.74 (m, 1H), 7.66 (d, J=10.2 Hz, 1H), 7.46-7.39 (m, 2H), 7.37 (m, 1H), 7.33 (m, 1H), 7.24 (m, 1H), 7.16 (m, 1H), 7.05 (d, J=8.3 Hz, 2H), 6.76-6.70 (s, 1H), 5.33 (s, 1H), 4.48 (m, 1H), 3.85 (s, 3H), 3.61 (t, J=6.6 Hz, 2H), 3.20-2.75 (m, 4H), 2.18 (m, 7H), 1.97 (m, 2H), 1.80-1.55 (m, 5H), 1.46 (s, 6H), 1.08 (m, 2H).

Compound 20

N-(3-(6-(4-(2-(9-(3-(2,4-Dioxotetrahydropyrimidin-1(2H)-yl)-4-methoxybenzoyl)-3,9-diazaspiro[5.5]undecan-3-yl)-2-methylpropyl)phenyl)-7H-pyrrolo[2,3-d]pyrimidin-4-yl)-5-fluoro-2-methylphenyl)-2-fluoro-4-(2-hydroxypropan-2-yl)benzamide

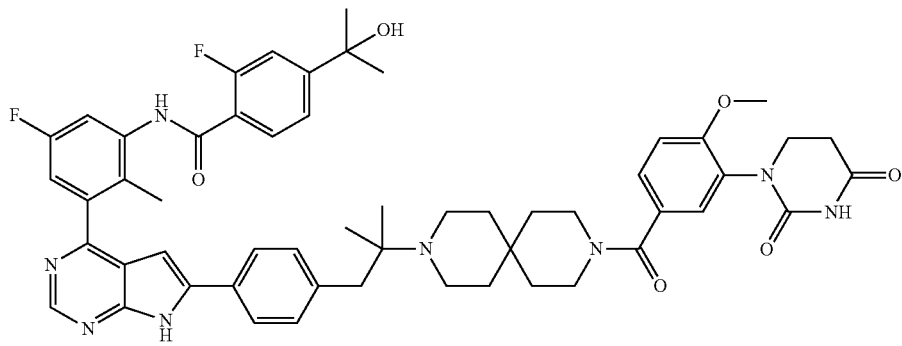 [SMILES: COc1ccc(C(=O)N2CCC3(CC2)CCN(C(C)(C)Cc2ccc(-c4cc5c(-c6cc(F)cc(NC(=O)c7ccc(C(C)(C)O)cc7F)c6C)ncnc5[nH]4)cc2)CC3)cc1N1CCC(=O)NC1=O]

Step 1: tert-butyl 9-(2-(4-bromophenyl)acetyl)-3,9-diazaspiro[5.5]undecane-3-carboxylate To a solution of 3,9-diaza-spiro[5.5]undecane-3-carboxylic acid tert-butyl ester (1269 mg, 4.99 mmol) in dry DMF (12 ml) at RT under argon was added DIPEA (1.743 ml, 9.98 mmol), 4-bromophenylacetic acid (1073 mg, 4.99 mmol) and dry DMF (6 ml). Solid HBTU (2081 mg, 5.49 mmol) was added and the RM was stirred at RT for 1 h, poured into water and the resulting mixture was stirred for 1 h. The liquid was decanted, water was added and the mixture was sonicated. The liquid was again decanted and the residue was dissolved in DCM, the solution was dried over MgSO$_4$ and evaporated to afford the title compound as an oil (2.2 g).

Method A: Rt=1.22 min; [M+H]$^+$=451.2.

Step 2: tert-butyl 9-(1-(4-bromophenyl)-2-methyl-propan-2-yl)-3,9-diazaspiro[5.5]undecane-3-carboxylate To a solution of tert-butyl 9-(2-(4-bromophenyl)acetyl)-3,9-diazaspiro[5.5]undecane-3-carboxylate (1.9 g, 4.21 mmol) in dry THF (15 ml) at −50° C. under argon, oven-dried ZrCl$_4$ (1.079 g, 4.63 mmol) was added and the RM was stirred between −50° C. and −45° C. for 30 minutes. A solution of methylmagnesium bromide (3 M) in Et$_2$O (8.42 ml, 25.3 mmol) was added drop by drop over 10 min., while keeping the reaction temperature between −45° C. and −40° C. The RM was allowed to warm to −20° C. before being stirred in an ice bath for 15 min and then at RT for 2 h. A sat. aq. solution of NH$_4$Cl and EtOAc were added and the phases were separated. The aqueous phase was extracted with EtOAc and the combined organic phases were dried over MgSO$_4$, evaporated and the residue was purified by reverse phase chromatography on a Redisep® C18 column eluting with ACN in an aq. solution of TFA (0.1%) (from 10 to 100%) to afford the title compound as a solid TFA salt (70 mg).

Method A: Rt=0.95 min; [M+H]$^+$=465.2.

Step 3: tert-butyl 9-(2-methyl-1-(4-(4,4,5,5-tetramethyl-1,3,2-dioxaborolan-2-yl)phenyl)propan-2-yl)-3,9-diazaspiro[5.5]undecane-3-carboxylate To a solution of tert-butyl 9-(1-(4-bromophenyl)-2-methylpropan-2-yl)-3,9-diazaspiro[5.5]undecane-3-carboxylate (70 mg, 0.121 mmol) in dry 1,4-dioxane (2 ml) was added KOAc (35.6 mg, 0.362 mmol) and BISPIN (36.8 mg, 0.145 mmol) and argon was passed through the mixture for 5 minutes. The mixture was heated at 35° C. and PdCl$_2$(dpp) (4.42 mg, 6.04 µmol) was added, the RM was again flushed with argon and then stirred at 90° C. for 6 h. The solvent was removed and the residue absorbed on silica and purified by chromatography on silica gel eluting with EtOAc in CHX (from 10 to 100%), then with MeOH in DCM (from 0 to 20%) to afford the title compound as an oil (94 mg).

Method A: Rt=1.09 min; [M+H]$^+$=513.4.

Step 4: tert-butyl 9-(1-(4-(4-chloro-7H-pyrrolo[2,3-d]pyrimidin-6-yl)phenyl)-2-methylpropan-2-yl)-3,9-diazaspiro[5.5]undecane-3-carboxylate Tert-butyl 9-(2-methyl-1-(4-(4,4,5,5-tetramethyl-1,3,2-dioxaborolan-2-yl)phenyl)propan-2-yl)-3,9-diazaspiro[5.5]undecane-3-carboxylate (94 mg, 0.182 mmol) and 4-chloro-6-iodo-7H-pyrrolo[2,3-d]pyrimidine (51 mg, 0.182 mmol) were suspended in a mixture of 1-propanol (5 ml) and an aq. solution of $Na_2CO_3$ (2 M) (0.182 ml, 0.365 mmol) at RT. Argon was passed through the mixture, $PdCl_2(PPh_3)_2$ (12.81 mg, 0.018 mmol) was added and the RM was stirred at 100° C. for 23 h under an argon atmosphere. 1-Propanol (3 ml) and an aq. solution of $Na_2CO_3$ (2 M) (0.540 ml, 1.08 mmol) were added, argon was passed through the RM for 5 min., $PdCl_2(PPh_3)_2$ (15 mg, 0.021 mmol) was added and the RM was stirred at 110° C. for 7 h. The RM was diluted with EtOAc, the mixture was dried over $MgSO_4$, adsorbed and dried on Isolute® HM-N, and purified by reverse phase chromatography on a Redisep® C18 column eluting with ACN in an aq. solution of TFA (0.1%) (from 5 to 100%) to afford the title compound as a solid TFA salt (33 mg).

Method A: Rt=0.94 min; $[M+H]^+$=538.3.

Step 5: Tert-butyl 9-(1-(4-(4-(5-fluoro-3-(2-fluoro-4-(2-hydroxypropan-2-yl)benzamido)-2-methylphenyl)-7H-pyrrolo[2,3-d]pyrimidin-6-yl)phenyl)-2-methylpropan-2-yl)-3,9-diazaspiro[5.5]undecane-3-carboxylate To a solution of tert-butyl 9-(1-(4-(4-chloro-7H-pyrrolo[2,3-d]pyrimidin-6-yl)phenyl)-2-methylpropan-2-yl)-3,9-diazaspiro[5.5]undecane-3-carboxylate (33 mg, 0.019 mmol) in 1-propanol (1 ml) at RT was added 2-fluoro-N-(5-fluoro-2-methyl-3-(4,4,5,5-tetramethyl-1,3,2-dioxaborolan-2-yl)phenyl)-4-(2-hydroxypropan-2-yl)benzamide (intermediate 2, 36 mg, 0.083 mmol), 1-propanol (1.5 ml) and an aq. solution of $Na_2CO_3$ (2 M) (0.08 ml, 0.160 mmol). Argon was passed through the mixture, $PdCl_2(PPh_3)_2$ (1.330 mg, 1.895 µmol) was added and the RM was heated at 140° C. using microwave radiation for 20 min. The RM was diluted with EtOAc, the mixture was dried over $MgSO_4$, adsorbed and dried on Isolute® HMN and purified by reverse phase chromatography on a Redisep® C18 column eluting with ACN in an aq. solution of TFA (0.1%) (from 5 to 100%) to afford the title compound as a solid TFA salt (9 mg).

Method A: Rt=1.00 min; $[M+H]^+$=807.4.

Step 6: N-(3-(6-(4-(2-(9-(3-(2,4-dioxotetrahydropyrimidin-1(2H)-yl)-4-methoxybenzoyl)-3,9-diazaspiro[5.5]undecan-3-yl)-2-methylpropyl)phenyl)-7H-pyrrolo[2,3-d]pyrimidin-4-yl)-5-fluoro-2-methylphenyl)-2-fluoro-4-(2-hydroxypropan-2-yl)benzamide A solution of tert-butyl 9-(1-(4-(4-(5-fluoro-3-(2-fluoro-4-(2-hydroxypropan-2-yl)benzamido)-2-methylphenyl)-7H-pyrrolo[2,3-d]pyrimidin-6-yl)phenyl)-2-methylpropan-2-yl)-3,9-diazaspiro[5.5]undecane-3-carboxylate (9 mg, 8.70 µmol) in DCM (0.8 ml) and TFA (0.8 ml) was stirred at RT for 10 min. The solvents were evaporated and the residue was dissolved in DMF (0.8 ml) and NMM (0.022 ml, 0.200 mmol). 3-(2,4-Dioxotetrahydropyrimidin-1(2H)-yl)-4-methoxybenzoic acid (intermediate 5, 4.60 mg, 0.017 mmol) and HATU (6.61 mg, 0.017 mmol) were added and the RM was stirred at RT for 15 h under argon. The mixture was adsorbed and dried on Isolute® and purified by reverse phase chromatography on a Redisep® C18 column eluting with ACN in an aq. solution of TFA (0.1%) (from 5 to 100%), to afford the title compound as a solid TFA salt (6.5 mg).

Method B: Rt=3.91 min, $[M+H]^+$=953.7.

$^1$H NMR (400 MHz, DMSO-$d_6$) δ 12.83 (s, 1H), 10.34 (s, 1H), 9.95 (s, 1H), 8.88 (s, 1H), 7.99 (d, J=8.2 Hz, 2H), 7.73 (t, J=7.9 Hz, 1H), 7.70-7.50 (m, 1H), 7.50-7.25 (m, 6H), 7.25 (d, J=8.8 Hz, 1H), 7.17 (d, J=8.7 Hz, 1H), 6.89 (s, 1H), 3.85 (s, 3H), 3.70-3.40 (m, 6H), 3.20-3.00 (m, 2H), 2.70-2.60 (m, 2H), 2.18 (s, 3H), 2.1-1.9 (m, 3H), 1.75-1.55 (m, 4H), 1.45 (s, 6H), 1.45-1.20 (m, 12H).

Compound 21

N-(3-(6-(4-(((1-(2-(4-(3-(2,4-dioxotetrahydropyrimidin-1(2H)-yl)-4-methoxybenzoyl)piperazin-1-yl)ethyl)piperidin-4-yl)oxy)methyl)phenyl)-7H-pyrrolo[2,3-d]pyrimidin-4-yl)-5-fluoro-2-methylphenyl)-2-fluoro-4-(2-hydroxypropan-2-yl)benzamide

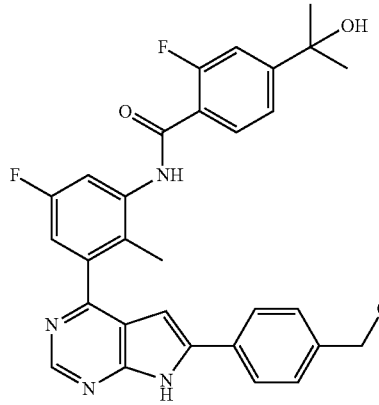
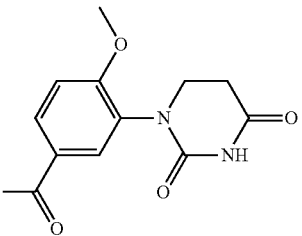

Step 1: tert-butyl 4-(2-chloroethyl)piperazine-1-carboxylate

To a 250 ml round bottom flask were added tert-butyl piperazine-1-carboxylate (10 g, 53.7 mmol), ACN (100 ml) and $K_2CO_3$ (11.1 g, 80.6 mmol) and the mixture was cooled to 5° C. 1-Bromo-2-chloroethane (15.0 g, 104 mmol) was slowly added at 5° C., the RM was allowed to warm to RT and stirring was continued for 18 h. The RM was filtered, the filtrate was concentrated and purified by chromatography on silica gel eluting with EtOAc in petroleum ether (from 0 to 50%) yielding the title compound as an oil (4.2 g).

Method J: Rt=1.93 min, MS m/z [M+H]$^+$ 249.

Step 2: tert-butyl 4-(4-bromobenzyloxy)piperidine-1-carboxylate

To a 250 ml round bottom flask was added NaH (60%) in mineral oil (1.17 g, 29.25 mmol) and DMF (30 ml) and the mixture was cooled to 5° C. A solution of tert-butyl 4-hydroxypiperidine-1-carboxylate (4.03 g, 20.0 mmol) in DMF (15 ml) was added drop by drop at 5° C. and the RM was stirred at 5° C. for 1 h. 1-Bromo-4-(bromomethyl)benzene (7.0 g, 28.0 mmol) was added at 5° C., the RM was stirred at 30° C. for 18 h and was then diluted with ice-water. The phases were separated and the aq. phase was extracted with a mixture of EtOAc and petroleum ether (2:1), the combined organic phases were dried, concentrated and purified by chromatography on silica gel eluting with EtOAc in petroleum ether (from 0 to 20%) yielding the title compound as an oil (6.1 g).

Method H: Rt=2.30 min, MS m/z [M−100+H]$^+$ 270.

Step 3: tert-butyl 4-(4-(4,4,5,5-tetramethyl-1,3,2-dioxaborolan-2-yl)benzyloxy)piperidine-1-carboxylate To a 100 ml round bottom flask, purged and maintained under inert atmosphere, were added tert-butyl 4-(4-bromobenzyloxy)piperidine-1-carboxylate (2.0 g, 5.4 mmol), BISPIN (2.7 g, 10.8 mmol), KOAc (1.59 g, 16.2 mmol) and PdCl$_2$(dpp) (630 mg, 0.86 mmol). 1,4-Dioxane (45 ml) was added and the RM was stirred at 85° C. for 18 h under N$_2$. The RM was evaporated and the residue was purified by chromatography on silica gel eluting with EtOAc in petroleum ether (from 0 to 20%) yielding the title compound as a solid (2.1 g).

Method F: Rt=1.70 min, MS m/z [M−100+H]$^+$ 318.

Step 4: 4-(4-(4,4,5,5-tetramethyl-1,3,2-dioxaborolan-2-yl)benzyloxy)piperidine

To a 50 ml round bottom flask was added tert-butyl 4-(4-(4,4,5,5-tetramethyl-1,3,2-dioxaborolan-2-yl)benzyloxy)piperidine-1-carboxylate (2.1 g, 5.0 mmol) and DCM (10 ml) and the solution was cooled to 5° C. A solution of HCl (4 M) in 1,4-dioxane (5 ml, 20 mmol) was slowly added and the RM was stirred at 30° C. for 2 h. The mixture was concentrated, triturated with a mixture of petroleum ether and TBME (2:1) and the solids were filtered, yielding the title compound as a solid HCl salt (1.2 g).

Method E: Rt=1.74 min, MS m/z [M+H]$^+$ 318.

Step 5: 4-((1-(2-(4-(tert-butoxycarbonyl)piperazin-1-yl)ethyl)piperidin-4-yloxy)methyl)phenylboronic Acid In a 100 ml round bottom flask were added 4-(4-(4,4,5,5-tetramethyl-1,3,2-dioxaborolan-2-yl)benzyloxy)piperidine hydrochloride (530 mg, 1.5 mmol), K$_2$CO$_3$ (518 mg, 3.75 mmol), NaI (80 mg, 0.53 mmol), ACN (30 ml) and tert-butyl 4-(2-chloroethyl)piperazine-1-carboxylate (374 mg, 1.5 mmol). The RM was stirred at 30° C. for 24 h, concentrated, rediluted in DMF (9 ml), stirred at 60° C. for 6 h and filtered to give the title compound as a solid (670 mg).

Method I: Rt=1.02 min, MS m/z [M+H]$^+$ 448.

Step 6: tert-butyl 4-(2-(4-(4-(4-(5-fluoro-3-(2-fluoro-4-(2-hydroxypropan-2-yl)benzamido)-2-methylphenyl)-7-(phenylsulfonyl)-7H-pyrrolo[2,3-d]pyrimidin-6-yl)benzyloxy)piperidin-1-yl)ethyl)piperazine-1-carboxylate To a 100 ml round bottom flask, purged and maintained under inert atmosphere, were added a solution of 4-((1-(2-(4-(tert-butoxycarbonyl)piperazin-1-yl)ethyl)piperidin-4-yloxy)methyl)phenylboronic acid (604 mg, 1.35 mmol) in DMF (9 ml), 4-chloro-6-iodo-7-(phenylsulfonyl)-7H-pyrrolo[2,3-d]pyrimidine (intermediate 7, 680 mg, 1.62 mmol), Na$_2$CO$_3$ (300 mg, 2.83 mmol), and PdCl$_2$(dpp) (120 mg, 0.16 mmol). ACN (25 ml) and water (7 ml) were added and the RM was stirred at 95° C. for 1 h under N$_2$. To the mixture was added 2-fluoro-N-(5-fluoro-2-methyl-3-(4,4,5,5-tetramethyl-1,3,2-dioxaborolan-2-yl)phenyl)-4-(2-hydroxypropan-2-yl)benzamide (intermediate 2, 815 mg, 1.89 mmol), Na$_2$CO$_3$ (520 mg, 4.9 mmol) and PdCl$_2$(dppf) (80 mg, 0.11 mmol) and the RM was stirred at 100° C. for 16 h under N$_2$. The mixture was concentrated, water was added, filtered and the solids were purified by chromatography on silica gel eluting with EtOAc in petroleum ether (from 0 to 50%) yielding the title compound as a solid (1.3 g).

Method I: Rt=1.51 min, MS m/z [M+H]$^+$ 965.

Step 7: tert-butyl 4-(2-(4-(4-(4-(5-fluoro-3-(2-fluoro-4-(2-hydroxypropan-2-yl)benzamido)-2-methylphenyl)-7H-pyrrolo[2,3-d]pyrimidin-6-yl)benzyloxy)piperidin-1-yl)ethyl)piperazine-1-carboxylate In a 100 ml round bottom flask was added a solution of tert-butyl 4-(2-(4-(4-(4-(5-fluoro-3-(2-fluoro-4-(2-hydroxypropan-2-yl)benzamido)-2-methylphenyl)-7-(phenylsulfonyl)-7H-pyrrolo[2,3-d]pyrimidin-6-yl)benzyloxy)piperidin-1-yl)ethyl)piperazine-1-carboxylate (1.3 g, 1.35 mmol) in DMSO (12 ml) and a solution of NaOH (630 mg, 15.75 mmol) in water (2.6 ml) was added at 0° C. The RM was stirred at 30° C. for 1 h and then ice-water was added. The solids were filtered, redissolved in DCM, the solution was dried over Na$_2$SO$_4$, concentrated and the residue was purified by chromatography on silica gel eluting with methanol in DCM (from 0 to 60%) yielding the title compound as a solid (600 mg).

Method I: Rt=1.34 min. MS m/z [M+H]$^+$ 825.

Step 8: 2-fluoro-N-(5-fluoro-2-methyl-3-(6-(4-((1-(2-(piperazin-1-yl)ethyl)piperidin-4-yloxy)methyl)phenyl)-7H-pyrrolo[2,3-d]pyrimidin-4-yl)phenyl)-4-(2-hydroxypropan-2-yl)benzamide To a 100 ml round bottom flask were added tert-butyl 4-(2-(4-(4-(4-(5-fluoro-3-(2-fluoro-4-(2-hydroxypropan-2-yl)benzamido)-2-methylphenyl)-7H-pyrrolo[2,3-d]pyrimidin-6-yl)benzyloxy)piperidin-1-yl)ethyl)piperazine-1-carboxylate (200 mg, 0.24 mmol), DCM (1.5 ml) and EtOH (4.5 ml). A solution of HCl (4 M) in 1,4-dioxane (1.8 ml, 7.2 mmol) was slowly added at 5° C. and the RM was stirred at 30° C. for 4 h. The RM was concentrated, triturated with a mixture of petroleum ether and TBME (1:1), TBME and a mixture of DCM and TBME (1:2) and filtered yielding the title compound as a solid HCl salt (160 mg).
Method I: Rt=1.15 min, MS m/z [M+H]⁺ 725.

Step 9: N-(3-(6-(4-(((1-(2-(4-(3-(2,4-dioxotetrahydropyrimidin-1(2H)-yl)-4-methoxybenzoyl)piperazin-1-yl)ethyl)piperidin-4-yl)oxy)methyl)phenyl)-7H-pyrrolo[2,3-d]pyrimidin-4-yl)-5-fluoro-2-methylphenyl)-2-fluoro-4-(2-hydroxypropan-2-yl)benzamide To a 100 ml round bottom flask were added 2-fluoro-N-(5-fluoro-2-methyl-3-(6-(4-(((1-(2-(piperazin-1-yl)ethyl)piperidin-4-yloxy)methyl)phenyl)-7H-pyrrolo[2,3-d]pyrimidin-4-yl)phenyl)-4-(2-hydroxypropan-2-yl)benzamide hydrochloride (160 mg, 0.21 mmol), 3-(2,4-dioxotetrahydropyrimidin-1(2H)-yl)-4-methoxybenzoic acid (intermediate 5, 63 mg, 0.24 mmol), DMF (2.5 ml) and DIPEA (163 mg, 1.26 mmol) and the mixture was cooled to 5° C. HATU (90 mg, 0.24 mmol) was added and the RM was stirred at 5° C. for 1 h. The mixture was filtered and the filtrate was purified by preparative HPLC on a XBridge C18 column (21.2×250 mm, 10 μm) eluting with ACN in an aq. solution of ammonium hydrogencarbonate (10 mM), yielding the title compound as a solid (79 mg).
Method G: Rt=1.95 min, MS m/z [M+H]⁺ 970.
¹H NMR (500 MHz, DMSO-d₆) δ 12.78 (s, 1H), 10.34 (s, 1H), 9.95 (s, 1H), 8.85 (s, 1H), 7.96 (d, J=8.2 Hz, 2H), 7.73 (t, J=8.0 Hz, 1H), 7.66 (dd, J=9.8, 1.7 Hz, 1H), 7.45-7.39 (m, 4H), 7.37 (dd, J=8.4, 2.1 Hz, 1H), 7.33 (d, J=2.0 Hz, 1H), 7.24 (dd, J=8.8, 2.7 Hz, 1H), 7.15 (d, J=8.6 Hz, 1H), 6.85 (s, 1H), 5.31 (s, 1H), 4.53 (s, 2H), 3.84 (s, 3H), 3.59 (t, J=6.6 Hz, 2H), 3.54-3.40 (m, 4H), 3.39-3.36 (m, 1H), 2.74-2.64 (m, 4H), 2.45-2.36 (m, 8H), 2.17 (s, 3H), 2.07 (t, J=9.3 Hz, 2H), 1.89-1.80 (m, 2H), 1.54-1.47 (m, 2H), 1.45 (s, 6H).

Compound 22

N-(3-(6-(4-((4-(4-(3-(2,4-Dioxotetrahydropyrimidin-1(2H)-yl)-4-methoxybenzoyl)piperazine-1-carbonyl)piperazin-1-yl)methyl)phenyl)-7H-pyrrolo[2,3-d]pyrimidin-4-yl)-5-fluoro-2-methylphenyl)-2-fluoro-4-(2-hydroxypropan-2-yl)benzamide Step 1: tert-butyl 4-(piperazine-1-carbonyl)piperazine-1-carboxylate To a 100 ml round bottom flask containing a solution of di(1H-imidazol-1-yl)methanone (1.95 g, 12.0 mmol) in THF (35 ml), tert-butyl piperazine-1-carboxylate (1.863 g, 10.0 mmol) was added at 0° C. The resulting solution was stirred at 0° C. for 2 h, then piperazine (2.59 g, 30.0 mmol) was added and the RM was stirred at 65° C. for 16 h, then additional piperazine (0.86 g, 10.0 mmol) was added and the RM was stirred at 65° C. for 24 h. The solvent was removed and the residue was redissolved in H₂O, Na₂CO₃ was added and the mixture was extracted with DCM. The combined organic phases were dried over Na₂SO₄ and the solvent was removed. The residue was triturated with TBME, the mixture was filtered, the solids were washed with TBME and dried, yielding the title compound as a solid (2.0 g).
¹H NMR (500 MHz, DMSO-d₆) δ 3.30 (s, 4H), 3.11-3.02 (m, 8H), 2.67-2.61 (m, 4H), 2.36 (s, 1H), 1.40 (s, 9H).

Step 2: tert-butyl 4-(4-(3-(2,4-dioxotetrahydropyrimidin-1(2H)-yl)-4-methoxybenzoyl)piperazine-1-carbonyl)piperazine-1-carboxylate To a 100 ml round bottom flask containing a solution of 3-(2,4-dioxotetrahydropyrimidin-1(2H)-yl)-4-methoxybenzoic acid (intermediate 5, 555 mg, 2.1 mmol) and HATU (783 mg, 2.06 mmol) in DMF (8 ml), DIPEA was added (517 mg, 4.0 mmol) and the RM was stirred at 15° C. for 5 min., then tert-butyl 4-(piperazine-1-carbonyl)piperazine-1-carboxylate (587 mg, 2.0 mmol) was added. The solution was stirred at 15° C. for 1 h, poured into ice-water containing KH₂PO₄ and the mixture was extracted with DCM. The combined organic phases were dried over Na₂SO₄ and evaporated yielding the title compound as a solid (1.1 g).
Method F: Rt=1.113 min, MS m/z [M+Na]⁺ 567.

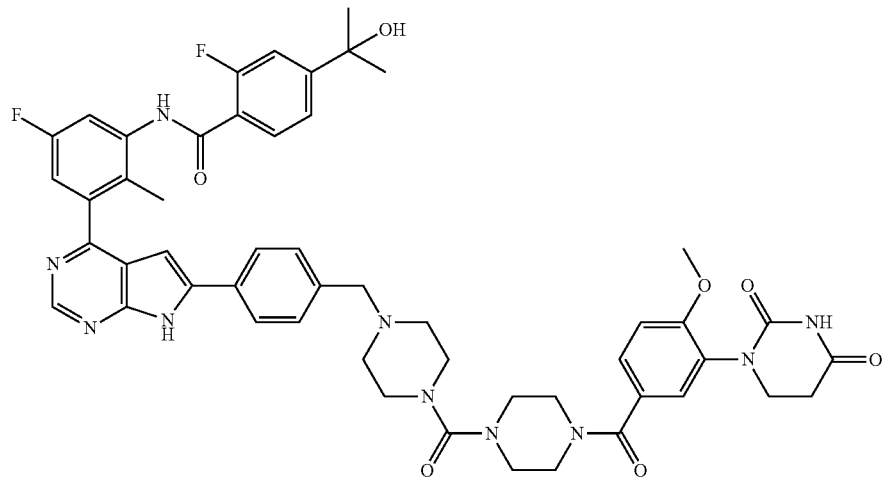 [SMILES: COc1ccc(C(=O)N2CCN(C(=O)N3CCN(Cc4ccc(-c5cc6c(-c7cc(F)cc(NC(=O)c8ccc(C(C)(C)O)cc8F)c7C)ncnc6[nH]5)cc4)CC3)CC2)cc1N1CCC(=O)NC1=O]

Step 3: 1-(2-methoxy-5-(4-(piperazine-1-carbonyl)piperazine-1-carbonyl)phenyl)dihydropyrimidine-2,4(1H,3H)-dione To a 100 ml round bottom flask containing a solution of tert-butyl 4-(4-(3-(2,4-dioxotetrahydropyrimidin-1(2H)-yl)-4-methoxybenzoyl)piperazine-1-carbonyl)piperazine-1-carboxylate (1.1 g, 2.0 mmol) in DCM (10 ml), anisole (1 ml) and TFA (3.5 ml) were added. The RM was stirred at 15° C. for 3 h, the solvent was removed, the residue was triturated with TBME, the mixture was filtered and the solids were dried, providing the title compound as a solid TFA salt (1.0 g).

Method F: Rt=0.750 min, MS m/z [M+Na]$^+$ 445.

J=8.7, 2.7 Hz, 1H), 7.16 (d, J=8.4 Hz, 1H), 6.84 (s, 1H), 5.31 (s, 1H), 3.84 (s, 3H), 3.60 (t, J=6.6 Hz, 2H), 3.53 (s, 2H), 3.49-3.41 (m, 2H), 3.31 (s, 2H), 3.24-3.13 (m, 8H), 2.68 (t, J=6.5 Hz, 2H), 2.40-2.34 (m, 4H), 2.18 (s, 3H), 1.45 (s, 6H).

Compound 23 rac-N-(3-(6-(4-((9-(3-(2,4-Dioxotetrahydropyrimidin-1(2H)-yl)-4-methoxybenzoyl)-1-(hydroxymethyl)-3,9-diazaspiro[5.5]undecan-3-yl)methyl)phenyl)-7H-pyrrolo[2,3-d]pyrimidin-4-yl)-5-fluoro-2-methylphenyl)-2-fluoro-4-(2-hydroxypropan-2-yl)benzamide

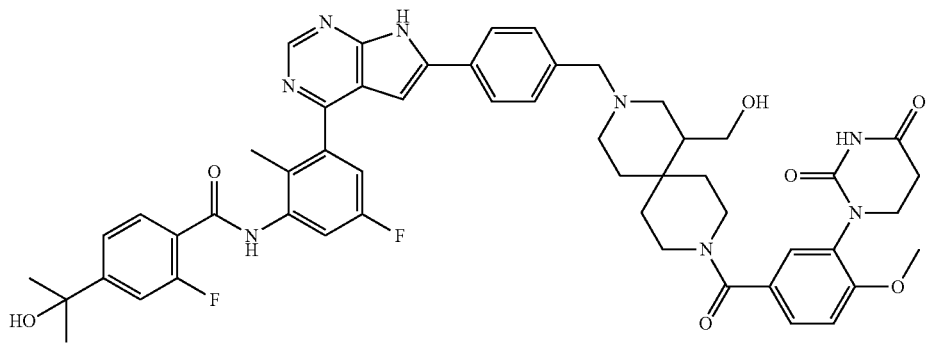 [SMILES: COc1ccc(C(=O)N2CCC3(CCN(Cc4ccc(-c5cc6c(-c7cc(F)cc(NC(=O)c8ccc(C(C)(C)O)cc8F)c7C)ncnc6[nH]5)cc4)CC3CO)CC2)cc1N1CCC(=O)NC1=O]

Step 4: N-(3-(6-(4-((4-(4-(3-(2,4-dioxotetrahydropyrimidin-1(2H)-yl)-4-methoxybenzoyl)piperazine-1-carbonyl)piperazin-1-yl)methyl)phenyl)-7H-pyrrolo[2,3-d]pyrimidin-4-yl)-5-fluoro-2-methylphenyl)-2-fluoro-4-(2-hydroxypropan-2-yl)benzamide To a 50 ml round bottom flask, containing a solution of 1-(2-methoxy-5-(4-(piperazine-1-carbonyl)piperazine-1-carbonyl)phenyl)dihydropyrimidine-2,4(1H,3H)-dione trifluoroacetate (440 mg, 0.788 mmol) and DIPEA (70 mg, 0.542 mmol) in MeOH (5 ml), was added a solution of 2-fluoro-N-(5-fluoro-3-(6-(4-formylphenyl)-7H-pyrrolo[2,3-d]pyrimidin-4-yl)-2-methylphenyl)-4-(2-hydroxypropan-2-yl)benzamide (intermediate 3, 206 mg, 0.391 mmol) in DMSO (5 ml) at 10° C. and the mixture was stirred for 5 min. A solution of ZnCl$_2$ (1 M) in THF (0.41 ml, 0.41 mmol) was added and the RM was stirred at 22° C. for 2 h. Solid NaBH$_3$CN (30 mg, 0.477 mmol) was added and stirring was continued at 22° C. for 18 h. The solvent was removed, ice-water and KH$_2$PO$_4$ were added, the mixture was filtered and the filtrate was purified by reversed phase chromatography on an Agela C18 column (spherical 20-35 μm, 100 Å, 40 g) eluting with ACN in an aq. solution of ammonium hydrogencarbonate (0.0075M), yielding the title compound as a solid (63 mg).

Method D: Rt=1.223 min, MS m/z [M+H]$^+$ 955.

$^1$H NMR (500 MHz, DMSO-d$_6$) δ 12.78 (s, 1H), 10.36 (s, 1H), 9.96 (s, 1H), 8.85 (s, 1H), 7.96 (d, J=8.1 Hz, 2H), 7.73 (m, 1H), 7.66 (d, J=9.9 Hz, 1H), 7.44-7.36 (m, 6H), 7.24 (dd,

To a mixture of 2-fluoro-N-(5-fluoro-3-(6-(4-formylphenyl)-7H-pyrrolo[2,3-d]pyrimidin-4-yl)-2-methylphenyl)-4-(2-hydroxypropan-2-yl)benzamide (intermediate 3, 200 mg, 0.380 mmol), rac-1-(5-(7-(hydroxymethyl)-3,9-diazaspiro[5.5]undecane-3-carbonyl)-2-methoxyphenyl)dihydropyrimidine-2,4(1H,3H)-dione trifluoroacetate (intermediate 20, 228 mg, 0.418 mmol) and TEA (0.079 ml, 0.570 mmol) in THF (3 ml) was added a solution of ZnCl$_2$ (0.5 M) in THF (0.798 ml, 0.399 mmol). The RM was stirred at RT for 3 h under argon, solid NaBH$_3$CN (47.7 mg, 0.760 mmol) was added and the RM was stirred at RT for 4 h. The mixture was diluted with DCM, the organic phase was washed with water, concentrated, the residue was absorbed and dried on Isolute® and purified by reverse phase chromatography on Redisep® C18 column eluting with ACN in an aq. solution of TFA (0.1%) (from 10 to 100%) to afford, after filtration through PL-HCO3 MP SPE cartridges and freeze drying, the title compound as a solid (161 mg).

Method B: Rt=3.53 min, [M+H]$^+$=942.3.

$^1$H NMR (400 MHz, DMSO-d$_6$) δ 12.77 (s, 1H), 10.33 (s, 1H), 9.95 (s, 1H), 8.85 (s, 1H), 8.2-7.85 (m, 2H), 7.73 (t, J=8 Hz, 1H), 7.66 (d, J=8.8 Hz, 1H), 7.57-7.28 (m, 6H), 7.24 (dd, J=8.8, 2.5 Hz, 1H), 7.14 (d, J=8.6 Hz, 1H), 6.84 (s, 1H), 5.30 (s, 1H), 4.38 (br. s, 1H), 3.84 (s, 3H), 3.7-3.40 (m, 6H), 3.3-3.0 (m, 4H), 2.75-2.55 (m, 3H), 2.35-2.25 (m, 2H), 2.18 (s, 3H), 2.0-1.7 (m, 2H), 1.58-1.15 (m, 6H), 1.45 (s, 6H).

Compound 24 and Compound 25

(R)—N-(3-(6-(4-((9-(3-(2,4-Dioxotetrahydropyrimi-din-1(2H)-yl)-4-methoxybenzoyl)-1-(hydroxymethyl)-3,9-diazaspiro[5.5]undecan-3-yl)methyl)phenyl)-7H-pyrrolo[2,3-d]pyrimidin-4-yl)-5-fluoro-2-methylphenyl)-2-fluoro-4-(2-hydroxypropan-2-yl)benzamide and (S)—N-(3-(6-(4-((9-(3-(2,4-Dioxotetrahydropyrimi-din-1(2H)-yl)-4-methoxybenzoyl)-1-(hydroxymethyl)-3,9-diazaspiro[5.5]undecan-3-yl)methyl)phenyl)-7H-pyrrolo[2,3-d]pyrimidin-4-yl)-5-fluoro-2-methylphenyl)-2-fluoro-4-(2-hydroxypropan-2-yl)benzamide methylphenyl)-2-fluoro-4-(2-hydroxypropan-2-yl)benzamide (50 mg, 50.6 μmol) using HPLC on a Chiralpak ID column (5 μm, 250×20 mm) eluting with a mixture of heptane, DCM and MeOH (40:35:25) containing IDEA (0.05%) at a flow rate of 10 ml/min (Method M) afforded the title compounds as single enantiomers in the following order:

first eluting enantiomer: 14.7 mg;
Method K: Rt=30.8 min;
Method B: Rt=3.45 min; [M+H]$^+$=941.5.
$^1$H NMR (400 MHz, DMSO-d$_6$) is in accordance with the NMR for the racemate reported above
second eluting enantiomer: 12.7 mg;

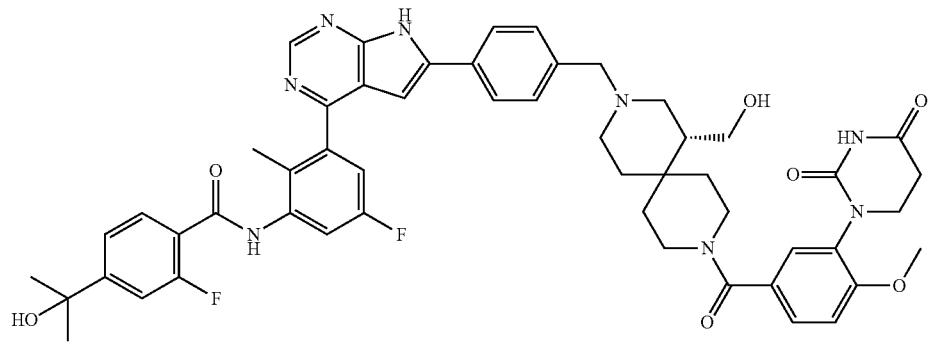

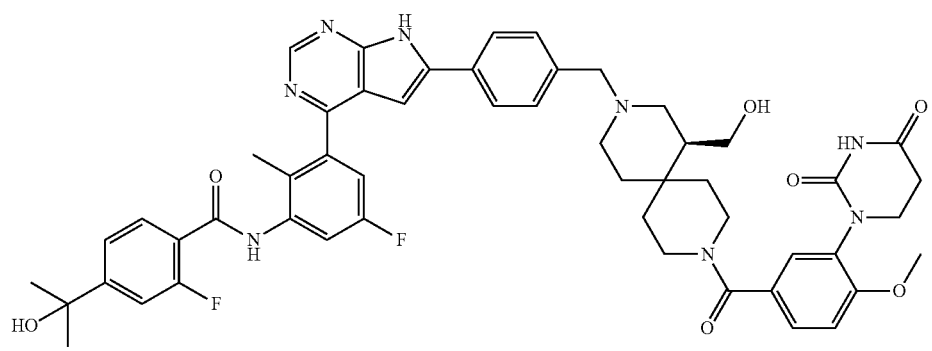

Chiral separation of rac-N-(3-(6-(4-((9-(3-(2,4-dioxotetrahydropyrimidin-1(2H)-yl)-4-methoxybenzoyl)-1-(hydroxymethyl)-3,9-diazaspiro[5.5]undecan-3-yl)methyl)phenyl)-7H-pyrrolo[2,3-d]pyrimidin-4-yl)-5-fluoro-2-

Method K: Rt=42.3 min;
Method B: Rt=3.48 min; [M+H]$^+$=941.5.
$^1$H NMR (400 MHz, DMSO-d$_6$) is in accordance with the NMR for the racemate reported above

Compound 26

N-(3-(6-(4-((4-(4-(3-(2,4-Dioxotetrahydropyrimidin-1(2H)-yl)-4-methoxybenzamido)butyl)piperazin-1-yl)methyl)phenyl)-7H-pyrrolo[2,3-d]pyrimidin-4-yl)-5-fluoro-2-methylphenyl)-2-fluoro-4-(2-hydroxypropan-2-yl)benzamide

Step 1: tert-butyl 4-(4-(3-(2,4-dioxotetrahydropyrimidin-1(2H)-yl)-4-methoxybenzamido)butyl)piperazine-1-carboxylate A solution of 3-(2,4-dioxotetrahydropyrimidin-1(2H)-yl)-4-methoxybenzoic acid (intermediate 5, 150 mg, 0.539 mmol), 4-(4-amino-butyl)-piperazine-1-carboxylic acid tert-butyl ester (146 mg, 0.539 mmol), HATU (293 mg, 0.755 mmol) and NMM (0.300 ml, 2.70 mmol) in DMF (5 ml) was stirred at RT for 3 h. The reaction mixture was purified by reverse phase chromatography on a Redisep® C18 column eluting with ACN in an aq. solution of TFA (0.1%) (from 2 to 100%) to afford the title compound as a solid TFA salt (348 mg).

Method A: Rt=0.98 min; [M+H]⁺=504.3.

Step 2: 3-(2,4-dioxotetrahydropyrimidin-1(2H)-yl)-4-methoxy-N-(4-(piperazin-1-yl)butyl)benzamide A solution of tert-butyl 4-(4-(3-(2,4-dioxotetrahydropyrimidin-1(2H)-yl)-4-methoxybenzamido)butyl)piperazine-1-carboxylate (305 mg, 0.469 mmol) in MeOH (2 ml) and a solution of HCl (4 M) in 1,4-dioxane (4 ml, 16 mmol) was stirred at RT for 1.5 h. The solvent was removed, the residue redissolved in a mixture of ACN and water and freeze dried, to afford the title compound as a solid HCl salt (249 mg).

Method A: Rt=0.70 min; [M+H]⁺=404.4.

Step 3: N-(3-(6-(4-((4-(4-(3-(2,4-dioxotetrahydropyrimidin-1(2H)-yl)-4-methoxybenzamido)butyl)piperazin-1-yl)methyl)phenyl)-7H-pyrrolo[2,3-d]pyrimidin-4-yl)-5-fluoro-2-methylphenyl)-2-fluoro-4-(2-hydroxypropan-2-yl)benzamide

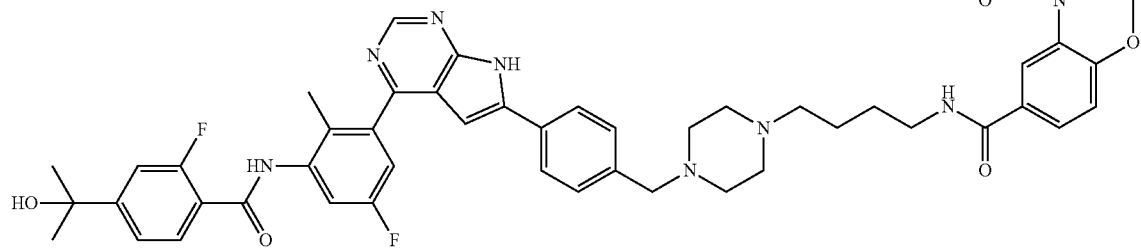

3-(2,4-Dioxotetrahydropyrimidin-1(2H)-yl)-4-methoxy-N-(4-(piperazin-1-yl)butyl)benzamide hydrochloride (136 mg, 0.303 mmol), TEA (0.100 ml, 0.717 mmol) and 2-fluoro-N-(5-fluoro-3-(6-(4-formylphenyl)-7H-pyrrolo[2,3-d]pyrimidin-4-yl)-2-methylphenyl)-4-(2-hydroxypropan-2-yl)benzamide (intermediate 3, 163 mg, 0.303 mmol) were dissolved in MeOH (2 ml) at RT, a solution of ZnCl₂ (0.5 M) in THF (0.75 ml, 0.375 mmol) was added and the RM was stirred at RT overnight. Solid NaBH₃CN (22 mg, 0.350 mmol) was added, the RM was stirred at RT overnight and the solvent was removed. The residue was purified by reverse phase chromatography on a Redisep® C18 column eluting with ACN in an aq. solution of TFA (0.1%) (from 2 to 100%) to afford, after filtration through PL-HCO₃ MP SPE cartridges and freeze drying, a solid. Additional purification of this material by SFC on a Reprospher PEI column (250×30 mm, 100 A, 5 μM) eluting with MeOH in CO₂ (from 33 to 50%) afforded the title compound as a solid (95 mg).

Method B: Rt=3.68 min; [M+H]⁺=914.5.

¹H NMR (400 MHz, DMSO-d6) δ 12.74 (s, 1H), 10.33 (s, 1H), 9.93 (s, 1H), 8.84 (s, 1H), 8.33 (t, J=5.6 Hz, 1H), 7.93 (d, J=7.8 Hz, 2H), 7.83 (dd, J=8.7, 2.3 Hz, 1H), 7.78-7.68 (m, 2H), 7.64 (d, J=9.7 Hz, 1H), 7.39 (m, 4H), 7.22 (dd, J=8.9, 2.8 Hz, 1H), 7.15 (d, J=8.7 Hz, 1H), 6.81 (s, 1H), 5.28 (s, 1H), 3.84 (s, 3H), 3.57 (t, J=6.7 Hz, 2H), 3.48 (s, 2H), 3.25-3.18 (m, 2H), 2.67 (t, J=6.6 Hz, 2H), 2.43-2.24 (m, 10H), 2.16 (s, 3H), 1.45 (m, 10H).

Compound 27

N-(3-(6-(4-((9-(3-(2,4-Dioxotetrahydropyrimidin-1 (2H)-yl)-4-methylbenzoyl)-3,9-diazaspiro[5.5]undecan-3-yl)methyl)phenyl)-7H-pyrrolo[2,3-d]pyrimidin-4-yl)-5-fluoro-2-methylphenyl)-2-fluoro-4-(2-hydroxypropan-2-yl)benzamide

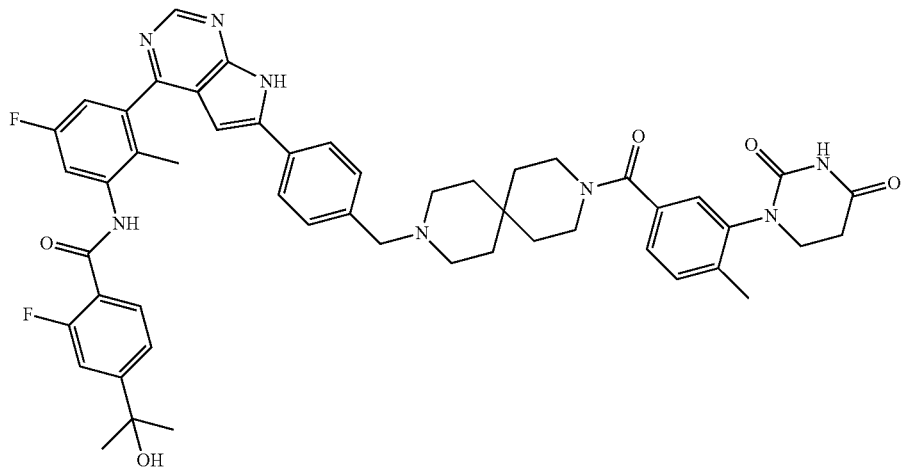 [SMILES: Cc1ccc(C(=O)N2CCC3(CCN(Cc4ccc(-c5cc6c(-c7cc(F)cc(NC(=O)c8ccc(C(C)(C)O)cc8F)c7C)ncnc6[nH]5)cc4)CC3)CC2)cc1N1CCC(=O)NC1=O]

Step 1: tert-butyl 9-(3-(2,4-dioxotetrahydropyrimidin-1(2H)-yl)-4-methylbenzoyl)-3,9-diazaspiro[5.5]undecane-3-carboxylate To a 100 ml round bottom flask were added 3-(2,4-dioxotetrahydropyrimidin-1(2H)-yl)-4-methylbenzoic acid (intermediate 8, 195 mg, 0.787 mmol), TEA (0.33 ml, 2.36 mmol), THF (8 ml) and HATU (420 mg, 1.1 mmol). The RM was stirred at RT for 5 min; tert-butyl 3,9-diazaspiro[5.5] undecane-3-carboxylate (200 mg, 0.787 mmol) was added portionwise at 0° C. and the mixture was stirred at RT for 1 h. The mixture was concentrated and the residue was purified by chromatography on silica gel eluting with EtOAc to give the title compound as a solid (350 mg).
Method J: Rt=1.77 min; MS m/z [M+H]$^+$ 485

Step 2: 1-(2-methyl-5-(3,9-diazaspiro[5.5]undecane-3-carbonyl)phenyl)dihydropyrimidine-2,4(1H,3H)-dione To a 100 ml round bottom flask was added tert-butyl 9-(3-(2,4-dioxotetrahydropyrimidin-1(2H)-yl)-4-methylbenzoyl)-3,9-diazaspiro[5.5]undecane-3-carboxylate (0.35 g, 0.723 mmol) and DCM (5 ml) and the mixture was cooled to 0° C. A solution of HCl (4 M) in 1,4-dioxane (20 ml, 80 mmol) was added drop by drop, the RM was allowed to warm to RT and stirring was continued for 3 h. The RM was concentrated and directly used for the next step without further purification and the title compound was obtained as a solid HCl salt (0.32 g).
Method D: Rt=1.62 min; MS m/z [M+H]$^+$ 384.

Step 3: N-(3-(6-(4-((9-(3-(2,4-dioxotetrahydropyrimidin-1(2H)-yl)-4-methylbenzoyl)-3,9-diazaspiro[5.5]undecan-3-yl)methyl)phenyl)-7H-pyrrolo[2,3-d]pyrimidin-4-yl)-5-fluoro-2-methylphenyl)-2-fluoro-4-(2-hydroxypropan-2-yl)benzamide In a 100 ml round bottom flask were added 1-(2-methyl-5-(3,9-diazaspiro[5.5]undecane-3-carbonyl)phenyl)dihydropyrimidine-2,4(1H,3H)-dione hydrochloride (0.32 g, 0.723 mmol), 2-fluoro-N-(5-fluoro-3-(6-(4-formylphenyl)-7H-pyrrolo[2,3-d]pyrimidin-4-yl)-2-methylphenyl)-4-(2-hydroxypropan-2-yl)benzamide (intermediate 3, 0.25 g, 0.462 mmol), MeOH (10 ml) and THF (30 ml). A solution of ZnCl$_2$ (1 M) in THF (1.38 ml, 0.462 mmol) was added at 0° C. and the RM was allowed to warm to RT and stirring was continued for 2 h. Solid NaBH$_3$CN (87 mg, 1.38 mmol) was added and the RM was stirred at RT for 16 h. The mixture was filtered, the solids were washed with MeOH (10 ml) and the combined filtrates were concentrated. The residue was purified by preparative HPLC on a XBridge C18 column (21.2×250 mm, 10 μm) eluting with ACN in an aq. solution of ammonium hydrogen carbonate (10 mM), to afford the title compound as a solid (109 mg).
Method I: Rt=1.28 min; MS m/z [M+H]$^+$ 896.
$^1$H-NMR (500 MHz, DMSO-d$_6$) δ 12.75 (s, 1H), 10.37 (s, 1H), 9.95 (s, 1H), 8.85 (s, 1H), 7.94 (d, J=8.0 Hz, 2H), 7.75 (t, J=8.0 Hz, 1H), 7.67 (d, J=9.0 Hz, 1H), 7.43-7.30 (m, 6H), 7.24 (d, J=7.5 Hz, 2H), 6.82 (s, 1H), 5.3 (s, 1H), 3.85-3.75 (m, 1H), 3.56-3.49 (m, 5H), 3.37-3.27 (m, 2H), 2.77-2.6 (m, 2H), 2.39-2.29 (m, 4H), 2.21 (s, 3H), 2.17 (s, 3H), 1.49-1.37 (m, 8H), 1.45 (s, 6H).

Compound 28

5-(2,4-Dioxotetrahydropyrimidin-1(2H)-yl)-2-fluoro-N-(5-((4-(4-(5-fluoro-3-(2-fluoro-4-(2-hydroxypropan-2-yl)benzamido)-2-methylphenyl)-7H-pyrrolo[2,3-d]pyrimidin-6-yl)benzyl)amino)pentyl)-N,4-dimethylbenzamide

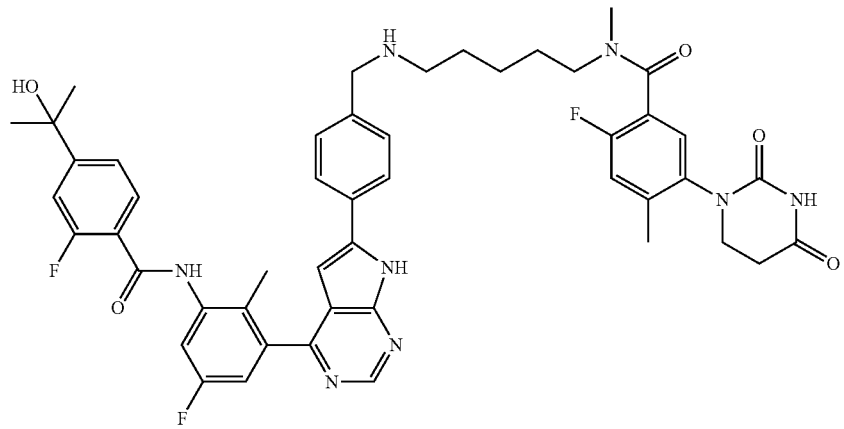 [SMILES: Cc1cc(F)c(C(=O)N(C)CCCCCNCc2ccc(-c3cc4c(-c5cc(F)cc(NC(=O)c6ccc(C(C)(C)O)cc6F)c5C)ncnc4[nH]3)cc2)cc1N1CCC(=O)NC1=O]

Step 1: Tert-butyl(5-(5-(2,4-dioxotetrahydropyrimidin-1(2H)-yl)-2-fluoro-N,4 dimethylbenzamido)pentyl)carbamate To a solution of 5-(2,4-dioxotetrahydropyrimidin-1(2H)-yl)-2-fluoro-4-methylbenzoic acid (intermediate 22, 80 mg, 0.300 mmol), 5-(methylamino)-N-Boc-pentanamine (73.7 mg, 0.331 mmol) and HBTU (128 mg, 0.331 mmol) in dry DMF (3 ml) under $N_2$ atmosphere was added DIPEA (210 µl, 1.202 mmol) and the resulting RM was stirred for 1 h at RT. The RM was diluted with DCM and citric acid buffer (pH=4, Sigma-Aldrich 33643) was added. The phases were separated, the aq. phase was extracted with DCM, the combined organic phases were dried over $MgSO_4$, evaporated and the residue was purified by chromatography on silica eluting with iPrOH in DCM (from 1 to 6%) to afford the title compound as a solid (124 mg).
Method A: Rt=0.88 min; [M+H]$^+$=465.4.

Step 2: N-(5-aminopentyl)-5-(2,4-dioxotetrahydropyrimidin-1(2H)-yl)-2-fluoro-N,4-dimethylbenzamide A suspension of tert-butyl (5-(5-(2,4-dioxotetrahydropyrimidin-1(2H)-yl)-2-fluoro-N,4 dimethylbenzamido)pentyl carbamate (123 mg, 0.244 mmol) in a solution of HCl (4 M) in 1,4-dioxane (1.827 ml, 7.31 mmol) was stirred at RT for 2 h under $N_2$ atmosphere. The RM was concentrated, redissolved in a mixture of ACN and water and freeze dried to afford the title compound as a solid HCl salt (116 mg).
Method A: Rt=0.46 min; [M+H]+=365.3.

Step 3: 5-(2,4-dioxotetrahydropyrimidin-1(2H)-yl)-2-fluoro-N-(5-((4-(4-(5-fluoro-3-(2-fluoro-4-(2-hydroxypropan-2-yl)benzamido)-2-methylphenyl)-7H-pyrrolo[2,3-d]pyrimidin-6-yl)benzyl)amino)pentyl)-N,4-dimethylbenzamide To a mixture of 2-fluoro-N-(5-fluoro-3-(6-(4-formylphenyl)-7H-pyrrolo[2,3-d]pyrimidin-4-yl)-2-methylphenyl)-4-(2-hydroxypropan-2-yl)benzamide (intermediate 3, 60 mg, 0.114 mmol), N-(5-aminopentyl)-5-(2,4-dioxotetrahydropyrimidin-1(2H)-yl)-2-fluoro-N,4-dimethylbenzamide hydrochloride (59.8 mg, 0.125 mmol) and TEA (0.017 ml, 0.125 mmol) in MeOH (2.1 ml) was added a solution of $ZnCl_2$ (0.5 M) in THF (0.251 ml, 0.125 mmol). The resulting mixture was stirred for 3 h at RT under $N_2$ atmosphere. Solid $NaBH_3CN$ (8.29 mg, 0.125 mmol) was added and the RM was stirred at RT for 18 h. The RM was diluted with ACN, adsorbed and dried on Isolute® and purified by reverse phase chromatography on a Redisep® C18 column eluting with ACN in an aq. solution of TFA (0.1%), to afford, after filtration through PL-HCO3 MP SPE cartridges and freeze drying, the title compound as a solid (77 mg).
Method A: Rt=0.81 min; [M+H]$^+$=875.4.
$^1$H NMR (400 MHz, DMSO-d$_6$) δ 12.71 (s, 1H), 10.35 (s, 1H), 9.92 (s, 1H), 8.83 (s, 1H), 7.91 (m, 2H), 7.72 (t, J=7.89 Hz, 1H), 7.64 (m, J=9.70 Hz, 1H), 7.44-7.35 (m, 4H), 7.31 (dd, J=6.48, 2.81 Hz, 1H), 7.24-7.18 (m, 2H), 6.81 (s, 1H), 5.28 (s, 1H), 3.80-3.62 (m, 3H), 3.51-3.40 (m, 2H), 3.11 (m, 1H), 2.93 (s, 1H), 2.80 (s, 3H), 2.64-2.77 (m, 2H), 2.52 (m, 1H), 2.39 (m, 1H), 2.17 (d, J=7.34 Hz, 6H), 1.41-1.57 (m, 9H), 1.25-1.36 (m, 2H), 1.02-1.14 (m, 1H).

Compound 29

5-(2,4-Dioxotetrahydropyrimidin-1(2H)-yl)-2-fluoro-N-(5-((4-(4-(5-fluoro-3-(2-fluoro-4-(2-hydroxypropan-2-yl)benzamido)-2-methylphenyl)-7H-pyrrolo[2,3-d]pyrimidin-6-yl)benzyl)amino)pentyl)-4-methylbenzamide

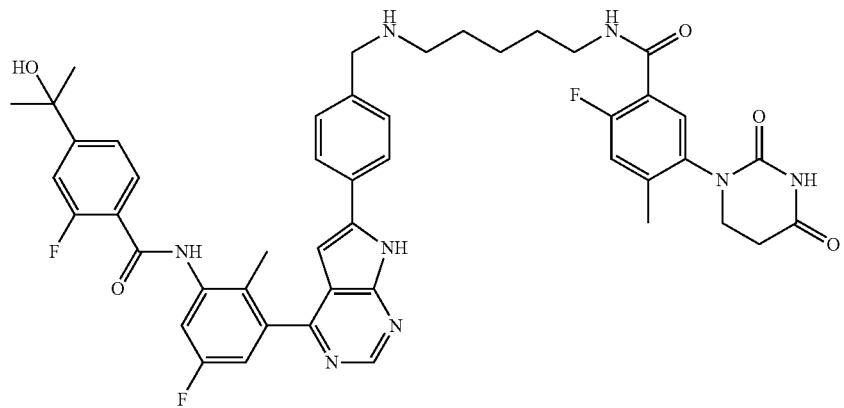 [SMILES: Cc1cc(F)c(C(=O)NCCCCCNCc2ccc(-c3cc4c(-c5cc(F)cc(NC(=O)c6ccc(C(C)(C)O)cc6F)c5C)ncnc4[nH]3)cc2)cc1N1CCC(=O)NC1=O]

Step 1: tert-butyl(5-(5-(2,4-dioxotetrahydropyrimidin-1(2H)-yl)-2-fluoro-4-methylbenzamido)pentyl) carbamate To a solution of 5-(2,4-dioxotetrahydropyrimidin-1(2H)-yl)-2-fluoro-4-methylbenzoic acid (intermediate 22, 80 mg, 0.300 mmol), N-Boc-cadaverine (0.071 ml, 0.331 mmol) and HBTU (128 mg, 0.331 mmol) in DMF (3 ml) under $N_2$ atmosphere was added DIPEA (210 µl, 1.202 mmol). The resulting RM was stirred for 2.5 h at RT, the RM was diluted with DCM and citric acid buffer (pH=4, Sigma-Aldrich 33643), the phases were separated and the aq. phase was extracted with DCM. The combined organic phases were dried over $MgSO_4$, filtered, evaporated and the residue purified by chromatography on silica gel eluting with iPrOH in DCM (from 1 to 6%) to afford the title compound as a solid (117 mg).

Method A: Rt=0.86 min; [M+H]$^+$=451.3.

Step 2: N-(5-aminopentyl)-5-(2,4-dioxotetrahydropyrimidin-1(2H)-yl)-2-fluoro-4-methylbenzamide A suspension of tert-butyl (5-(5-(2,4-dioxotetrahydropyrimidin-1(2H)-yl)-2-fluoro-4-methylbenzamido)pentyl)carbamate (117 mg, 0.234 mmol) in a solution of HCl (4 M) in 1,4-dioxane (1.753 ml, 7.01 mmol) under $N_2$ atmosphere was stirred for 2 h at RT. The RM was concentrated, redissolved in a mixture of ACN and water and freeze dried to afford the title compound as a solid HCL salt (106 mg).

Method A: Rt=0.43 min; [M+H]$^+$=351.2.

Step 3: 5-(2,4-dioxotetrahydropyrimidin-1(2H)-yl)-2-fluoro-N-(5-((4-(4-(5-fluoro-3-(2-fluoro-4-(2-hydroxypropan-2-yl)benzamido)-2-methylphenyl)-7H-pyrrolo[2,3-d]pyrimidin-6-yl)benzyl)amino)pentyl)-4-methylbenzamide To a mixture of 2-fluoro-N-(5-fluoro-3-(6-(4-formylphenyl)-7H-pyrrolo[2,3-d]pyrimidin-4-yl)-2-methylphenyl)-4-(2-hydroxypropan-2-yl)benzamide (intermediate 3, 53 mg, 0.101 mmol), N-(5-aminopentyl)-5-(2,4-dioxotetrahydropyrimidin-1(2H)-yl)-2-fluoro-4-methylbenzamide hydrochloride (50.4 mg, 0.111 mmol) and TEA (0.015 ml, 0.111 mmol) in MeOH (2 ml) was added a solution of $ZnCl_2$ (0.5 M) in THF (0.221 ml, 0.111 mmol). The RM was stirred at RT for 3 h under $N_2$ atmosphere. Solid $NaBH_3CN$ (7.32 mg, 0.111 mmol) was added and the RM was stirred at RT for 18 h. The mixture was diluted with ACN, adsorbed and dried on Isolute® and purified by reverse phase chromatography on a Redisep® C18 column eluting with ACN in an aq. solution of TFA (0.1%) (from 10 to 100%), to afford, after filtration through PL-HCO$_3$ MP SPE cartridges and freeze drying, the title compound as a solid (65 mg).

Method A: Rt=0.80 min, [M+H]$^+$=861.5.

$^1$H NMR (400 MHz, DMSO-d$_6$) δ 12.71 (s, 1H), 10.35 (s, 1H), 9.92 (s, 1H), 8.83 (s, 1H), 8.18-8.24 (m, 1H), 7.90 (d, J=8.19 Hz, 2H), 7.72 (t, J=7.95 Hz, 1H), 7.64 (d, J=10.51 Hz, 1H), 7.50 (d, J=6.97 Hz, 1H), 7.37-7.43 (m, 4H), 7.17-7.24 (m, 2H), 6.80 (s, 1H), 5.28 (s, 1H), 3.67-3.80 (m, 4H), 3.45-3.52 (m, 1H), 3.21 (m, 2H), 2.67-2.80 (m, 2H), 2.43-2.47 (m, 2H), 2.17 (d, J=7.46 Hz, 6H), 1.40-1.52 (m, 10H), 1.29-1.38 (m, 2H).

Compound 30

3-(2,4-Dioxotetrahydropyrimidin-1(2H)-yl)-N-(5-((4-(4-(5-fluoro-3-(2-fluoro-4-(2-hydroxypropan-2-yl)benzamido)-2-methylphenyl)-7H-pyrrolo[2,3-d]pyrimidin-6-yl)benzyl)amino)pentyl)-N,4-dimethylbenzamide

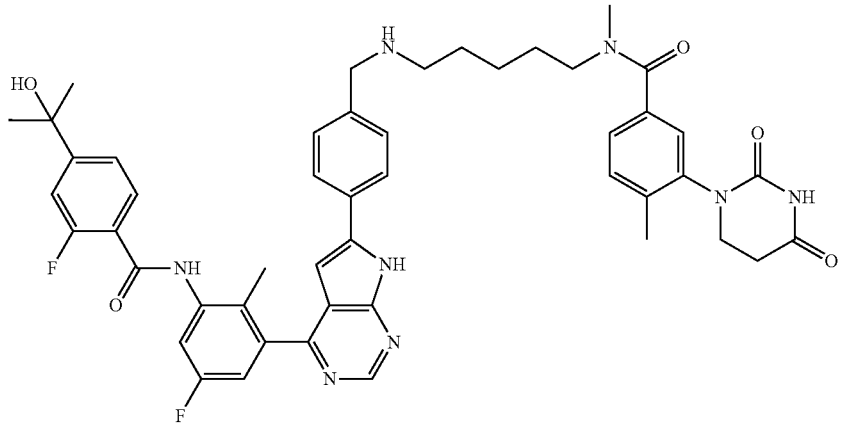 [SMILES: Cc1ccc(C(=O)N(C)CCCCCNCc2ccc(-c3cc4c(-c5cc(F)cc(NC(=O)c6ccc(C(C)(C)O)cc6F)c5C)ncnc4[nH]3)cc2)cc1N1CCC(=O)NC1=O]

Step 1: tert-butyl (5-(3-(2,4-dioxotetrahydropyrimidin-1(2H)-yl)-N,4-dimethylbenzamido)pentyl)carbamate To a solution of 3-(2,4-dioxotetrahydropyrimidin-1(2H)-yl)-4-methylbenzoic acid (intermediate 8, 125 mg, 0.504 mmol), 5-(methylamino)-N-Boc-pentanamine (124 mg, 0.554 mmol) and HBTU (214 mg, 0.554 mmol) in dry DMF (5 ml) was added DIPEA (352 µl, 2.014 mmol) and the resulting RM was stirred for 1 h at RT under $N_2$ atmosphere. The RM was diluted with DCM and citric acid buffer (pH=4, Sigma-Aldrich 33643), the phases were separated, the aq. phase was extracted with DCM, the combined organic phases were dried over $MgSO_4$, concentrated and the residue was purified by chromatography on silica gel eluting with iPrOH in DCM (from 2 to 10%), to afford the title compound as a solid (188 mg).

Method A: Rt=0.86 min: [M+H]$^+$=447.4.

Step 2: N-(5-aminopentyl)-3-(2,4-dioxotetrahydropyrimidin-1(2H)-yl)-N,4-dimethylbenzamide A suspension of tert-butyl (5-(3-(2,4-dioxotetrahydropyrimidin-1(2H)-yl)-N,4-dimethylbenzamido)pentyl)carbamate (187 mg, 0.385 mmol) in a solution of HCl (4 M) in 1,4-dioxane (2.89 ml, 11.56 mmol) was stirred for 1 h at RT under $N_2$ atmosphere. The RM was concentrated, the residue redissolved in a mixture of ACN and water and freeze dried to afford the title compound as a solid HCl salt (171 mg).

Method A: Rt=0.43 min; [M+H]$^+$=347.3.

Step 3: 3-(2,4-dioxotetrahydropyrimidin-1(2H)-yl)-N-(5-((4-(4-(5-fluoro-3-(2-fluoro-4-(2-hydroxypropan-2-yl)benzamido)-2-methylphenyl)-7H-pyrrolo[2,3-d]pyrimidin-6-yl)benzyl)amino)pentyl)-N,4-dimethylbenzamide To a mixture of 2-fluoro-N-(5-fluoro-3-(6-(4-formylphenyl)-7H-pyrrolo[2,3-d]pyrimidin-4-yl)-2-methylphenyl)-4-(2-hydroxypropan-2-yl)benzamide (intermediate 3, 90 mg, 0.171 mmol), N-(5-aminopentyl)-3-(2,4-dioxotetrahydropyrimidin-1(2H)-yl)-N,4-dimethylbenzamide hydrochloride (90 mg, 0.171 mmol) and TEA (0.026 ml, 0.188 mmol) in MeOH (3.5 ml) was added a solution of $ZnCl_2$ (0.5 M) in THF (0.376 ml, 0.188 mmol). The RM was stirred at RT for 3 h under N2 atmosphere. Solid $NaBH_3CN$ (12.44 mg, 0.188 mmol) was added and stirring was continued at RT for 18 h. The mixture was diluted with ACN, adsorbed and dried on Isolute® and the residue was purified by reverse phase chromatography on a Redisep® C18 column eluting with ACN in an aq. solution of TFA (0.1%) to afford, after filtration through PL-$HCO_3$ MP SPE cartridges and freeze drying, the title compound as a solid (110 mg).

Method A: Rt=0.80 min; [M+H]$^+$=857.6.

$^1$H NMR (400 MHz, DMSO-d$_6$) δ 12.72 (s, 1H), 10.34 (s, 1H), 9.92 (s, 1H), 8.83 (s, 1H), 7.91 (d, J=8.07 Hz, 2H), 7.68-7.76 (m, 1H), 7.64 (d, J=9.78 Hz, 1H), 7.35-7.45 (m, 4H), 7.25-7.32 (m, 2H), 7.22 (m, 2H), 6.80 (s, 1H), 5.28 (s, 1H), 3.63-3.81 (m, 3H), 3.46-3.53 (m, 1H), 3.39 (m, 2H), 3.16 (m, 1H), 2.88 (m, 3H), 2.64-2.76 (m, 2H), 2.52-2.61 (m, 1H), 2.38 (m, 1H), 2.18 (s, 3H), 2.16 (s, 3H), 1.44 (m, 10H), 1.31 (m, 1H), 1.09 (m, 1H).

Compound 31

N-(3-(6-(4-(2-(9-(3-(2,4-Dioxotetrahydropyrimidin-1(2H)-yl)-4-methoxybenzoyl)-3,9-diazaspiro[5.5]undecan-3-yl)ethyl)phenyl)-7H-pyrrolo[2,3-d]pyrimidin-4-yl)-5-fluoro-2-methylphenyl)-2-fluoro-4-(2-hydroxypropan-2-yl)benzamide

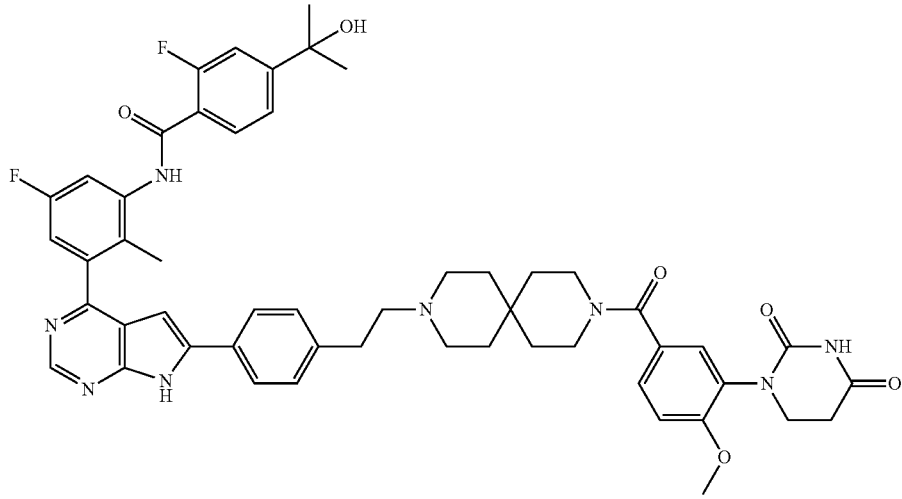

1-(2-Methoxy-5-(3,9-diazaspiro[5.5]undecane-3-carbonyl)phenyl)dihydropyrimidine-2,4(1H,3H)-dione (intermediate 21, 94 mg, 0.182 mmol) was dissolved in dry ACN (2 ml) at RT under argon atmosphere, K$_2$CO$_3$ (144 mg, 1.042 mmol) was added, followed by a solution of 4-(4-(5-fluoro-3-(2-fluoro-4-(2-hydroxypropan-2-yl)benzamido)-2-methylphenyl)-7H-pyrrolo[2,3-d]pyrimidin-6-yl)phenethyl methanesulfonate (intermediate 13, 94 mg, 0.151 mmol) in a mixture of dry DMF (1 ml) and dry ACN (1 ml). The RM was stirred for 24 h at 55° C. and was then allowed to cool to 0° C. before TFA (0.198 ml, 2.57 mmol) was added. The mixture was adsorbed and dried on Isolute® HMN and the residue was purified by reverse phase chromatography on a Redisep® C18 column eluting with ACN in an aq. solution of TFA (0.1%) (from 5 to 100%) to afford, after filtration through PL-HCO3 MP SPE cartridges and freeze drying, the title compound as a solid (21.2 mg).

Method B: Rt=3.69 min, [M+H]$^+$=925.5.

$^1$H NMR (400 MHz, DMSO-d$_6$) δ 12.71 (s, 1H), 10.31 (s, 1H), 9.92 (s, 1H), 8.83 (s, 1H), 7.88 (d, J=7.8 Hz, 2H), 7.72 (t, J=7.8 Hz, 1H), 7.64 (d, J=10.0 Hz, 1H), 7.46-7.26 (m, 6H), 7.22 (d, J=8.7 Hz, 1H), 7.14 (d, J=8.4 Hz, 1H), 6.79 (s, 1H), 5.28 (s, 1H), 3.83 (s, 3H), 3.58 (t, J=6.5 Hz, 2H), 3.6-3.3 (m, 4H), 2.8-2.7 (m, 2H), 2.67 (t, J=6.2 Hz, 2H), 2.6-2.5 (m, 2H), 2.45-2.35 (m, 4H), 2.16 (s, 3H), 1.60-1.30 (m, 8H), 1.44 (s, 6H).

A second and alternative synthesis route for compound 31 is described below:

Step 1: tert-butyl 9-(4-(4-(5-fluoro-3-(2-fluoro-4-(2-hydroxypropan-2-yl)benzamido)-2-methylphenyl)-7-(phenylsulfonyl)-7H-pyrrolo[2,3-d]pyrimidin-6-yl)phenethyl)-3,9-diazaspiro[5.5]undecane-3-carboxylate A mixture of tert-butyl 9-(4-(4-chloro-7-(phenylsulfonyl)-7H-pyrrolo[2,3-d]pyrimidin-6-yl)phenethyl)-3,9-diazaspiro[5.5]undecane-3-carboxylate (intermediate 24, 6.2 g, 9.55 mmol), 2-fluoro-N-(5-fluoro-2-methyl-3-(4,4,5,5-tetramethyl-1,3,2-dioxaborolan-2-yl)phenyl)-4-(2-hydroxypropan-2-yl)benzamide (intermediate 2, 4.32 g, 10.03 mmol), K$_2$CO$_3$ (2.64 g, 19.1 mmol), and PdCl$_2$(dpp) (698 mg, 0.955 mmol) in dioxane (100 ml) and water (20 ml) was stirred under N$_2$ at 80° C. for 4 h. The mixture was diluted with water, the phases were separated and the organic phase was extracted with EtOAc. The combined organic phases were washed with brine, dried over Na$_2$SO$_4$, concentrated, and the residue was purified by chromatography on silica gel eluting with EtOAc in DCM (from 0 to 100%) to afford the title compound as a solid (5.1 g).

Method D: Rt=1.53 min; [M+H]$^+$=919.0.

Step 2: tert-butyl 9-(4-(4-(5-fluoro-3-(2-fluoro-4-(2-hydroxypropan-2-yl)benzamido)-2-methylphenyl)-7H-pyrrolo[2,3-d]pyrimidin-6-yl)phenethyl)-3,9-diazaspiro[5.5]undecane-3-carboxylate To a solution of tert-butyl 9-(4-(4-(5-fluoro-3-(2-fluoro-4-(2-hydroxypropan-2-yl)benzamido)-2-methylphenyl)-7-(phenylsulfonyl)-7H-pyrrolo[2,3-d]pyrimidin-6-yl)phenethyl)-3,9-diazaspiro[5.5]undecane-3-carboxylate (5.1 g, 5.55 mmol) in DMSO (50 ml) cooled at 0° C. was slowly added a solution of NaOH (888 mg, 22.2 mmol) in water (2 ml). The RM was stirred at RT for 2 h, diluted with water, the phases were separated, and the organic phase was extracted with EtOAc. The combined organic phases were washed with brine, dried over Na$_2$SO$_4$, and concentrated to afford the title compound as a solid (4.5 g).

Method D: Rt=1.42 min; [M+H]$^+$=779.

Step 3: N-(3-(6-(4-(2-(3,9-diazaspiro[5.5]undecan-3-yl)ethyl)phenyl)-7H-pyrrolo[2,3-d]pyrimidin-4-yl)-5-fluoro-2-methylphenyl)-2-fluoro-4-(2-hydroxypropan-2-yl)benzamide To a solution of tert-butyl 9-(4-(4-(5-fluoro-3-(2-fluoro-4-(2-hydroxypropan-2-yl)benzamido)-2-methylphenyl)-7H-pyrrolo[2,3-d]pyrimidin-6-yl)phenethyl)-3,9-diazaspiro[5.5]undecane-3-carboxylate (4.5 g, 5.5 mmol) in DCM (100 ml), stirred at RT, was slowly added a solution of HCl (4 M) in 1,4-dioxane (10 ml, 40 mmol). The RM was stirred at RT for 8 h and concentrated to afford the title compound as a solid HCl salt (4.5 g).

Method I: Rt=0.59 min; [(M+H)/2]$^+$=340.

Step 4: N-(3-(6-(4-(2-(9-(3-(2,4-dioxotetrahydropyrimidin-1(2H)-yl)-4-methoxybenzoyl)-3,9-diazaspiro[5.5]undecan-3-yl)ethyl)phenyl)-7H-pyrrolo[2,3-d]pyrimidin-4-yl)-5-fluoro-2-methylphenyl)-2-fluoro-4-(2-hydroxypropan-2-yl)benzamide To a solution of N-(3-(6-(4-(2-(3,9-diazaspiro[5.5]undecan-3-yl)ethyl)phenyl)-7H-pyrrolo[2,3-d]pyrimidin-4-yl)-5-fluoro-2-methylphenyl)-2-fluoro-4-(2-hydroxypropan-2-yl)benzamide hydrochloride (4.5 g, 5.5 mmol) and DIPEA (2.8 g, 22 mmol) in DMF (100 ml) at RT was added pentafluorophenyl 3-(2,4-dioxotetrahydropyrimidin-1(2H)-yl)-4-methoxybenzoate (intermediate 23, 2.5 g, 5.8 mmol) and the RM was stirred at RT for 3 h. The RM was poured into water, the mixture was filtered, the solids were washed with water and dried and purified by reverse phase chromatography on a C18 column eluting with ACN in an aq. solution of ammonium hydrogen carbonate (10 mM) afforded the title compound as a solid (3.7 g).

Method E: Rt=1.44 min, [M/2+H]$^+$=463.5.

Compound 32

N-(3-(6-(4-((2-(3-(2,4-Dioxotetrahydropyrimidin-1(2H)-yl)-4-methoxybenzoyl)-2,7-diazaspiro[3.5]nonan-7-yl)methyl)phenyl)-7H-pyrrolo[2,3-d]pyrimidin-4-yl)-5-fluoro-2-methylphenyl)-2-fluoro-4-(2-hydroxypropan-2-yl)benzamide

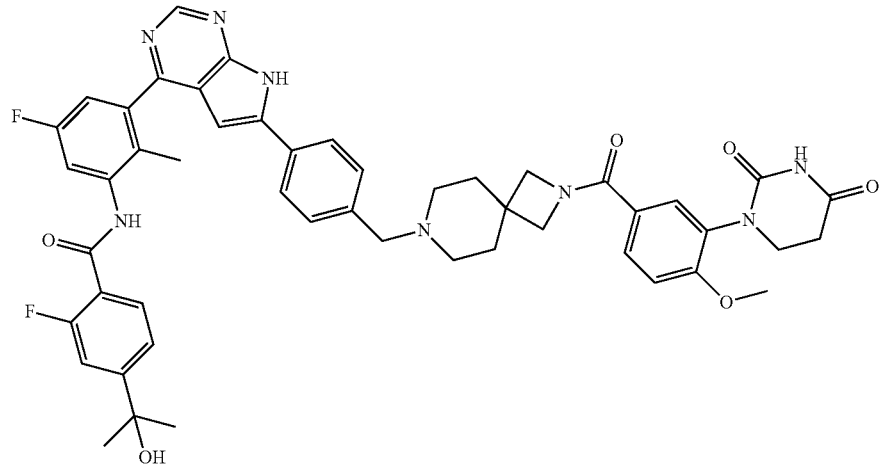 [SMILES: COc1ccc(C(=O)N2CC3(CCN(Cc4ccc(-c5cc6c(-c7cc(F)cc(NC(=O)c8ccc(C(C)(C)O)cc8F)c7C)ncnc6[nH]5)cc4)CC3)C2)cc1N1CCC(=O)NC1=O]

Step 1: tert-butyl 2-(3-(2,4-dioxotetrahydropyrimidin-1(2H)-yl)-4-methoxybenzoyl)-2,7-diazaspiro[3.5]nonane-7-carboxylate To a 25 ml round bottom flask were added 3-(2,4-dioxotetrahydropyrimidin-1(2H)-yl)-4-methoxybenzoic acid (intermediate 5, 100 mg, 0.38 mmol), tert-butyl 2,7-diazaspiro[3.5]nonane-7-carboxylate (94 mg, 0.42 mmol), DMF (2 ml) and DIPEA (147 mg, 1.14 mmol) at RT. HATU (174 mg, 0.46 mmol) was added and the RM was stirred at RT for 16 h. The mixture was concentrated and the residue was purified by reversed phase chromatography on an Agela C18 column (spherical 20-35 µm, 100 Å, 80 g) eluting with ACN in an aq. solution of ammonium hydrogen carbonate (0.05%), yielding the title compound as a solid (151 mg).

Method G: Rt=1.90 min, MS m/z [M−55]$^+$ 417.

Step 2: 1-(2-methoxy-5-(2,7-diazaspiro[3.5]nonane-2-carbonyl)phenyl)dihydropyrimidine-2,4(1H,3H)-dione To a solution of tert-butyl 2-(3-(2,4-dioxotetrahydropyrimidin-1(2H)-yl)-4-methoxybenzoyl)-2,7-diazaspiro[3.5]nonane-7-carboxylate (151 mg, 0.32 mmol) in DCM (1 ml) was added a solution of HCl (4 M) in 1,4-dioxane (1 ml, 4 mmol). The RM was stirred at RT for 3 h. The RM was concentrated and directly used for the next step without further purification. The title compound was obtained as a solid HCl salt (119 mg).

Method G: Rt=1.42 min, MS m/z [M+H]$^+$ 373.

Step 3: N-(3-(6-(4-((2-(3-(2,4-dioxotetrahydropyrimidin-1(2H)-yl)-4-methoxybenzoyl)-2,7-diazaspiro[3.5]nonan-7-yl)methyl)phenyl)-7H-pyrrolo[2,3-d]pyrimidin-4-yl)-5-fluoro-2-methylphenyl)-2-fluoro-4-(2-hydroxypropan-2-yl)benzamide To a 25 ml round bottom flask were added 1-(2-methoxy-5-(2,7-diazaspiro[3.5]nonane-2-carbonyl)phenyl) dihydropyrimidine-2,4(1H,3H)-dione hydrochloride (119 mg, 0.32 mmol), K$_2$CO$_3$ (132 mg, 0.96 mmol) and DMSO (2 ml). After stirring the mixture at RT for 30 min, a solution of ZnCl$_2$ (1 M) in THF (0.35 ml, 0.35 mmol), 2-fluoro-N-(5-fluoro-3-(6-(4-(4-formylphenyl)-7H-pyrrolo[2,3-d]pyrimidin-4-yl)-2-methylphenyl)-4-(2-hydroxypropan-2-yl)benzamide (intermediate 3, 168 mg, 0.32 mmol) and NaBH$_3$CN (30 mg, 0.48 mmol) were successively added. The RM was stirred at RT for 30 min., MeOH (2 ml) was added and the resulting mixture was stirred at RT for 16 h. The mixture was concentrated, the residue was purified by reversed phase chromatography on an Agela C18 column (spherical 20-35 µm, 100 Å, 80 g) eluting with ACN in an aq. solution of ammonium hydrogen carbonate (0.05%) and additionally repurified by preparative HPLC on a XBridge C18 column (21.2×250 mm, 10 µm) eluting with ACN in an aq. solution of ammonium hydrogen carbonate (10 mM) yielding the title compound as a solid (64 mg).

Method J: Rt=1.707 min, MS m/z [M+H]$^+$ 883.

$^1$H NMR (400 MHz, DMSO-d$_6$) δ 12.76 (s, 1H), 10.34 (s, 1H), 9.95 (s, 1H), 8.85 (s, 1H), 7.94 (d, J=8.2 Hz, 2H), 7.77-7.65 (m, 1H), 7.65-7.57 (m, 2H), 7.55 (s, 1H), 7.48-

7.35 (m, 4H), 7.27-7.20 (m, 1H), 7.20-7.10 (m, 1H), 6.83 (s, 1H), 5.30 (s, 1H), 4.03 (s, 2H), 3.85 (s, 3H), 3.72 (s, 2H), 3.58 (t, J=6.6 Hz, 2H), 3.47 (s, 2H), 2.70-2.60 (m, 2H), 2.40-2.20 (m, 4H), 2.18 (s, 3H), 1.8-1.6 (m, 4H), 1.45 (s, 6H).

Compound 33

N-(3-(6-(4-((4-(1-(3-(2,4-dioxotetrahydropyrimidin-1(2H)-yl)-4-methoxybenzoyl)piperidine-4-carbonyl)piperazin-1-yl)methyl)phenyl)-7H-pyrrolo[2,3-d]pyrimidin-4-yl)-5-fluoro-2-methylphenyl)-2-fluoro-4-(2-hydroxypropan-2-yl)benzamide

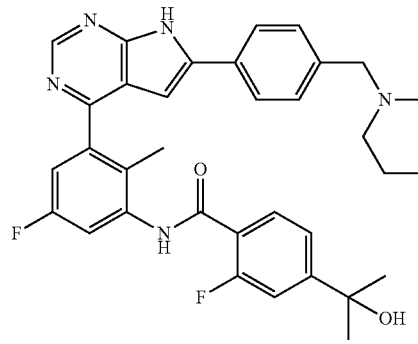
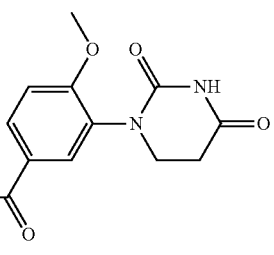

Step 1: tert-butyl 4-(1-(benzyloxycarbonyl)piperidine-4-carbonyl)piperazine-1-carboxylate In a 250 ml round bottom flask containing a solution of 1-(benzyloxycarbonyl)piperidine-4-carboxylic acid (2.63 g, 10 mmol) in THF (50 ml) was added HATU (4.56 g, 12 mmol) and the mixture was stirred at RT for 30 min. Tert-butyl piperazine-1-carboxylate (1.86 g, 10 mmol) and DIPEA (2.58 g, 20 mmol) were added and the RM was stirred at RT for 2 h. The solvent was removed, the residue was dissolved in EtOAc, washed with water and brine, the combined organic phases were dried over Na$_2$SO$_4$, evaporated, and the residue was purified by chromatography on silica gel eluting with MeOH in DCM (from 0 to 15%) yielding the title compound as a solid (4.17 g).
Method G: Rt=1.94 min; MS m/z [M+H]$^+$ 432.

Step 2: tert-butyl 4-(piperidine-4-carbonyl)piperazine-1-carboxylate

To a 500 ml round bottom flask, purged and maintained under inert atmosphere, were added tert-butyl 4-(1-(benzyloxycarbonyl)piperidine-4-carbonyl)piperazine-1-carboxylate (4.17 g, 9.67 mmol), THF (120 ml) and Pd/C (1 g, 10% w/w). The RM was stirred at RT for 16 h under H$_2$ atmosphere. The RM was filtered and the filtrate concentrated yielding the title compound as a solid (2.85 g).
Method J: Rt=1.51 min; MS m/z [M+H]$^+$ 298.
$^1$H NMR (500 MHz, DMSO-d$_6$) δ 3.43 (d, J=26.3 Hz, 4H), 3.29 (d, J=25.9 Hz, 4H), 2.91 (d, J=12.2 Hz, 2H), 2.70-2.59 (m, 1H), 2.55-2.51 (m, 1H), 2.48-2.4 (m, 1H), 1.59-1.32 (m, 13H).

Step 3: tert-butyl 4-(1-(3-(2,4-dioxotetrahydropyrimidin-1(2H)-yl)-4-methoxybenzoyl)piperidine-4-carbonyl)piperazine-1-carboxylate To a 250 ml round bottom flask were added 3-(2,4-dioxotetrahydropyrimidin-1(2H)-yl)-4-methoxybenzoic acid (intermediate 5, 197 mg, 0.75 mmol), DMF (5 ml) and HATU (309 mg, 0.81 mmol) and the RM was stirred at RT for 0.5 h. Tert-butyl 4-(piperidine-4-carbonyl)piperazine-1-carboxylate (200 mg, 0.68 mmol) and K$_2$CO$_3$ (280 mg, 2.03 mmol) were added and the RM was stirred at RT for 3 h. The mixture was poured into water, extracted with EtOAc and DCM, the combined organic phases were washed with brine, dried over Na$_2$SO$_4$ evaporated and the residue was purified by revered phase chromatography on an Agela C18 column (spherical 20-35 μm, 100 Å, 40 g) eluting with ACN in an aq. solution of ammonium hydrogen carbonate (10 mM), yielding the title compound as a solid (380 mg).
Method J: Rt=1.63 min; MS m/z [M+H]$^+$ 544.

Step 4: 1-(2-methoxy-5-(4-(piperazine-1-carbonyl)piperidine-1-carbonyl)phenyl)-dihydropyrimidine-2,4(1H,3H)-dione To a 100 ml round bottom flask were added tert-butyl 4-(1-(3-(2,4-dioxotetrahydropyrimidin-1(2H)-yl)-4-methoxybenzoyl)piperidine-4-carbonyl)piperazine-1-carboxylate (350 mg, 0.64 mmol), MeOH (0.5 ml) and 1,4-dioxane (4 ml) and the RM was cooled to 5° C. A solution of HCl (4 M) in 1,4-dioxane (1 ml, 4 mmol) was slowly added, the RM was stirred at RT for 1 h, concentrated, the residue was redissolved in DMF (2 ml) and NaHCO$_3$ (200 mg) was added. The mixture was stirred at RT for 0.5 h and then purified by reversed phase chromatography on an Agela C18 column (spherical 20-35 μm, 100 Å, 40 g) eluting with ACN in an aq. solution of ammonium hydrogencarbonate (10 mM) yielding the title compound as a solid (233 mg).
Method F: Rt=0.75 min: MS m/z [M+H]$^+$ 444.

Step 5: N-(3-(6-(4-((4-(1-(3-(2,4-dioxotetrahydropyrimidin-1(2H)-yl)-4-methoxybenzoyl)piperidine-4-carbonyl)piperazin-1-yl)methyl)phenyl)-7H-pyrrolo[2,3-d]pyrimidin-4-yl)-5-fluoro-2-methylphenyl)-2-fluoro-4-(2-hydroxypropan-2-yl)benzamide To a 10 ml round bottom flask were added 1-(2-methoxy-5-(4-(piperazine-1-carbonyl)piperidine-1-carbonyl)phenyl)-dihydropyrimidine-2,4(1H,3H)-dione (233 mg, 0.53 mmol), 2-fluoro-N-(5-fluoro-3-(6-(4-formylphenyl)-7H-pyrrolo[2,3-d]pyrimidin-4-yl)-2-methylphenyl)-4-(2-hydroxypropan-2-yl)benzamide (intermediate 3, 251 mg, 0.48 mmol) and DMSO (2 ml). At RT a solution of ZnCl$_2$ (1 M) in THF (0.5 ml, 0.5 mmol) was added and the RM was stirred for 30 min. Solid NaBH$_3$CN (60 mg, 0.96 mmol) was added and the RM was stirred at RT for 30 min. MeOH (2 ml) was added and the resulting RM was stirred at RT for 16 h, concentrated, poured into water, filtered, the solids were washed with water, dried, and the residue was then purified by chromatography on silica gel eluting with MeOH in DCM (from 0 to 10%) yielding the title compound as a solid (209 mg).

Method J: Rt=1.22 min, MS m/z [M+H]⁺ 955.

¹H NMR (500 MHz, DMSO-d₆) δ 12.77 (s, 1H), 10.32 (s, 1H), 9.94 (s, 1H), 8.85 (s, 1H), 7.96 (d, J=8.2 Hz, 2H), 7.78-7.61 (m, 2H), 7.45-7.15 (m, 8H), 6.84 (s, 1H), 5.30 (s, 1H), 3.80 (s, 3H), 3.64-3.32 (m, 8H), 3.22-2.93 (m, 4H), 2.69-2.64 (m, 2H), 2.41-2.33 (m, 5H), 2.18 (s, 3H), 1.76-1.38 (m, 10H).

Compound 34

N-(3-(6-(4-(2-(4-((1-(3-(2,4-Dioxotetrahydropyrimidin-1(2H)-yl)-4-methoxybenzoyl)piperidin-4-yl)oxy)piperidin-1-yl)ethyl)phenyl)-7H-pyrrolo[2,3-d]pyrimidin-4-yl)-5-fluoro-2-methylphenyl)-2-fluoro-4-(2-hydroxypropan-2-yl)benzamide

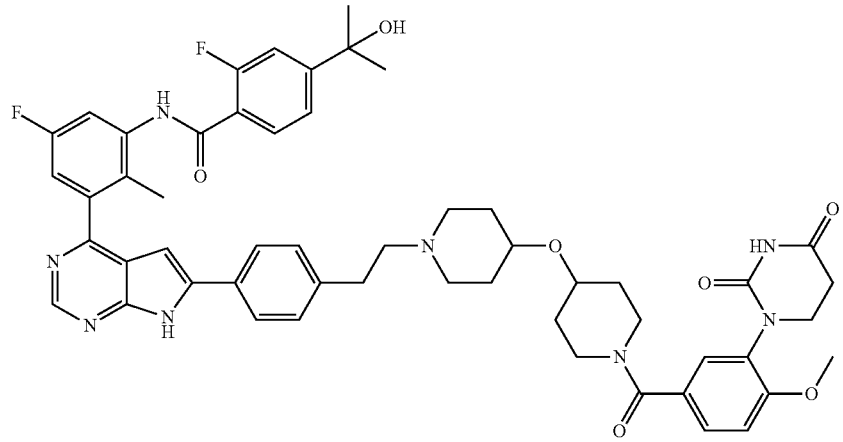 [SMILES: COc1ccc(C(=O)N2CCC(OC3CCN(CCc4ccc(-c5cc6c(-c7cc(F)cc(NC(=O)c8ccc(C(C)(C)O)cc8F)c7C)ncnc6[nH]5)cc4)CC3)CC2)cc1N1CCC(=O)NC1=O]

Step 1: tert-butyl 4-((1-(3-(2,4-dioxotetrahydropyrimidin-1(2H)-yl)-4-methoxybenzoyl)piperidin-4-yl)oxy)piperidine-1-carboxylate 3-(2,4-Dioxotetrahydropyrimidin-1(2H)-yl)-4-methoxybenzoic acid (intermediate 5, 1.20 g, 4.54 mmol) was dissolved in DMF (15 ml), tert-butyl 4-(piperidin-4-yloxy)piperidine-1-carboxylate (intermediate 10, 1.292 g, 4.54 mmol) and DIPEA (1.586 ml, 9.08 mmol) were added, followed by HBTU (2.067 g, 5.45 mmol) and the RM was stirred at RT for 2.5 h. The RM was poured into ice-water and the mixture was extracted with DCM. The combined organic phases were dried over MgSO₄, evaporated and the residue was purified by chromatography on silica gel eluting with MeOH in DCM (from 0 to 20%) to afford an oil. The oil was dissolved in EtOAc, the solution was washed with a mixture of water and brine (1:1), brine, dried over MgSO₄, and concentrated to afford the title compound as a solid (2.43 g).

Method A: Rt=0.93 min; [M+H]⁺=531.4.

Step 2: 1-(2-methoxy-5-(4-(piperidin-4-yloxy)piperidine-1-carbonyl)phenyl)dihydropyrimidine-2,4(1H,3H)-dione Tert-butyl 4-((1-(3-(2,4-dioxotetrahydropyrimidin-1(2H)-yl)-4-methoxybenzoyl)piperidin-4-yl)oxy)piperidine-1-carboxylate (1 g, 1.885 mmol) was dissolved in DCM (3 ml) at RT, TFA (3 ml, 38.9 mmol) was added and the RM was stirred for 2 h at RT. The RM was evaporated to dryness and dried to afford the title compound as a TFA salt (1.15 g).

Method A: Rt=0.43 min; [M+H]+=431.4.

Step 3: N-(3-(6-(4-(2-(4-((1-(3-(2,4-dioxotetrahydropyrimidin-1(2H)-yl)-4-methoxybenzoyl)piperidin-4-yl)oxy)piperidin-1-yl)ethyl)phenyl)-7H-pyrrolo[2,3-d]pyrimidin-4-yl)-5-fluoro-2-methylphenyl)-2-fluoro-4-(2-hydroxypropan-2-yl)benzamide 4-(4-(5-Fluoro-3-(2-fluoro-4-(2-hydroxypropan-2-yl)benzamido)-2-methylphenyl)-7H-pyrrolo[2,3-d]pyrimidin-6-yl)phenethyl methanesulfonate (intermediate 13, 300 mg, 0.411 mmol) was dissolved in a mixture of dry DMF and dry ACN 2:5 (7 ml) at RT under argon atmosphere and 1-(2-methoxy-5-(4-(piperidin-4-yloxy)piperidine-1-carbonyl)phenyl)dihydropyrimidine-2,4(1H,3H)-dione trifluoroacetate (460 mg, 0.845 mmol), K₂CO₃ (341 mg, 2.465 mmol) and dry ACN (3 ml) were added. The RM was stirred at 50° C. for 63 h, cooled to 0° C., diluted with ACN and TFA (0.380 ml, 4.93 mmol) was added. The mixture was adsorbed and dried on Isolute® HM-N and the residue was purified by reverse phase chromatography on a Redisep® C18 column eluting with ACN in an aq. solution of TFA (0.1%) (from 5 to 100%), to afford, after filtration over PL-HCO3 MP SPE cartridges and freeze drying, the title compound as a solid (190 mg).

Method B: Rt=3.88 min; [M+H]⁺=955.6.

¹H NMR (600 MHz, DMSO-d₆) δ 12.74 (s, 1H), 10.35 (s, 1H), 9.95 (s, 1H), 8.84 (s, 1H), 7.89 (d, J=8.1 Hz, 2H), 7.73 (t, J=7.8 Hz, 1H), 7.66 (d, J=10.0 Hz, 1H), 7.45-7.39 (m, 2H), 7.38 (dd, J=8.4, 2.2 Hz, 1H), 7.34 (d, J=2.1 Hz, 1H), 7.32 (d, J=8.1 Hz, 2H), 7.23 (dd, J=8.8, 2.8 Hz, 1H), 7.15 (d, J=8.6 Hz, 1H), 6.8-6.75 (m, 1H), 5.31 (s, 1H), 3.84 (s, 3H), 3.7-3.6 (m, 2H), 3.59 (t, J=6.6 Hz, 3H), 3.5-3.4 (m, 1H), 3.20 (t, J=11.3 Hz, 2H), 2.8-2.7 (m, 4H), 2.7-2.6 (m, 2H), 2.6-2.5 (m, 2H), 2.17 (s, 3H), 2.15-2.05 (m, 2H), 1.75-1.60 (m, 4H), 1.45 (s, 6H), 1.45-1.3 (m, 4H).

Compound 35

N-(3-(6-(4-((8-(2-(3-(2,4-Dioxotetrahydropyrimidin-1(2H)-yl)-4-methoxybenzamido)ethyl)-2,8-diazaspiro[4.5]decan-2-yl)methyl)phenyl)-7H-pyrrolo[2,3-d]pyrimidin-4-yl)-5-fluoro-2-methylphenyl)-2-fluoro-4-(2-hydroxypropan-2-yl)benzamide

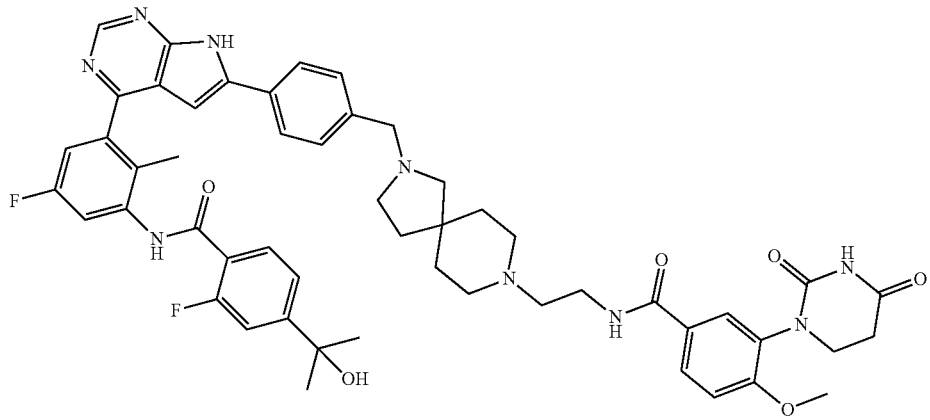 [SMILES: COc1ccc(C(=O)NCCN2CCC3(CC2)CCN(Cc2ccc(-c4cc5c(-c6cc(F)cc(NC(=O)c7ccc(C(C)(C)O)cc7F)c6C)ncnc5[nH]4)cc2)C3)cc1N1CCC(=O)NC1=O]

Step 1: tert-butyl 8-(2-(1,3-dioxoisoindolin-2-yl)ethyl)-2,8-diazaspiro[4.5]decane-2-carboxylate To a 50 ml round bottom flask was added tert-butyl 2,8-diazaspiro[4.5]decane-2-carboxylate (320 mg, 1.41 mmol), 2-(1,3-dioxoisoindolin-2-yl)acetaldehyde (321 mg, 1.70 mmol), MeOH (15 ml) and AcOH (20 drops) at 15° C. and the RM was stirred at 15° C. for 1 h. Solid NaBH$_3$CN (133 mg, 2.12 mmol) was added and the RM was stirred at 15° C. for 6 h. The RM was concentrated, redissolved in a mixture of EtOAc and an aq. solution of NaHCO$_3$ (10%) and the phases were separated. The aq. phase was extracted with EtOAc, the combined organic phases were washed with water, concentrated and directly used for the next step without further purification. The title compound was obtained as a solid (520 mg).
Method F: Rt=1.44 min; MS m/z [M+H]$^+$ 414.

Step 2: tert-butyl 2-(2-aminoethyl)-2,8-diazaspiro[4.5]decane-8-carboxylate

To a 100 ml round bottom flask were added tert-butyl 8-(2-(1,3-dioxoisoindolin-2-yl)ethyl)-2,8-diazaspiro[4.5]decane-2-carboxylate (320 mg, 0.774 mmol), EtOH (15 ml) and hydrazine hydrate (240 mg, 4.8 mmol) at 15° C. The RM was stirred at 40° C. for 18 h, filtered, concentrated, and the residue was redissolved in a mixture of DCM and an aq. solution of NaHCO$_3$ (10%). The phases were separated and the aq. phase was extracted with DCM, the combined organic phases were concentrated and the residue was purified by chromatography on silica gel eluting with MeOH in DCM (from 0 to 7%) yielding the title compound as a solid (160 mg).
Method J: Rt=1.57 min; MS m/z [M+H]$^+$ 284.
$^1$H NMR (500 MHz, CDCl$_3$) δ 3.45-3.27 (m, 4H), 2.77 (t, J=6.2 Hz, 2H), 2.58 (s, 2H), 2.48 (t, J=6.2 Hz, 2H), 2.39 (s, 2H), 1.66-1.61 (m, 2H), 1.51 (dd, J=9.5, 5.1 Hz, 4H), 1.45 (s, 9H).

Step 3: tert-butyl 8-(2-(3-(2,4-dioxotetrahydropyrimidin-1(2H)-yl)-4-methoxybenzamido)ethyl)-2,8-diazaspiro[4.5]decane-2-carboxylate To a 50 ml round bottom flask were added 3-(2,4-dioxotetrahydropyrimidin-1(2H)-yl)-4-methoxybenzoic acid (intermediate 5, 150 mg, 0.56 mmol), tert-butyl 2-(2-aminoethyl)-2,8-diazaspiro[4.5]decane-8-carboxylate (100 mg, 0.62 mmol), DIPEA (220 mg, 1.70 mmol), DMF (4 ml), and HATU (323 mg 0.85 mmol) at RT. The RM was stirred at RT for 3 h, concentrated and the residue was purified by reversed phase chromatography on an Agela C18 column (spherical 20-35 μm, 100 Å, 80 g) eluting with ACN in an aq. solution of ammonium hydrogencarbonate (10 mM), yielding the title compound as a solid (175 mg).
Method G: Rt=1.66 min; MS m/z [M+H]$^+$ 530.

Step 4: N-(2-(2,8-diazaspiro[4.5]decan-8-yl)ethyl)-3-(2,4-dioxotetrahydropyrimidin-1(2H)-yl)-4-methoxybenzamide To a 100 ml round bottom flask was added a solution of tert-butyl 8-(2-(3-(2,4-dioxotetrahydropyrimidin-1(2H)-yl)-4-methoxybenzamido)ethyl)-2,8-diazaspiro[4.5]decane-2-carboxylate (175 mg, 0.33 mmol) in DCM (5 ml) and TFA (1 ml) was slowly added at RT. The RM was stirred at RT for 3 h, concentrated and the residue was directly used for the next step without further purification. The title compound was obtained as an oil as a TFA salt (170 mg).
Method G: Rt=1.20 min; MS m/z [M+H]$^+$ 430.

Step 5: N-(3-(6-(4-((8-(2-(3-(2,4-dioxotetrahydropyrimidin-1(2H)-yl)-4-methoxybenzamido)ethyl)-2,8-diazaspiro[4.5]decan-2-yl)methyl)phenyl)-7H-pyrrolo[2,3-d]pyrimidin-4-yl)-5-fluoro-2-methylphenyl)-2-fluoro-4-(2-hydroxypropan-2-yl)benzamide To a 50 ml round bottom flask were added N-(2-(2,8-diazaspiro[4.5]decan-8-yl)ethyl)-3-(2,4-dioxotetrahydropyrimidin-1(2H)-yl)-4-methoxybenzamide trifluoroacetate (170 mg), DMSO (5 ml), and K$_2$CO$_3$ (114 mg, 0.83 mmol) and the solution was stirred at RT for 30 min. 2-Fluoro-N-(5-fluoro-3-(6-(4-formylphenyl)-7H-pyrrolo[2,3-d]pyrimidin-4-yl)-2-methylphenyl)-4-(2-hydroxypropan-2-yl)benzamide (intermediate 3, 145 mg, 0.27 mmol) and a solution of ZnCl$_2$ (1 M) in THF (0.3 ml, 0.3 mmol) were added at RT and the RM was stirred at RT for 30 min. Solid NaBH$_3$CN (26 mg, 0.41 mmol) was added and the RM was stirred at RT for 30 min., then MeOH (5 ml) was added and the RM was stirred at RT for 16 h. The mixture was concentrated and the residue purified by reversed phase chromatography on an Agela C18 column (spherical 20-35 µm, 100 Å, 40 g) eluting with ACN in an aq. solution of ammonium hydrogencarbonate (10 mM), yielding the title compound as a solid (130 mg).

Method G: Rt=1.86 min; MS m/z [M+H]$^+$ 940.

$^1$H NMR (500 MHz, DMSO-d$_6$) δ 12.77 (s, 1H), 10.37 (s, 1H), 9.96 (s, 1H), 8.86 (s, 1H), 8.30 (br. s, 1H), 7.94 (d, J=8.0 Hz, 2H), 7.83 (d, J=8.5 Hz, 1H), 7.76-7.72 (m, 2H), 7.66 (d, J=8.5 Hz, 1H), 7.44-7.35 (m, 4H), 7.24 (dd, J=8.7, 2.6 Hz, 1H), 7.18 (d, J=8.8 Hz, 1H), 6.84 (s, 1H), 5.31 (s, 1H), 3.85 (s, 3H), 3.62-3.55 (m, 4H), 2.72-2.55 (m, 5H), 2.47-2.22 (m, 9H), 2.18 (s, 3H), 1.60-1.39 (m, 6H), 1.45 (s, 6H).

Compound 36

N-(3-(6-(4-(4-((2-(4-(3-(2,4-dioxotetrahydropyrimidin-1(2H)-yl)-4-methoxybenzoyl)piperazin-1-yl)ethyl)amino)butoxy)phenyl)-7H-pyrrolo[2,3-d]pyrimidin-4-yl)-5-fluoro-2-methylphenyl)-2-fluoro-4-(2-hydroxypropan-2-yl)benzamide

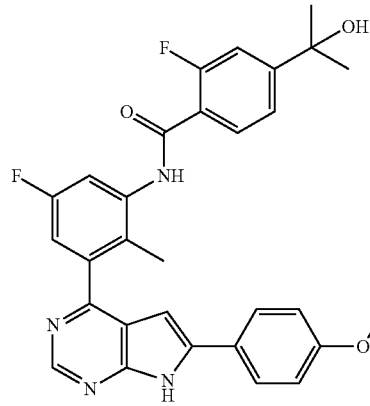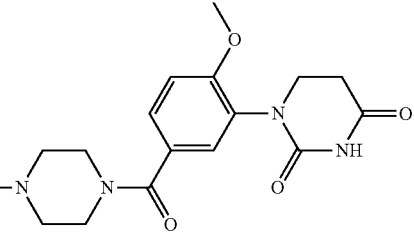

Step 1: tert-butyl 4-(4-(4,4,5,5-tetramethyl-1,3,2-dioxaborolan-2-yl)phenoxy)butylcarbamate To a 100 ml round bottom flask, purged and maintained under inert atmosphere, were added 4-(4,4,5,5-tetramethyl-1,3,2-dioxaborolan-2-yl)phenol (1.95 g, 8.86 mmol), tert-butyl 4-hydroxybutylcarbamate (1.843 g, 9.75 mmol), triphenylphosphine (3.483 g, 13.3 mmol) and dry THF (50 ml). The RM was cooled to 0° C. and DIAD (3.223 g, 15.98 mmol) was added dropwise at 0° C. over a period of 20 min. The RM was then allowed to warm to RT and stirring was continued for 16 h. The mixture was concentrated and the residue was purified by chromatography on silica gel eluting with EtOAc in petroleum ether (from 10 to 25%) yielding the title compound as an oil (3.19 g).

Method H: Rt=2.26 min, MS m/z [M+H−55]$^+$ 336.

$^1$H NMR (400 MHz, DMSO-d$_6$) δ 7.73 (dd, J=8.5, 1.7 Hz, 2H), 6.90-6.85 (m, 2H), 4.61 (s, 1H), 4.00 (t, J=6.2 Hz, 2H), 3.25-3.14 (m, 2H), 1.86-1.77 (m, 2H), 1.71-1.63 (m, 2H), 1.44 (s, 9H), 1.33 (s, 14H).

Step 2: tert-butyl 3-(4-(4-chloro-7-(phenylsulfonyl)-7H-pyrrolo[2,3-d]pyrimidin-6-yl)phenoxy)propylcarbamate To a 100 ml round bottom flask, purged and maintained under inert atmosphere, were added tert-butyl 4-(4-(4,4,5,5-tetramethyl-1,3,2-dioxaborolan-2-yl)phenoxy)butylcarbamate (1.500 g, 3.836 mmol), 4-chloro-6-iodo-7-(phenylsulfonyl)-7H-pyrrolo[2,3-d]pyrimidine (intermediate 7, 1.768 g, 4.22 mmol), PdCl$_2$(dppf-CH$_2$Cl$_2$ adduct (235 mg, 0.288 mmol), and NaHCO$_3$ (806 mg, 9.591 mmol). 1,4-Dioxane (16 ml) and water (4 ml) were added and the RM was stirred at 90° C. for 2 h. The mixture was concentrated, rediluted with water and extracted with DCM. The combined organic phases were washed with brine, dried over Na$_2$SO$_4$, concentrated, and purified by chromatography on silica gel eluting with EtOAc in petroleum ether (from 10 to 40%) yielding the title compound as a solid (1.08 g).

Method J: Rt=2.27 min: MS m/z [M+H]$^+$ 543.2.

Step 3: tert-butyl 3-(4-(4-(5-fluoro-3-(2-fluoro-4-(2-hydroxypropan-2-yl)benzamido)-2-methylphenyl)-7-(phenylsulfonyl)-7H-pyrrolo[2,3-d]pyrimidin-6-yl)phenoxy)propylcarbamate To a 100 ml round bottom flask, purged and maintained under inert atmosphere, were added tert-butyl 3-(4-(4-chloro-7-(phenylsulfonyl)-7H-pyrrolo[2,3-d]pyrimidin-6-yl)phenoxy)propyl carbamate (515 mg, 0.814 mmol), 2-fluoro-N-(5-fluoro-2-methyl-3-(4,4,5,5-tetramethyl-1,3,2-dioxaborolan-2-yl)phenyl)-4-(2-hydroxypropan-2-yl)benzamide (intermediate 2, 374 mg, 0.867 mmol), PdCl$_2$(dppf-CH$_2$Cl$_2$ adduct (69 mg, 0.084 mmol), and Na$_2$CO$_3$ (223 mg, 2.1 mmol). ACN (8 ml) and water (2 ml) were added and the RM was stirred at 90° C. for 1 h. The mixture was concentrated, rediluted with water and extracted with DCM. The combined organic phases were washed with brine, dried over Na$_2$SO$_4$, concentrated and the residue was purified by chromatography on silica gel eluting with EtOAc in petroleum ether (from 10 to 50%) yielding the title compound as an oil (509 mg).

Method J: Rt=2.21 min; MS m/z [M+H]$^+$ 812.3.

Step 4: N-(3-(6-(4-(3-aminopropoxy)phenyl)-7-(phenylsulfonyl)-7H-pyrrolo[2,3-d]pyrimidin-4-yl)-5-fluoro-2-methylphenyl)-2-fluoro-4-(2-hydroxypropan-2-yl)benzamide To a 100 ml round bottom flask was added tert-butyl 3-(4-(4-(5-fluoro-3-(2-fluoro-4-(2-hydroxypropan-2-yl)benzamido)-2-methylphenyl)-7-(phenylsulfonyl)-7H-pyrrolo[2,3-d]pyrimidin-6-yl)phenoxy)propylcarbamate (280 mg, 0.49 mmol) in DCM (9 ml) and EtOH (3 ml). A solution of HCl (4 M) in 1,4-dioxane (4.93 ml, 19.72 mmol) was slowly added and the RM was stirred at RT for 2 h. The mixture was concentrated, rediluted with a mixture of DCM and MeOH (1:1) and an aq. saturated solution of NaHCO$_3$ was added until the mixture reached pH 9. The mixture was concentrated, adsorbed and dried on silica gel and purified by chromatography on silica gel eluting with MeOH in DCM (from 4 to 8%) yielding the title compound as a white solid (280 mg).

Method E: Rt=1.58 min; MS m/z [M+H]$^+$ 712.2.

Step 5: N-(3-(6-(4-(3-aminopropoxy)phenyl)-7H-pyrrolo[2,3-d]pyrimidin-4-yl)-5-fluoro-2-methylphenyl)-2-fluoro-4-(2-hydroxypropan-2-yl)benzamide To a 100 ml round bottom flask were added N-(3-(6-(4-(3-aminopropoxy)phenyl)-7-(phenylsulfonyl)-7H-pyrrolo[2,3-d]pyrimidin-4-yl)-5-fluoro-2-methylphenyl)-2-fluoro-4-(2-hydroxypropan-2-yl)benzamide (200 mg, 0.28 mmol), DMSO (2 ml) and an aq. solution of NaOH (1.1 ml, 1.1 mmol, 1.0 M). The RM was stirred at RT for 1 h, acidified with an aq. solution of HCl (1.0 M) to pH 6 and was then directly purified by reversed phase chromatography on an Agela C18 column (spherical 20-35 µm, 100 Å, 25 g) eluting with ACN in an aq. solution of ammonium hydrogen carbonate (10 mM), yielding the title compound as a solid (152 mg).

Method J: Rt=2.15 min: MS m/z [M+H]$^+$ 572.3.

Step 6: 1-(5-(4-(2-hydroxyethyl)piperazine-1-carbonyl)-2-methoxyphenyl)dihydropyrimidine-2,4(1H,3H)-dione To a 100 ml round bottom flask were added 2-(piperazin-1-yl)ethanol (400 mg, 3.07 mmol), 3-(2,4-dioxotetrahydropyrimidin-1(2H)-yl)-4-methoxybenzoic acid (intermediate 5, 812 mg. 3.07 mmol), HATU (1.286 g, 3.39 mmol), DIPEA (794 mg, 6.15 mmol), and DMF (5 ml). The RM was stirred at RT for 16 h and was then directly purified by reversed phase chromatography on an Agela C18 column (spherical 20-35 µm, 100 Å, 80 g) eluting with ACN in an aq. solution of ammonium hydrogen carbonate (10 mM), yielding the title compound as a solid (382 mg).

Method F: Rt=1.53 min; MS m/z [M+H]$^+$ 377.2.

Step 7: 2-(4-(3-(2,4-dioxotetrahydropyrimidin-1(2H)-yl)-4-methoxybenzoyl)piperazin-1-yl)acetaldehyde To a 100 ml round bottom flask, purged and maintained under inert atmosphere, was added DCM (3 ml) and oxalyl chloride (0.21 ml, 2.53 mmol). A solution of DMSO (0.36 ml, 5.05 mmol) in dry DCM (1 ml) was added at −78° C. and after stirring the RM at −78° C. for 30 min, a solution of 1-(5-(4-(2-hydroxyethyl)piperazine-1-carbonyl)-2-methoxyphenyl)dihydropyrimidine-2,4(1H,3H)-dione (380 mg, 1.01 mmol) in DCM (6 ml) was added. The mixture was stirred at −78° C. for 1 h, then TEA (1.4 ml, 10.11 mmol) was added at −78° C. and the mixture was allowed to warm to RT in a period of 30 min. The mixture was diluted with water, extracted with a mixture of chloroform and iPrOH (3:1), the combined organic phases were dried over Na$_2$SO$_4$, concentrated, and the residue was purified by chromatography on silica gel eluting with MeOH in DCM (from 2 to 5%) yielding the title compound as a solid (225 mg).

Method H: Rt=1.23 min; MS m/z [M+H]$^+$ 375.1.

Step 8: N-(3-(6-(4-(4-((2-(4-(3-(2,4-dioxotetrahydropyrimidin-1(2H)-yl)-4-methoxybenzoyl)piperazin-1-yl)ethyl)amino)butoxy)phenyl)-7H-pyrrolo[2,3-d]pyrimidin-4-yl)-5-fluoro-2-methylphenyl)-2-fluoro-4-(2-hydroxypropan-2-yl)benzamide To a 100 ml round bottom flask were added N-(3-(6-(4-(3-aminopropoxy)phenyl)-7H-pyrrolo[2,3-d]pyrimidin-4-yl)-5-fluoro-2-methylphenyl)-2-fluoro-4-(2-hydroxypropan-2-yl)benzamide (156 mg, 0.27 mmol), freshly prepared 2-(4-(3-(2,4-dioxotetrahydropyrimidin-1(2H)-yl)-4-methoxybenzoyl)piperazin-1-yl)acetaldehyde (100 mg, 0.27 mmol) and dry THF (6 ml). A solution of ZnCl$_2$ (1 M) in THF (0.4 ml, 0.4 mmol) was slowly added and after stirring the mixture at RT for 30 min, solid NaBH$_3$CN (50 mg, 0.8 mmol) and MeOH (1 ml) were added at 0° C. and the RM was stirred at RT for 16 h. An aq. solution of HCl (1 M) was added until the mixture reached pH 6, the mixture was concentrated and adsorbed on silica gel and purified by chromatography on silica gel eluting with MeOH in DCM (from 2 to 5%). The purified material was repurified by reversed phase chromatography on an Agela C18 column (spherical 20-35 µm, 100 Å, 40 g) eluting with ACN in an aq. solution of ammonium hydrogen carbonate (10 mM), yielding the title compound as a solid (80 mg).

Method J: Rt=1.89 min; MS m/z [M+H]$^+$ 944.

$^1$H NMR (500 MHz, DMSO-d$_6$) δ 12.7 (br. s, 1H), 10.34 (s, 1H), 9.95 (s, 1H), 8.82 (s, 1H), 7.92 (d, J=8.8 Hz, 2H), 7.73 (t, J=7.9 Hz, 1H), 7.65 (d, J=9.2 Hz, 1H), 7.5-7.3 (m, 4H), 7.23 (dd, J=8.8, 2.7 Hz, 1H), 7.14 (d, J=8.6 Hz, 1H), 7.02 (d, J=8.9 Hz, 2H), 6.72 (s, 1H), 5.30 (s, 1H), 4.03 (t, J=6.5 Hz, 2H), 3.84 (s, 3H), 3.6-3.4 (m, 6H), 2.8-2.5 (m, 6H), 2.45-2.30 (m, 6H), 2.17 (s, 3H), 1.8-1.7 (m, 2H), 1.6-1.5 (m, 2H), 1.45 (s, 6H), 1.2 (s, 1H).

Compound 37

N-(3-(6-(4-((4-(2-(4-chloro-3-(2,4-dioxotetrahydro-pyrimidin-1(2H)-yl)benzamido)ethyl)-1-oxa-4,9-diazaspiro[5.5]undecan-9-yl)methyl)phenyl)-7H-pyrrolo[2,3-d]pyrimidin-4-yl)-5-fluoro-2-methylphenyl)-2-fluoro-4-(2-hydroxypropan-2-yl)benzamide

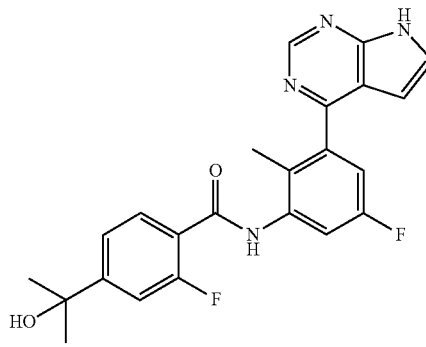

Step 1: Tert-butyl 9-(4-(4-(5-fluoro-3-(2-fluoro-4-(2-hydroxypropan-2-yl)benzamido)-2-methylphenyl)-7H-pyrrolo[2,3-d]pyrimidin-6-yl)benzyl)-1-oxa-4,9-diazaspiro[5.5]undecane-4-carboxylate A mixture of tert-butyl 1-oxa-4,9-diazaspiro[5.5]undecane-4-carboxylate (155 mg, 0.605 mmol) and 2-fluoro-N-(5-fluoro-3-(6-(4-formylphenyl)-7H-pyrrolo[2,3-d]pyrimidin-4-yl)-2-methylphenyl)-4-(2-hydroxypropan-2-yl)benzamide (intermediate 3, 350 mg, 0.665 mmol) in THF (6 ml) was stirred overnight at 60° C. Solid NaBH(OAc)$_3$ (384 mg, 1.814 mmol) was added and stirring was continued at 60° C. for 9 h and at RT overnight. The RM was diluted with EtOAc, and washed with an aq. solution of NaHCO$_3$ and brine. The organic phase was dried over Na$_2$SO$_4$ and concentrated to afford the title compound as a solid (0.42 g).
Method A: Rt=0.90 min; [M+H]+=767.5.

Step 2: N-(3-(6-(4-(1-oxa-4,9-diazaspiro[5.5]undecan-9-ylmethyl)phenyl)-7H-pyrrolo[2,3-d]pyrimidin-4-yl)-5-fluoro-2-methylphenyl)-2-fluoro-4-(2-hydroxypropan-2-yl)benzamide To a solution of tert-butyl 9-(4-(4-(5-fluoro-3-(2-fluoro-4-(2-hydroxypropan-2-yl)benzamido)-2-methylphenyl)-7H-pyrrolo[2,3-d]pyrimidin-6-yl)benzyl)-1-oxa-4,9-diazaspiro[5.5]undecane-4-carboxylate (0.42 g, 0.531 mmol) in DCM (5 ml) was added TFA (1.228 ml, 15.94 mmol). The RM was stirred at RT for 1 h, evaporated and the residue was purified by reverse phase HPLC on a Reprosil® C18 column eluting with ACN in an aq. solution of TFA (0.1%) (from 5 to 95%), to afford the title compound as a solid TFA salt (0.11 g).
Method A: Rt=0.68 min; [M+H]+=667.5.

Step 3: 3-((2-carboxyethyl)amino)-4-chlorobenzoic Acid

To a mixture of 3-amino-4-chlorobenzoic acid (0.63 g, 3.67 mmol) in a mixture of water and AcOH (5:1) (4.8 ml) was added acrylic acid (0.264 ml, 3.86 mmol). The RM was stirred at 110° C. for 5 h and then at 120° C. overnight. An additional amount of acrylic acid (1.260 ml, 18.36 mmol) was added and the RM was stirred at 120° C. overnight, cooled to RT and filtered. The solids were washed with water and diisopropylether and dried to afford the title compound as a solid (0.67 g).
Method A: Rt=0.65 min; [M+H]+=244.1.

Step 4: 4-chloro-3-(2,4-dioxotetrahydropyrimidin-1 (2H)-yl)benzoic Acid

To 3-((2-carboxyethyl)amino)-4-chlorobenzoic acid (0.64 g, 2.469 mmol) was added AcOH (14.14 ml, 247 mmol), followed by urea (2.97 g, 49.4 mmol) and the RM was stirred at 120° C. overnight. An additional amount of urea (2.97 g, 49.4 mmol) was added and the RM was stirred at 120° C. overnight and then left at RT for 3 days. The RM was diluted with an aq. solution of NaOH and extracted with EtOAc. The phases were separated, the aq. phase was poured into an ice cold concentrated aq. solution of HCl (pH=1) and the mixture was extracted with DCM. The combined organic phases were dried over Na$_2$SO$_4$ and concentrated. The residue was taken up in a mixture of diisopropylether and EtOAc (10:1), sonicated, and filtered. The solids were washed with diisopropylether and dried to afford the title compound as a solid (0.11 g).
Method A: Rt=0.50 min; [M+H]+=267.1.

Step 5: N-((1,3-dioxolan-2-yl)methyl)-4-chloro-3-(2,4-dioxotetrahydropyrimidin-1(2H)-yl)benzamide To mixture of 4-chloro-3-(2,4-dioxotetrahydropyrimidin-1(2H)-yl)benzoic acid (95 mg, 0.329 mmol) in DMA (2 ml) was added HATU (163 mg, 0.428 mmol), followed by DIPEA (0.230 ml, 1.315 mmol). After 15 min, (1,3-dioxolan-2-yl)methanamine (40.7 mg, 0.395 mmol) was added and the RM was stirred at RT overnight. The RM was filtered and the filtrate purified by reverse phase HPLC on a Reprosil® C18 column eluting with ACN in an aq. solution of TFA (0.1%) (from 5 to 95%) to afford the title compound as a solid (30 mg).

Method A: Rt=0.53 min; [M+H]⁺=354.2.

Step 6: 4-chloro-3-(2,4-dioxotetrahydropyrimidin-1(2H)-yl)-N-(2-oxoethyl)benzamide N-((1,3-dioxolan-2-yl)methyl)-4-chloro-3-(2,4-dioxotetrahydropyrimidin-1(2H)-yl)benzamide (30 mg, 0.085 mmol) was dissolved in formic acid (0.325 ml, 8.48 mmol) and the RM was stirred at RT overnight. The RM was then diluted with water and freeze-dried to afford the title compound as a solid (20 mg).
Method A: Rt=0.44 min; [M+H]⁺=310.1.

Step 7: N-(3-(6-(4-((4-(2-(4-chloro-3-(2,4-dioxotetrahydropyrimidin-1(2H)-yl)benzamido)ethyl)-1-oxa-4,9-diazaspiro[5.5]undecan-9-yl)methyl)phenyl)-7H-pyrrolo[2,3-d]pyrimidin-4-yl)-5-fluoro-2-methylphenyl)-2-fluoro-4-(2-hydroxypropan-2-yl)benzamide To a mixture of N-(3-(6-(4-(1-oxa-4,9-diazaspiro[5.5]undecan-9-ylmethyl)phenyl)-7H-pyrrolo[2,3-d]pyrimidin-4-yl)-5-fluoro-2-methylphenyl)-2-fluoro-4-(2-hydroxypropan-2-yl)benzamide trifluoroacetate (0.050 g, 0.065 mmol) and 4-chloro-3-(2,4-dioxotetrahydropyrimidin-1(2H)-yl)-N-(2-oxoethyl)benzamide (0.02 g, 0.065 mmol) in MeOH (3 ml) was added TEA (0.027 ml, 0.194 mmol), followed by a solution of ZnCl₂ (0.5 M) in THF (0.142 ml, 0.071 mmol) and the RM was stirred at RT for 3 h. Solid NaBH₃CN (4.46 mg, 0.071 mmol) was added, the RM was stirred at RT overnight and filtered. The filtrate was concentrated, a few drops of TFA were added and the residue was purified by reverse phase HPLC on a Reprosil® C18 column eluting with ACN in an aq. solution of TFA (0.1%) (from 5 to 95%). Fractions containing pure material were combined, basified with an aq. solution of NaHCO₃ and extracted with EtOAc. The combined organic phases were concentrated, the residue was dissolved in tert-butanol containing a few drops of water and freeze dried to afford the title compound as a solid (30.5 mg).
Method B: Rt=3.42 min, [M+H]⁺=960.6.
¹H NMR (600 MHz, DMSO-d₆) δ 12.79 (s, 1H), 10.56 (s, 1H), 9.97 (s, 1H), 8.87 (s, 1H), 8.52 (t, J=5.7 Hz, 1H), 8.02-7.89 (m, 3H), 7.81 (dd, J=8.4, 2.2 Hz, 1H), 7.74 (t, J=7.9 Hz, 1H), 7.72-7.64 (m, 2H), 7.49-7.34 (m, 4H), 7.25 (dd, J=8.8, 2.8 Hz, 1H), 6.9-6.8 (m, 1H), 5.32 (s, 1H), 3.8-3.7 (m, 1H), 3.67-3.57 (m, 4H), 3.55-3.45 (m, 2H), 3.4-3.3 (m, 2H), 3.32 (s, 2H), 2.8-2.7 (m, 2H), 2.41 (s, 1H), 2.45-2.2 (m, 9H), 1.8-1.7 (m, 2H), 1.51 (m, 2H), 1.46 (s, 6H).

The compounds described in Table 1 were obtained in analogous ways as the compounds described above and by following the principles outlined in the general synthesis schemes.

TABLE 1

| Compound number | analytical method | retention time [min] | [M + H]⁺ | IUPAC name |
| --- | --- | --- | --- | --- |
| 038 | Method G | 2.05 | 956.4 | N-(3-(6-(4-((1-(2-(1-(3-(2,4-dioxotetrahydropyrimidin-1(2H)-yl)-4-methoxybenzoyl)piperidin-4-yl)ethyl)piperidin-4-yl)oxy)phenyl)-7H-pyrrolo[2,3-d]pyrimidin-4-yl)-5-fluoro-2-methylphenyl)-2-fluoro-4-(2-hydroxypropan-2-yl)benzamide |
| 039 | Method I | 0.90 | 478.8 [(M + H)/2]⁺ | N-(3-(6-(4-((4-(2-(3-(2,4-dioxotetrahydropyrimidin-1(2H)-yl)-4-methoxybenzamido)ethyl)-1-oxa-4,9-diazaspiro[5.5]undecan-9-yl)methyl)phenyl)-7H-pyrrolo[2,3-d]pyrimidin-4-yl)-5-fluoro-2-methylphenyl)-2-fluoro-4-(2-hydroxypropan-2-yl)benzamide |
| 040 | Method B | 3.03 | 914.6 | N-(3-(6-(4-(((4-(4-(3-(2,4-dioxotetrahydropyrimidin-1(2H)-yl)-4-methoxybenzoyl)piperazin-1-yl)butyl)amino)methyl)phenyl)-7H-pyrrolo[2,3-d]pyrimidin-4-yl)-5-fluoro-2-methylphenyl)-2-fluoro-4-(2-hydroxypropan-2-yl)benzamide |
| 041 | Method J | 1.90 | 956.4 | N-(3-(6-(4-((((1s,4s)-4-((1-(3-(2,4-dioxotetrahydropyrimidin-1(2H)-yl)-4-methoxybenzoyl)piperidin-4-yl)oxy)cyclohexyl)oxy)methyl)phenyl)-7H-pyrrolo[2,3-d]pyrimidin-4-yl)-5-fluoro-2-methylphenyl)-2-fluoro-4-(2-hydroxypropan-2-yl)benzamide |
| 042 | Method B | 3.74 | 877.5 | 4-chloro-3-(2,4-dioxotetrahydropyrimidin-1(2H)-yl)-N-(5-((4-(4-(5-fluoro-3-(2-fluoro-4-(2-hydroxypropan-2-yl)benzamido)-2-methylphenyl)-7H-pyrrolo+2,3-d+pyrimidin-6-yl)benzyl)amino)pentyl)-N-methylbenzamide |
| 043 | Method B | 4.03 | 969.6 | N-(3-(6-(4-((1-(2-(1-(3-(2,4-dioxotetrahydropyrimidin-1(2H)-yl)-4-methoxybenzoyl)piperidin-4-yl)ethyl)piperidin-4-yl)methoxy)phenyl)-7H-pyrrolo[2,3-d]pyrimidin-4-yl)-5-fluoro-2-methylphenyl)-2-fluoro-4-(2-hydroxypropan-2-yl)benzamide |
| 044 | Method J | 1.76 | 954.3 | N-(3-(6-(4-((9-(2-(3-(2,4-dioxotetrahydropyrimidin-1(2H)-yl)-4-methoxybenzamido)ethyl)-3,9-diazaspiro[5.5]undecan-3-yl)methyl)phenyl)-7H-pyrrolo[2,3-d]pyrimidin-4-yl)-5-fluoro-2-methylphenyl)-2-fluoro-4-(2-hydroxypropan-2-yl)benzamide |

TABLE 1-continued

| Compound number | analytical method | retention time [min] | [M + H]⁺ | IUPAC name |
|---|---|---|---|---|
| 045 | Method G | 1.93 | 945.3 | N-(3-(6-(4-((3-((2-(4-(3-(2,4-dioxotetrahydropyrimidin-1(2H)-yl)-4-methoxybenzoyl)piperazin-1-yl)ethyl)amino)propoxy)methyl)phenyl)-7H-pyrrolo[2,3-d]pyrimidin-4-yl)-5-fluoro-2-methylphenyl)-2-fluoro-4-(2-hydroxypropan-2-yl)benzamide |
| 046 | Method J | 1.85 | 943.2 | N-(3-(6-(4-(((1r,4r)-4-((1-(3-(2,4-dioxotetrahydropyrimidin-1(2H)-yl)-4-methoxybenzoyl)piperidin-4-yl)oxy)cyclohexyl)oxy)phenyl)-7H-pyrrolo[2,3-d]pyrimidin-4-yl)-5-fluoro-2-methylphenyl)-2-fluoro-4-(2-hydroxypropan-2-yl)benzamide |
| 047 | Method J | 1.79 | 914.3 | N-(3-(6-(4-(2-(9-(3-(2,4-dioxotetrahydropyrimidin-1(2H)-yl)-4-fluorobenzoyl)-3,9-diazaspiro[5.5]undecan-3-yl)ethyl)phenyl)-7H-pyrrolo[2,3-d]pyrimidin-4-yl)-5-fluoro-2-methylphenyl)-2-fluoro-4-(2-hydroxypropan-2-yl)benzamide |
| 048 | Method B | 3.26 | 974.7 | N-(3-(6-(4-((4-(3-(4-chloro-3-(2,4-dioxotetrahydropyrimidin-1(2H)-yl)benzamido)propyl)-1-oxa-4,9-diazaspiro[5.5]undecan-9-yl)methyl)phenyl)-7H-pyrrolo[2,3-d]pyrimidin-4-yl)-5-fluoro-2-methylphenyl)-2-fluoro-4-(2-hydroxypropan-2-yl)benzamide |
| 049 | Method D | 1.30 | 898.3 | N-(3-(6-(4-((8-(3-(2,4-dioxotetrahydropyrimidin-1(2H)-yl)-4-methoxybenzoyl)-2,8-diazaspiro[4.5]decan-2-yl)methyl)phenyl)-7H-pyrrolo[2,3-d]pyrimidin-4-yl)-5-fluoro-2-methylphenyl)-2-fluoro-4-(2-hydroxypropan-2-yl)benzamide |
| 050 | Method F | 1.30 | 926.2 | N-(3-(6-(4-((4-((1-(3-(2,4-dioxotetrahydropyrimidin-1(2H)-yl)-4-methylbenzoyl)piperidin-4-yl)oxy)piperidin-1-yl)methyl)phenyl)-7H-pyrrolo[2,3-d]pyrimidin-4-yl)-5-fluoro-2-methylphenyl)-2-fluoro-4-(2-hydroxypropan-2-yl)benzamide |
| 051 | Method F | 1.52 | 485.6 [(M + H)/2]⁺ | N-(3-(6-(4-((1-(2-(4-(3-(2,4-dioxotetrahydropyrimidin-1(2H)-yl)-4-methoxybenzoyl)piperazin-1-yl)ethyl)piperidin-4-yl)methoxy)phenyl)-7H-pyrrolo[2,3-d]pyrimidin-4-yl)-5-fluoro-2-methylphenyl)-2-fluoro-4-(2-hydroxypropan-2-yl)benzamide |
| 052 | Method H | 1.72 | 927.0 | N-(3-(6-(4-((2-(2-(3-(2,4-dioxotetrahydropyrimidin-1(2H)-yl)-4-methoxybenzamido)ethyl)-2,7-diazaspiro[3.5]nonan-7-yl)methyl)phenyl)-7H-pyrrolo[2,3-d]pyrimidin-4-yl)-5-fluoro-2-methylphenyl)-2-fluoro-4-(2-hydroxypropan-2-yl)benzamide |
| 053 | Method J | 1.79 | 940.4 | N-(3-(6-(4-((2-(2-(3-(2,4-dioxotetrahydropyrimidin-1(2H)-yl)-4-methoxybenzamido)ethyl)-2,8-diazaspiro[4.5]decan-8-yl)methyl)phenyl)-7H-pyrrolo[2,3-d]pyrimidin-4-yl)-5-fluoro-2-methylphenyl)-2-fluoro-4-(2-hydroxypropan-2-yl)benzamide |
| 054 | Method J | 1.86 | 942.3 | N-(3-(6-(4-(((1s,4s)-4-((1-(3-(2,4-dioxotetrahydropyrimidin-1(2H)-yl)-4-methoxybenzoyl)piperidin-4-yl)oxy)cyclohexyl)oxy)phenyl)-7H-pyrrolo[2,3-d]pyrimidin-4-yl)-5-fluoro-2-methylphenyl)-2-fluoro-4-(2-hydroxypropan-2-yl)benzamide |
| 055 | Method J | 1.77 | 897.3 | N-(3-(6-(4-((2-(3-(2,4-dioxotetrahydropyrimidin-1(2H)-yl)-4-methoxybenzoyl)-2,8-diazaspiro[4.5]decan-8-yl)methyl)phenyl)-7H-pyrrolo[2,3-d]pyrimidin-4-yl)-5-fluoro-2-methylphenyl)-2-fluoro-4-(2-hydroxypropan-2-yl)benzamide |
| 056 | Method J | 1.88 | 956.4 | N-(3-(6-(4-((((1r,4r)-4-((1-(3-(2,4-dioxotetrahydropyrimidin-1(2H)-yl)-4-methoxybenzoyl)piperidin-4-yl)oxy)cyclohexyl)oxy)methyl)phenyl)-7H-pyrrolo[2,3-d]pyrimidin-4-yl)-5-fluoro-2-methylphenyl)-2-fluoro-4-(2-hydroxypropan-2-yl)benzamide |

TABLE 1-continued

| Compound number | analytical method | retention time [min] | [M + H]+ | IUPAC name |
|---|---|---|---|---|
| 057 | Method B | 3.06 | 972.9 | N-(3-(6-(4-((9-(3-(4-chloro-3-(2,4-dioxotetrahydropyrimidin-1(2H)-yl)benzamido)propyl)-3,9-diazaspiro[5.5]undecan-3-yl)methyl)phenyl)-7H-pyrrolo[2,3-d]pyrimidin-4-yl)-5-fluoro-2-methylphenyl)-2-fluoro-4-(2-hydroxypropan-2-yl)benzamide |
| 058 | Method B | 3.82 | 971.5 | N-(3-(6-(4-((1-(2-((1-(3-(2,4-dioxotetrahydropyrimidin-1(2H)-yl)-4-methoxybenzoyl)piperidin-4-yl)oxy)ethyl)piperidin-4-yl)oxy)phenyl)-7H-pyrrolo[2,3-d]pyrimidin-4-yl)-5-fluoro-2-methylphenyl)-2-fluoro-4-(2-hydroxypropan-2-yl)benzamide |

Assay Description

Compounds of the invention were tested in the following cellular assays. The data obtained is shown in Table 2. The terms in Table 2 are defined as follows: $DC_{50}$ refers to the concentration at which 50% maximal degradation was observed; deg Amax is the extent of degradation and the value refers to the % protein remaining at the concentration at which maximum degradation is seen; Prol $GI_{50}$ refers to the proliferation data and defines the concentration at which 50% growth inhibition was observed compared to the vehicle treated control at the end of the incubation time. TMD8 cells are BTK dependent and OCI-LY3 cells are BTK independent.

BTK-GFP and IKZF3-GFP Protein Abundance Flow Cytometry Assay in HEK293A Cells:

Degradation of BTK or IKZF3 was measured in HEK293A cells (Invitrogen R70507) expressing either BTK-GFP and RFP or IKZF3-GFP and RFP from a stably integrated bicistronic BTK-GFP-iresRFP or IKZF3-GFP-iresRFP construct, respectively. Reduction of the GFP signal measured by flow cytometry served as readout for BTK or IKZF3 degradation after degrader treatment.

i) Cloning of the pLenti6-BTK-GFP-Ires-RFP and IKZF3-GFP-Ires-RFP Sensor Vectors The bicistronic BTK-GFP-iresRFP construct is based on a pLenti6-DEST vector backbone where GFP was introduced into the unique XhoI site downstream of the destination cassette (DEST) and RFP was cloned behind an internal ribosomal entry site (Ires).

In detail, the sensor construct was engineered by replacing NanoLuciferase (NLuc) by GFP and FireFly luciferase (FF) by RFP from pLenti6-DEST-NLuc-Ires-FF.

The pLenti6-DEST-NLuc-Ires-FF sensor construct was cloned by replacing eGFP from pLenti6-DEST-Ires-eGFP with a synthesized stuffer element (encoding Ires-FF with FF flanked by two Nhe1 restriction sites) using blunt end cloning replacing Ires-eGFP between the two PmlI. To enable C-terminal tagging with NanoLuciferase (NLuc), NLuc was amplified from pNL1.1 (Promega #N1001) using linker primers with XhoI sites for ligating into linearized pLenti6-DEST-Ires-FF using XhoI digest resulting in the construct pLenti6-DEST-NLuc-Ires-FF.

The pLenti6-DEST-NLuc-Ires-FF served as base vector for cloning pLenti6-DEST-GFP-Ires-RFP using Gibson assembly to replace FF with RFP and NLuc with GFP. In a first round FF was replaced by RFP by amplifying RFP from a template using the following Gibson assembly linker primers (Gibson-Nhe1 RFPfw, CGATGAATTCGC-CACCgctagcATGGTGAGCAAGGGCGAGGAGC (SEQ ID NO: 1); Gibson-Nhe1 RFP-Stoprev, CTCAT-TACTAACCGGctagcTTACTTGTACAGCTCGTCCATGC (SEQ ID NO: 2)) to clone into pLenti6-DEST-NLuc-Ires-FF digested with Nhe1 and gel-purified to remove the FF fragment. The resulting pLenti6-DEST-NLuc-Ires-RFP vector served as the template to replace NLuc with GFP by amplifying GFP from a template using following Gibson assembly linker primers (Gibson-XhoI GFPfw, CCAGCACAGTGGCGGCCGCTCGAGcATGGT-GAGCAAGGGCGAGGAGCTGTTCACC (SEQ ID NO: 3); Gibson-XhoI GFP-Stoprev, CCGCGGGCCCTCTA-GACTCGAGTTACTTGTACAGCTCGTC-CATGCCGAGAGT (SEQ ID NO: 4)) to clone into pLenti6-DEST-NLuc-Ires-RFP digested with XhoI and gel-purified to remove the NLuc fragment. All Gibson assembly reactions were performed with Gibson assembly Master Mix (New England Biolabs NEB E2611L) according to manufacturer's manual, resulting in the destination vector pLenti6-DEST-GFP-Ires-RFP to allow Gateway cloning.

To enable gateway cloning and C-terminal GFP tagging of BTK, the BTK open reading frame (ORF) was first shuttled from a pcDNA-DEST40-BTK vector (Invitrogen library ID INV_20090504v1) into pDONR221 (Invitrogen 12536-017) vector using a gateway BP reaction according to the manufacturer's manual (Invitrogen 11789-013) resulting in the novel construct pENTR221-BTK. For C-terminal tagging the STOP codon was mutated to a leucine performing a mutagenesis reaction with the following primers (pENTR221-BTK Quikchange STOP-Leu fw, gtcatggat-gaagaatccTTGaacccagctttcttgtac; pENTR221-BTK Quikchange STOP-Leu REVC, gtacaagaaagctgggtt-CAAggattcttcatccatgac) using the QuikChange Lightning mutagenesis kit (Agilent Technologies #210518) according to the manufacturer's manual, resulting in pENTR221-BTK (STOP-Leu).

To get the final pLenti6-BTK-GFP-Ires-RFP sensor construct, a Gateway LR reaction was performed between pLenti6-DEST-GFP-Ires-RFP and pENTR221-BTK (STOP-Leu) using the LR Clonase kit (Invitrogen 11791-019) according to the manufacturer's manual. All vectors described have been sequenced for verification.

By analogy the bicistronic pLenti6-IKZF3-GFP-iresRFP was engineered by gateway cloning of IKZF3 from a pENTR221-IKZF3 (STOP-Leu) construct into the previously described pLenti6-DEST-GFP-Ires-RFP vector using the LR Clonase kit (Invitrogen 11791-019) according to the manufacturer's manual. All vectors described have been sequenced for verification.

To enable gateway cloning and C-terminal GFP tagging of IKZF3 the STOP codon was mutated to a leucine from pENTR221-IKZF3 (Invitrogen #INVE089_A8) performing a mutagenesis reaction with following primers (pENTR221-IKZF3 Quikchange STOP-Leu fw, AGAGCCCTGCTGAAGttgaaccCAGCTTTcttgtac (SEQ ID NO: 5); pENTR221-IKZF3 Quikchange STOP-Leu REVC, gtacaagAAAGCTGggttcaaCTTCAGCAGGGCTCT (SEQ ID NO: 6)) using the QuikChange Lightning mutagenesis kit (Agilent Technologies #210518) according to the manufacturer's manual, resulting in pENTR221-IKZF3 (STOP-Leu).

ii) Engineering of Stably Expressing 293A BTK-GFP-Ires-RFP and IKZF3-GFP-Ires-RFP Sensor Cells 293A BTK-GFP-Ires-RFP and IKZF3-GFP-Ires-RFP sensor cells were generated by lentiviral vector transduction using the pLenti6-BTK-GFP-Ires-RFP or pLenti6-IKZF3-GFP-Ires-RFP sensor construct described before. Lentiviral particles were produced in HEK293FT cells (Invitrogen R70007) by co-transfection of 500 ng pLenti6-BTK-GFP-Ires-RFP or pLenti6-IKZF3-GFP-Ires-RFP, 500 ng delta8.71 and 200 ng pVSVG diluted in 100 µl OptiMEM serum free medium (Invitrogen #11058-021) that was mixed after 5 min preincubation with 3 µl of Lipofectamine2000 (Invitrogen #11668-019) in 97 µl OptiMEM serum free medium. The mix was incubated for another 20 min at RT and then added on 1 ml of a freshly prepared suspension of HEK293FT cells in a well of a 6-well plate (concentration $1.2 \times 10^6$ cells/ml). 1 day after transfection, the medium was replaced with 1.5 ml of complete growth medium (DMEM high Glucose+10% FCS+1% L-Glutamine+1% NEAA+1% NaPyr.). 48 h post transfection supernatant containing viral transducing particles was collected and frozen at $-80°$ C.

Two days before transduction with viral particles $1 \times 10^5$ HEK293A cells (Invitrogen R70507) were seeded in 2 ml growth medium in a well of a 6-well plate. Infection was performed with 90 µl of collected supernatant containing viral transducing particles in 1 ml medium including 8 µg/ml polybrene. 24 h post infection, stably transfected cells were selected with blasticidin at a concentration of 8 µg/ml.

iii) Quantitative BTK-GFP and IKZF3-GFP Abundance Measurements

Stable HEK293A-BTK-GFP-iresRFP cells were maintained in complete growth medium (DMEM high Glucose+10% FCS+1% L-Glutamine+1% NEAA+1% NaPyr.) with passaging performed twice per week. On Day 0, HEK293A-BTK-GFP-iresRFP or HEK293A-IKZF3-GFP-iresRFP and HEK293A-iresRFP cells were seeded at 10,000 cells/well in a 96-well microtiter plate in 260 µl complete medium. On Day 1, cells were treated in duplicate with 10-point 1:3 dilution series of compound using the HP D300 Digital Dispenser (Tecan). DMSO concentrations were normalized across the plate to 0.1%. On Day 2, after 24 h of incubation at 37° C., treatment media was discarded, cells rinsed with 100 ul/well PBS and then detached using 40 ul trypsin/well for 5 min. Trypsin was neutralized with 100 ul/well PBS+20% FCS). Flow cytometry was performed on the samples using the BD FACS CANTO II (Becton Dickinson). Cell identification was then performed using forward (FSC) vs. side scatter (SSC) plots. Single cell discrimination is performed using SSC-Width (SSC-W) vs. SSC-Height (SSC-H) plots. Median GFP values for 5,000 single cells are used to determine BTK levels. Median GFP values from HEK293A-iresRFP are used as a background signal and thus defining 0% BTK signal. Median GFP values from DMSO treated HEK293A-BTK-GFP-iresRFP or HEK293A-IKZF3-GFP-iresRFP are used to define 100% BTK signal for subsequent $DC_{50}$ curves (concentration at 50% BTK degradation). GFP and RFP are read in the channels called FITC and PE, respectively.

Concentration response curves plotting relative reduction of the GFP signal (measured by flow cytometry) versus 10 compound concentrations (starting concentration 10 µM, 3 fold dilution steps) of the compounds allowed generation of $DC_{50}$ values.

For the IKZF3 abundance assay, the literature molecules pomalidomide and lenalidomide were tested as positive control compounds. Data is shown in table 3, in which, $DC_{50}$ refers to the concentration at which 50% maximal degradation was observed; deg Amax is the extent of degradation and the value refers to the % protein remaining at the concentration at which maximum degradation is seen.

BTK(C481S)-GFP Protein Abundance Flow Cytometry Assay in TMD8 Cells:

Degradation of BTK(C481S) was measured in TMD8 cells expressing BTK(C481S)-GFP and mCherry from a stably integrated second generation bicistronic BTK(C481S)-GFP-CHYSEL-mCherry construct. Reduction of the GFP signal measured by flow cytometry served as readout for BTK(C481S) degradation after degrader treatment.

Cloning of the pLenti6-BTK(C481S)-GFP-CHYSEL-mCherry Sensor Vectors

The BTK(C481S) protein abundance sensor is based on a second generation bicistronic construct, where the 2 reading frames BTK(C481S) and mCherry control are separated by a cis-acting hydrolase element (see: Lo et al., 2015 Cell Reports 13, 2634), replacing the Ires from the first generation vector described before.

The bicistronic BTK(C481S)-GFP-CHYSEL-mCherry construct is based on a pLenti6-DEST vector backbone where a GFP-CHYSEL-mCherry cassette was synthesized and inserted downstream of the DEST cassette by Gibson assembly resulting in the new gateway compatible vector pLenti6-DEST-GFP-CHYSEL-mCherry to allow Gateway cloning with pENTR221-BTK(C481S)(STOP-Leu) to obtain the final sensor construct pLenti6-BTK(C481S)-GFP-CHYSEL-mCherry. The pENTR221-BTK(C481S) (STOP-Leu) was generated by mutating wild-type BTK to BTK(C481S) with a mutagenesis reaction on pENTR221-BTK (STOP-Leu) with the following primers (BTK C481S Quikchange fw, gagtacatggccaatggctCcctcctgaactacctgagg (SEQ ID NO: 7); BTK C481S Quikchange REVC, cctcaggtagttcaggaggGagccattggccatgtactc (SEQ ID NO: 8)) using the QuikChange Lightning mutagenesis kit (Agilent Technologies #210518) performed according to the manufacturer's manual, resulting in pENTR221-BTK(C481S) (STOP-Leu).

Sequence of the synthesized construct (Xho1 sites are shown in bold, mCherry-ORF is shown in small letters):

(SEQ ID NO: 9)
GATATCCAGCACAGTGGCGGCCGCTCGAGcATGGTGAGCAAGGGCGAGGAG

CTGTTCACCGGGGTGGTGCCCATCCTGGTCGAGCTGGACGGCGACGTAAAC

GGCCACAAGTTCAGCGTGTCCGGCGAGGGCGAGGGCGATGCCACCTACGGC

AAGCTGACCCTGAAGTTCATCTGCACCACCGGCAAGCTGCCCGTGCCCTGG

CCCACCCTCGTGACCACCCTGACCTACGGCGTGCAGTGCTTCAGCCGCTAC

CCCGACCACATGAAGCAGCACGACTTCTTCAAGTCCGCCATGCCCGAAGGC

TACGTCCAGGAGCGCACCATCTTCTTCAAGGACGACGGCAACTACAAGACC

CGCGCCGAGGTGAAGTTCGAGGGCGACACCCTGGTGAACCGCATCGAGCTG

-continued
```
AAGGGCATCGACTTCAAGGAGGACGGCAACATCCTGGGGCACAAGCTGGAG

TACAACTACAACAGCCACAACGTCTATATCATGGCCGACAAGCAGAAGAAC

GGCATCAAGGTGAACTTCAAGATCCGCCACAACATCGAGGACGGCAGCGTG

CAGCTCGCCGACCACTACCAGCAGAACACCCCCATCGGCGACGGCCCCGTG

CTGCTGCCCGACAACCACTACCTGAGCACCCAGTCCGCCCTGAGCAAAGAC

CCCAACGAGAAGCGCGATCACATGGTCCTGCTGGAGTTCGTGACCGCCGCC

GGGATCACTCTCGGCATGGACGAGCTGTACAAGGGAAGCGGAGCGACGAAT

TTTAGTCTACTGAAACAAGCGGGAGACGTGGAGGAAAACCCTGGACCTatg gtgagcaagggcgaggaggataacatggccatcatcaaggagttcatgcgc ttcaaggtgcacatggagggctccgtgaacggccacgagttcgagatcgag ggcgagggcgagggccgcccctacgagggcacccagaccgccaagctgaag gtgaccaagggtggcccctgccttcgctgggacatcctgtcccctcag ttcatgtacggctccaaggcctacgtgaagcacccgccgacatccccgac tacttgaagctgtccttccccgagggcttcaagtgggagcgcgtgatgaac ttcgaggacggcggcgtggtgaccgtgaccaggactcctccctgcaggac ggcgagttcatctacaaggtgaagctgcgcggcaccaacttccctccgac ggccccgtaatgcagaagaagaccatgggctgggaggcctcctccgagcgg atgtacccgaggacggcgccctgaagggcgagatcaagcagaggctgaag ctgaaggacggcggccactacgacgctgaggtcaagaccacctacaaggcc aagaagcccgtgcagctgcccggcgcctacaacgtcaacatcaagttggac atcacctcccacaacgaggactacaccatcgtggaacagtacgaacgcgcc gagggccgccactccaccggcggcatggacgagctgtacaagtagCTCGAG

TCTAGAGGGCCCGCGGTTAAC
```

Engineering of Stably Expressing TMD8 BTK(C481S)-GFP-CHYSEL-mCherry Sensor Cells TMD8 BTK(C481S)-GFP-CHYSEL-mCherry sensor cells were generated by lentiviral vector transduction using the pLenti6-BTK(C481S)-GFP-CHYSEL-mCherry sensor construct described before. Lentiviral particles were produced in HEK293FT cells (Invitrogen R70007) by co-transfection of 500 ng pLenti6-BTK-GFP-Ires-RFP or pLenti6-IKZF3-GFP-Ires-RFP, 500 ng delta8.71 and 200 ng pVSVG diluted in 100 µl OptiMEM serum free medium (Invitrogen #11058-021) that was mixed after 5 min preincubation with 3 µl of Lipofectamine2000 (Invitrogen #11668-019) in 97 µl OptiMEM serum free medium. The mix was incubated for another 20 min at RT and then added to 1 ml of a freshly prepared suspension of HEK293FT cells in a well of a 6-well plate (concentration $1.2 \times 10^6$ cells/ml). 1 day after transfection, the medium was replaced with 1.5 ml of complete growth medium (DMEM high Glucose+10% FCS+1% L-Glutamine+1% NEAA+1% NaPyr.). 48 h post transfection supernatant containing viral transducing particles was collected and frozen at −80° C.

Two days before transduction with viral particles $1 \times 10^5$ HEK293A cells (Invitrogen R70507) were seeded in 2 ml growth medium in a well of a 6-well plate. Infection was performed with 90 µl of collected supernatant containing viral transducing particles in 1 ml medium including 8 µg/ml polybrene. 24 h post infection, stably transfected cells were selected with blasticidin at a concentration of 8 µg/ml.

Cell Viability Assay in DLBCL (Diffuse Large B-Cell Lymphoma) Cells:

The effect of the BTK compounds on cell proliferation was measured by a Resazurin (Sigma, #R7017) based cell viability assay. TMD8 (BTK compound sensitive) and OCI-LY3 (BTK compound insensitive) cells were incubated for 72 h at 37° C. and 5% $CO_2$ with the corresponding compound. Resazurin is a non-toxic, cell-permeable substrate that is virtually non-fluorescent. Upon entering living cells, Resazurin (Sigma, #R7017) is reduced to highly fluorescent Resorufin. The metabolic activity was assessed by measuring the fluorescence signal (ex. 530 nm; em. 600 nm).

TMD8 and OCI-Ly3 cells were seeded at day 0 in triplicates at a cell density of $1 \times 10^4$ cells per 150 µl/well in a 96-well plate (Costar #3904). Additional plates were prepared, in order to assess the basal metabolic activity of both cell lines at the beginning of the experiment. For these reference plates, Resazurin (Sigma, #R7017) was added to a final concentration of 13 µg/ml 3 h post seeding and was incubated for 2 h at 37° C. and 5% $CO_2$. Following incubation, the fluorescent signal intensity of the 96-well plates was measured on a Mithras LB940 multimode plate reader at 530/600 nm (Berthold Technologies, Germany).

In parallel, 3 h post-seeding, test-plates were treated with compound at various concentrations, or with vehicle (DMSO) alone for 3 days. The compound addition to the plates was performed by using a HP D300 digital dispenser (TECAN, Switzerland). The compounds were tested in triplicate, 8-point serial dilution (1:4), with a start concentration of 10 µM for OCI-LY3 and 1 µM for the TMD8 cells, respectively. To assess the relative proliferation of the cells, Resazurin was added to each well directly to the medium to a final concentration of 13 µg/ml. The plates were incubated for 2 h at 37° C. and 5% $CO_2$ to result in a 72 h endpoint. Following incubation, the fluorescent signal intensity of the 96-well plates were measured on a Mithras LB940 multi-mode plate reader at 530/600 nm (Berthold Technologies, Germany). The formation of Resorufin dye directly correlates with the number of metabolically active cells. For each triplicate treatment the mean and standard deviation were calculated and analyzed via curve fitting software to determine the respective compound concentration resulting in 50% growth inhibition ($GI_{50}$) values. For each compound $GI_{50}$ values were typically determined from at least 2 entirely independent experiments.

OCI-LY3 cells were acquired through a license agreement with University Health Network, Toronto, Canada. Cells are cultivated in RPM1640 media (Gibco, #61870-010, lot. 1894759), supplemented with 10% FCS (HyClone, GE #SH30066.03, lot AB217603), 2 mM L-Glutamine (Bio-Concept, #5-10K50-H, lot. LA03467P), 1 mM Sodium Pyruvate (BioConcept, #5-60F00-H, lot. LB10510P), 10 mM HEPES (Gibco, #15630-056, lot. 1854074), 1% Pen/Strep (BioConcept, #4-01F00-H, lot. LB04235P).

TMD8 cells were acquired through a license agreement with Tokyo Medical and Dental University, Japan. Cells are cultivated in MEM Alpha (BioConcept, #1-23F01-1. lot. LB04262P) supplemented with 10% FCS (HyClone, GE #SH30066.03, lot AB217603), 2 mM L-Glutamine (Bio-Concept, #5-10K50-H, lot. LA03467P), 1% Pen/Strep (Bio-Concept, #4-01F00-H, lot. LB04235P).

TABLE 2

| Compound No | BTK DC50 [uM] | BTK deg Amax % | BTK (C481S) DC50 [uM] | BTK (C481S) Amax % | TMD8 Prol $GI_{50}$ [uM] | OCI-LY3 Prol $GI_{50}$ [uM] | IKZF3 $DC_{50}$ [uM] | IKZF3 deg Amax % |
|---|---|---|---|---|---|---|---|---|
| 1 | 0.0262 | 4.2 | n.d. | n.d. | 0.00389 | >10 | n.d. | n.d. |
| 2 | 0.0385 | 4.6 | n.d. | n.d. | 0.00357 | >10 | n.d. | n.d. |
| 3 | 0.0191 | 3.6 | n.d. | n.d. | 0.00224 | >10 | n.d. | n.d. |
| 4 | 0.0037 | 7.8 | 0.00208 | 2.2 | 0.00184 | 4.685 | >1.1 | 101.3 |
| 5 | 0.001 | 3.1 | 0.00057 | 2.5 | 0.00047 | 6.550 | >0.370 | 103.3 |
| 6 | 0.0007 | 4.1 | 0.00072 | 2.1 | 0.00053 | 3.426 | >10 | 100.8 |
| 7 | 0.0007 | 3.3 | n.d. | n.d. | 0.00039 | 6.115 | n.d. | n.d. |
| 8 | 0.0026 | 5.5 | 0.00208 | 2.7 | 0.00039 | 4.853 | >2.6 | 103.3 |
| 9 | 0.0021 | 4.5 | 0.00192 | 4.5 | 0.00052 | 3.870 | >7.8 | 99.1 |
| 10 | 0.0007 | 2.3 | n.d. | n.d. | 0.00036 | 5.943 | n.d. | n.d. |
| 11 | 0.005 | 4.7 | n.d. | n.d. | 0.00084 | >10 | n.d. | n.d. |
| 12 | 0.0299 | 40.6 | 0.00158 | 2.9 | 0.00093 | 3.835 | >1.1 | 100.4 |
| 13 | 0.0008 | 1.8 | n.d. | n.d. | 0.00018 | 3.393 | n.d. | n.d. |
| 14 | 0.0038 | 11.7 | 0.00152 | 2.8 | 0.00102 | 5.980 | >1.1 | 100.2 |
| 15 | 0.0004 | 1.6 | n.d. | n.d. | 0.00056 | 3.385 | n.d. | n.d. |
| 16 | 0.0042 | 4.1 | n.d. | n.d. | 0.00067 | >10 | n.d. | n.d. |
| 17 | 0.0023 | 11.0 | n.d. | n.d. | 0.00050 | 4.145 | n.d. | n.d. |
| 18 | 0.0108 | 3.4 | n.d. | n.d. | 0.00158 | 4.315 | n.d. | n.d. |
| 19 | 0.0006 | 2.7 | 0.00062 | 2.7 | 0.00045 | 4.455 | >10 | 100.5 |
| 20 | 0.002 | 1.1 | 0.00068 | 2.4 | 0.00053 | 7.900 | >1.1 | 93.3 |
| 21 | 0.0018 | 3.7 | n.d. | n.d. | 0.00060 | 6.830 | n.d. | n.d. |
| 22 | 0.0237 | 6.5 | 0.00247 | 4.5 | 0.00482 | 4.113 | >10 | 99.7 |
| 23 | 0.0468 | 10.4 | n.d. | n.d. | 0.00535 | >10 | n.d. | n.d. |
| 24 | 0.0771 | 10.8 | n.d. | n.d. | 0.00598 | >10 | n.d. | n.d. |
| 25 | 0.0784 | 7.2 | n.d. | n.d. | 0.01136 | >10 | n.d. | n.d. |
| 26 | 0.025 | 4.3 | n.d. | n.d. | 0.00192 | 4.760 | n.d. | n.d. |
| 27 | 0.0015 | 4.1 | 0.00081 | 2.8 | 0.00040 | 4.085 | >1.1 | 102.2 |
| 28 | 0.0937 | 12.1 | n.d. | n.d. | 0.00716 | 6.115 | n.d. | n.d. |
| 29 | 0.0199 | 3.1 | n.d. | n.d. | 0.00225 | 8.625 | >3.3 | 98.6 |
| 30 | 0.0471 | 5.4 | 0.00818 | 3.1 | 0.00520 | >10 | >3.3 | 101.1 |
| 31 | 0.0025 | 3.4 | 0.00121 | 3.0 | 0.00046 | 5.641 | >5.5 | 99.8 |
| 32 | 0.0342 | 15.4 | n.d. | n.d. | 0.00631 | 7.445 | n.d. | n.d. |
| 33 | 0.0222 | 5.9 | n.d. | n.d. | 0.00397 | 4.285 | n.d. | n.d. |
| 34 | 0.0039 | 1.7 | 0.00194 | 1.6 | 0.00170 | >10 | >10 | 94.7 |
| 35 | 0.0611 | 7.6 | n.d. | n.d. | 0.00346 | 9.160 | n.d. | n.d. |
| 36 | 0.037 | 2.4 | n.d. | n.d. | 0.00294 | >10 | n.d. | n.d. |
| 37 | 0.0113 | 6.5 | n.d. | n.d. | 0.00193 | 4.218 | n.d. | n.d. |
| 38 | 0.0009 | 4.1 | n.d. | n.d. | 0.00051 | 4.440 | n.d. | n.d. |
| 39 | 0.1494 | 12.7 | n.d. | n.d. | 0.00479 | 7.160 | >10 | 94.5 |
| 40 | 0.0532 | 4.6 | 0.00303 | 2.9 | 0.00343 | >10 | n.d. | n.d. |
| 41 | 0.0124 | 4.4 | n.d. | n.d. | 0.01750 | >10 | n.d. | n.d. |
| 42 | 0.0595 | 8.8 | n.d. | n.d. | 0.00534 | 8.920 | n.d. | n.d. |
| 43 | 0.001 | 2.3 | n.d. | n.d. | 0.00068 | 3.340 | n.d. | n.d. |
| 44 | 0.2355 | 48.4 | n.d. | n.d. | 0.00374 | 3.050 | >3.3 | 99.7 |
| 45 | 0.284 | 3.2 | n.d. | n.d. | 0.01910 | >10 | n.d. | n.d. |
| 46 | 0.0017 | 3.6 | n.d. | n.d. | 0.00359 | >10 | n.d. | n.d. |
| 47 | 0.0022 | 6.7 | 0.00072 | 2.4 | 0.00053 | 4.575 | >1.1 | 99.7 |
| 48 | 0.0208 | 9.4 | n.d. | n.d. | 0.00223 | 3.595 | n.d. | n.d. |
| 49 | 0.0703 | 49.4 | n.d. | n.d. | 0.00535 | 4.845 | n.d. | n.d. |
| 50 | 0.0012 | 4.1 | n.d. | n.d. | 0.00066 | 7.773 | n.d. | n.d. |
| 51 | 0.0008 | 3.9 | n.d. | n.d. | 0.00058 | 4.370 | n.d. | n.d. |
| 52 | 2.5756 | 43.7 | n.d. | n.d. | 0.02273 | >10 | n.d. | n.d. |
| 53 | 0.1498 | 17.4 | n.d. | n.d. | 0.00314 | >10 | n.d. | n.d. |
| 54 | 0.0015 | 4.4 | n.d. | n.d. | 0.00356 | >10 | n.d. | n.d. |
| 55 | >0.1235 | 53.8 | n.d. | n.d. | 0.00701 | 7.940 | n.d. | n.d. |
| 56 | 0.004 | 4.4 | n.d. | n.d. | 0.01543 | 6.335 | n.d. | n.d. |
| 57 | 0.0144 | 8.9 | n.d. | n.d. | 0.00116 | 4.400 | n.d. | n.d. |
| 58 | 0.0009 | 1.8 | n.d. | n.d. | 0.00056 | 4.915 | n.d. | n.d. | n.d. = not determined

TABLE 3

| Compound name | IKZF3 DC50 [uM] | IKZF deg Amax % |
|---|---|---|
| Lenalidomide | 0.069 | 16.8 |
| Pomalidomide | 0.039 | 13.2 |

The invention claimed is:

1. A compound of formula (I):

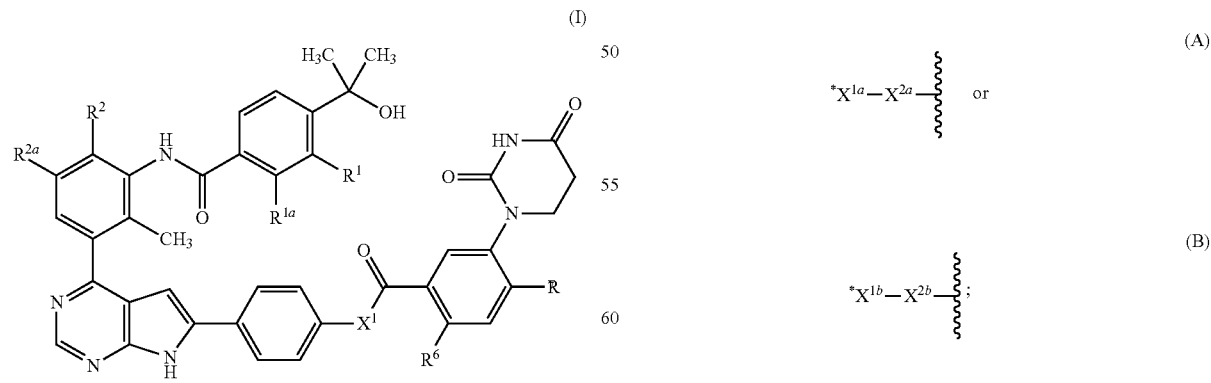

or a pharmaceutically acceptable salt or stereoisomer thereof, wherein:

$X^1$ is formula (A) or formula (B):

$*X^{1a}-X^{2a}-\xi$  (A)

or $*X^{1b}-X^{2b}-\xi$;  (B)

$X^{1a}$ is $*-(CH_2)_{1-3}-$ or $*-CH_2C(CH_3)_2-$;

$X^{1b}$ is $*-CH_2O-$, $*-O-$, or $*-OCH_2-$;

$X^{2a}$ is formula (C), formula (D), formula (E), formula (F), or formula (G):

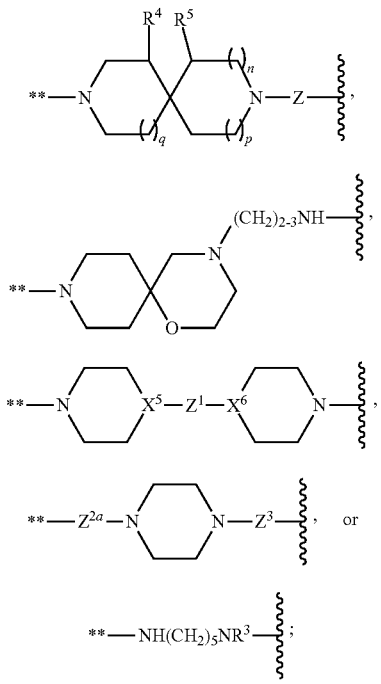

$X^{2b}$ is formula (E1) or formula (F1):

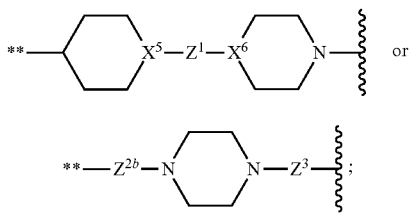

$X^5$ is CH or N;
$X^6$ is CH or N;
$R^1$ is H or F;
$R^{1a}$ is H or F;
$R^2$ is H or F;
$R^{2a}$ is H or F;
$R^3$ is H or $CH_3$;
$R^4$ is H or $CH_2OH$;
$R^5$ is H or $CH_2OH$;
$R^6$ is H or F;
$R^7$ is H, F, Cl, $CH_3$, $OCH_3$, or $OCH_2CH_3$;
Z is absent or *—$(CH_2)_{2-3}$NH—, wherein * is the point of attachment of Z to the N atom in formula (C);
$Z^1$ is *—$(CH_2)_{1-3}$—, *—$CH_2CH_2O$—, *—$CH_2CH(CH_2OH)O$—, *—C(O)—, or *—O—, wherein * is the point of attachment of $Z^1$ to $X^5$ in formula (E) or formula (E1);
$Z^{2a}$ is absent or —$(CH_2)_4$NH—, wherein  is the point of attachment to N in formula (F);
$Z^{2b}$ is —$(CH_2)_2NH(CH_2)_{3-4}$—, wherein  is the point of attachment to N in formula (F1);

$Z^3$ is absent or —$(CH_2)_4$NH—, wherein  is the point of attachment to N in formula (F);
n is 0 or 1;
p is 0 or 1;
q is 0 or 1;
* is the point of attachment of $X^{1a}$ or $X^{1b}$ to the phenyl ring in formula (I); and
** is the point of attachment to $X^{1a}$ or $X^{1b}$;
with the provisos that:
(1) $Z^{2a}$ and $Z^3$ are not both simultaneously absent;
(2) if $Z^1$ is *—$CH_2CH_2O$— or *—$CH_2CH(CH_2OH)O$— in formula (E) or formula (E1), then $X^6$ is not N; and
(3) if $Z^1$ is *—O— in formula (E) or formula (E1), then $X^5$ is not N and $X^6$ is not N.

2. The compound according to claim 1, or a pharmaceutically acceptable salt or stereoisomer thereof, wherein:
$X^1$ is formula (A):

$X^{1a}$ is *—$(CH_2)_{1-3}$— or *—$CH_2C(CH_3)_2$—;
$X^{2a}$ is formula (C), formula (E), or formula (F):

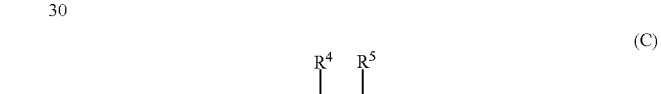

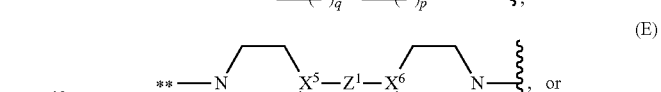

* is the point of attachment of $X^{1a}$ to the phenyl ring in formula (I); and
** is the point of attachment to $X^{1a}$.

3. The compound according to claim 1, or a pharmaceutically acceptable salt or stereoisomer thereof, wherein:
$X^1$ is:

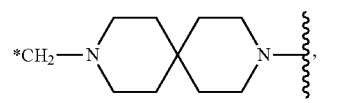

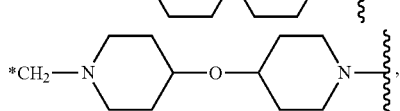

193

-continued

*CH₂CH₂—N⟨piperidine⟩—O—⟨piperidine⟩N—⟩,

*CH₂—N⟨piperazine⟩N—CH₂CH₂—N⟨piperazine⟩N—⟩, or

*CH₂NHCH₂CH₂CH₂CH₂—N⟨piperazine⟩N—⟩;

and
* is the point of attachment to the phenyl ring in formula (I).

4. The compound according to claim 1, wherein the compound is of formula (Ia):

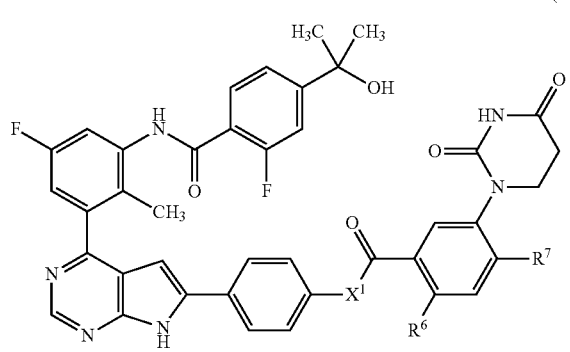

(Ia)

or a pharmaceutically acceptable salt or stereoisomer thereof.

5. The compound according to claim 1, or a pharmaceutically acceptable salt or stereoisomer thereof, wherein $R^6$ is H.

6. The compound according to claim 1, or a pharmaceutically acceptable salt or stereoisomer thereof, wherein $R^7$ is $OCH_3$.

7. The compound according to claim 1, or a stereoisomer thereof, wherein the compound, or stereoisomer thereof, is selected from the group consisting of:
rac-N-(3-(6-(4-((9-(3-(2,4-dioxotetrahydropyrimidin-1(2H)-yl)-4-methoxybenzoyl)-7-(hydroxymethyl)-3,9-diazaspiro[5.5]undecan-3-yl)methyl)phenyl)-7H-pyrrolo[2,3-d]pyrimidin-4-yl)-5-fluoro-2-methylphenyl)-2-fluoro-4-(2-hydroxypropan-2-yl)benzamide,
(R)—N-(3-(6-(4-((9-(3-(2,4-dioxotetrahydropyrimidin-1(2H)-yl)-4-methoxybenzoyl)-7-(hydroxymethyl)-3,9-diazaspiro[5.5]undecan-3-yl)methyl)phenyl)-7H-pyrrolo[2,3-d]pyrimidin-4-yl)-5-fluoro-2-methylphenyl)-2-fluoro-4-(2-hydroxypropan-2-yl)benzamide,
(S)—N-(3-(6-(4-((9-(3-(2,4-dioxotetrahydropyrimidin-1(2H)-yl)-4-methoxybenzoyl)-7-(hydroxymethyl)-3,9-diazaspiro[5.5]undecan-3-yl)methyl)phenyl)-7H-pyrrolo[2,3-d]pyrimidin-4-yl)-5-fluoro-2-methylphenyl)-2-fluoro-4-(2-hydroxypropan-2-yl)benzamide,
N-(3-(6-(4-((9-(3-(2,4-dioxotetrahydropyrimidin-1(2H)-yl)-4-ethoxybenzoyl)-3,9-diazaspiro[5.5]undecan-3-yl)methyl)phenyl)-7H-pyrrolo[2,3-d]pyrimidin-4-yl)-5-fluoro-2-methylphenyl)-2-fluoro-4-(2-hydroxypropan-2-yl)benzamide,

194

N-(3-(6-(4-(2-(9-(3-(2,4-dioxotetrahydropyrimidin-1(2H)-yl)-4-methylbenzoyl)-3,9-diazaspiro[5.5]undecan-3-yl)ethyl)phenyl)-7H-pyrrolo[2,3-d]pyrimidin-4-yl)-5-fluoro-2-methylphenyl)-2-fluoro-4-(2-hydroxypropan-2-yl)benzamide,
N-(3-(6-(4-(((1-(2-(1-(3-(2,4-dioxotetrahydropyrimidin-1(2H)-yl)-4-fluorobenzoyl)piperidin-4-yl)ethyl)piperidin-4-yl)oxy)methyl)phenyl)-7H-pyrrolo[2,3-d]pyrimidin-4-yl)-5-fluoro-2-methylphenyl)-2-fluoro-4-(2-hydroxypropan-2-yl)benzamide,
N-(3-(6-(4-((4-((1-(3-(2,4-dioxotetrahydropyrimidin-1(2H)-yl)-4-methoxybenzoyl)piperidin-4-yl)methyl)piperazin-1-yl)methyl)phenyl)-7H-pyrrolo[2,3-d]pyrimidin-4-yl)-5-fluoro-2-methylphenyl)-2-fluoro-4-(2-hydroxypropan-2-yl)benzamide,
N-(3-(6-(4-((4-((1-(3-(2,4-dioxotetrahydropyrimidin-1(2H)-yl)-4-methoxybenzoyl)piperidin-4-yl)oxy)piperidin-1-yl)methyl)phenyl)-7H-pyrrolo[2,3-d]pyrimidin-4-yl)-5-fluoro-2-methylphenyl)-2-fluoro-4-(2-hydroxypropan-2-yl)benzamide,
N-(3-(6-(4-((9-(3-(2,4-dioxotetrahydropyrimidin-1(2H)-yl)-4-methoxybenzoyl)-3,9-diazaspiro[5.5]undecan-3-yl)methyl)phenyl)-7H-pyrrolo[2,3-d]pyrimidin-4-yl)-5-fluoro-2-methylphenyl)-2-fluoro-4-(2-hydroxypropan-2-yl)benzamide,
N-(3-(6-(4-(2-(4-((1-(3-(2,4-dioxotetrahydropyrimidin-1(2H)-yl)-4-methylbenzoyl)piperidin-4-yl)oxy)piperidin-1-yl)ethyl)phenyl)-7H-pyrrolo[2,3-d]pyrimidin-4-yl)-5-fluoro-2-methylphenyl)-2-fluoro-4-(2-hydroxypropan-2-yl)benzamide,
N-(3-(6-(4-(3-(9-(3-(2,4-dioxotetrahydropyrimidin-1(2H)-yl)-4-methoxybenzoyl)-3,9-diazaspiro[5.5]undecan-3-yl)propyl)phenyl)-7H-pyrrolo[2,3-d]pyrimidin-4-yl)-5-fluoro-2-methylphenyl)-2-fluoro-4-(2-hydroxypropan-2-yl)benzamide,
N-(3-(6-(4-(2-(9-(3-(2,4-dioxotetrahydropyrimidin-1(2H)-yl)benzoyl)-3,9-diazaspiro[5.5]undecan-3-yl)ethyl)phenyl)-7H-pyrrolo[2,3-d]pyrimidin-4-yl)-5-fluoro-2-methylphenyl)-2-fluoro-4-(2-hydroxypropan-2-yl)benzamide,
N-(3-(6-(4-(((1-(2-(1-(3-(2,4-dioxotetrahydropyrimidin-1(2H)-yl)-4-methoxybenzoyl)piperidin-4-yl)ethyl)piperidin-4-yl)oxy)methyl)phenyl)-7H-pyrrolo[2,3-d]pyrimidin-4-yl)-5-fluoro-2-methylphenyl)-2-fluoro-4-(2-hydroxypropan-2-yl)benzamide,
N-(3-(6-(4-((9-(3-(2,4-dioxotetrahydropyrimidin-1(2H)-yl)-4-fluorobenzoyl)-3,9-diazaspiro[5.5]undecan-3-yl)methyl)phenyl)-7H-pyrrolo[2,3-d]pyrimidin-4-yl)-5-fluoro-2-methylphenyl)-2-fluoro-4-(2-hydroxypropan-2-yl)benzamide,
N-(3-(6-(4-((1-(3-(1-(3-(2,4-dioxotetrahydropyrimidin-1(2H)-yl)-4-methoxybenzoyl)piperidin-4-yl)propyl)piperidin-4-yl)oxy)phenyl)-7H-pyrrolo[2,3-d]pyrimidin-4-yl)-5-fluoro-2-methylphenyl)-2-fluoro-4-(2-hydroxypropan-2-yl)benzamide,
N-(3-(6-(4-((4-(2-(4-(3-(2,4-dioxotetrahydropyrimidin-1(2H)-yl)-4-methoxybenzoyl)piperazin-1-yl)ethyl)piperazin-1-yl)methyl)phenyl)-7H-pyrrolo[2,3-d]pyrimidin-4-yl)-5-fluoro-2-methylphenyl)-2-fluoro-4-(2-hydroxypropan-2-yl)benzamide,
N-(3-(6-(4-((4-(2-(1-(3-(2,4-dioxotetrahydropyrimidin-1(2H)-yl)-4-methoxybenzoyl)piperidin-4-yl)ethyl)piperazin-1-yl)methyl)phenyl)-7H-pyrrolo[2,3-d]pyrimidin-4-yl)-5-fluoro-2-methylphenyl)-2-fluoro-4-(2-hydroxypropan-2-yl)benzamide,
rac-N-(3-(6-(4-((1-(2-((1-(3-(2,4-dioxotetrahydropyrimidin-1(2H)-yl)-4-methoxybenzoyl)piperidin-4-yl)oxy)-

3-hydroxypropyl)piperidin-4-yl)oxy)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-(((1-((1-(3-(2,4-dioxotetrahydropyrimidin-1(2H)-yl)-4-methoxybenzoyl)piperidin-4-yl)methyl)piperidin-4-yl)oxy)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-(2-(9-(3-(2,4-dioxotetrahydropyrimidin-1(2H)-yl)-4-methoxybenzoyl)-3,9-diazaspiro[5.5]undecan-3-yl)-2-methylpropyl)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-(((1-(2-(4-(3-(2,4-dioxotetrahydropyrimidin-1(2H)-yl)-4-methoxybenzoyl)piperazin-1-yl)ethyl)piperidin-4-yl)oxy)methyl)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-((4-(4-(3-(2,4-dioxotetrahydropyrimidin-1(2H)-yl)-4-methoxybenzoyl)piperazine-1-carbonyl)piperazin-1-yl)methyl)phenyl)-7H-pyrrolo[2,3-d]pyrimidin-4-yl)-5-fluoro-2-methylphenyl)-2-fluoro-4-(2-hydroxypropan-2-yl)benzamide, rac-N-(3-(6-(4-((9-(3-(2,4-dioxotetrahydropyrimidin-1(2H)-yl)-4-methoxybenzoyl)-1-(hydroxymethyl)-3,9-diazaspiro[5.5]undecan-3-yl)methyl)phenyl)-7H-pyrrolo[2,3-d]pyrimidin-4-yl)-5-fluoro-2-methylphenyl)-2-fluoro-4-(2-hydroxypropan-2-yl)benzamide, (S)—N-(3-(6-(4-((9-(3-(2,4-dioxotetrahydropyrimidin-1(2H)-yl)-4-methoxybenzoyl)-1-(hydroxymethyl)-3,9-diazaspiro[5.5]undecan-3-yl)methyl)phenyl)-7H-pyrrolo[2,3-d]pyrimidin-4-yl)-5-fluoro-2-methylphenyl)-2-fluoro-4-(2-hydroxypropan-2-yl)benzamide, (R)—N-(3-(6-(4-((9-(3-(2,4-dioxotetrahydropyrimidin-1(2H)-yl)-4-methoxybenzoyl)-1-(hydroxymethyl)-3,9-diazaspiro[5.5]undecan-3-yl)methyl)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-((4-(4-(3-(2,4-dioxotetrahydropyrimidin-1(2H)-yl)-4-methoxybenzamido)butyl)piperazin-1-yl)methyl)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-((9-(3-(2,4-dioxotetrahydropyrimidin-1(2H)-yl)-4-methylbenzoyl)-3,9-diazaspiro[5.5]undecan-3-yl)methyl)phenyl)-7H-pyrrolo[2,3-d]pyrimidin-4-yl)-5-fluoro-2-methylphenyl)-2-fluoro-4-(2-hydroxypropan-2-yl)benzamide, 5-(2,4-dioxotetrahydropyrimidin-1(2H)-yl)-2-fluoro-N-(5-((4-(4-(5-fluoro-3-(2-fluoro-4-(2-hydroxypropan-2-yl)benzamido)-2-methylphenyl)-7H-pyrrolo[2,3-d]pyrimidin-6-yl)benzyl)amino)pentyl)-N,4-dimethylbenzamide, 5-(2,4-dioxotetrahydropyrimidin-1(2H)-yl)-2-fluoro-N-(5-((4-(4-(5-fluoro-3-(2-fluoro-4-(2-hydroxypropan-2-yl)benzamido)-2-methylphenyl)-7H-pyrrolo[2,3-d]pyrimidin-6-yl)benzyl)amino)pentyl)-4-methylbenzamide, 3-(2,4-dioxotetrahydropyrimidin-1(2H)-yl)-N-(5-((4-(4-(5-fluoro-3-(2-fluoro-4-(2-hydroxypropan-2-yl)benzamido)-2-methylphenyl)-7H-pyrrolo[2,3-d]pyrimidin-6-yl)benzyl)amino)pentyl)-N,4-dimethylbenzamide, N-(3-(6-(4-(2-(9-(3-(2,4-dioxotetrahydropyrimidin-1(2H)-yl)-4-methoxybenzoyl)-3,9-diazaspiro[5.5]undecan-3-yl)ethyl)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-((2-(3-(2,4-dioxotetrahydropyrimidin-1(2H)-yl)-4-methoxybenzoyl)-2,7-diazaspiro[3.5]nonan-7-yl)methyl)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-((4-(1-(3-(2,4-dioxotetrahydropyrimidin-1(2H)-yl)-4-methoxybenzoyl)piperidine-4-carbonyl)piperazin-1-yl)methyl)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-(2-(4-((1-(3-(2,4-dioxotetrahydropyrimidin-1(2H)-yl)-4-methoxybenzoyl)piperidin-4-yl)oxy)piperidin-1-yl)ethyl)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-((8-(2-(3-(2,4-dioxotetrahydropyrimidin-1(2H)-yl)-4-methoxybenzamido)ethyl)-2,8-diazaspiro[4.5]decan-2-yl)methyl)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-(4-((2-(4-(3-(2,4-dioxotetrahydropyrimidin-1(2H)-yl)-4-methoxybenzoyl)piperazin-1-yl)ethyl)amino)butoxy)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-((4-(2-(4-chloro-3-(2,4-dioxotetrahydropyrimidin-1(2H)-yl)benzamido)ethyl)-1-oxa-4,9-diazaspiro[5.5]undecan-9-yl)methyl)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-((1-(2-(1-(3-(2,4-dioxotetrahydropyrimidin-1(2H)-yl)-4-methoxybenzoyl)piperidin-4-yl)ethyl)piperidin-4-yl)oxy)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-((4-(2-(3-(2,4-dioxotetrahydropyrimidin-1(2H)-yl)-4-methoxybenzamido)ethyl)-1-oxa-4,9-diazaspiro[5.5]undecan-9-yl)methyl)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-(((4-(4-(3-(2,4-dioxotetrahydropyrimidin-1(2H)-yl)-4-methoxybenzoyl)piperazin-1-yl)butyl)amino)methyl)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-((((1s,4s)-4-((1-(3-(2,4-dioxotetrahydropyrimidin-1(2H)-yl)-4-methoxybenzoyl)piperidin-4-yl)oxy)cyclohexyl)oxy)methyl)phenyl)-7H-pyrrolo[2,3-d]pyrimidin-4-yl)-5-fluoro-2-methylphenyl)-2-fluoro-4-(2-hydroxypropan-2-yl)benzamide, 4-chloro-3-(2,4-dioxotetrahydropyrimidin-1(2H)-yl)-N-(5-((4-(4-(5-fluoro-3-(2-fluoro-4-(2-hydroxypropan-2-yl)benzamido)-2-methylphenyl)-7H-pyrrolo[2,3-d]pyrimidin-6-yl)benzyl)amino)pentyl)-N-methylbenzamide, N-(3-(6-(4-((1-(2-(1-(3-(2,4-dioxotetrahydropyrimidin-1(2H)-yl)-4-methoxybenzoyl)piperidin-4-yl)ethyl)piperidin-4-yl)methoxy)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-((9-(2-(3-(2,4-dioxotetrahydropyrimidin-1(2H)-yl)-4-methoxybenzamido)ethyl)-3,9-diazaspiro[5.5]undecan-3-yl)methyl)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-((3-((2-(4-(3-(2,4-dioxotetrahydropyrimidin-1(2H)-yl)-4-methoxybenzoyl)piperazin-1-yl)ethyl)amino)propoxy)methyl)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-(((1r,4r)-4-((1-(3-(2,4-dioxotetrahydropyrimidin-1(2H)-yl)-4-methoxybenzoyl)piperidin-4-yl)oxy)cyclohexyl)oxy)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-(2-(9-(3-(2,4-dioxotetrahydropyrimidin-1(2H)-yl)-4-fluorobenzoyl)-3,9-diazaspiro[5.5]undecan-3-yl)ethyl)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-((4-(3-(4-chloro-3-(2,4-dioxotetrahydropyrimidin-1(2H)-yl)benzamido)propyl)-1-oxa-4,9-diazaspiro[5.5]undecan-9-yl)methyl)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-((8-(3-(2,4-dioxotetrahydropyrimidin-1(2H)-yl)-4-methoxybenzoyl)-2,8-diazaspiro[4.5]decan-2-yl)methyl)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-((4-((1-(3-(2,4-dioxotetrahydropyrimidin-1(2H)-yl)-4-methylbenzoyl)piperidin-4-yl)oxy)piperidin-1-yl)methyl)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-((1-(2-(4-(3-(2,4-dioxotetrahydropyrimidin-1(2H)-yl)-4-methoxybenzoyl)piperazin-1-yl)ethyl)piperidin-4-yl)methoxy)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-((2-(2-(3-(2,4-dioxotetrahydropyrimidin-1(2H)-yl)-4-methoxybenzamido)ethyl)-2,7-diazaspiro[3.5]nonan-7-yl)methyl)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-((2-(2-(3-(2,4-dioxotetrahydropyrimidin-1(2H)-yl)-4-methoxybenzamido)ethyl)-2,8-diazaspiro[4.5]decan-8-yl)methyl)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-(((1s,4s)-4-((1-(3-(2,4-dioxotetrahydropyrimidin-1(2H)-yl)-4-methoxybenzoyl)piperidin-4-yl)oxy)cyclohexyl)oxy)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-((2-(3-(2,4-dioxotetrahydropyrimidin-1(2H)-yl)-4-methoxybenzoyl)-2,8-diazaspiro[4.5]decan-8-yl)methyl)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-(((((1r,4r)-4-((1-(3-(2,4-dioxotetrahydropyrimidin-1(2H)-yl)-4-methoxybenzoyl)piperidin-4-yl)oxy)cyclohexyl)oxy)methyl)phenyl)-7H-pyrrolo[2,3-d]pyrimidin-4-yl)-5-fluoro-2-methylphenyl)-2-fluoro-4-(2-hydroxypropan-2-yl)benzamide, N-(3-(6-(4-((9-(3-(4-chloro-3-(2,4-dioxotetrahydropyrimidin-1(2H)-yl)benzamido)propyl)-3,9-diazaspiro[5.5]undecan-3-yl)methyl)phenyl)-7H-pyrrolo[2,3-d]pyrimidin-4-yl)-5-fluoro-2-methylphenyl)-2-fluoro-4-(2-hydroxypropan-2-yl)benzamide, and N-(3-(6-(4-((1-(2-((1-(3-(2,4-dioxotetrahydropyrimidin-1(2H)-yl)-4-methoxybenzoyl)piperidin-4-yl)oxy)ethyl)piperidin-4-yl)oxy)phenyl)-7H-pyrrolo[2,3-d]pyrimidin-4-yl)-5-fluoro-2-methylphenyl)-2-fluoro-4-(2-hydroxypropan-2-yl)benzamide, or a pharmaceutically acceptable salt thereof.

8. A combination comprising a compound according to claim 1, or a pharmaceutically acceptable salt or stereoisomer thereof, and one or more therapeutically active agents.

9. A pharmaceutical composition comprising a compound according to claim 1, or a pharmaceutically acceptable salt or stereoisomer thereof, and one or more pharmaceutically acceptable carriers.

10. A method for inhibiting Bruton's tyrosine kinase activity in a subject, wherein the method comprises administering to the subject in need thereof a therapeutically effective amount of a compound according to claim 1, or a pharmaceutically acceptable salt or stereoisomer thereof.

11. The method according to claim 10, wherein the subject has an airway disease, an allergic disease, an autoimmune disorder, or an inflammatory disorder.

12. The method according to claim 11, wherein the allergic disease is allergic asthma or anaphylaxis.

13. The method according to claim 10, wherein the subject has cancer.

14. The method according to claim 13, wherein the cancer is selected from the group consisting of acute lymphoblastic leukemia, B-cell prolymphocytic leukemia, Burkitt lymphoma, chronic lymphocytic leukemia, a dendritic neoplasm, diffuse large B-cell lymphoma, extranodal marginal zone B-cell lymphoma, follicular lymphoma, hairy cell leukemia, a histiocytic neoplasm, Hodgkin lymphoma, immunoblastic large cell lymphoma, intravascular large B-cell lymphoma, lymphomatoid granulomatosis, lymphoplasmacytic lymphoma, mantle cell lymphoma, marginal zone lymphoma, mediastinal large B-cell lymphoma, nodal marginal zone B-cell lymphoma, non-Hodgkin lymphoma, plasma cell myeloma, plasmacytoma, post-transplant lymphoproliferative disorder, precursor B-lymphoblastic lymphoma, primary effusion lymphoma, primary multiple myeloma, Richter syndrome, secondary multiple myeloma, small lymphocytic lymphoma, and Waldenstrom's macroglobulinemia.

* * * * *

SEQUENCE LISTING

<160> NUMBER OF SEQ ID NOS: 11

<210> SEQ ID NO 1
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1
cgatgaattc gccaccgcta gcatggtgag caagggcgag gagc                 44

<210> SEQ ID NO 2
<211> LENGTH: 43
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 2
ctcattacta accggctagc ttacttgtac agctcgtcca tgc                  43

<210> SEQ ID NO 3
<211> LENGTH: 55
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 3
ccagcacagt ggcggccgct cgagcatggt gagcaagggc gaggagctgt tcacc     55

<210> SEQ ID NO 4
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 4
ccgcgggccc tctagactcg agttacttgt acagctcgtc catgccgaga gt        52

<210> SEQ ID NO 5
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 5
agagccctgc tgaagttgaa cccagctttc ttgtac                          36

<210> SEQ ID NO 6
<211> LENGTH: 36
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic primer"

<400> SEQUENCE: 6
gtacaagaaa gctgggttca acttcagcag ggctct                              36

<210> SEQ ID NO 7
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 7
gagtacatgg ccaatggctc cctcctgaac tacctgagg                           39

<210> SEQ ID NO 8
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 8
cctcaggtag ttcaggaggg agccattggc catgtactc                           39

<210> SEQ ID NO 9
<211> LENGTH: 1551
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 9
gatatccagc acagtggcgg ccgctcgagc atggtgagca agggcgagga gctgttcacc    60
ggggtggtgc ccatcctggt cgagctggac ggcgacgtaa acggccacaa gttcagcgtg   120
tccggcgagg gcgagggcga tgccacctac ggcaagctga ccctgaagtt catctgcacc   180
accggcaagc tgcccgtgcc ctggcccacc ctcgtgacca cctgacctac ggcgtgcag    240 tgcttcagcc gctaccccga ccacatgaag cagcacgact tcttcaagtc cgccatgccc   300
gaaggctacg tccaggagcg caccatcttc ttcaaggacg acggcaacta caagacccgc   360
gccgaggtga agttcgaggg cgacaccctg gtgaaccgca tcgagctgaa gggcatcgac   420
ttcaaggagg acggcaacat cctggggcac aagctggagt acaactacaa cagccacaac   480
gtctatatca tggccgacaa gcagaagaac ggcatcaagg tgaacttcaa gatccgccac   540
aacatcgagg acggcagcgt gcagctcgcc gaccactacc agcagaacac ccccatcggc   600
gacggccccg tgctgctgcc cgacaaccac tacctgagca cccagtccgc cctgagcaaa   660
gaccccaacg agaagcgcga tcacatggtc ctgctggagt tcgtgaccgc cgccgggatc   720
actctcggca tggacgagct gtacaaggga agcggagcga cgaattttag tctactgaaa   780
caagcgggag acgtggagga aaaccctgga cctatggtga gcaagggcga ggaggataac   840
atggccatca tcaaggagtt catgcgcttc aaggtgcaca tggagggctc cgtgaacggc   900
cacgagttcg agatcgaggg cgagggcgag ggccgcccct acgagggcac ccagaccgcc   960
```

```
aagctgaagg tgaccaaggg tggcccctg cccttcgcct gggacatcct gtcccctcag    1020
ttcatgtacg gctccaaggc ctacgtgaag caccccgccg acatccccga ctacttgaag    1080
ctgtccttcc ccgagggctt caagtgggag cgcgtgatga acttcgagga cggcggcgtg    1140
gtgaccgtga cccaggactc ctccctgcag gacggcgagt tcatctacaa ggtgaagctg    1200
cgcggcacca acttcccctc cgacggcccc gtaatgcaga agaagaccat gggctgggag    1260
gcctcctccg agcggatgta ccccgaggac ggcgccctga agggcgagat caagcagagg    1320
ctgaagctga aggacggcgg ccactacgac gctgaggtca agaccaccta caaggccaag    1380
aagcccgtgc agctgcccgg cgcctacaac gtcaacatca gttggacat cacctcccac    1440 aacgaggact acaccatcgt ggaacagtac gaacgcgccg agggccgcca ctccaccggc    1500
ggcatggacg agctgtacaa gtagctcgag tctagagggc ccgcggttaa c            1551

<210> SEQ ID NO 10
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 10
gtcatggatg aagaatcctt gaacccagct ttcttgtac                            39

<210> SEQ ID NO 11
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 11
gtacaagaaa gctgggttca aggattcttc atccatgac                            39
```